(12) United States Patent
Kochendoerfer et al.

(10) Patent No.: US 7,118,737 B2
(45) Date of Patent: Oct. 10, 2006

(54) POLYMER-MODIFIED SYNTHETIC PROTEINS

(75) Inventors: Gerd G. Kochendoerfer, Oakland, CA (US); Paolo Botti, Piacenza (IT); James A. Bradburne, Redwood City, CA (US); Shiah-yun Chen, Mountain View, CA (US); Sonya Cressman, Ladysmith (CA); Christie L. Hunter, San Mateo, CA (US); Stephen B. H. Kent, San Francisco, CA (US); Donald W. Low, Burlingame, CA (US); Jill G. Wilken, Walnut Creek, CA (US)

(73) Assignee: Amylin Pharmaceuticals, Inc., San Diego, CA (US)

( * ) Notice: Subject to any disclaimer, the term of this patent is extended or adjusted under 35 U.S.C. 154(b) by 74 days.

(21) Appl. No.: 10/332,385

(22) PCT Filed: Jul. 12, 2001

(86) PCT No.: PCT/US01/21930

§ 371 (c)(1),
(2), (4) Date: Jan. 8, 2003

(87) PCT Pub. No.: WO02/20033

PCT Pub. Date: Mar. 14, 2002

(65) Prior Publication Data

US 2004/0115774 A1    Jun. 17, 2004

Related U.S. Application Data

(60) Provisional application No. 60/231,339, filed on Sep. 8, 2000, provisional application No. 60/236,377, filed on Sep. 29, 2000.

(51) Int. Cl.
*A61K 38/16* (2006.01)
*A61K 38/17* (2006.01)
*A61K 39/19* (2006.01)
*C07K 1/113* (2006.01)
*C07K 14/00* (2006.01)
*C07K 14/435* (2006.01)
*C07K 14/52* (2006.01)

(52) U.S. Cl. ............... 424/85.1; 530/350; 530/351; 530/395; 530/402; 530/409; 530/410; 424/85.2; 424/85.4; 514/2; 514/8; 514/21

(58) Field of Classification Search ............... 424/85.1, 424/85.2, 85.4, 85.5, 85.6, 85.7; 514/2, 8, 514/12, 21; 530/350, 351, 395, 397, 399, 530/402, 408, 409, 410; 525/420, 432; 528/335, 528/338, 339, 340; 564/160
See application file for complete search history.

(56) References Cited

U.S. PATENT DOCUMENTS 4,002,531 A    1/1977  Royer ..................... 195/68

(Continued)

FOREIGN PATENT DOCUMENTS

EP    0 154 316    9/1989

(Continued)

OTHER PUBLICATIONS

Goodson et al. Site-Directed Pegylation of Recombinant Interleukin-2 At Its Glycosylation Site. Bio/Technology. Apr. 1990, vol. 8, pp. 343-346.*

(Continued)

*Primary Examiner*—Jeffrey Edwin Russel
(74) *Attorney, Agent, or Firm*—Edell, Shapiro & Finnan, LLC

(57) ABSTRACT

The present invention relates to methods and compositions for modifying peptides, polypeptides and proteins with polymers, especially glyco-mimetic polymers, so as to improve their biological activity or pharmacokinetic properties. The invention further provides methods and uses for such polymer-modified peptides, polypeptides and proteins. The invention is particularly suitable for use in the synthesis of polymer-modified synthetic bioactive proteins (FIG. 1D), and of pharmaceutical compositions that contain such proteins.

62 Claims, 52 Drawing Sheets

U.S. PATENT DOCUMENTS

| | | | |
|---|---|---|---|
| 4,179,337 A | 12/1979 | Davis et al. | 435/181 |
| 4,833,127 A * | 5/1989 | Ono et al. | 514/21 |
| 4,904,584 A | 2/1990 | Shaw | 435/69.4 |
| 5,075,046 A | 12/1991 | Stoll | 560/410.6 |
| 5,089,261 A | 2/1992 | Nitecki et al. | 424/85.2 |
| 5,100,992 A | 3/1992 | Cohn et al. | 528/26 |
| 5,122,614 A | 6/1992 | Zalipsky | 548/520 |
| 5,134,192 A | 7/1992 | Feijen et al. | 525/54.1 |
| 5,166,309 A | 11/1992 | Maj et al. | 528/272 |
| 5,171,264 A | 12/1992 | Merrill | 623/3 |
| 5,213,891 A | 5/1993 | Maj et al. | 428/364 |
| 5,218,092 A | 6/1993 | Sasaki et al. | 530/351 |
| 5,219,564 A | 6/1993 | Zalipsky et al. | 424/78.17 |
| 5,264,209 A | 11/1993 | Mikayama et al. | 424/85.2 |
| 5,275,838 A | 1/1994 | Merrill | 427/2 |
| 5,281,698 A | 1/1994 | Nitecki | 530/351 |
| 5,298,643 A | 3/1994 | Greenwald | 558/6 |
| 5,312,808 A | 5/1994 | Shorr et al. | 514/6 |
| 5,321,095 A | 6/1994 | Greenwald | 525/404 |
| 5,324,844 A | 6/1994 | Zalipsky | 548/520 |
| 5,349,001 A | 9/1994 | Greenwald et al. | 525/408 |
| 5,352,756 A | 10/1994 | Meldal | 525/50 |
| 5,405,877 A | 4/1995 | Greenwald et al. | 514/772.3 |
| 5,428,128 A * | 6/1995 | Mensi-Fattohi et al. | 530/302 |
| 5,446,090 A | 8/1995 | Harris | 525/54.1 |
| 5,455,027 A | 10/1995 | Zalipsky et al. | 424/78.17 |
| 5,457,089 A | 10/1995 | Fibi et al. | 514/8 |
| 5,470,829 A | 11/1995 | Prisell et al. | 514/12 |
| 5,478,805 A | 12/1995 | Shorr et al. | 514/6 |
| 5,567,422 A | 10/1996 | Greenwald | 424/78.3 |
| 5,589,356 A | 12/1996 | Tam | 435/68.1 |
| 5,595,732 A | 1/1997 | Hakini et al. | 424/85.7 |
| 5,605,976 A | 2/1997 | Martinez et al. | 525/408 |
| 5,612,460 A | 3/1997 | Zalipsky | 530/391.9 |
| 5,614,184 A | 3/1997 | Sytkowski et al. | 424/85.1 |
| 5,614,549 A | 3/1997 | Greenwald et al. | 514/449 |
| 5,618,528 A | 4/1997 | Cooper et al. | 424/78.3 |
| 5,631,018 A | 5/1997 | Zapilsky et al. | 424/450 |
| 5,637,749 A | 6/1997 | Greenwald | 558/6 |
| 5,643,575 A | 7/1997 | Martinez et al. | 424/194.1 |
| 5,646,285 A | 7/1997 | Baindur et al. | 546/298 |
| 5,650,388 A | 7/1997 | Shorr et al. | 514/6 |
| 5,672,662 A | 9/1997 | Harris et al. | 525/408 |
| 5,681,567 A | 10/1997 | Martinez et al. | 424/178.1 |
| 5,686,110 A | 11/1997 | Greenwald et al. | 424/486 |
| 5,723,147 A | 3/1998 | Kim et al. | 424/450 |
| 5,730,990 A | 3/1998 | Greenwald et al. | 424/279.1 |
| 5,739,208 A | 4/1998 | Harris | 525/54.1 |
| 5,756,593 A | 5/1998 | Martinez et al. | 525/403 |
| 5,756,672 A | 5/1998 | Builder et al. | 530/350 |
| 5,766,627 A | 6/1998 | Sankaram et al. | 424/450 |
| 5,808,096 A | 9/1998 | Zalipsky | 548/520 |
| 5,824,778 A | 10/1998 | Ishikawa et al. | 530/351 |
| 5,824,784 A * | 10/1998 | Kinstler et al. | 530/399 |
| 5,840,900 A | 11/1998 | Greenwald et al. | 546/48 |
| 5,856,298 A | 1/1999 | Strickland | 514/8 |
| 5,858,347 A | 1/1999 | Bauer et al. | 424/85.2 |
| 5,874,500 A | 2/1999 | Rhee et al. | 525/54.1 |
| 5,879,712 A | 3/1999 | Bomberger et al. | 424/489 |
| 5,880,131 A | 3/1999 | Greenwald et al. | 514/279 |
| 5,880,255 A | 3/1999 | Delgado et al. | 530/303 |
| 5,888,772 A | 3/1999 | Okasinski et al. | 15/19 |
| 5,900,461 A | 5/1999 | Harris | 525/54.11 |
| 5,902,588 A | 5/1999 | Greenwald et al. | 424/278.1 |
| 5,919,442 A | 7/1999 | Yin et al. | 424/178.1 |
| 5,919,455 A | 7/1999 | Greenwald et al. | 424/178.1 |
| 5,932,462 A | 8/1999 | Harris et al. | 435/188 |
| 5,951,974 A | 9/1999 | Gilbert et al. | 424/85.7 |
| 5,955,422 A | 9/1999 | Lin | 514/8 |
| 5,965,119 A | 10/1999 | Greenwald et al. | 424/78.37 |
| 5,965,566 A | 10/1999 | Greenwald et al. | 514/279 |
| 5,985,263 A | 11/1999 | Lee et al. | 424/85.2 |
| 5,985,265 A | 11/1999 | Kinstler et al. | 424/85.4 |
| 5,990,237 A | 11/1999 | Bentley et al. | 525/54.2 |
| 6,011,042 A | 1/2000 | Greenwald et al. | 514/283 |
| 6,013,283 A | 1/2000 | Greenwald et al. | 424/486 |
| 6,042,822 A | 3/2000 | Gilbert et al. | 424/85.7 |
| 6,077,939 A | 6/2000 | Wei et al. | 530/402 |
| 6,090,388 A | 7/2000 | Wang | 424/185.1 |
| 6,113,906 A | 9/2000 | Greenwald et al. | 424/194.1 |
| 6,127,355 A | 10/2000 | Greenwald et al. | 514/183 |
| 6,140,064 A | 10/2000 | Loetscher et al. | 435/7.2 |
| 6,168,784 B1 | 1/2001 | Offord et al. | 424/85.1 |
| 6,177,087 B1 | 1/2001 | Greenwald et al. | 424/278.1 |
| 6,180,095 B1 | 1/2001 | Greenwald et al. | 424/85.1 |
| 6,180,336 B1 | 1/2001 | Osbourn et al. | 435/5 |
| 6,184,358 B1 | 2/2001 | Loetscher et al. | 530/388.22 |
| 6,194,580 B1 | 2/2001 | Greenwald et al. | 546/48 |
| 6,214,540 B1 | 4/2001 | DeVico et al. | 435/5 |
| 6,214,966 B1 | 4/2001 | Harris | 528/322 |
| 6,515,027 B1 * | 2/2003 | Bondinell et al. | 514/617 |
| 6,552,167 B1 | 4/2003 | Rose | 530/326 |

FOREIGN PATENT DOCUMENTS

| | | |
|---|---|---|
| EP | 0 459 630 | 4/1991 |
| EP | 0 668 353 | 8/1995 |
| EP | 0 401 384 | 3/1996 |
| EP | 0 442 724 | 10/1999 |
| WO | WO 90/02135 | 3/1990 |
| WO | WO 90/02136 | 3/1990 |
| WO | WO 90/13540 | 11/1990 |
| WO | WO 91/19735 | 12/1991 |
| WO | WO 92/00748 | 1/1992 |
| WO | WO 92/01047 | 1/1992 |
| WO | WO 92/16555 | 10/1992 |
| WO | WO 94/04193 | 3/1994 |
| WO | WO 94/14758 | 7/1994 |
| WO | WO 94/17039 | 8/1994 |
| WO | WO 94/18247 | 8/1994 |
| WO | WO 94/28937 | 12/1994 |
| WO | WO 95/00846 | 1/1995 |
| WO | WO 95/11924 | 5/1995 |
| WO | WO 95/13312 | 5/1995 |
| WO | WO 96/00080 | 1/1996 |
| WO | WO 96/21469 | 7/1996 |
| WO | WO 96/23794 | 8/1996 |
| WO | WO 96/34878 | 11/1996 |
| WO | WO 96/41813 | 12/1996 |
| WO | WO 97/03106 | 1/1997 |
| WO | WO 97/44054 | 11/1997 |
| WO | WO 98/07713 | 2/1998 |
| WO | WO 98/28434 | 7/1998 |
| WO | WO 98/41562 | 9/1998 |
| WO | WO 98/48837 | 11/1998 |
| WO | WO 98/49198 * | 11/1998 |
| WO | WO 99/03887 A1 * | 1/1999 |
| WO | WO 99/11655 | 3/1999 |
| WO | WO 99/11666 | 3/1999 |
| WO | WO 99/30727 | 6/1999 |
| WO | WO 99/32134 | 7/1999 |
| WO | WO 99/33483 | 7/1999 |
| WO | WO 99/45964 | 9/1999 |
| WO | WO 99/53951 | 10/1999 |
| WO | WO 00/04926 | 2/2000 |
| WO | WO 00/12587 A2 * | 3/2000 |
| WO | WO 00/32772 | 6/2000 |
| WO | WO 01/26692 | 4/2001 |
| WO | WO 02/004015 | 1/2002 |
| WO | WO 02/20033 | 3/2002 |
| WO | WO 02/20034 | 3/2002 |

OTHER PUBLICATIONS

Zhao et al. Site-Specific Modification of a Single-Chain Antibody . . . Bioconjugate Chemistry. 1999, vol. 10, No. 3, pp. 424-430.*

Radha Krishnan et al. Stability And Physical Characteristics Of Orally Active Amphiphilic . . . Proceedings of the International Symposium on Controlled Release of Bioactive Materials. Jul. 7-13, 2000, vol. 27, pp. 1038-1039.*

Ahuja, Satinder, 'Chiral separations and technology: an overview.' *Chiral Sep.* (1997), 1-7.

Ahuja, Satinder. 'Chiral separations. An overview.' *ACS Symp. Ser.* (1991), 471 Chiral Sep. Liq. Chromatogr.

Aiuti et al, "The Chemokine SDF-1 Is a Chemoattractant for Human CD34+ Hematopoietic Progenitor Cells and Provides a New Mechanism to Explain the Mobilization of CD34+ Progenitors to Peripheral Blood," *J. Exp. Med.* (1997) 185(1):111-120 (1997).

Albericio, F. et al., "Methods for Solid-Phase Assembly of Peptides," *Methods Enzymol.* (1997) 289:313-36.

Angiololo, et al., "A Role for the Interferon-Inductible Protein 10 in Inhibition of Angiogenesis by Interleukin-12," *Annals NY Acad. Sci.* (1996) 795:158-167.

Appay et al., "Aggregation of RANTES Is Responsible for Its Inflammatory Properties," *J. Biol. Chem.* (1999) 274(39):27505-27512.

Arenzana-Seisdedos, et al., "HIV blocked by chemokine antagonist," *Nature* (1996) 383:400.

Baggiolini M, et al., "Human chemokines: an update," *Ann. Rev. Immunol* (1997) 15:675-705.

Bartels et al., "Human Dermal Fibroblasts Express Eotaxin: Molecular Cloning, mRNA Expression, and Identification of Eotaxin Sequence Cariants," *Biochem. Biophys. Res. Comm.* (1996) 225(3):1045-51.

Bazan et al., "A new class of membrane-bound chemokine with a $CX_3C$ motif," *Nature* (1997) 385(6617):640-644.

Belcheva, N. et al., "Synthesis and Biological Activity of Polyethylene Glycol-Mouse Nerve Growth Gactor Conjugate," *Bioconjugate Chem.* (1999) 10: 932-937.

Bettinger, T. et al., "Convenient Polymer-Supported SyntheticRoute to Heterobifunctional Polyethylene Glycols," Bioconjugate Chem. (1998) 9:842-846.

Bleul et al., "A Highly Efficacious Lymphocyte Chemoattractant, Stromal Cell-derived Factor 1 (SDF-1)," *J. Exp. Med.* (1996) 184(3):1101-1109 (1996).

Bleul et al., "The lymphocyte chemoattractant SDF-1 is a Ligand for LESTR/fusin and blocks HIV-1 entry," *Nature* (1996) 382(6594):829-833.

Bolin et al., "NMR Structure of a Minimized Human Agouti related protein prepared by total chemical synthesis," *FEBS Letters* (1999) 451:125-131.

Botti, P. et al., "Native Chemical Ligation Using Removable N.alpha -(1-phenyl-2-mercaptoethyl) Auxiliaries," *Tetrahedron Letters* 42, 1831-1833 (2001).

Brems et al., "Equilibrium denaturation of pituitary- and recombinant-derived bovine growth hormone" *Biochemistry* Dec. 17, 1985;24(26):7662-8.

Cain, S.A. et al. "Selection of novel ligands from a whole-molecule randomly mutated C5a library," *Protein Eng* Mar. 2001;14(3):189-93.

Canne et al., "A General Method for the Synthesis of Thioester Resin Linkers for Use in the Solid Phase Synthesis of Peptide-alpha-Thioacids," *Tetrahedron Lett.* (1995) 36:1217-1220.

Canne L.E. et al., "Solid Phase Protein Synthesis by Chemical Ligation of Unprotected Peptide Segments in Aqueous Solution," *Peptides: Frontiers of Peptide Science, Proceedings of the American Peptide Symposium*, 15th, Nashville, Tennessee, Jun. 14-19, 1997, 301-302 (1999).

Canne L.E. et al., "The Total Chemical Synthesis of L- and D-superoxide Dismutase," *Protein Engineering*, 10-23 (1997).

Chait, BT, "Mass spectrometry—a useful tool for the protein X-ray crystalographer and NMR spectroscopist," *Structure* (1994) 2:465-467.

Chan, T.-H. et al., "Synthesis of Phosphonic Acid Analogues of Sialic Acids (Neu5Ac and KDN) as Potential Sialidase Inhibitors," *J. Org. Chem.* (1997) 62:3500-3504.

Chang, C. et al., "Dissection of the LXXLL nuclear receptor-coactivator interaction motif using combinatorial peptide libraries: discovery of peptide antagonists of estrogen receptors alpha and beta," *Mol Cell Biol* Dec. 1999;19(12):8226-39.

Cheng, T.-L. et al., "Accelerated Clearance of Polyethylene Glycol-Modified Proteins by Anti-Polyethylene Glycol IgM," *Bioconjugate Chem.* (1999) 10:520-528.

Chong et al., "Single-column purification of free recombinant proteins using a self-cleavable affinity tag derived from a protein splicing element," *Gene* Jun. 19, 1997;192(2):271-281.

Chong et al., "Utilizing the C-terminal cleavage activity of a protein splicing element to purify recombinant proteins in a single chromatographic step," *Nucleic Acids Res.* Nov. 15, 1998;26(22):5109-5115.

Collet, Andre. "Separation and Purification of Enantiomers by Crystallization Methods", *Enantiomer* (1999) 4:157-172.

Coltart, DM., "Peptide Segment Coupling byPrior Ligation and Proximity-Induced Itramolecular Acyl Transfer," *Tetrahedron* (2000) 56:3449-3491.

Combadiere et al, "Identificaiton of $CX_3CR1$,". *J. Biol. Chem.* (1998) 273(37):23799-23804.

Cotton et al., "Peptide Ligation and Its application to protein engineering," *Chemistry & Biology* (1999) 6(9):247-256.

Cyster, J.G., "Chemokines and Cell Migration in Secondary Lymphoid Organs," *Science* (1999) 286:2098-2102.

Czaplewski et al., "Identification of Amino Acid Residues Critical for Aggregation of Human CC Chemokines Macrophage Inflammatory Protein (MIP)-1 alpha, MIP-1 beta, and RANTES,"*The Journal of Biological Chemistry* (1999) 274:16077-16084.

D'Apuzzo et al., "The Chemokine SDF-1, Stromal cell-derived factor 1, attracts early stage B cell precursors via the chemokine receptor CXCR4," *European J. Immunol.* (1997) 27(7):1788-1793.

Daugherty, B.L. et al., "Radiolabeled chemokine binding assays," *Methods Mol Biol.* 2000;138:129-34.

Dawson et al., "Synthesis of Chemokines by Native Chemical Ligation," *Methods Enzymol.* (1997) 287:34-45.

Dawson et al., "Synthesis of Native Proteins By Chemical Ligation," *Ann. Rev. Biochem* (2000) 69:923-960.

Dawson, P.E. et al. Synthesis of Proteins by Native Chemical Ligation, Science 266, 776-779 (1994).

Delgado et al., "Polymer-derivatized Proteins: Analytical and Preparative Problems," *Pharmaceutical Sciences* (1997) 3:59-66.

Doorbar, J. et al., "Isolation of a peptide antagonist to the thrombin receptor using phage display," *J. Mol. Biol.*, 244: 361-9 (1994).

Doscher, M.S., "Solid-Phase Peptide Synthesis," *Methods Enzymol.* (1977) 47:578-617.

Efraim, B., et al., "Secondary Structure and Membrane Localization of Synthetic Segments and a Truncated Form of the IsK (minK) Protein," *Biochemistry* (1994) 33:6966.

Englebretsen, et al., "A Novel Thioether Linker: Chemical Synthesis of a HIV-1 Protease Analogue by Thioether Ligation," *Tet. Letts.* (1995) 36(48):8871-8874.

Evans et al., "Semisynthesis of cytotoxic proteins using a modified protein splicing element," *Protein Science* (1998) 7:2256-2264.

Faure et al., "Rapid Progression to AIDS in HIV+ Individuals with a Structural Variant of the Chemokine Receptor $CX_3CR1$," *Science* (2000) 287:2274-2277.

Fenn et al., "Electrospray ionization-principles and practice," *Mass Spectr Rev* (1990) 9:37-70.

Fielding, A.K. et al., "A hyperfusogenic gibbon ape leukemia envelope glycoprotein: targeting of a cytotoxic gene by ligand display," *Hum Gene Ther* Apr. 10, 2000;11(6):817-26.

Fischer et al., "Dendrimers: From Design to Application—A Progress Report," *Angew. Chem. Int. Ed.* (1999) 38:884.

Friedlander, et al., "Definition of Two Angiogenic Pathways by District Alpha v Integrins," *Science* (1995) 870:1500-1502.

Gaertner et al., "Site Specific Attachment of Functionalized Poly(ethylene glycol) to the Amino Terminus of Proteins," *Bioconjug. Chem.* (1996) 7(1):38-44.

Gaertner H.F.G., et al., "Chemical Ligation of Proteins and Other Macromolecules, Peptides: Chemistry, Structure and Biology," *Proceedings of the American Peptide Symposium*, 14th, Columbus, Ohio, Jun. 18-23, 1995, 18-20 (1996).

Gaertner, et al., "Site-specific religation of G-CSF fragments through a thioether bond," *Bioconjug Chem.* Jul.-Aug. 1994;5(4):333-338.

Gauthier, et al., "A New, Sensitive Fluorogenic Substrate for Papain Based on the Sequence of the Cystatin Inhibitory Site," *Arch Biochem. Biophys.* (1993) 306:304.

Geahlen, et al., "A General Method for Preparation of Peptides Biotinylated at the Carboxy Terminus," *Anal. Biochem.* (1992) 202:68.

Gieselman et al., "Synthesis of a selenocysteine-containing peptide by native chemical ligation," *Org Lett.* May 3, 2001;3(9):1331-1334.

Gordon. et al., "Enhancement of Human Immunodeficiency Virus Type I Infection by the CC-Chemokine RANTES Is Independent of the Mechanism of Virus-Cell Fusion," *J. Virol.* (1999) 73:684-694.

Hackeng et al., "Protein synthesis by native chemical ligation: expanded scope by using straightforward methodology," *Proc Natl Acad Sci U S A.* Aug. 31, 1999;96(18):10068-73.

Hancock, D.C. et al., "Synthetic Peptides in Biochemical Research," *Mol Biotechnol.* (1995) 4(1):73-86.

Heller, T. et al., "Selection of a C5a receptor antagonist from phage libraries attenuating the inflammatory response in immune complex disease and ischemia/reperfusion injury," *J. Immunol.* Jul. 15, 1999;163(2):985-94.

Hillenkamp et al., "Matrix-Assisted Laser Desorption/Ionization Mass Spectrometry of Biopolymers," *Anal Chem* (1991) 63:AI 193-1201.

Hojo H, et al., "Polypeptide Synthesis Using the S-Alkyl Thioester of a Partially Protected Peptide Segment. Synthesis of the DNA-Binding Domain of c-Myb Protein (142-193)-$NH_2$" (1991) *Bull Chem Soc Jpn* 64:111-117.

Honeycutt et al. "Comparison of Pharmacokinetic Parameters of a Polypeptide, the Bowman-Birk Protease Inhibitor (BBI), and Its Palmitic Acid Conjugate," *Pharm.Res.* (1996) 13:1373-1377.

Huang, S.-Y. et al., "A Polyethylene Glycol Copolymer for Carrying and Releasing Multiple Copies of Cysteine-Containing Peptides," *Bioconjugate Chem.* (1998) 9:612-617.

Ingenito et al., "Solid Phase Synthesis of Peptide C-Terminal Thioesters by Fmoc/t-Bu Chemistry," *JACS* (1999) 121(49):11369-11374.

Jacobs, K.J. et al,. "Isolation and characterization of genomic and cDNA clones of human erythropoietin," *Nature* Feb. 28-Mar. 6, 1985;313(6005):806-10.

Jelkmann, W., "Erythropoietin: structure, control of production, and function," *Physiol Rev.* Apr. 1992;72(2):449-89.

Jiang, et al., "Synthesis of a-factor analogues containing photoactivatable and labeling groups," *Intl. J. Peptide Prot. Res.* (1995) 45:106.

Jose et al., "Eotaxin: A Potent Eosinophil Chemoattractant Cytokine Detected in a Guinea Pig Model of Allergic Airways Inflammation," *J. Exp. Med.* (1994) 179:881-887.

Kaiser et al. "Chemical Mutation Of Enzyme Active Sites," *Science* Nov. 2, 1984, vol. 226, No. 4674, pp. 505-511.

Kent S., et al., "Determining the Structure of HIV-1 Protease," *Science* 288, 1590 (2000).

Kent, S.B.H. "Chemical Synthesis of Peptides And Proteins," (1988) *Ann. Rev. Biochem.* 57, 957-984.

Kochendoerfer G.G. et al., "Total Chemical Synthesis of the Integral Membrane Protein Influenza A Virus M2: Role of Its C-Terminal Domain in Tetramer Assembly," *Biochemistry* 38, 11905-11913 (1999).

Kochendoerfer, G.G. et al. "Chemical Protein Synthesis Methods in Drug Discovery," *Current Opinion in Drug Discovery & Development* 4, 205-214 (2001).

Kochendoerfer, G.G. et al. "Total Chemical Synthesis of a 27 kDa TASP Protein Derived from the MscL Ion Channel of M. Tuberulosis by Ketoxime-forming Ligation," *Bioconjugate Chemistry* 13, 474-480 (2002).

Kochendoerfer, G.G. et al., "Chemical Protein Synthesis," *Current Opinion in Chemical Biology* 3, 665-671 (1999).

Komatsu N, et al., "Establishment and characterization of a human leukemic cell line with megakaryocytic features:dependency on granulocyte-macrophage colony-stimulating factor, interleukin 3, or erythropoietin for growth and survival," *Cancer Res.* Jan. 1, 1991;51(1):341-8.

Konigsberg WH, "Limited Proteolysis of DNA Polymerases," *Methods Enzymol* (1995) 262:331-346.

Kotecha S., "Cytokines in chronic lung disease of prematurity," *Eur J Pediatr.* Aug. 1996;155 Suppl 2:S14-7.

Krantz, S.B., "Erythropoietin," *Blood* Feb. 1, 1991;77(3):419-34.

Kriwacki et al., "Probing protein structure using biochemical and biophysical methods. Proteolysis, matrix-assisted laser desorption/ionization mass spectrometry, high-performance liquid chromatography and size-exclusion chromatography of p21," *J Chromatogr A* (1997) 777:23-30.

Kurtzhals et al., "Effect of Fatty Acids and Selected Drugs on the Albumin Binding of a Long-Acting, Acylated Insulin Analogue," *J. Pharm. Sci.* (1997) 86:1365-1368.

Lin, F-K. et al, "Cloning and expression of the human erythropoietin gene," *Proc Natl Acad Sci U S A* Nov. 1985;82(22):7580-4.

Lopata et al., "Quantitative Approaches to Optical Resolution," *J. Chem. Res. Minipprint* (1984) 10:2930-2962.

Low D.W. et al., "Rational Fine-Tuning of the Redox Potentials in Chemically Synthesized Rubredoxins," *Journal of the American Chemical Society* 120, 11536-11537 (1998).

Low, D.W. et al., "Backbone-engineered High-potential Iron Proteins: Effects of Active-Site Hydrogen Bonding on Reduction Potential," *Journal of the American Chemical Society* 122, 11039-11040 (2000).

Low, D.W. et al., "Total Synthesis of Cytochrome b562 by Native Chemical Ligation Using a Removable Auxiliary," *Proceedings of the National Academy of Sciences of the United States of America* 98, 6554-6559 (2001).

Lowy, P.H. et al., "Inactivation of Erythropoietin by Neuraminidase and by Mild Substitution Reactions," (1960) *Nature* 185:102.

Lu W. et al. "Total Chemical Synthesis of Bovine Pancreatic Trypsin Inhibitor by Native Chemical Ligation," *FEBS Letters* 429, 31-35 (1998).

Lu W. et al., "Probing Intermolecular Backbone H-bonding in Serine Proteinase-Protein Inhibitor Complexes," *Chemistry & Biology* 6, 419-427 (1999).

Lu, W-Y, et al., "Deciphering the Role of the Electrostatic Interactions Involving Gly70 in eglin C by Total Chemical Protein Synthesis," *Biochemistry* 39, 3575-3584 (2000).

Lundblad RL., "Chemical Reagents for Protein Modification," *CRC Press* (1991,).

Mack, et al., "Aminooxypentane-RANTES Induces CCR5 Internalization but Inhibits Recycling: A Novel Inhibitory Mechanism of HIV Infectivity," *J. Exp. Med.* (1998) 187:1215-1224.

Mack, M. et al. "Downmodulation and recycling of chemokine receptors," *Methods Mol Biol.* 2000;138:191-5.

Maggiora, et al., "A General Method for the Preparation of Internally Quenched Fluorogenic Protease Substrates Using Solid-Phase Peptide Synthesis," *J Med Chem* (1992) 35:3727.

Mahajan et al., "Resin-bound Dendrimers as High Loading Supports for Solid Phase Chemistry," *Tetrahedron Letters* (1999) 40:4909-49-12.

Markussen et al., "Soluble, fatty acid acylated insulins bind to albumin and show protracted action in pigs," *Diabetologia* (1996) 39:281-288.

Marston et al., "Solubilization of protein aggregates," *Methods Enzymol.* 1990;182:264-76.

Matthews et al., "Dendrimers-Branching Out From Curiosities Into New Technologies," *Prog. Polym. Sci.* (1998) 1-56.

McGoff P. et al., "Analysis of Polyethylene Glycol Modified Superoxide Dismutase by Chromatographic, Electrophoretic, Light Scattering, Chemical and Enzymatic Methods," *Chem. Pharm. Bull.* (1988) 36:3079-3091.

McKnight, et al., "HIV-2 and SIV Infection of Nonprimate Cell Lines Expressing Human CD4: Restrictions to Replication at Distinct Stages," *Virology* (1994) 201:8-18.

Melkonian et al., "Role of Lipid Modifications in Targeting Proteins to Detergent-resistant membrane Rafts," *J. Biol. Chem.* (1999) 274:3910-3917.

Milton, R.C..D. et al. Total Chemical Synthesis of a D-Enzyme: The Enantiomers of HIV-1 Protease Show Reciprocal Chiral Substrate Specificity, *Science* 256, 1445-1448 (1992).

Mitraki and King, "Protein Folding Intermediates and Inclusion Body Formation," *Bio/Technology*, 7: 690 (1989).

Miura Y, et al., "Regulation of Both Erythroid and Megakaryocytic Differentiation of a Human Leukemia Cell Line, UT-7," *Acta Haematol* (1998) 99:180-184.

Moser et al., "Lymphocyte Responses to Chemokines," *Intl. Rev. Immunology* (1998) 16(3-4):323-344.

Mosier et al., " Highly Potent RANTES Analogues either Prevent CCR5-Using Human Immunodeficiency Virus Type 1 Infection In Vivo or Rapidly Select for CXCR4-Using Variants," *J. Virology* (1999) 73(5):3544-3550.

Mosier, *Adv.* "Human Immunodeficiciency Virus Infection of Human Cells Transplanted to Severe Combined Immunodeficient Mice," *Immunol.* (1996) 63:79-125.

Mosier, et al., "Rapid Loss of CD4+ T Cells in Human-PBL-SCID Mice by Noncytopathic HIV Isolates," *Science* (1993) 260:689-692.

Muir et al., "Probing the chemical basis of binding activity in an SH3 domain by protein signature analysis," *Chemistry & Biology* (1 996) 3:817-825.

Muir et al., "Protein Synthesis by chemical Ligation of Unprotected Peptides in Aqueous Solution," *Methods Enzymol.* (1997) 289:266-298.

Mulders et al., "Synthesis of a Novel Amino Acid Based Dendrimer," *Tetrahedron Lett.* (1997) 38:631-634.

Nagasawa et al., "Defects of B-Cell Lymphopoiesis and Bone-Marrow myelopoiesis in mice lacking the CXC Chemokine PBSF/SDF-1," *Nature* (1996) 382:635-638.

Nierengarten et al., "Complexation of fullerenes with dendritic cyclotriveratrylene derivatives," *Tetrahedron Lett.* (1999) 40:5681-5684.

Nissenson, A.R., "Erythropoietin Overview—1993," (1994) *Blood Purif.* 12:6-13.

Oberlin et al., "The CXC chemokine SDF-1 is the ligand for LESTR/fusin and prevents infection by T-cell-line-adapted HIV-1," *Nature* (1996) 382(6594):833-835.

Oikawa, et al., "Angiogenic factor of a rat mammary tumor cell line (RMT-1) (I) Secretion of two distinct angiogenic factors into serum-free conditioned medium by RMT-1 cells," *Cancer Lett.* (1991) 59:57-66.

Ouali et al., "Backbone Streching of Wormlike Carbosilane Dendrimers," *Macromolecules* (2000) 33:6185.

Pelchen-Matthews, A. et al., "Chemokine receptor trafficking and viral replication," *Immunol Rev.* Apr. 1999;168:33-49.

Peled, et al., "Synthetic S-2 and H-5 Segments of the Shaker K+ Channel: Secondary Structure, Membrane Interaction, and Assembly within Phospholipid Membranes," *Biochemistry* (1994) 33:7211.

Picchio, et al., "Chemokine Receptor CCR5 Genotype Influences the Kinetics of Human Immunodeficiency Virus Type 1 Infection in Human PBL-SCID Mice," *J. Virol.* (1997) 71:7124-7127.

Picchio, et al., "The Cell Tropism of Human Immunodeficiency Virus Type 1 Determines the Kinetics of Plasma Viremia in SCID Mice Reconstituted with Human Peripheral Blood Leukocytes," *J. Virol.* (1998) 72:2002-2009.

Plaue, S et al., "Recent Advances in Solid-phase Peptide Synthesis and Preparation of Antibodies to Synthetic Peptides," *Biologicals.* (1990) 18(3):147-57.

Ponath et al., "Cloning of the Human Eosinophil Chemoattractant, Eotaxin," *J. Clinical Investigation* (1996) 97(3):604-12.

Ponath et al., "Molecular Cloning and Characterization of a Human Eotaxin Receptor Expressed Selectively on Eosinophils," *J. Exp. Med.* (1996) 183(6):2437-2448.

Posnett, D. N. et al., "A Novel Method for Producing Anti-Peptide Antibodies," (1988) *J. Biol. Chem.* 263, 1719-1725.

Proudfoot, et al., "Extension of Recombinant Human RANTES by the Retention of the Initiating Methionine Produces a Potent Antagonist," *J. Biol. Chem.* (1996) 271:2599-2603.

Reuter, J. D. et al., "Inhibition of Viral Adhesion and Infection by Sialic-Acid-Conjugated Dendritic Polymers," *Bioconjugate Chem.* (1999) 10:271-278.

Robson B., et al. "Doppelganger Proteins as Drug Leads," *Nature Biotechnology* 14, 892-893 (1996).

Rose et al., "Stepwise Solid-Phase Synthesis of Polyamides As Linkers," *J. Am. Chem. Soc.* Aug. 4, 1999, 121:7034-7038.

Rose, et al., "Facile Synthesis of Homogeneous Artificial Proteins," *J. Amer. Chem. Soc.* (1994) 116:30-34.

Rose, K. et al., "Natural Peptides as Building Blocks for the Synthesis of Large Protein-like Molecules with Hydrazone and Oxime Linkages," *Bioconjugate Chem.* (1996) 7:552-556.

Rossi et al., "Cloning and Characterization of a New Type of Mouse Chemokine," *Genomics* (1998) 47(2):163-170.

Sarin, et al., "Quantitative Monitoring of Solid-Phase Peptide Synthesis by the Ninhydrin Reaction," *Anal. Biochem.* (1981) 117:147-157.

Sawyer, S.T. et al., "Erythropoietin cell biology," *Hematol Oncol Clin North Am.* Oct. 1994;8(5):895-911.

Saxon, E. et al., "A "traceless" Staudinger ligation for the chemoselective synthesis of amide bonds," *Org Lett*. Jul. 13, 2000;2(14):2141-3.

Schlüter et al., "Dendronized Polymers: Synthesis, Characterization, Assembly at Interfaces, and Manipulation," *Angew Chem. Int. Ed.* (2000) 39:864-883.

Schnölzer, M. et al., "Constructing proteins by dovetailing unprotected synthetic peptides: backbone-engineered HIV protease," *Science.* Apr. 10, 1992;256(5054):221-5.

Schnölzer, M., "In situ neutralization in Boc-chemistry solid phase peptide synthesis. Rapid, high yield assembly of difficult sequences," *Int J Pept Protein Res.* Sep.-Oct. 1992;40(3-4):180-193.

Schwarz, J. B. et al., "A Broadly Applicable Method for the Efficient Synthesis of alpha-O-Linked Glycopeptides and Clustered Sialic Acid Residues," *J. Amer. Chem. Soc.* (1999) 121:2662-2673.

Shao Y. et al., "A Novel Method to Synthesize Cyclic Peptides," *Tetrahedron Letters* 39, 3911-3914 (1998).

Shao Y. et al., "Protein Splicing: Occurrence, Mechanisms, and Related Phenomena," *Chemistry & Biology* 4, 187-194 (1997).

Shin et al., "Fmoc-Based Synthesis of Peptide-Thioesters: Application to the Total Chemical Synthesis of a Glycoprotein by Native Chemical Ligation," (1999) *J. Am. Chem. Soc.*, 121, 11684-11689.

Siani M.A. et al., "Rapid Modular Total Chemical Synthesis of Proteins Based on Genome Sequence Data," *Peptides: Frontiers of Peptide Science, Proceedings of the American Peptide Symposium*, 15th, Nashville, Tennessee, Jun. 14-19, 1997, 643-644 (1999).

Sidhu, S.S. et al., "High copy display of large proteins on phage for functional selections," *J Mol Biol* Feb. 18, 2000;296(2):487-95.

Signoret, N. et al., "Analysis of chemokine receptor endocytosis and recycling," *Methods Mol Biol.* 2000;138:197-207.

Signoret, N. et al., "Endocytosis and recycling of the HIV coreceptor CCR5," *J Cell Biol.* 2000 151(6):1281-94.

Simmons, et al, "Potent Inhibition of HIV-1 Infectivity in Macrophages and Lymphocytes by a Novel CCR Antagonist," *Science* (1997) 276:276-279.

Simon R. et al., "Peptoids: A Modular Approach to Drug Discovery," *Proc. Natl. Acad. Sci. U.S.A.* (1992) 89: 9367-71.

Strahilevitz, et al., "Spectrum of Antimicrobial Activity and Assembly of Dermaseptin-b and Its Precursor Form in Phospholipid Membranes," *Biochemistry* (1994) 33:10951.

Sunder et al., "Hyperbranched Polyether Polyols: A Modular Approach to Complex Polymer Architectures," *Adv. Mater.* (2000) 12:235.

Sunder et al., "Chiral Hyperbranched Dendron Analogues," *Macromolecules* (2000) 33:253.

Tam et al. "Methionine Ligation Strategy in the Biomimetic Synthesis of Parathyroid Hormones," *Biopolymers*, 1998, vol. 46, pp. 319-327.

Trkola, et al., "CD4-dependent, antibody-sensitive interactions between HIV-1 and itsco-receptor CCR-5," *Nature* (1996) 384:184-187.

Turnbull et al., "Synthetic Carbohydrate Dendrimers," *Chembiocehm* (2000) 1(1):70-74.

Wade, J.D. et al., "Solid Phase Peptide Synthesis Recent Advances and Applications," *Australas Biotechnol.* (1993) 3(6):332-6.

Wang et al., "Chemokines and their role in tumor growth and metastasis," *J. Immunological Methods* (1998) 220(1-2):1-17.

Wells et al., "Solid-Phase Dendrimer Synthesis," *Biopolymers* (1998) 47:381-396.

Wilken J. et al., "Chemical Protein Synthesis," *Current Opinion in Biotechnology* 9, 412-426 (1998).

Wilken J. et al., "Rational Development of an Anti-HIV Protein Active at Low Picomolar Concentrations," *Peptides for the New Millennium, Proceedings of the American Peptide Symposium*, 16th, Minneapolis, Minnesota, Jun. 26-Jul. 1, 1999, 513-515 (2000).

Wilken J. et al., "Total Chemical Synthesis and High-Resolution Crystal Structure of the Potent Anti-HIV Protein AOP-RANTES," *Chemistry & Biology* 6, 43-51 (1999).

Wu, et al., "CCR5 Levels and Expression Pattern Correlate with Infectability by Macrophage-tropic HIV-1, In Vitro," *J. Exp. Med.* (1997) 185:1681-1691.

Xu, B. et al., "Synthesis, Characterization, and Rheological Behavior of Polyethylene Glycols End-Capped with Fluorocarbon Hydrophobes," *Langmuir* (1997) 13:2447-2456.

Yamada et al., "Eotaxin is a Potent Chemotaxin for Human Basophils," *Biochem. Biophys. Res. Communications* (1997) 231(2): 365-368.

Yan, L.Z. et al. "Synthesis of peptides and proteins without cysteine residues by native chemical ligation combined with desulfurization," *J Am Chem Soc.* Jan. 31, 2001;123(4):526-33.

Yoshida et al. "Identification of Single C Motif-1/Lymphotactin Receptor XCR1," *J. Biol. Chem.* (1998) 273(216):16551-16554.

Yoshida et al., "Molecular cloning of a novel C or gamma type chemokine, SCM-1," *FEBS Letters* (1995) 360(2):155-159.

Zalipsky S., et al., "Functionalized Poly(ethylene glycol) for Preparations of Biologically Relevant Conjugates," *Bioconjugate Chemistry* (1995) 6:150-165.

Zeng et al., "Synthesis of a New Template with a Built-in Adjuvant and Its Use in Constructing peptide Vaccine Candidates Through Polyoxime Chemistry," *J. Pept. Sci.* (1996) 2:66-72.

Zhan et al. "Modification of ricin A chain, by addition of endoplasmic reticulum (KDEL) or Golgi (YQRL) retention sequences, enhances its cytotoxicity and translocation," *Cancer Immunol. Immunother.* (1998) 46:55-60.

Zhang, et al., "Preparation of functionally active cell-permeable peptides by single-step ligation of two peptide modules," *Proc Employable for chemical ligation

FIG. 12

```
         ┌─────────────────────────────┐
         │   G-CSF Residues 1-174      │
         └─┬─┬─┬──────────────┬──────┬─┘
    ┌────┐ │ │ │              │   ┌──┴──┐
    │ T1J├─┘ │ │              │   │P174 │
    └────┘   │ │              │   └─────┘
  ┌────┐  ┌──┴─┐              │   ┌─────┐
  │ P2J├──┤ P5J│              │   │ Q173│
  └────┘  └────┘              │   └─────┘
        ┌──┴─┐                │
        │ L3J│                │
        └────┘                │
   ┌──────────────┐    ┌──────┴──────┐
   │  S64X-pPEG   │    │ T134X-pPEG  │
   └──────────────┘    └─────────────┘
```

FIG. 13

```
 ┌───┐ ┌─────────────────────────┬──┐ ┌──────┐ ┌──┐
 │NNY├─┤  RANTES Residues 2-68   │  ├─┤Linker├─┤FA│
 └───┘ └─┬──┬──────────┬─────────┴──┘ └──────┘ └──┘
       ┌─┴┐┌┴─┐  ┌─────┴──────┐   ┌────────────┐
       │P2││Y3│  │ E66X -pPEG │   │ M68X -pPEG │
       └──┘└──┘  └────────────┘   └────────────┘
                                  ┌────────────┐
                                  │ S67X -pPEG │
                                  └────────────┘
       ┌──────────────────────────────┐
       │One or more N-loop residues 12-20 to X│
       └──────────────────────────────┘
```

1. Remove *Fmoc*
2. Synthesize/elaborate *Fmoc*-Lys branching core
3. Couple S-acetyl thiologlycolic acid
4. Remove *Boc*
5. Couple *Boc*-aminooxy acetic acid
6. Remove S-linked acetyl groups
7. Cleave/remove *Boc*

Alternate representation of same compound

GP17

SEP3-L42

FIG.23A
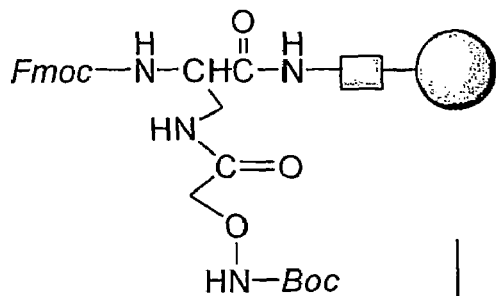
1. Remove *Fmoc*
2. Synthesize TTD-Succ Linker
3. Synthesize/elaborate *Fmoc*-Lys branching core
4. Cleave/remove *Fmoc*
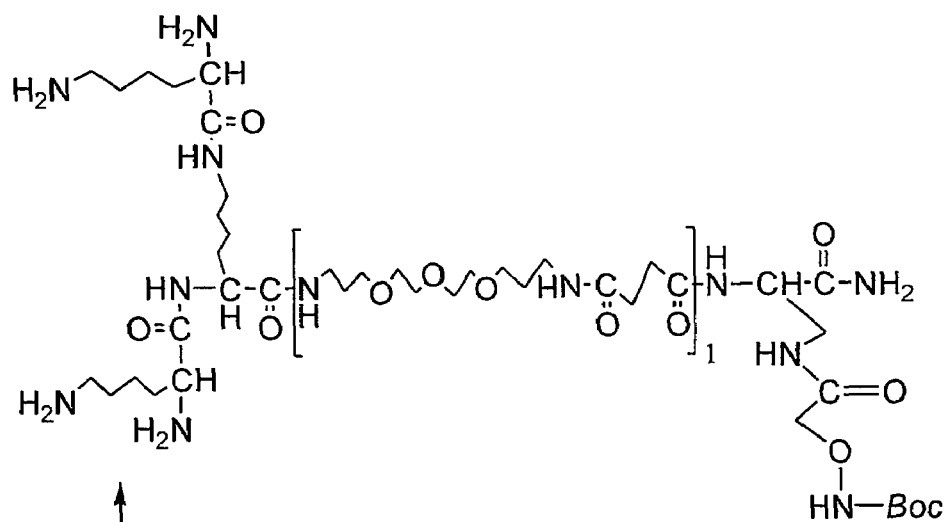
Alternate representation of same compound
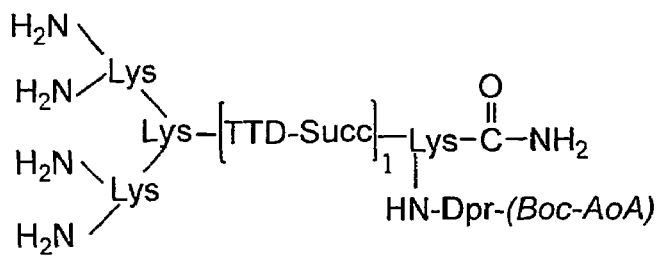
GP40

SEP1-B51

FIG. 25A
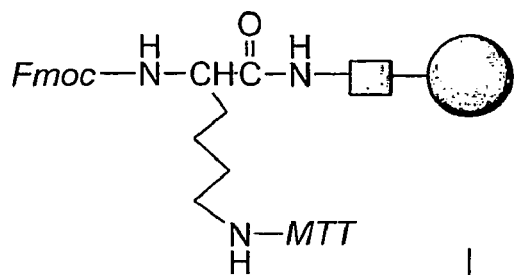
1. Remove *Fmoc*
2. Synthesize Succ-TTD Linker
3. Synthesize/elaborate Boc-Lys branching core
4. Remove *MTT*
5. Couple pyruvic acid
6. Cleave/remove *Boc*
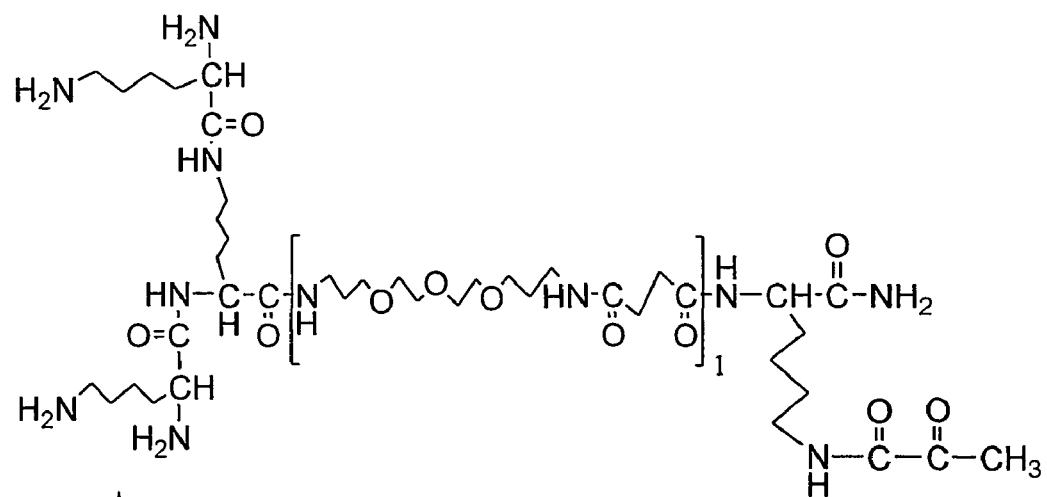
Alternate representation of same compound
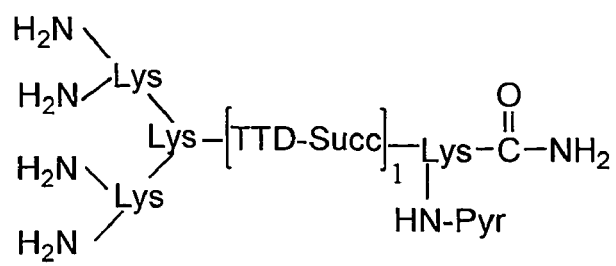
GP42

SEP1-B52

```
                        SEQUENCE LISTING

<160> NUMBER OF SEQ ID NOS: 7

<210> SEQ ID NO 1
<211> LENGTH: 166
<212> TYPE: PRT
<213> ORGANISM: Homo sapiens

<400> SEQUENCE: 1

Ala Pro Pro Arg Leu Ile Cys Asp Ser Arg Val Leu Glu Arg Tyr Leu
1               5                   10                  15

Leu Glu Ala Lys Glu Ala Glu Lys Ile Thr Thr Gly Cys Ala Glu His
            20                  25                  30

Cys Ser Leu Asn Glu Lys Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Lys Ser Ser Gln Pro Trp Cys Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Cys Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 2
<211> LENGTH: 166
<212> TYPE: PRT
<213> ORGANISM: Homo sapiens

<400> SEQUENCE: 2

Ala Pro Pro Arg Leu Ile Cys Asp Ser Arg Val Leu Glu Arg Tyr Leu
1               5                   10                  15

Leu Glu Ala Lys Glu Ala Glu Lys Ile Thr Thr Gly Cys Ala Glu His
            20                  25                  30
```

```
Cys Ser Leu Asn Glu Lys Ile Thr Val Pro Asp Thr Lys Val Asn Phe
            35                  40                  45

Tyr Ala Trp Lys Arg Met Glu Val Gly Gln Gln Ala Val Glu Val Trp
 50                      55                  60

Gln Gly Leu Ala Leu Leu Ser Glu Ala Val Leu Arg Gly Gln Ala Leu
 65                  70                  75                  80

Leu Val Lys Ser Ser Gln Pro Trp Cys Pro Leu Gln Leu His Val Asp
                85                  90                  95

Lys Ala Val Ser Gly Leu Arg Ser Leu Thr Thr Leu Leu Arg Ala Leu
               100                 105                 110

Gly Ala Gln Lys Cys Ala Ile Ser Pro Pro Asp Ala Ala Lys Ala Ala
               115                 120                 125

Pro Leu Arg Thr Ile Thr Ala Asp Thr Phe Arg Lys Leu Phe Arg Val
               130                 135                 140

Tyr Ser Asn Phe Leu Arg Gly Lys Leu Lys Leu Tyr Thr Gly Glu Ala
145                 150                 155                 160

Cys Arg Thr Gly Asp Arg
               165

<210> SEQ ID NO 3
<211> LENGTH: 166
<212> TYPE: PRT
<213> ORGANISM: Homo sapiens

<400> SEQUENCE: 3

Ala Pro Pro Arg Leu Ile Cys Asp Ser Arg Val Leu Glu Arg Tyr Leu
 1               5                  10                  15

Leu Glu Ala Lys Glu Ala Glu Cys Ile Thr Thr Gly Cys Ala Glu His
                20                  25                  30

Cys Ser Leu Asn Glu Cys Ile Thr Val Pro Asp Thr Lys Val Asn Phe
            35                  40                  45

Tyr Ala Trp Lys Arg Met Glu Val Gly Gln Gln Ala Val Glu Val Trp
 50                      55                  60

Gln Gly Leu Ala Leu Leu Ser Glu Ala Val Leu Arg Gly Gln Ala Leu
 65                  70                  75                  80

Leu Ala Cys Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
               100                 105                 110

Gly Ala Gln Lys Glu Ala Ile Ser Pro Pro Asp Ala Ala Cys Ala Ala
               115                 120                 125

Pro Leu Arg Thr Ile Thr Ala Asp Thr Phe Arg Lys Leu Phe Arg Val
               130                 135                 140

Tyr Ser Asn Phe Leu Arg Gly Lys Leu Lys Leu Tyr Thr Gly Glu Ala
145                 150                 155                 160

Cys Arg Thr Gly Asp Arg
               165

<210> SEQ ID NO 4
<211> LENGTH: 69
<212> TYPE: PRT
<213> ORGANISM: Homo sapiens

<400> SEQUENCE: 4

Pro Tyr Ser Ser Asp Thr Thr Pro Cys Cys Phe Ala Tyr Ile Ala Arg
 1               5                  10                  15
```

```
Pro Leu Pro Arg Ala His Ile Lys Glu Tyr Phe Tyr Thr Ser Gly Lys
            20                  25                  30

Cys Ser Asn Pro Ala Val Val Phe Val Thr Arg Lys Asn Arg Gln Val
            35                  40                  45

Cys Ala Asn Pro Glu Lys Lys Trp Val Arg Glu Tyr Ile Asn Ser Leu
            50                  55                  60

Glu Met Ser Lys Leu
65

<210> SEQ ID NO 5
<211> LENGTH: 69
<212> TYPE: PRT
<213> ORGANISM: Homo sapiens

<400> SEQUENCE: 5

Pro Tyr Ser Ser Asp Thr Thr Pro Cys Cys Phe Ala Tyr Ile Ala Arg
1               5                   10                  15

Pro Leu Pro Arg Ala His Ile Lys Glu Tyr Phe Tyr Thr Ser Gly Lys
            20                  25                  30

Cys Ser Asn Pro Ala Val Val Phe Val Thr Arg Lys Asn Arg Gln Val
            35                  40                  45

Cys Ala Asn Pro Glu Lys Lys Trp Val Arg Glu Tyr Ile Asn Ser Leu
            50                  55                  60

Glu Met Ser Lys Leu
65

<210> SEQ ID NO 6
<211> LENGTH: 71
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: X is L-cyclohexylglycine

<400> SEQUENCE: 6

Pro Xaa Ala Ala Ser Ser Asp Thr Thr Pro Cys Cys Phe Ala Tyr Ile
1               5                   10                  15

Ala Arg Pro Leu Pro Arg Ala His Ile Lys Glu Tyr Phe Tyr Thr Ser
            20                  25                  30

Gly Lys Cys Ser Asn Pro Ala Val Val Phe Val Thr Arg Lys Asn Arg
            35                  40                  45

Gln Val Cys Ala Asn Pro Glu Lys Lys Trp Val Arg Glu Tyr Ile Asn
        50                  55                  60

Ser Leu Glu Lys Ser Lys Leu
65                  70

<210> SEQ ID NO 7
<211> LENGTH: 69
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: X is L-cyclohexylglycine

<400> SEQUENCE: 7

Pro Xaa Ser Ser Asp Thr Thr Pro Cys Cys Phe Ala Tyr Ile Ala Arg
1               5                   10                  15

Pro Leu Pro Arg Ala His Ile Lys Glu Tyr Phe Tyr Thr Ser Gly Lys
```

```
                    20                  25                  30
Cys Ser Asn Pro Ala Val Val Phe Val Thr Arg Lys Asn Arg Gln Val
        35                  40                  45
Cys Ala Asn Pro Glu Lys Lys Trp Val Arg Glu Tyr Ile Asn Ser Leu
    50                  55                  60
Glu Lys Ser Lys Leu
65
```

POLYMER-MODIFIED SYNTHETIC PROTEINS

CROSS-REFERENCE TO RELATED APPLICATIONS

This application claims the benefit of U.S. patent applications Ser. Nos. 60/231,339 (filed Sep. 8, 2000) and 60/236,377 (filed Sep. 29, 2000), both of which applications are herein incorporated by reference in their entirety.

FIELD OF THE INVENTION

The present invention relates to methods and compositions for modifying biologically active synthetic peptides, polypeptides and proteins with polymers, especially glycomimetic polymers so as to improve their biological activity or pharmacokinetic properties. The invention further provides methods and uses for such polymer-modified peptides, polypeptides and proteins.

BACKGROUND OF THE INVENTION

Over the past 30 years, medical attention has increasingly turned to the possibility of using proteins as therapeutic drugs for the treatment of disease (See, e.g., "Therapeutic Proteins 1999," Datamonitor plc, London, 1999). Most protein therapeutics are based on naturally occurring animal or human forms of the protein (such as insulin, growth hormone, erythropoietin, interleukin-2 etc.) and produced in recombinant DNA engineered bacterial or eukaryotic cells. Unfortunately, recombinant proteins made in bacterial cells, such as E. coli, often lack post-translational modifications that are normally found in the protein's naturally produced form. This lack of modification can have a significant negative impact on the pharmaceutical properties of the protein when introduced to a patient.

Glycosylation is one example of a common post-translational modification in eukaryotes that involves the enzymatic attachment of complex sugar chains to the protein. Because recombinant proteins made in bacterial expression systems lack the ability to glycosylate proteins, eukaryotic expression systems such as plant, yeast, insect or mammalian cells have been used in their place when a glycosylated form or 'glycoprotein' is required. A significant problem in making recombinant glycoproteins is that the resulting product typically consists of a complex mixture of different 'glycoforms', which may have widely varying physiological or pharmacological properties.

Nevertheless, recombinant DNA techniques have become the primary method for commercial production of many polypeptides and proteins because of the large quantities that can be produced in bacteria and other host cells. Recombinant protein production involves transfecting or transforming host cells with DNA encoding the desired exogenous protein and growing the cells under conditions favoring expression of the recombinant protein. E. coli and yeast are favored as hosts because they can be made to produce recombinant proteins at high titers (see, U.S. Pat. No. 5,756,672).

Numerous U.S. patents have been issued with respect to general bacterial expression of recombinant-DNA-encoded proteins (see, for example, U.S. Pat. Nos. 4,565,785; 4,673,641; 4,738,921; 4,795,706; 4,710,473). Unfortunately, the use of recombinant DNA techniques has not been universally successful. Under some conditions, certain heterologous proteins expressed in large quantities from bacterial hosts are precipitated within the cells in dense aggregates, recognized as bright spots visible within the enclosure of the cells under a phase-contrast microscope. These aggregates of precipitated proteins are referred to as "retractile bodies," and can constitute a significant portion of the total cell protein (Brems et al., Biochemistry (1985)24: 7662.

Recovery of protein from these bodies has presented numerous problems, such as how to separate the protein encased within the cell from the cellular material and proteins harboring it, and how to recover the inclusion body protein in biologically active form. For general review articles on refractile bodies, see Marston, supra; Mitraki and King, Bio/Technology, 7:690 (1989); Marston and Hartley, Methods in Enzymol., 182: 264–276 (1990); Wetzel, "Protein Aggregation In Vivo: Bacterial Inclusion Bodies and Mammalian Amyloid," in Stability of Protein Pharmaceuticals: In Vivo Pathways of Degradation and Strategies for Protein Stabilization, Ahern and Manning (eds.) (Plenum Press, 1991); and Wetzel, "Enhanced Folding and Stabilization of Proteins by Suppression of Aggregation In Vitro and In Vivo," in Protein Engineering—A Practical Approach, Rees, A. R. et al. (eds.) (IRL Press at Oxford University Press, Oxford, 1991).

Proteins also have been produced as research reagents by total chemical synthesis (See, e.g., Wilkin et al., Curr. Opinion Biotech. (1999) 9:412–426). This process involves chemical synthesis of proteins by the stepwise coupling of individual amino acids, or convergent strategies that employ the separate synthesis of peptide or polypeptide segments followed by linking of the segments, including chemical ligation of such segments, to generate full-length products (See, e.g., Dawson et al., Ann. Rev. Biochem (2000) 69:923–960). In some instances chemical synthesis has been utilized to make small glycoproteins modified with simple low molecular weight sugars (Shin et al., J. Am. Chem. Soc. (1999) 121:11684–11689). In other cases, proteins have been made chemically to contain detectable labels and the like (Bolin et al., FEBS Letters (1999) 451:125–131). Unfortunately, such labeled proteins offer little to no therapeutic advantage over their recombinantly produced counterparts. However, a few proteins showing therapeutic potential have been made by chemical synthesis with a focus on improving potency by use of small molecule-type changes to pharmacophore regions of the target protein (U.S. Pat. No. 6,168, 784). While potency is an important aspect in making a therapeutic, other factors remain problems with protein therapeutics.

Efforts to develop therapeutically usable protein drugs have long suffered from the undesirable bioactivity, bioavailability and biokinetics (such as clearing time, etc.) of putative drug candidates upon in vivo administration. The principal factors that have severely limited the use of proteins, and of polypeptides in particular, as therapeutic agents has been the fact that these compounds often elicit an immunogenic response in the circulatory system (see, U.S. Pat. No. 4,179,337 (Davis et al.)). This effect has one or both of two secondary consequences. The first being the destruction of polypeptides by the elicited antibodies, and the second more seriously, being the emergence of an allergic response. For example, the antibody-mediated destruction of insulin is believed to be responsible for the rather low residence time of insulin in the human circulatory system. In the case of enzymes, not only is there a problem of destruction of the polypeptide and the subsequent negation of its physiological activity but also the most undesired elicitation of an allergic reaction. Conversely, certain proteins, such as clotting factors, growth factors and cytokines, etc., may exhibit a biological half-life that is disadvantageously prolonged upon their in vivo administration.

One approach to improving proteins for use as therapeutics has involved derivatizing the protein with water-soluble polymers. Such conjugation has been proposed as a means for improving the circulating life, water solubility or antigenicity of administered proteins, in vivo (see, U.S. Pat. No. 4,179,337 Davis et al.). Many different water-soluble polymers and attachment chemistries have been used towards this goal, such as polyethylene glycol, copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers) and the like. Polyethylene glycol ("PEG") is one such chemical moiety that has been used in efforts to obtain therapeutically usable proteins (Zalipsky, S. (*Bioconjugate Chemistry* (1995) 6:150–165; Mehvar, R. (*J. Pharm. Pharmaceut. Sci.* (2000) 3(1):125–136)). Its backbone $(CH_2CH_2O)_n$ is flexible, amphiphilic, not susceptible to proteases, and non-immunogenic. Attachment of PEG also has been shown to protect proteins against proteolysis (Blomhoff, H. K. et al., *Biochim Biophys Acta* (1983) 757:202–208). It also can improve other physical-chemical properties of proteins.

For example, pegademase bovine (Adagen®), a formulation of adenosine deaminase with an attached PEG polymer, has been developed for treating severe combined immunodeficiency disease (SCID); superoxide dismutase with an attached PEG moiety has been in clinical trials for treating head injury; alpha interferon with an attached PEG moiety has been tested for treating hepatitis. Pegylated IL-6 has been described (see, EP 0 442 724, and U.S. Pat. No. 5,264,209). EP 0 154 316 reports reacting a lymphokine with an aldehyde of polyethylene glycol. European Patent Publication EP 0 401 384, describes materials and methods for preparing granulocyte colony stimulating factor ("G-CSF") to which polyethylene glycol molecules are attached. Modified G-CSF and analogs thereof are also reported in EP 0 473 268, stating the use of various G-CSF and derivatives covalently conjugated to a water-soluble particle polymer, such as polyethylene glycol. U.S. Pat. No. 5,880,255 summarizes many of the proteins that have been modified with PEG chains.

A variety of means have been used to attach polymer moieties such as PEG and related polymers to reactive groups found on the protein (see, U.S. Pat. No. 4,179,337 (Davis et al.), and U.S. Pat. No. 4,002,531 (Royer). For a review, see Abuchowski et al., in "Enzymes as Drugs," (J. S. Holcerberg and J. Roberts, eds. pp. 367–383 (1981) and Zalipsky, S. (*Bioconjugate Chemistry* (1995) 6:150–165. The use of PEG and other polymers to modify proteins also is discussed by Cheng, T.-L. et al., Bioconjugate Chem. (1999) 10:520–528; Belcheva, N. et al., Bioconjugate Chem. (1999) 10: 932–937; Bettinger, T. et al., Bioconjugate Chem. (1998) 9:842–846; Huang, S.-Y. et al., Bioconjugate Chem. (1998) 9:612–617; Xu, B. et al. Langmuir (1997) 13:2447–2456; Schwarz, J. B. et al., J. Amer. Chem. Soc. (1999) 121:2662–2673; Reuter, J. D. et al., Bioconjugate Chem. (1999) 10:271–278; Chan, T.-H. et al., J. Org. Chem. (1997) 62:3500–3504. Typical attachment sites in proteins include primary amino groups, such as those on lysine residues or at the N-terminus, thiol groups, such as those on cysteine side-chains, and carboxyl groups, such as those on glutamate or aspartate residues or at the C-terminus. Some of the most common sites of attachment are to the sugar residues of glycoproteins, cysteines or to the N-terminus and lysines of the target proteins.

Although many different approaches have been described for conjugation of polymers to proteins, the conjugation process is not without complications. Care must be taken to limit the loss of biological activity caused by the conjugation reaction. For example, folded or re-folded proteins are typically used to minimize the number of sites of attachment. However, if too much of the activated polymer is attached to the target protein or polypeptide, biological activity can be severely reduced or lost. Likewise, if the wrong linker joining the polymer to the protein is used or an insufficient amount of polymer is attached to the target, the therapeutic value of the resultant conjugate may be limited, and may not demonstrate enough of an increase in circulating life to compensate for the loss in its bioactivity. Problems can also result due to a blockage of the protein's active site by the modifying polymer. This problem can be difficult to avoid since the polymer and protein are typically joined in solution-based reactions. Pre-blocking the active sites with materials such as pyridoxal phosphate has been suggested, but the results have been inconsistent (see, U.S. Pat. No. 4,179,337 (Davis et al.)). These problems are particularly acute with lower molecular weight proteins and peptides, which often have few attachment sites not associated with bioactivity.

For instance, a common technique has been the attachment of water-soluble polymers to the primary amines in the target protein (e.g., the N-terminal amino group and the epsilon amino groups of lysines). Thiol-reactive polymer conjugates also have been used to attach polymers to the thiol side-chains of cysteines. Both approaches represent significant problems as most proteins contain multiple copies of such reactive groups spread out over various regions of the polypeptide backbone that play an important role in defining the activity, folding, re-folding and stability of a protein. Thus although widely used, such approaches suffer from more or less incomplete or unwanted reduction in bioactivity of a protein, and usually complex mixtures that are difficult to separate and characterize (Delgada et al., *Pharmaceutical Sciences* (1997) 3:59–66).

In an attempt to reduce random attachment, proteins have been made in which the natural lysines are removed in conjunction with adding lysines at the desired sites of polymer attachment (U.S. Pat. No. 4,904,584). For example G-CSF and IL-2 have been modified in this manner. Other attempts to avoid random attachment has been to make proteins in which the natural cysteines are removed in conjunction with adding cysteines at the desired sites of polymer attachment, or cysteines are added without removing the natural cysteines if present (EP 0 668 353). For example, G-CSF, IL-3 and EPO have been made this way. While such cysteine or lysine variants theoretically allow site-specific polymer attachment, there still is no guarantee that all selected sites can be modified in a controlled manner.

Given the inability to site-specifically modify proteins containing multiple amino acids with side-chains bearing the same or similar reactive functional groups, recent efforts have focused on the modification of the amino or carboxy terminus of proteins. Modification of the amino or carboxy terminus has relied on the ability of some chemical conjugation techniques to uniquely modify these sites (WO 90/02136 and WO 90/02135). For example, this technique was utilized for the attachment of PEG chains to the N-terminal residue of G-CSF and the chemokine IL-8 (Gaertner et al., *Bioconjug. Chem.* (1996) 7(1):38–44; and WO 96/41813). However, modification of the N- or C-termini typically reduces a protein's activity (See, e.g., U.S. Pat. No. 5,985,265 discussing attachment of PEG to the N-terminus and lysine side chains of G-CSF). Despite the drawbacks with modification of proteins with water-soluble polymers, PEGylation and attachment of other water-soluble polymers to proteins continues to be pursued. For example, attachment of PEG to histidine in IF-alpha has been described in U.S. Pat. Nos. 5,951,974 and 6,042,822. Attachment of PEG to lysines in alpha interferon is described in U.S. Pat. No. 5,595,732. Attachment of PEG to sugar chains of erythropoietin (EPO) and internal amino acids such as lysines (EP 0 605 963 and WO 00/32772), and the N-terminus (U.S. Pat. No. 6,077,939 and WO 00/32772) also has been described.

Another problem is that all of the above-discussed polymers are highly non-homogeneous, which render analytical characterization and purification of the mixtures of polymer-modified proteins difficult (Delgada et al., *Pharmaceutical Sciences* (1997) 3:59–66). For example, techniques used to prepare PEG or PEG-based chains, even those of fairly low relative molecular mass such as 3400, involve a poorly controlled polymerization step which leads to preparations having a spread of chain lengths about a mean value; that is, they involve polymer preparations of $(CH_2CH_2O)_n$ where n does not have a discrete value but rather has a range of values about a mean. The resulting heterogeneity of the derivatized proteins is often associated with a range of properties that one cannot easily identify much less separate. Although the use of polypeptide adducts might be considered to offer a possible solution in principle, the use of polypeptides is disadvantageous since they are susceptible to proteolytic cleavage and can render the derivatized protein immunogenic.

Unfortunately, however, the problem of identifying and employing a suitable polymer is exacerbated by the fact that all proteins currently employed for therapeutic use are derived from recombinant DNA technologies. The use of recombinant DNA technologies puts severe limitations on the types and specificity of linkages that can be formed between a performance-enhancing moiety and the recombinantly produced protein. This is because firstly there are only a very limited number of functional groups suitable for linkage, and secondly there will generally be several copies of the reactive functional group in the protein being modified, thus precluding any specificity of modification. For example, it has been shown that in the case of nonselective conjugation of superoxide dismutase with PEG, several fractions of the modified enzyme were completely inactive (P. McGoff et al., Chem. Pharm. Bull. (1988) 36:3079–3091). Also, if differing numbers of such moieties are randomly attached, the pharmacokinetics of the therapeutic protein cannot be precisely predictable, making dosing a large problem. The lack of control of attachment furthermore may lead to (a) reduced potency, (b) a need for elaborate purification schemes to separate a vast mixture of derivatives and (c) possibly unstable attachment of the modifying moiety. Several linkages, such as tresylchloride-based linkages, known to the art are also known to be immunogenic.

Thus to improve circulating half-life, reduce proteolysis and immunogenicity and improve other properties of biologically produced proteins, water-soluble polymers such as PEG can be attached, but with mixed results given the difficulty of attaching them in a controlled manner and with user-defined precision. Also, because of the limited success in attaching polymers at precise user-defined sites, very little is known about preferred sites of attachment that could be applicable to proteins in general. In addition, because of the stochastic nature of attachment, and the hetero-disperse nature of PEG and other water-soluble polymers currently employed for such purposes, purification and analytical characterization of PEG-protein conjugates has been difficult. Thus the combined problem of poor control over reproducible attachment and polymer heterogeneity has severely hampered the routine approval of polymer-modified proteins as therapeutics (only a few approved to date for therapeutic use despite its introduction in the early 1970's).

Accordingly, a need exists for methods of forming bioactive proteins that are distinct from recombinant DNA technologies, and that could be used to form proteins capable of polymer modification. A need also exists for a preferred polymer that can be employed to form derivatized proteins that have polymer adducts of defined structure rather than a mixture of chains of different lengths. Polymers that can be employed to form derivatized proteins having polymer adducts with structures that can be tailored to mimic desirable properties of natural proteins also is needed. Moreover, a need exists for derivatizing proteins that has general applicability to many proteins. The present invention satisfies these and other needs.

SUMMARY OF THE INVENTION

The present invention concerns polymer-modified synthetic bioactive proteins, pharmaceutical compositions that contain them and methods for their production and use. The polymer-modified synthetic bioactive proteins of the invention are produced in whole or in part by chemical synthesis, and thus differ markedly from biologically produced proteins.

In detail, the invention provides polymer-modified synthetic bioactive proteins having a monomer molecular weight greater than about 25 kilo Daltons ("kDa"). The invention further provides polymer-modified synthetic bioactive proteins having one or more irregular amino acid residues. The invention particularly provides polymer-modified synthetic bioactive proteins that possess a bioactivity that mimics a bioactivity associated with a ribosomally specified protein such as a natural mammalian protein (e.g., human, simian, bovine, murine, porcine, ovine, or equine, avian, or piscine protein). The invention more particularly provides such polymer-modified synthetic bioactive proteins having a bioactivity that mimics a bioactivity associated with a ribosomally specified protein selected from the group consisting of a protein receptor or fragment thereof, a protein receptor ligand or fragment thereof, and a cytokine.

In preferred embodiment, the invention is directed to a molecularly homogenous polymer-modified synthetic bioactive protein of the formula:

Protein-Un-s1-B-s2-Polymer-s3-J* where Protein comprises a polypeptide chain of a ribosomally specified protein, where the polypeptide chain comprises one or more non-overlapping peptide segments covalently bonded by one or more chemical ligation sites, U is a residue of a unique functional group covalently bonded to a mutually reactive unique functional group of a side chain n of one or more amino acids of one or more of the non-overlapping peptide segments, where n is a discrete integer from 1 to 6, B is a branching core having three or more arms that may be the same or different and may be present or absent, Polymer is a substantially non-antigenic water-soluble polymer that may be the same or different where B is present, J* is a residue of pendant group having a net charge under physiological conditions selected from the group consisting of negative, positive and neutral, and where s1, s2, and s3 are spacer or linker moieties that may be the same or different, and may be individually present or absent. A preferred molecularly homogenous polymer-modified synthetic bioactive protein of the invention is one that is mono-disperse having a monomer molecular weight of greater than 25 kDa.

In another embodiment, the invention is directed to a polymer-modified synthetic bioactive protein having a polypeptide chain comprising an amino acid sequence of a ribosomally specified glycoprotein, where the polypeptide chain has one or more water-soluble polymers attached thereto. In a more preferred embodiment, one or more of the water-soluble polymers is covalently attached at one or more sites of the polypeptide chain that correspond to a glycosylation site of the ribosomally specified glycoprotein. Preferred water-soluble polymers are polyalkylene oxide, polyamide alkylene oxide and derivatives thereof that are glyco-mimetic water-soluble polymers. The most preferred are polymer-modified synthetic proteins comprising a polypeptide chain of a cytokine glycoprotein.

The invention further concerns pharmaceutical compositions comprising such polymer-modified synthetic bioactive proteins of the invention. The invention further provides a method of treating a human disease or condition that comprises administering to an individual in need of such treatment an effective amount of a pharmaceutical composition comprising one or more of such pharmaceutical compositions of the invention.

The invention also is directed to methods of producing polymer-modified synthetic bioactive proteins of the invention. A preferred method for producing the synthetic bioactive proteins of the invention comprises chemically ligating peptide segments comprising non-overlapping amino acid sequences of a polypeptide chain of the polymer-modified synthetic protein, where one or more of the peptide segments used for ligation has a water-soluble polymer attached thereto at a user-defined and pre-selected site. The polymer-modified polypeptide chain may then be folded to produce a polymer-modified synthetic bioactive protein of the invention.

Another preferred method for producing the synthetic bioactive proteins of the invention comprises chemically ligating peptide segments comprising non-overlapping amino acid sequences of a polypeptide chain of a synthetic bioactive polymer-modified protein of the invention, and attaching one or more water-soluble polymers to a side-chain of an amino acid at one or more chemical ligation sites thereof. The polymer-modified polypeptide chain may then be folded to produce a polymer-modified synthetic bioactive protein of the invention.

The invention also is drawn to a method of producing a polymer-modified synthetic bioactive protein comprising (1) chemically ligating peptide segments comprising non-overlapping amino acid sequences of a polypeptide chain of a synthetic bioactive protein to form a full-length polypeptide chain corresponding to the synthetic bioactive protein, where at least one peptide segment comprises an irregular amino acid having a first chemoselective functional group, (2) folding the polypeptide chain, and (3) attaching a water-soluble polymer thereto that comprises a second chemoselective group that is uniquely and mutually reactive with the first chemoselective group.

Another embodiment of the invention is directed to molecularly homogeneous glyco-mimetic water-soluble polymers of the formula U-s1-B-s2-Polymer-s3-J*, where U is a residue of a unique functional group, B is a branching core having three or more arms that may be the same or different and may be present or absent, Polymer is a polyamide having a molecular weight greater than about 5,000 Daltons of the formula —[C(O)—X—C(O)—NH—Y—NH]n- or —[NH—Y—NH—C(O)—X—C(O)]n-, where X and Y are divalent radicals that may be the same or different and may be branched or linear, and n is a discrete integer from 2 to 50, and where either or both of X and Y comprises a substantially non-antigenic water-soluble repeat unit that may be linear or branched, J* is a residue of a substantially non-antigenic pendant group having a net charge under physiological conditions selected from the group consisting of negative, positive and neutral, and where s1, s2, and s3 are spacer or linker moieties that may be the same or different, and may be individually present or absent.

The invention further concerns a molecularly homogeneous water-soluble polymer of the formula:

U-s1-B-s2-Polymer-s3-J* where U is a residue of a unique functional group, B is a branching core having three or more arms that may be the same or different and may be present or absent, Polymer is a polyamide having a molecular weight greater than about 5,000 Da of the formula —[C(O)—X—C(O)—NH—Y—NH]n- or —[NH—Y—NH—C(O)—X—C(O)]n-, where X and Y are divalent radicals that may be the same or different and may be branched or linear, and n is a discrete integer from 2 to 50, and where either or both of X and Y comprises a substantially non-antigenic water-soluble repeat unit that may be linear or branched, J* is a residue of a substantially non-antigenic pendant group having a net charge under physiological conditions selected from the group consisting of negative, positive and neutral, and where s1, s2, and s3 are spacer or linker moieties that may be the same or different, and may be individually present or absent, and if present preferably comprise from 1 to 18 carbons.

The invention particularly concerns such molecularly homogeneous water-soluble polymers wherein U is a residue of a functional group selected from the group consisting of acrylate, aldehyde, ketone, aminooxy, amine, carboxylic acid, ester, thioester, halogen, thiol, cyanoacetate, dipalmitoyl phosphatidylethanolamine, distearoyl phosphatidylethanolamine, epoxide, hydrazide, azide, isocyanate, maleimide, methacrylate, nitrophenyl carbonate, orthopyridyl disulfide, silane, sulfhydryl, vinyl sulfones, succinimidyl glutarate, succimidyl succinate, succinic acid, tresylate and an activatable functional group.

The invention further concerns such molecularly homogeneous water-soluble polymers wherein U is a residue of a functional group capable of forming a bond selected from the group carbonate, ester, urethane, orthoester, amide, amine, oxime, imide, urea, thiourea, thioether, thiourethane, thioester, ether, thaizolidine, hydrazone, and oxazolidine, and particularly such polymers wherein U is protected.

The invention further concerns such molecularly homogeneous water-soluble polymers, wherein the polymer has a molecular weight greater than about 10,000 Da, and more preferably greater than about 15,000 Da.

The invention further concerns such molecularly homogeneous water-soluble polymers wherein B comprises four or more arms, and/or wherein B comprises a branching core joined to s2 or Polymer through one or more amide bonds, and/or wherein B comprises a branching core joined to Polymer through amide bonds.

The invention further concerns such molecularly homogeneous water-soluble polymers wherein the repeat unit comprises an ethylene oxide of the formula —($CH_2$—$CH_2$—O)— or ($CH_2$—$CH_2$—O)—; and/or wherein X, Y, or X and Y are selected from: —(($CH_2$)$_{n1}$—($CH_2$—$CH_2$—O)$_{n2}$—($CH_2$)$_{n1}$—)— or —(($CH_2$)$_{n1}$—(O—$CH_2$—$CH_2$)$_{n2}$—($CH_2$)$_{n1}$—), where n1 is a discrete integer from 1 to 6, n2 is a discrete integer from 2 to 50; and/or wherein one of X or Y is selected from the group consisting of phenyl, a $C_1$–$C_{10}$ alkylene moiety, a $C_1$–$C_{10}$ alkyl group, a heteroatom-containing phenyl, a heteroatom-containing $C_1$–$C_{10}$ alkylene moiety, a heteroatom-containing $C_1$–$C_{10}$ alkyl group, and a combination thereof.

The invention particularly concerns such molecularly homogeneous water-soluble polymers wherein X is —($CH_2$—$CH_2$)—, or —X'—NH— or —NH—X'—.

The invention particularly concerns such molecularly homogeneous water-soluble polymers wherein Y is —($CH_2$—($CH_2$—$CH_2$—O)$_3$—$CH_2$—$CH_2$—$CH_2$)n- or —($CH_2$—$CH_2$—$CH_2$—(O—$CH_2$—$CH_2$)$_3$—$CH_2$)-n, where n is 6 to 36; or —Y'—NH— or —NH—Y'—, especially wherein at least one of X' and Y' comprise a polyethylene oxide of formula (—$CH2$—$CH_2$—O—)n or (O—$CH_2$—$CH_2$—)n where n is 2 to 50.

The invention particularly concerns such molecularly homogeneous water-soluble polymers wherein J* is protected, or comprises (i) a non-ionizable group having a net neutral charge under physiological conditions, or (ii) an ionizable group that comprises a net positive charge under physiological conditions, or (iii) an ionizable group that comprises a net negative charge under physiological conditions.

The invention particularly concerns such molecularly homogeneous water-soluble polymers wherein the water-soluble polymer is mono-disperse.

BRIEF DESCRIPTION OF THE FIGURES

FIG. 12 shows the basic structure of synthetic bioactive GCSF proteins. In the figure, "J" designates a non-naturally encoded residue having a hydrophobic side chain.

FIG. 13 shows the structure of preferred synthetic RANTES analogs. In the Figure, NNY=nonanoyl, X=non-naturally encoded amino acid having a hydrophobic side chain, and FA=fatty acid.

Figure 1A:
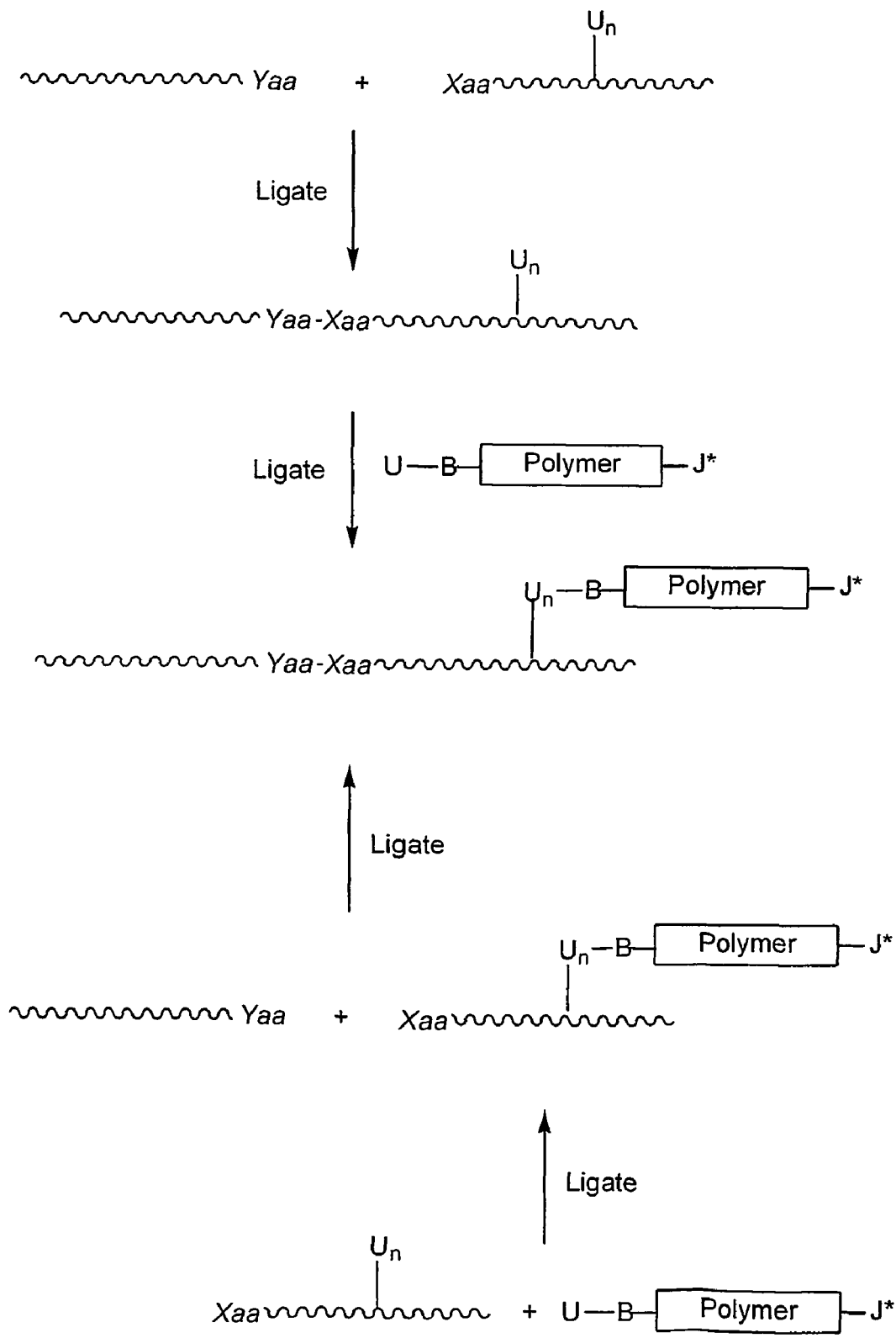
FIGS. 1A–1E depict schematics of processes for preparing the polymer-modified synthetic bioactive proteins of the invention.

DESCRIPTION OF THE PREFERRED EMBODIMENTS

The invention relates to polymer-modified synthetic bioactive proteins, methods of production and use. The invention also relates to glyco-mimetic water-soluble polyamide polymers.

I. Polymer-Modified Synthetic Bioactive Proteins of The Invention

Although polymer-modified proteins have been previously described, the nature and manner of the possible polymer-modifications of the present invention markedly differ from such prior efforts. For instance, the polymer-modified synthetic bioactive proteins of the present invention are chemically synthesized, in whole. In addition, the polymer-modified synthetic bioactive proteins of the invention are modified with water-soluble polymers at one or more particular, user-selected and user-defined sites.

Moreover, the synthetic production of the proteins in the present invention permits one to ensure that such modifications are present at each of the user-selected and user-defined sites of every molecule in a preparation. Such uniformity and control of synthesis markedly distinguishes the present invention from the random modifications permitted to the use of the methods of the prior art. Significantly, the present invention permits one to design a synthetic protein in which any non-critical residue may be derivatized to contain a polymer adduct. Moreover, for each such user-selected and user-defined site, the user may define the precise linkage (amide, thioester, thioether, oxime, etc.) through which such adducts will be bonded to the polypeptide or protein backbone. Additionally, the particular polymer adducts desired to be present at a particular site may be varied and controlled, such that a final preparation is obtained in which every protein or polypeptide present contains precisely the same derivatized adducts at precisely the same derivatized sites. Thus, the present invention permits the formation of homogeneous preparations of polymer-modified polypeptides and proteins.

In addition to providing a means for varying the position and number of attachment sites to which a water-soluble polymer can be bound, the present invention permits one to vary the nature of the bound polymer. The polymer adducts that may be incorporated into any particular user-selected and user-defined site can be of any defined length. Likewise, consistent with the methods of present invention, it is possible to employ polymers of different lengths at different sites. Thus, in one embodiment, the polymer-modified synthetic bioactive proteins of the present invention may be either mono-modified, or poly-modified, with a water-soluble polymer adduct. Where more than one polymer adduct is introduced into a particular polypeptide or protein, the employed polymers may be "mono-speciated," "poly-speciated," "uniformly speciated," or to "diversely speciated in." As used herein, the term "mono-speciated" is intended to refer to a polypeptide or protein that has been modified by a single species of polymer. In contrast, the term "poly-speciated" is intended to refer to a polypeptide or protein that has been modified by more than a single polymer species. Such poly-speciated polypeptides or proteins are said to be "uniformly-speciated" if, at each modified site of the polypeptide or protein, the same, single species of polymer is present. In contrast, a poly-speciated polypeptide or protein is said to be "diversely-speciated" if, the modified sites of the polypeptide or protein are modified with different species of polymer.

Moreover, it is possible to vary the extent of linearity or branchedness of the polymer adduct at each of the user-selected in user-defined sites. Thus the polymer adducts may be linear, branched, or uniformly branched. The term "uniformly branched" is intended to mean that all branches of a polymer at a particular site have the same structure and length. As we appreciate, the present invention permits one to independently vary both the length of any individual branch, as well as the structure of the polymer present at such branch point.

In sum, the present invention permits one to define (1) the location and (2) frequency of polymer-modified, user-selected and user-defined sites in a polypeptide or protein backbone, as well as to control the (3) length, (4) species, and (5) degree of branching present at each such site. Additionally, with respect to polypeptide and proteins having multiple polymer modifications, the present invention permits one to independently define each of the above-identified five variables for each site. Moreover, with respect polypeptides and proteins having branched polymer modifications, the present invention permits one to independently define each of the above-identified five variables for each branch point. This allows for the synthesis of homogenous compositions of precision polymer-modified synthetic bioactive proteins having multiple copies of any or all of the 20 genetically encoded amino acid side chains present and left unencumbered by unwanted polymer attachment.

Thus the invention affords significant flexibility in the design, synthesis and use of polymer-modified synthetic bioactive proteins, particularly those that target receptors for cytokines, growth factors and the like. For instance, the amino acid sequence of the synthetic bioactive proteins of the invention may comprise one or more deletions, insertions or substitutions relative to the amino acid sequence of a genetically encoded protein on which it is based. The amino acid sequence can be substituted with one or more irregular amino acids, such as a pseudo amino acid and or other amino acid bearing an unnatural side chain the like, for example, one that is modified to bear a unique chemoselective functional group for attaching a water-soluble polymer adduct thereto. Thus, the water-soluble polymer can be attached through an irregular amino acid, or a genetically encoded amino acid. The water-soluble polymer can be linear or branched, and it can have a terminal group comprising a chemical moiety such as a carboxylic acid, aliphatic, amide or amine. Moreover, the water-soluble polymer can be monodisperse, i.e., it can be made to comprise a single molecular species of precisely defined structure and composition. Thus, the water-soluble polymer can be designed to contain features to precisely tune half-life, immunogenicity, potency, storage stability, dosage, deliverability and the like of the target protein modified therewith.

In a preferred embodiment, the invention is directed to molecularly homogenous polymer-modified synthetic bioactive proteins. These proteins have the formula:

Protein-Un-s1-B-s2-Polymer-s3-J*

In this formula, Protein comprises a polypeptide chain of a ribosomally specified protein. The polypeptide chain comprises one or more non-overlapping peptide segments covalently bonded by one or more chemical ligation sites.

By "ribosomally specified protein" is intended a protein produced ribosomally in a cell. In a preferred embodiment, the polymer-modified polypeptide chain possess a bioactivity that mimics a bioactivity associated with such ribosomally specified protein such as a natural mammalian protein (e.g., human, simian, bovine, murine, porcine, ovine, or equine, avian, or piscine protein). More preferable is a bioactivity that mimics a bioactivity associated with a ribosomally specified protein selected from the group consisting of a protein receptor or fragment thereof, a protein receptor ligand or fragment thereof, and a cytokine. Bioactive polypeptide chains of ribosomally specified proteins include novel and well as those obtainable from various gene or protein databases. Examples of such databases include, but are not limited to, GeneBank (Benson, et al., *Nucleic Acids Res* (1998) 26(1):1–7; USA National Center for Biotechnology Information, National Library of Medicine, National Institutes of Health, Bethesda, Md., USA), TIGR Database (The Institute for Genomic Research, Rockville, Md., USA), Protein Data Bank (Brookhaven National Laboratory, USA), and the ExPASy and Swiss-Protein database (Swiss Institute of Bioinformatics, Geneve, Switzerland). The most preferred ribosomally specified proteins are cytokines, of which polypeptide chains and their specific amino acid sequences are well known (See e.g., "The Cytokine Handbook", $3^{rd}$ Edition, Ed. A. Thomas, Associated Press, 1998; "Cytokines", Ed. A. Mire-Sluis & R. Thorpe, Academic Press, 1998; and "Cytokine Reference", Vol. 1, Ligands, A compendium of cytokines and other mediators of host defense, Eds. J. J. Oppendheim and M. Feldmann, Acedemic Press, 2001)).

By "chemical ligation site" is intended the N-terminal amino acid of a first peptide or polypeptide and the C-terminal amino acid of a second peptide or polypeptide that form or are capable of forming a non-reversible covalent bond therein between by chemical ligation. As used herein, "chemical ligation" refers to a chemoselective reaction involving the covalent joining of two chemical moieties, each of which moieties bears a mutually reactive functional group that is uniquely capable of forming a non-reversible covalent bond with the other. Chemical ligation includes covalent ligation of (1) a first peptide or polypeptide bearing a uniquely reactive C-terminal group with (2) a second peptide or polypeptide bearing a uniquely reactive N-terminal group, where the C-terminal and N-terminal reactive groups form a non-reversible covalent bond therein between. In particular, chemical ligation includes any chemoselective reaction chemistry that can be applied to ligation of unprotected peptide segments.

U is a residue of a unique functional group covalently bonded to a mutually reactive unique functional group of a side chain n of one or more amino acids of one or more of the non-overlapping peptide segments, and where M is a discrete integer from 1 to 6. Most preferably side chain n is a discrete integer from 1 to 4. As used herein the term "amino acid" is intended to include the 20 genetically coded amino acids, rare or unusual amino acids that are found in nature, and any of the non-naturally occurring amino acids, such as irregular amino acids; sometimes referred to as amino acid residues when in the context of a peptide, polypeptide or protein. Preferred embodiments of U and side chain n are covalent bonds formed from unique mutually reactive groups, where such bonds are selected from oxime, amide, amine, urethane, ether, thioether, ester, hydrazide, oxazolidine, thaizolidine, thioether, ether, and ester. The most preferred U and n bond is one where U is covalently bonded to side chain n through a bond formed by chemical ligation selected from the group consisting of amide, oxime, thioester, hydrazone, thaizolidine, oxazolidine.

B is a branching core having three or more arms that may be the same or different and may be present or absent. Most preferably B is present and comprises three or more arms, and even more preferably four or more arms. In particular, one arm of B is joined to U (optionally through a spacer or linker s1), and a second arm of B is joined to Polymer (optionally through a spacer or linker s2). A favored polymer-modified synthetic bioactive protein is one in which at least one of the branching arms of moiety B comprises a residue of bond selected from the group consisting of oxime, amide, amine, urethane, thioether, ester, hydrazide, oxazolidine, and thaizolidine. A preferred branching group B of a polymer-modified synthetic bioactive protein of the invention comprises a branching core selected from the group consisting of amino, carboxylate and mixed amino-carboxylate. Preferred amino branching core comprise lysine, preferred carboxylate branching core comprise glutamic or aspartic acid, and preferred mixed amino-carboxylate branching core comprises gamma-glutamic acid, or derivatives thereof.

The Polymer component is a substantially non-antigenic water-soluble polymer that may be the same or different where B is present. By "water-soluble polymer" is intended a substantially non-antigenic polymer that is soluble in water and has an atomic molecular weight greater than about 1,000

Daltons. The Polymer will preferably have an effective hydrodynamic molecular weight of greater than 10,000 Da, and more preferably about 20,000 to 500,000 Da, and most preferably about 40,000 to 300,000 Da. By "effective hydrodynamic molecular weight" is intended the effective water-solvated size of a polymer chain as determined by aqueous-based size exclusion chromatography (SEC). When the water-soluble polymer contains polymer chains having polyalkylene oxide repeat units, such as ethylene oxide repeat units, it is preferred that each chain have an atomic molecular weight of between about 200 and about 80,000 Da and preferably between about 1,500 and about 42,000 Da, with 2,000 to about 20,000 Da being most preferred. Unless referred to specifically, molecular weight is intended to refer to atomic molecular weight.

The Polymer component can have a wide range of molecular weight, and polymer subunits. These subunits may include a biological polymer, a synthetic polymer, or a combination thereof. Examples of such water-soluble polymers include: dextran and dextran derivatives, including dextran sulfate, P-amino cross linked dextrin, and carboxymethyl dextrin, cellulose and cellulose derivatives, including methylcellulose and carboxymethyl cellulose, starch and dextrines, and derivatives and hydroylactes of starch, polyalklyene glycol and derivatives thereof, including polyethylene glycol, methoxypolyethylene glycol, polyethylene glycol homopolymers, polypropylene glycol homopolymers, copolymers of ethylene glycol with propylene glycol, wherein said homopolymers and copolymers are unsubstituted or substituted at one end with an alkyl group, heparin and fragments of heparin, polyvinyl alcohol and polyvinyl ethyl ethers, polyvinylpyrrolidone, aspartamide, and polyoxyethylated polyols, with the dextran and dextran derivatives, dextrine and dextrine derivatives. It will be appreciated that various derivatives of the specifically recited water-soluble polymers are also contemplated.

Water-soluble polymers such as those described above are well known, particularly the polyalkylene oxide based polymers such as polyethylene glycol "PEG" (See. e.g., "Poly (ethylene glycol) Chemistry: Biotechnical and Biomedical Applications", J. M. Harris, Ed., Plenum Press, New York, N.Y. (1992); and "Poly(ethylene glycol) Chemistry and Biological Applications", J. M. Harris and S. Zalipsky, Eds., ACS (1997); and International Patent Applications: WO 90/13540, WO 92/00748, WO 92/16555, WO 94/04193, WO 94/14758, WO 94/17039, WO 94/18247, WO 94/28937, WO 95/11924, WO 96/00080, WO 96/23794, WO 98/07713, WO 98/41562, WO 98/48837, WO 99/30727, WO 99/32134, WO 99/33483, WO 99/53951, WO 01/26692, WO 95/13312, WO 96/21469, WO 97/03106, WO 99/45964, and U.S. Pat. Nos. 4,179,337; 5,075,046; 5,089,261; 5,100,992; 5,134,192; 5,166,309; 5,171,264; 5,213,891; 5,219,564; 5,275,838; 5,281,698; 5,298,643; 5,312,808; 5,321,095; 5,324,844; 5,349,001; 5,352,756; 5,405,877; 5,455,027; 5,446,090; 5,470,829; 5,478,805; 5,567,422; 5,605,976; 5,612,460; 5,614,549; 5,618,528; 5,672,662; 5,637,749; 5,643,575; 5,650,388; 5,681,567; 5,686,110; 5,730,990; 5,739,208; 5,756,593; 5,808,096; 5,824,778; 5,824,784; 5,840,900; 5,874,500; 5,880,131; 5,900,461; 5,902,588; 5,919,442; 5,919,455; 5,932,462; 5,965,119; 5,965,566; 5,985,263; 5,990,237; 6,011,042; 6,013,283; 6,077,939; 6,113,906; 6,127,355; 6,177,087; 6,180,095; 6,194,580; 6,214,966).

The more preferred Polymer component comprises a polyalkylene oxide, polyamide alkylene oxide, or derivatives thereof. An even more preferred Polymer component is a polyamide having a molecular weight greater than about 1,000 Daltons of the formula —[C(O)—X—C(O)—NH—Y—NH]n— or —[NH—Y—NH—C(O)—X—C(O)]n-, where X and Y are divalent radicals that may be the same or different and may be branched or linear, and n is a discrete integer from 2–100, and more preferably from 2 to 50, and where either or both of X and Y comprises a biocompatible, substantially non-antigenic water-soluble repeat unit that may be linear or branched. The most preferred water-soluble repeat unit comprises an ethylene oxide of the formula —(CH$_2$—CH$_2$—O)— or —(CH$_2$—CH$_2$—O)—. The number of such water-soluble repeat units can vary significantly, but the more preferred number of such units is from 2 to 500, 2 to 400, 2 to 300, 2 to 200, 2 to 100, and most preferably 2 to 50. An example of a more preferred embodiment is where one or both of X and Y is selected from: —((CH$_2$)$_{n1}$—(CH$_2$—CH$_2$—O)$_{n2}$—(CH$_2$)$_{n1}$—)— or —((CH$_2$)$_{n1}$—(O—CH$_2$—CH$_2$)$_{n2}$—(CH$_2$)$_{n1}$—), where n1 is 1 to 6, 1 to 5, 1 to 4 and most preferably 1 to 3, and where n2 is 2 to 50, 2 to 25, 2 to 15, 2 to 10, 2 to 8, and most preferably 2 to 5. An example of a highly preferred embodiment is where X is —(CH$_2$—CH$_2$)—, and where Y is —(CH$_2$—(CH$_2$—CH$_2$—O)$_3$—CH$_2$—CH$_2$—CH$_2$)— or —(CH$_2$—CH$_2$—CH$_2$—(O—CH$_2$—CH$_2$)$_3$—CH$_2$)—.

The Polymer component or one or more of the spacers or linkers, when present, may include polymer chains or units that are biostable or biodegradable. For example, Polymers with repeat linkages have varying degrees of stability under physiological conditions depending on bond lability. Polymers with such bonds can be categorized by their relative rates of hydrolysis under physiological conditions based on known hydrolysis rates of low molecular weight analogs, e.g., from less stable to more stable polycarbonates (—O—C(O)—O—)>polyesters (—C(O)—O—)>polyurethanes (—NH—C(O)—O—)>polyorthoesters (—O—C((OR)(R'))—O—)>polyamides (—C(O)—NH—). Similarly, the linkage systems attaching a water-soluble polymer to a target molecule may be biostable or biodegradable, e.g., from less stable to more stable carbonate (—O—C(O)—O—)>ester (—C(O)—O—)>urethane (—NH—C(O)—O—)>orthoester (—O—C((OR)(R'))—O—)>amide (—C(O)—NH—). These bonds are provided by way of example, and are not intended to limit the types of bonds employable in the polymer chains or linkage systems of the water-soluble polymers of the invention.

Component J* is a residue of pendant group having a net charge under physiological conditions selected from the group consisting of negative, positive and neutral. This includes alkyl, aryl, heteroalkyl, heteroaryl, arylalkyl, acyl, alkoxy, alkenyl, allkynyl, amideo, amino, carbonyl groups and the like, that are substituted or unsubstituted, and as well as salts thereof. Neutral groups preferably are alkyl or alkoxy groups, and can include, but are not limited to moieties containing from 1 to 18 carbons, and may be linear or branched. When provided as a charged group, J* comprise an ionizable functional group. Examples of functional groups include, but are not limited to, carboxylic acids, esters, amides, nitrites, thiols, and hydroxyls. Such J* groups may be a component of amino acids, nucleic acids, fatty acids, carbohydrates, and derivatives thereof, and moieties such as chitin, chitosan, heparin, heparan sulfate, chondroitin, chondroitin sulfate, dermatan and dermatan sulfate, cyclodextrin, dextran, hyaluronic acid, phospholipid, sialic acid and the like. J* preferably comprises an ionizable moiety selected from carboxyl, amino, thiol, hydroxyl, phosphoryl, guanidinium, imidazole and salts thereof. The most preferred is where J* comprises an ionizable carboxylate moiety and has a net negative charge under physiological conditions.

The components s1, s2, and s3 are spacer or linker moieties that may be the same or different, and may be individually present or absent. Preferred spacers or linkers include linear or branched moieties comprising one or more repeat units employed in a water-soluble polymer, diamino and or diacid units, natural or unnatural amino acids or derivatives thereof, as well as aliphatic moieties, including alkyl, aryl, heteroalkyl, heteroaryl, alkoxy, and the like, which preferably contain up to 18 carbon atoms or even an additional polymer chain. Most preferably the spacer or linker comprises a polymer chain.

Alternatively, the above formula Protein-Un-s1-B-s2-Polymer-s3-J* can be represented as "Protein-Un-B-Polymer-J*" where the s1, s2 and s3 groups may be present or absent. The more preferred Polymer component is where the water-soluble polymer U-s1-B-s2-Polymer-s3-J* is produced in total by stepwise synthesis. This means that these polymers will have a precise molecular weight and defined structure. In contrast, normal polymer synthesis, which is a polymerization process, results in a mixture in which chains are of differing lengths, and so there is a distribution of molecular weights and sizes that are difficult if not impossible to separate. The ability to control molecular purity is advantageous in that a synthetic protein can be constructed that has a water-soluble polymer attached thereto and that is monodisperse. This represents a significant advantage in that variable properties resulting from heterogeneous compounds can be avoided, and only those compounds with the most preferred properties can be prepared and isolated with relative ease.

Alternatively, the above formula Protein-Un-s1-B-s2-Polymer-s3-J* can be represented as "Protein-Un-B-Polymer-J*" where the s1, s2 and s3 groups may be present or absent.

More preferred compounds of the formula Protein-Un-s1-B-s2-Polymer-s3-J* have a polypeptide chain comprising an amino acid sequence of a ribosomally specified protein, and more preferably where the polypeptide chain has one or more irregular amino acids. As used here, "irregular amino acid" refers to an amino acid having a non-genetically encoded side chain, a non-genetically encoded backbone, a non-genetically encoded substituted Nα or αC(O) moiety, or a combination thereof, i.e., other than one of the ribosomally installed 20 genetically encoded amino acids. Examples of preferred irregular amino acids include amino acids having side chains bearing a unique functional group other than a genetically encoded functional group, as well as pseudo amino acids and various amino acid derivatives. In this regard, the present invention permits wide selectability and flexibility in the design and/or construction of synthetic bioactive proteins. Examples of non-ribosomally installed amino acids that may be used in accordance with a present invention include, but are not limited to: D-amino acids, β-amino acids, pseudo-glutamate, γ-aminobutyrate, ornithine, homocysteine, N-substituted amino acids (R. Simon et al., Proc. Natl. Acad. Sci. U.S.A. (1992) 89: 9367–71; WO 91/19735 (Bartlett et al.), U.S. Pat. No. 5,646,285 (Baindur), α-aminomethyleneoxy acetic acids (an amino acid-Gly dipeptide isostere), and α-aminooxy acids and other amino acid derivatives having non-genetically non-encoded side chain function groups etc. Peptide analogs containing thioamide, vinylogous amide, hydrazino, methyleneoxy, thiomethylene, phosphonamides, oxyamide, hydroxyethylene, reduced amide and substituted reduced amide isosteres and β-sulfonamide(s) may be employed. By "pseudo amino acid" is intended an amino acid having an identical backbone structure and side-chain group as a genetically encoded amino acid, but differing in the atomic composition of the side chain atoms.

In a preferred embodiment, synthetic bioactive proteins are provided that have a water-soluble polymer attached to an irregular amino acid of a polypeptide chain thereof. Most preferred irregular amino acids for attachment of a water-soluble polymer thereto employ chemoselective ligation chemistry that can be used in the presence of genetically encoded functional groups without reacting with them.

In another embodiment, the invention is directed to a synthetic bioactive protein comprising a polypeptide chain comprising an amino acid sequence of a ribosomally specified glycoprotein, where the polypeptide chain has one or more water-soluble polymers attached thereto, and that preferably has a monomer molecular weight of greater than 25 kDa. This includes synthetic bioactive proteins that possess a bioactivity that mimics a bioactivity associated with the ribosomally specified glycoprotein. As used herein, "glycoprotein" refers to a protein containing a carbohydrate chain covalently linked to an amino acid side chain of the protein through a sugar residue, and is sometimes referred to as glycosylated protein. The carbohydrate of a glycoprotein may be in the form of a monosaccharide, disaccharide(s), oligosaccharide(s), polysaccharide(s), or their derivatives (e.g., sulfo- or phospho-substituted). Includes glycoproteins having more than one carbohydrate attached to the protein, and are exemplified by glycoproteins having N-linked and O-linked glycosylation. Includes glycosylated bioactive domains of natural or non-natural glycoproteins. It will be appreciated that glycoproteins that have been mutated to eliminate one or more glycosylation sites, or that are expressed in cells that do not glycosylate the protein (e.g., *E. coli*) are embodied in this definition, as the residual site for polymer modification will be positionally the same.

Preferred polypeptide chains of a polymer-modified synthetic bioactive protein of the invention comprise an amino acid sequence of a ribosomally specified mammalian glycoprotein, such as a human glycoprotein. More preferred polypeptide chains comprise an amino acid sequence of a ribosomally specified glycoprotein that is a cytokine, of which many polypeptide chains and their specific amino acid sequences and associated biological properties are well known (See e.g., "The Cytokine Handbook", 3$^{rd}$ Edition, Ed. A. Thomas, Associated Press, 1998; "Cytokines", Ed. A. Mire-Sluis & R. Thorpe, Academic Press, 1998; and "Cytokine Reference", Vol. 1, Ligands, A compendium of cytokines and other mediators of host defense, Eds. J. J. Oppendheim and M. Feldmann, Acedemic Press, 2001)). In a preferred embodiment, the ribosomally specified glycoprotein comprises one or more glycosylation sites, and a water-soluble polymer is attached to the polypeptide chain of the synthetic bioactive protein at one or more sites corresponding to one or more the glycosylation sites of the ribosomally specified glycoprotein. In a more preferred embodiment, the water-soluble polymer is attached to the polypeptide chain exclusively at one or more sites corresponding to one or more such glycosylation sites. This aspect of the invention includes synthetic bioactive proteins where the ribosomally specified glycoprotein is a recombinantly produced glycoprotein, which can be a natural glycoprotein or a non-natural glycoprotein, the latter of which can further include one or more non-natural glycosylation sites. By "glycosylation site" is intended an amino acid sequence of a protein that encodes for the enzymatic attachment of an oligosaccharide (carbohydrate) chain to the side-chain of an amino acid residue of the amino acid sequence of the protein; exemplified by N-linked and O-linked glycosylation sites. It will be appreciated that glycoproteins that have been mutated to eliminate one or more of such glycosylation sites are embodied in the definition of 'glycosylation site', as the residual site for polymer modification will be positionally the same. By "naturally occurring glycosylation site" is intended a glycosylation site of a glycoprotein found in nature. By "non-naturally occurring glycosylation site" is intended a glycosylation site that has been engineered into a protein. For instance, recombinant human EPO and GCSF have been engineered in this manner (see, e.g., U.S. Pat. Nos. 5,856, 298 and 5,218,092).

This preferred embodiment of the invention is based in part on the finding that when a synthetic protein having a polypeptide chain of a glycoprotein is modified at one or more glycosylation sites thereof with a water-soluble polymer, such as the polymers described herein, the water-soluble polymer can be utilized to take advantage of one or more of the biological effects attributed to a carbohydrate chain normally found at that position in the counterpart naturally occurring glycoprotein, glycoproteins that have been engineered to contain additional glycosylation sites, or non-glycoproteins that have been engineered to be glycosylated. Such biological effects include modulation of protease resistance, immunogenicity, receptor-specificity, specific activity, potency and pharmacokinetics. However, by eliminating the presence of a carbohydrate chain, and replacing it with preferred water-soluble polymers of the invention, significant benefits are obtained including the avoidance of enzymatic degradation and clearance such as when pendant sialic acid residues of the sugar chains are removed, instability, limited circulation half-life, distribution, poor handling properties etc. Significantly, its has been found that such polymer-modified synthetic bioactive proteins of the invention retain such advantageous biological properties in the substantive absence of loss of biological activity when compared to a non-modified counterpart protein, including increased bioactivity, even when the monomer molecular weight of the synthetic protein is greater than 25 kDa.

Thus, in another preferred embodiment, the invention is directed to a synthetic bioactive protein comprising a polypeptide chain comprising an amino acid sequence of a ribosomally specified glycoprotein, where the polypeptide chain has one or more water-soluble polymers attached thereto and a monomer molecular weight of greater than 25 kDa, and where the synthetic bioactive protein comprises a bioactivity that is equal to or better than a corresponding synthetic bioactive protein having a polypeptide chain that is devoid of said water-soluble polymer. The bioactivity can be in vitro, in vivo or both. In a preferred embodiment, the bioactivity is in vivo. In another preferred embodiment, the invention is directed to a synthetic bioactive protein comprising a polypeptide chain comprising an amino acid sequence of a ribosomally specified glycoprotein, where the polypeptide chain has one or more water-soluble polymers attached thereto and a monomer molecular weight of greater than 25 kDa, and where the synthetic bioactive protein comprises a bioactivity that is equal to or better than the ribosomally specified glycoprotein. Here again, the bioactivity can be in vitro, in vivo or both. In a preferred embodiment, the bioactivity is in vivo. Most preferably, such polymer modified synthetic bioactive proteins will have a discrete number of water-soluble polymers attached thereto.

A benefit of targeting the non-naturally occurring glycosylation sites of a protein is that a protein found in nature, whether a natural glycoprotein or not, can be modified to contain a glycosylation site at one or more sites or regions, such as those unprotected disordered or surface-exposed regions responsible for immunogenicity or protease sensitivity, using recombinant DNA techniques (e.g., site-directed mutagenesis or directed evolution). For instance, non-naturally occurring glycosylation sites are designed at potential immunogenic or protease sensitive sites of a target polypeptide sequence, and screened in a recombinant system for production (e.g., CHO cell and yeast cell expression systems etc.) and assayed for the relevant desired bioactivity. New sites found to be amenable to glycosylation are then utilized in the design and synthesis of synthetic bioactive proteins of the invention that have a water-soluble polymer attached exclusively one or more of those positions.

In another embodiment, the invention is directed to a synthetic bioactive protein comprising a pseudo amino acid at a ligation site of the protein, and optionally, a water-soluble polymer attached to the protein. These compounds are produced by forming a ligation product having an unprotected side-chain functional group at the ligation site by ligating a first peptide or polypeptide segment having an N-terminal amino acid comprising a chemoselective reactive functional group, such as a cysteine, to a second peptide or polypeptide having a chemical ligation compatible C-terminal functional group, such as a α-carboxy thioester, and chemically converting the unprotected side-chain functional group at the ligation site to a pseudo amino acid, such as carboxymethylation of the cysteine thiol side-chain to form a pseudo glutamate amino acid. Pseudo amino acids formed by conversion of cysteines at native chemical ligation sites is referred to herein as "Pseudo Native Chemical Ligation," which is described in detail below.

Also provided is a synthetic bioactive protein comprising a water-soluble polymer attached to a side-chain of an amino acid at a ligation site of the protein. These compounds are synthesized by forming a ligation product having an unprotected side-chain functional group at the ligation site by ligating a first peptide or polypeptide segment having an N-terminal amino acid comprising a chemoselective reactive functional group, such as a cysteine, to a second peptide or polypeptide having a ligation compatible C-terminal functional group, such as a α-carboxy thioester, and attaching a water-soluble polymer to the unprotected side-chain functional group at the ligation site.

Utilization of pseudo amino acid chemical ligation and the chemical ligation site polymer modification methods of the invention afford several advantages over the prior art, including the robust synthesis of synthetic bioactive proteins that are otherwise devoid of suitable ligation sites, expansion of the sites (and attachment chemistries) to which site-specific polymer modification can be exploited in a routine and cost-effective manner, as well as the synthesis of synthetic bioactive proteins of substantial molecular weight, among others. They also are particularly suited for high throughput analoging for fine-tuning of desired biological properties, including scanning individual or multiple sites for water-soluble polymer attachment.

As noted above, the biological properties of the polymer-modified synthetic bioactive proteins of the invention can be modified by precisely adjusting the sites and linkage chemistries of polymer attachment in combination with the precision adjustment of the molecular weight, the polymer composition, the structure (e.g., linear versus branched, or mixtures thereof), and the pendant group (e.g., charged versus uncharged, or mixtures thereof) of the water-soluble polymer. In particular, in addition to increasing the molecular weight of a protein to improve half-life, and branching etc., the water-soluble polymer attached thereto can render the synthetic protein to have a precise charge, as measured by isoelectric point that is approximately equal to the charge of a corresponding biologically produced protein on which the amino acid sequence of the synthetic bioactive protein is based. This has the advantage of mimicking the natural charge of a corresponding ribosomally specified protein. A preferred embodiment of the invention is thus directed to synthetic bioactive proteins that combine the above features, as well as the water-soluble polymers utilized therefor, particularly structurally defined polymer adducts that are capable of being attached at preselected positions.

As also indicated above, the polymer-modified synthetic bioactive proteins of the present invention can have substantial total molecular weight, being greater than about 25 kDa. For the purposes of the present invention, such determinations of molecular weight are to be made by denaturing SDS polyacrylamide electrophoresis. The term "monomer molecular weight" is intended to refer to the molecular weight of a monomer synthetic protein, as distinguished from synthetic proteins that may possess multiple copies of a protein or polypeptide. The term "monomer polypeptide molecular weight" is intended to refer to the molecular weight of a monomer polypeptide, as distinguished from synthetic proteins that may possess polymers attached thereto and/or multiple copies of a protein or polypeptide.

As used herein, a protein is said to be "synthetic" if non-recombinant technology has been employed to polymerize some, and most preferably all, of its amino acid residues. The term "non-recombinant technology" is intended to distinguish technologies that involve organic chemistry and other synthetic polymerization approaches from technologies involving the translation of RNA into protein, either in vivo or in vitro. Synthetic proteins include totally synthetic and semi-synthetic proteins. A totally synthetic protein is produced where all ligation components are man-made by chemical synthesis, i.e., ribosomal-free synthesis. A semi-synthetic protein is produced where at least part of a ligation component is made by biological synthesis, i.e., ribosomally in a cell or cell-free translation system, and another part is made by chemical synthesis.

As used herein, a synthetic protein is said to be "bioactive" if it possesses a discernible bioactivity that is dependent upon the synthetic protein's structure or amino acid sequence, such the variation in such structure or sequence enhances, modifies, or attenuates the protein's bioactivity. Without limitation, such "bioactivity" includes the capacity of the protein to mediate a catalytic, signaling or inducing reaction. As used herein, a protein is said to "mediate a catalytic reaction" by converting a substrate into a product without itself being consumed or permanently modified. A protein is said to "mediate a signaling or inducing reaction" if its presence causes an organism, or its tissues or cells, to initiate, continue, enhance, modify, or attenuate gene expression, cellular differentiation, or cellular proliferation. Examples on such signaling or inducing reactions include inducing cytokine expression or a response to cytokine expression, inducing erythropoiesis, inducing or attenuating inflammation and/or an inflammatory process, initiating angiogenesis or vascularization, inducing apoptosis, affecting the cell cycle, etc.

Accordingly, by "polymer-modified synthetic bioactive protein" as used herein refers to a synthetic bioactive protein having one or more water-soluble polymers attached thereto. The bioactivity of the synthetic bioactive proteins of the present invention also includes the capacity of the protein to bind specifically to a receptor, ligand or antibody. As used herein, the term "specific" binding is intended to refer to a structurally-based binding interaction, such as that existing between a hormone and its receptor, or an antibody and an antigenic epitope, as distinguished from "non-specific" binding based upon charge, solubility, hydrophobicity, etc.

The polymer-modified synthetic bioactive proteins of the present invention may be designed to possess a bioactivity that mimics a bioactivity associated with a mammalian (including human, simian, bovine, murine, porcine, ovine, equine, etc.), avian, or piscine protein. As used herein, a first protein is said to mimic a second protein if the first protein possesses a bioactivity that is modified, enhanced, or attenuated with respect to the bioactivity of the second protein. A bioactivity is said to be "associated" with the protein if its presence is directly or indirectly dependent upon the amino acid sequence of the protein. In an alternative embodiment, the bioactive proteins of the present invention may be wholly or partly engineered, without reference to any corresponding natural bioactive counterpart.

Preferred synthetic bioactive proteins of the present invention include polymer-modified proteins other than receptors, and polymer-modified soluble receptor domains. For instance, synthetic bioactive proteins comprising a polymer-modified soluble receptor domain are particularly preferred. Examples of soluble receptor domains that are preferred for polymer modification are described in PCT/US00/06297, and include soluble domains of adrenocorticotropic hormone receptor and its bioactive fragments, angiotensin receptor, atrial natriuretic receptor, bradykininin receptor, growth hormone receptor, chemotatic receptor, dynorphin receptor, endorphin receptor, the receptor for β-lipotropin and its bioactive fragments, enkephalin receptor, enzyme inhibitor receptors, the receptor for fibronectin and its bioactive fragments, gastrointestinal- and growth hormone-releasing peptide receptors, the receptor for luteinizing hormone releasing peptide, the receptor for melanocyte stimulating hormone, neurotensin receptor, opioid receptor, oxytocin receptor, vasopressin receptor, vasotocin receptor, the receptor for parathyroid hormone and fragments, protein kinase receptor, somatostatin receptor, substance P receptor.

Polymer-modified synthetic cytokines are particularly preferred embodiments of the invention. In particular, the polymer-modified synthetic bioactive proteins of the invention include synthetic cytokines, including synthetic chemokines, which mediate specific effects on cell-cell interaction, communication and on the behavior of other cells in a biological setting. As used herein, the term "cytokine" is intended to include the interleukins ("IL") (such as IL-1, IL-2, IL-3, IL-4, IL-5, IL-6, IL-7, IL-9, IL-10, IL-11, IL-12, IL-13, IL14, etc.), lymphokines and signaling molecules such as erythropoiesis stimulating proteins (e.g., erythropoietin (EPO), thrombopoietin (TPO)), tumor necrosis factor (TNF), interferons, etc., growth factors, such as transforming growth factor, nerve growth factor, brain derived growth factor, neurotrophin-3, neurotrophin-4, heptaocyte growth factor, T-cell Growth Factor (TGF, TGF-β1, TGF-β2, TGF-β3, etc.), Colony Stimulating Factors (G-CSF, GM-CSF, M-CSF etc.), Epidermal Growth Factors (EGF, LIF, KGF, OSM, PDGF, IGF-I, etc.), Fibroblast Growth Factor (αFGF, βFGF, etc.), and hormones, particularly signal peptide hormones, such as growth hormone, and chemokines. As used herein, the term "chemokine" is intended to refer to the chemotactic cytokines, such as 6Ckine, 9E3, ATAC, ABCD-1, ACT-2, ALP, AMAC-1, AMCF-1, AMCF-2, AIF, ANAP, Angie, beta-R1, Beta-Thromboglobulin, BCA-1, BLC, blr-1 ligand, BRAK, C10, CCF18, Ck-beta-6, Ck-beta-8, Ck-beta-8-1, Ck-beta-10, Ckbeta-11, cCAF, CEF-4, CINC, C7, CKA-3, CRG-2, CRG-10, CTAP-3, DC-CK1, ELC, Eotaxin, Eotaxin-2, Exodus-1, Exodus-2, ECIP-1, ENA-78, EDNAP, ENAP, FIC, FDNCF, FINAP, Fractalkine, G26, GDCF, GOS-19-1, GOS-19-2, GOS-19-3, GCF, GCP-2, GCP-2-like, GRO1, GRO2, GRO3, GRO-alpha, GRO-beta, GRO-gamma, H400, HC-11, HC-14, HC-21, HCC-1, HCC-2, HCC-3, HCC-4 H174, Heparin neutralizing protein, Humig, I-309, ILINCK, I-TAC, Ifi10, IL8, IP-9, IP-10, IRH, JE, KC, Lymphotactin, L2G25B, LAG-1, LARC, LCC-1, LD78-alpha, LD78-beta, LD78-gamma, LDCF, LEC, Lkn-1, LMC, LAI, LCF, LA-PF4, LDGF, LDNAP, LIF, LIX, LUCT, Lungkine, LYNAP, Manchester inhibitor, MARC, MCAF, MCP-1, MCP-2, MCP-3, MCP-4, MCP-5, MDC, MIP-1-alpha, MIP-1-beta, MIP-1-delta, MIP-1-gamma, MIP-3, MIP-3-alpha, MIP-3-beta, MIP-4, MIP-5, Monotactin-1, MPIF-1, MPIF-2, MRP-1, MRP-2, M119, MDNAP, MDNCF, Megakaryocyte-stimulatory-factor, MGSA, Mig, MIP-2, mob-1, MOC, MONAP, NC28, NCC-1, NCC-2, NCC-3, NCC-4 N51, NAF, NAP-1, NAP-2, NAP-3, NAP-4, NAP S, NCF, NCP, Neurotactin, Oncostatin A, P16, P500, PARC, pAT464, pAT744, PBP, PBP-like, PBSF, PF4, PF4-like, PF4-ALT, PF4V1, PLF, PPBP, RANTES, SCM-1-alpha, SCI, SCY A26, SLC, SMC-CF, ST38, STCP-1, SDP-1-alpha, SDF-1-beta, TARC, TCA-3, TCA-4, TDCF, TECK, TSG-8, TY5, TCF, TLSF-alpha, TLSF-beta, TPAR-1, and TSG-1.

Such cytokines, and their chemokine subfamilies and their corresponding polypeptide chains, variants thereof and associated bioactivities are well know and publicly available through multiple sources (See e.g., "The Cytokine Handbook", 3$^{rd}$ Edition, Ed. A. Thomas, Associated Press, 1998; "Cytokines", Ed. A. Mire-Sluis & R. Thorpe, Academic Press, 1998; and "Cytokine Reference", Vol. 1, Ligands, A compendium of cytokines and other mediators of host defense, Eds. J. J. Oppendheim and M. Feldmann, Acedemic Press, 2001)).

II. Production of the Polymer-Modified Synthetic Bioactive Proteins of the Invention The production of the polymer-modified bioactive proteins of the invention can be envisioned as having the following steps: design, peptide synthesis, peptide ligation, folding of the full-length ligation product to generate protein, and assessment of the protein's bioactivity. We have found that polymer modification can be performed at one or more of the peptide synthesis, ligation or on the folded product steps. It is preferred, however, to attach polymer to the peptides or to the ligation product prior to folding. Proteins produced in this manner that exhibit a desired bioactivity are selected and represent the synthetic bioactive proteins of the invention.

In a particularly preferred embodiment, a method is provided for producing the synthetic bioactive proteins of the invention that comprises chemically ligating peptide segments comprising non-overlapping amino acid sequences of a polypeptide chain of a target synthetic bioactive polymer-modified protein of the invention, where one or more of the peptide segments used for ligation has a water-soluble polymer attached thereto at a user-defined and pre-selected site. The polymer-modified polypeptide chain may then be folded to produce a polymer-modified synthetic bioactive protein of the invention.

Another preferred method for producing the synthetic bioactive proteins of the invention comprises chemically ligating peptide segments comprising non-overlapping amino acid sequences of a polypeptide chain of a synthetic bioactive polymer-modified protein of the invention, and attaching one or more water-soluble polymers to a side-chain of an amino acid at one or more chemical ligation sites thereof. The polymer-modified polypeptide chain may then be folded to produce a polymer-modified synthetic bioactive protein of the invention.

The invention also is drawn to a method for producing a polymer-modified synthetic bioactive protein, the method comprising (1) chemically ligating peptide segments comprising non-overlapping amino acid sequences of a polypeptide chain of a synthetic bioactive protein to form a full-length polypeptide chain corresponding to the synthetic bioactive protein, where at least one peptide segment comprises an irregular amino acid having a first chemoselective functional group, (2) folding the polypeptide chain, and (3) attaching a water-soluble polymer thereto that comprises a second chemoselective group that is uniquely and mutually reactive with the first chemoselective group.

Figure 1B:
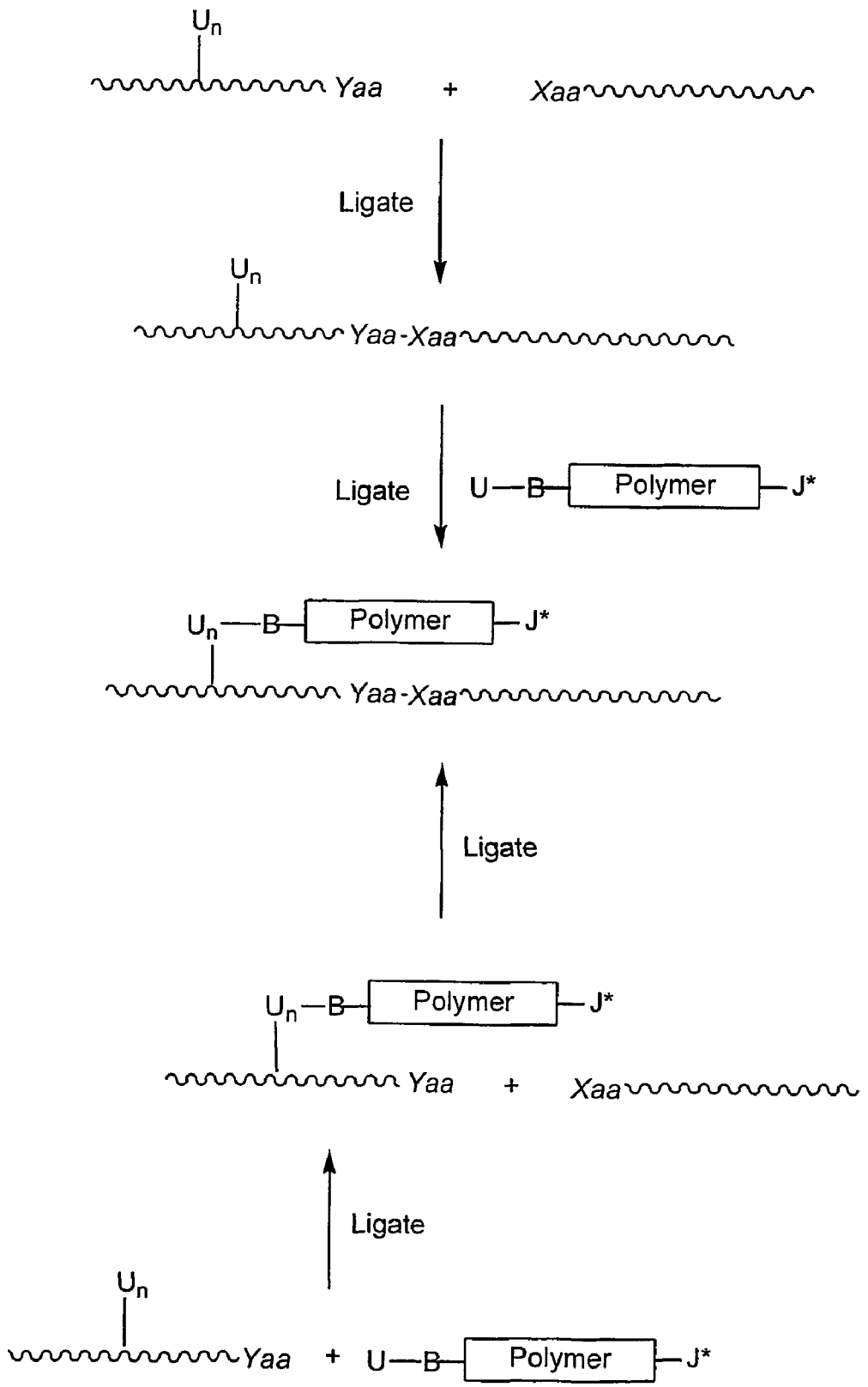
Figure 1C:
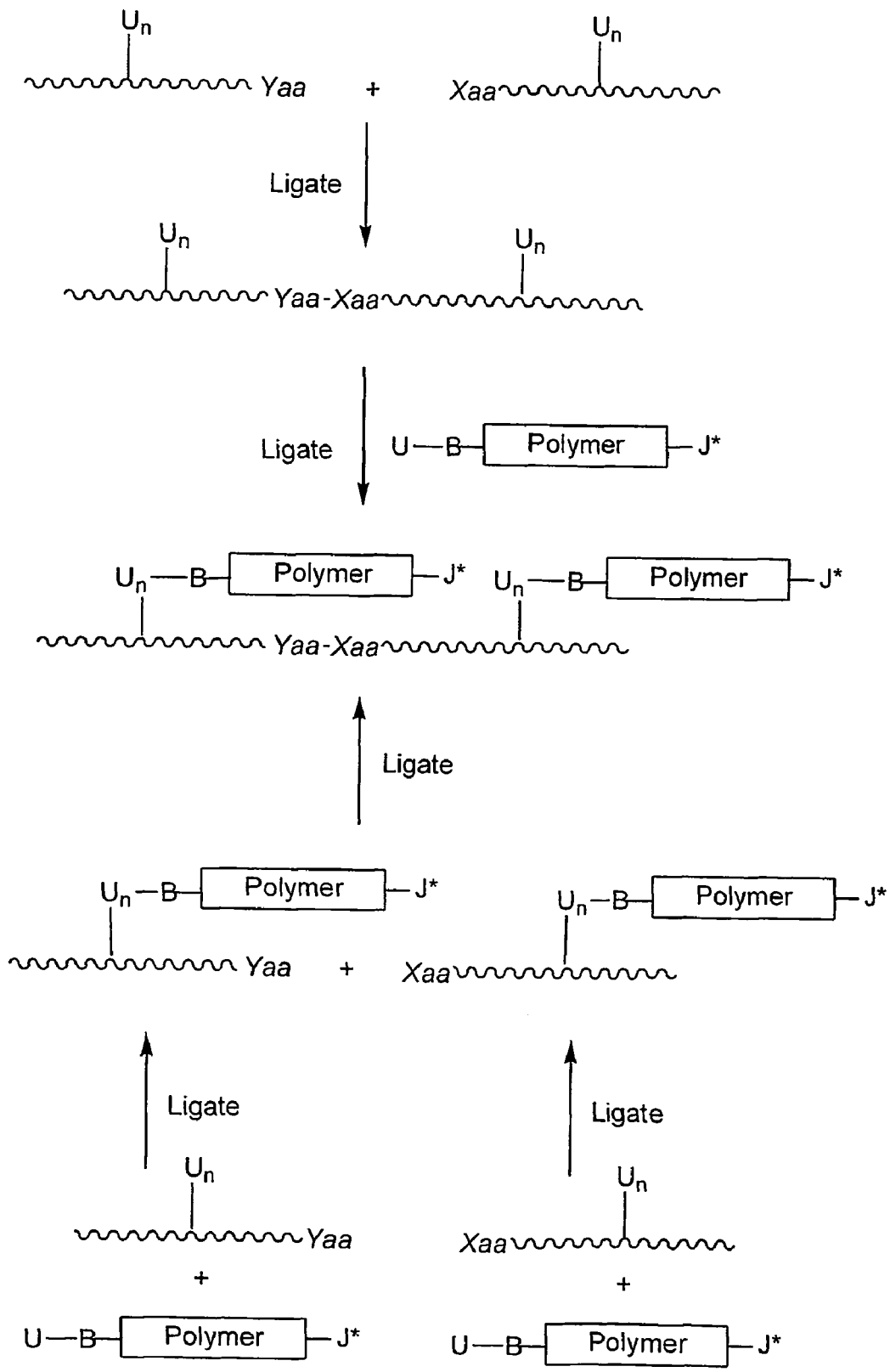
Figure 1D:
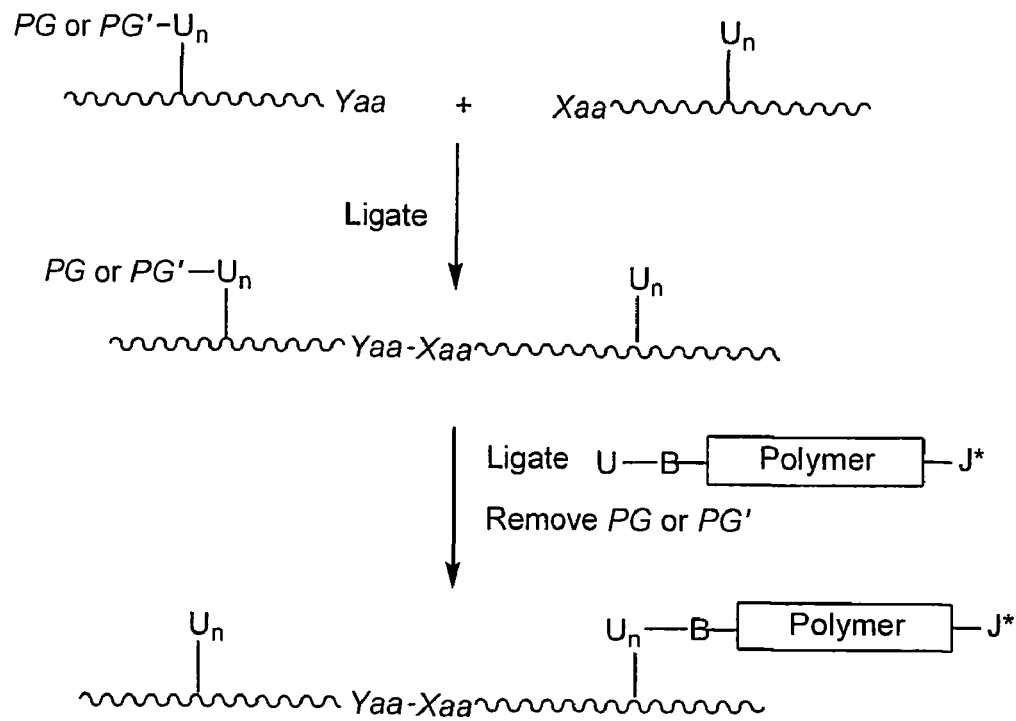

In particular, these various processes embodied in the invention, and as exemplified in the Examples, can be illustrated as shown in the Figures. For example, FIGS. 1A–1E depict ligation schemes involving the attachment of a water-soluble polymer (U-B-Polymer-J* as defined herein) to partially or fully unprotected peptide segments ∼∼∼before or after ligation, or combinations thereof. In FIGS. 1A–1D, $Y_{aa}$ represents the C-terminal amino acid on a first peptide segment that bears a unique chemoselective moiety (e.g., amino acid bearing alpha-carboxyl thioester) for chemical ligation to a second peptide segment bearing a unique and mutually reactive N-terminal amino acid $X_{aa}$ (e.g., amino terminal cysteine) moiety that is capable of chemoselective chemical ligation with $Y_{aa}$. Chemoselective reaction between $Y_{aa}$ and $X_{aa}$ generate a covalent linkage therein between (e.g., amide bond). Thus $Y_{aa}$ and $X_{aa}$ form a chemoselective ligation pairing. $U_n$-, as shown in the Figures, represents a second unique chemoselective moiety that has been incorporated at a precise user-defined site on the side chain of an amino acid and is chemoselective for, and mutually reactive with group U- of the water-soluble polymer U-B-Polymer-J*. For example, when $U_n$ is a side chain that has been modified to bear a ketone group, U- of the water-soluble polymer U-Polymer-J* is a group chemoselective for reacting with the ketone, e.g., an aminooxy group which yields an oxime bond therein between. The subscript "n" of $U_n$- represent the number of amino acids and their side chains designed to bear chemoselective group U, for example, where two specific and user-defined sites are to be polymer modified n=2, which also can be represented as $U_2$ or $U_{n=2}$. In all cases, n is a positive integer that is precisely controlled by design. Thus $U_n$ and U represent a second chemoselective ligation pairing that is compatible and unreactive with chemoselective groups of $X_{aa}$ and $Y_{aa}$. FIGS. 1A and 1B illustrate two different potential reactions. In the first depicted reaction, a polypeptide chain bearing a $U_n$ functionality is ligated to a second polypeptide, and is then reacted with a U-B-Polymer-J* moiety in order to obtain a polymer-modified polypeptide. In the second depicted reaction, the polypeptide chain bearing the $U_n$ functionality is reacted with a U-B-Polymer-J* moiety in order to obtain a polymer-modified polypeptide, and then ligated to a second polypeptide, to obtain a larger polymer-modified polypeptide. The figures differ in that in FIG. 1A, the polypeptide bearing the Xaa residue is to receive the polymer modification, whereas in FIG. 1B, the polypeptide bearing the Yaa residue receives the polymer modification. FIG. 1C illustrates the ability of the present invention to modify multiple polypeptide chains, either before or after their ligation to form a larger polypeptide. In FIG. 1D, PG and PG' represent protecting groups, where PG' depicts an orthogonal protecting group, i.e., PG and PG' are removable under different conditions, and are useful where different water-soluble polymers are attached via same chemistry to $U_n$ groups, or where $U_n$ groups represent side-chain functional groups that one does not wish to modify with a polymer (e.g., side chains bearing reactive —NH$_2$ or —SH where U group of water-soluble polymer is designed to react exclusively with primary amino or side chain thiols). FIG. 1D shows that protecting groups can be employed in order to protect desired side chains of the polypeptides being ligated in accordance with the methods of the present invention.

Figure 1E:
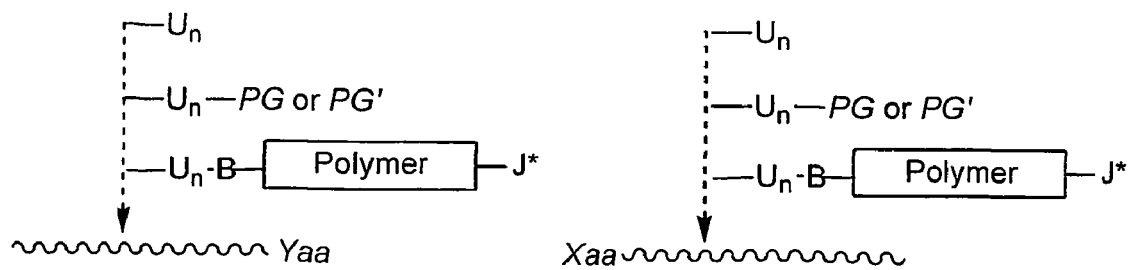

FIG. 1E illustrates the diversity of groups that may be present or absent in the peptide segments employed in ligation and polymer modification according to FIGS. 1A–1D.

Figure 2A:
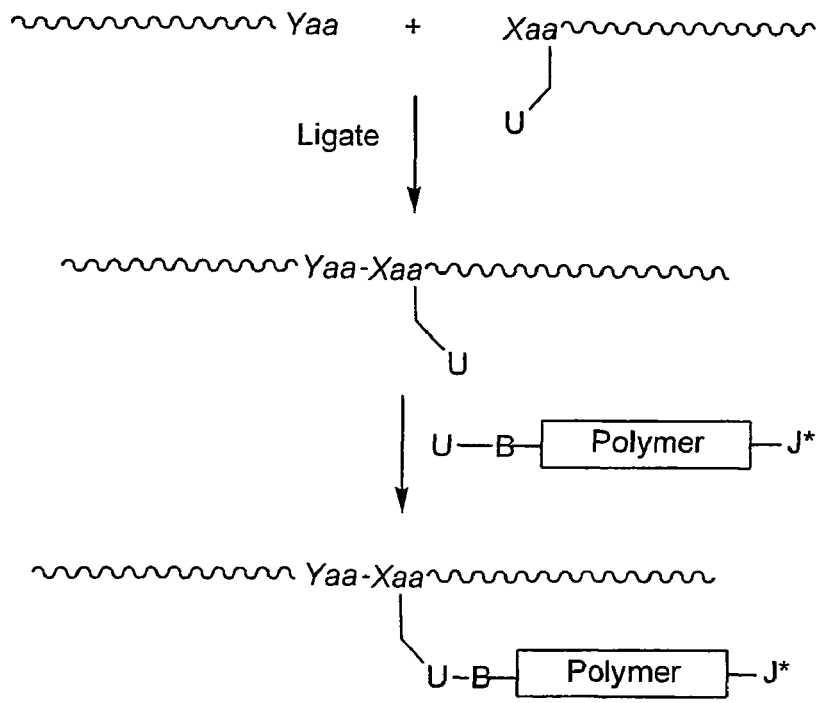
FIGS. 2A–2C depict schematics of processes for preparing synthetic bioactive proteins of the invention.
Figure 2B:
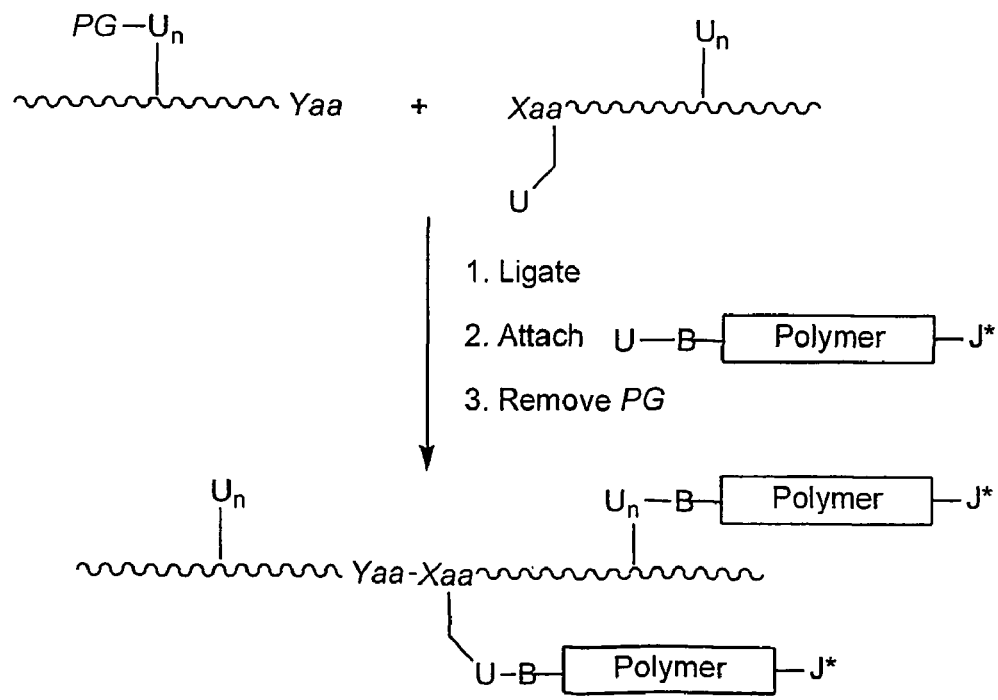
Figure 2C:
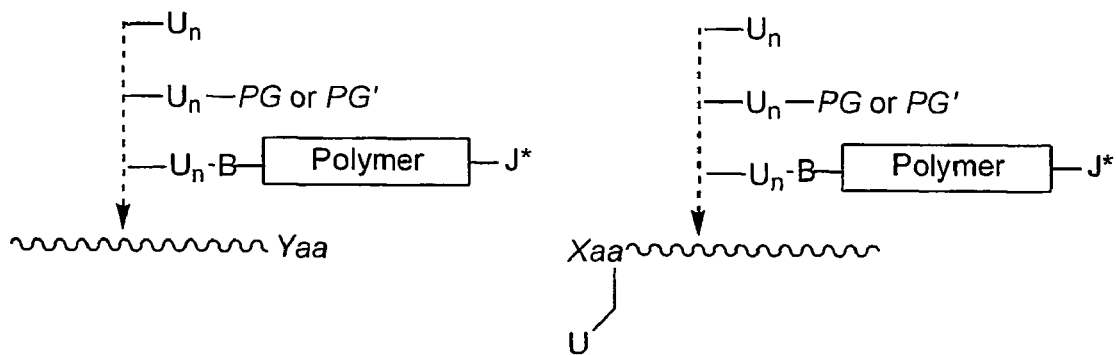

FIGS. 2A–2C depict additional schematics of processes for preparing synthetic bioactive proteins of the invention. In particular, FIGS. 2A–2B depict ligation scheme involving the attachment of a water-soluble polymer U-B-Polymer-J* to the side chain of amino terminal group Xaa at a ligation site (e.g., side chain thiol of cysteine). FIG. 2C illustrates the diversity of groups that may be present or absent in the peptide segments employed in ligation and polymer modification according to FIGS. 2A–2B.

Figure 3A:
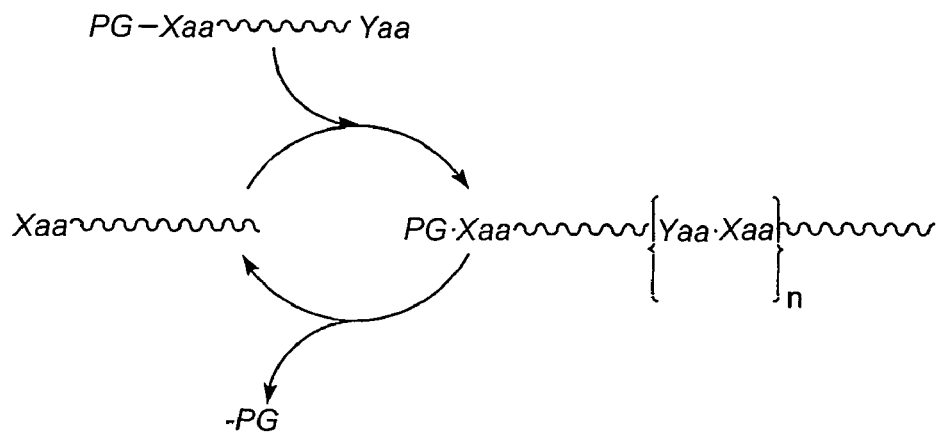
FIGS. 3A–3B depict schematics of processes for multi-segment ligations that involve the chemical ligation of three or more non-overlapping peptide segments, i.e., at least one segment is a middle segment corresponding to the final full-length ligation product.
Figure 3B:
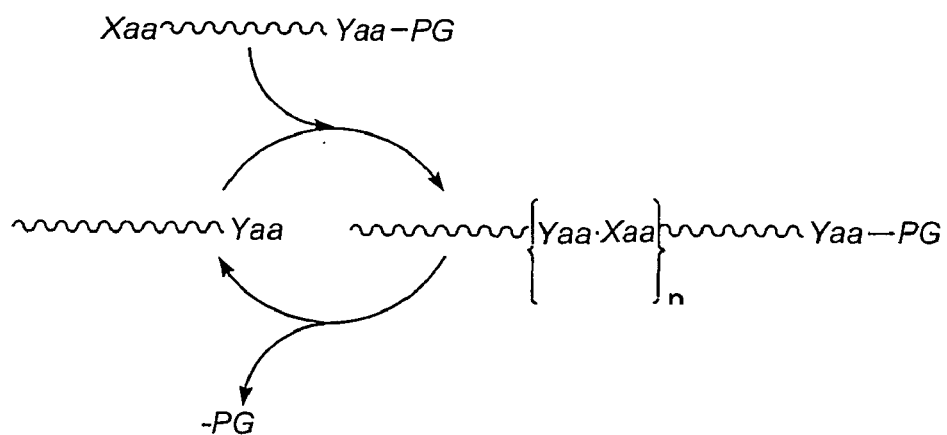

FIGS. 3A–3B depict additional schematics of processes for accomplishing multi-segment ligations that involve the chemical ligation of three or more non-overlapping peptide segments, i.e., at least one segment is a middle segment corresponding to the final full-length ligation product. Peptides prepared in this manner can be used for preparing peptide segments involved in another ligation reaction, for example, as shown in FIG. 1A–1E, FIGS. 2A–2C, and FIGS. 4A–4C. In general, for multi-segment ligations, the middle segment(s) has either a protected Xaa group or a protected Yaa group to avoid cyclization or concatemer formation of that peptide depending on the ligation chemistry employed. For sequential or serial ligations, the Xaa group of a middle segment is protected (e.g., Cys(Acm)) while the Yaa group is unprotected (e.g., Yaa-COSR, where —COSR is an alpha-carboxyl thioester). Here the Yaa group is free to react with a second peptide bearing an unprotected Xaa group, where the second peptide is devoid of a free Yaa group. Following ligation, the protecting group is removed to regenerate the Xaa group for the next ligation reaction. This process can be continued, as needed thereby generating an elongated polypeptide chain. Protection of the Yaa group is particularly useful for convergent chemical ligation involving the production of a final ligation product composed of four or more segments. For example, for a protein target generated from a four-segment ligation (i.e., three ligation reactions), two segments corresponding to one end of the protein and two segments corresponding to the other end of the protein can be ligated in parallel, as opposed to sequentially, and the two ends joined in a final ligation reaction. Such a convergent chemical ligation schemes also can employ orthogonal ligation chemistries. Here again the diversity of groups that may be present or absent in such peptide segments are illustrated in FIGS. 1E, 2C and 4C.

Figure 4A:
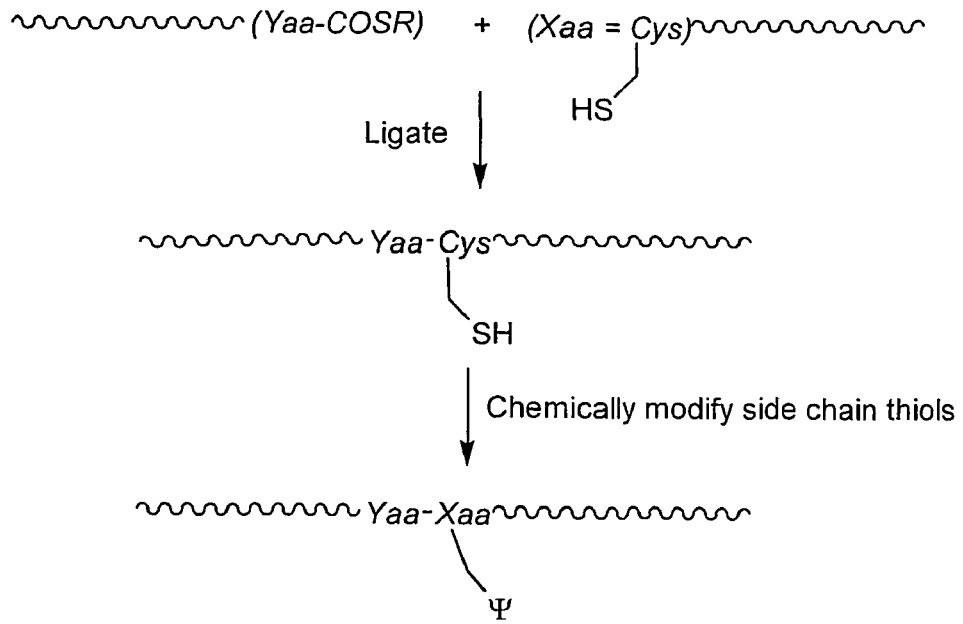
FIGS. 4A–4C illustrate native chemical ligation and chemical modification of the resulting side-chain thiol.
Figure 4B:
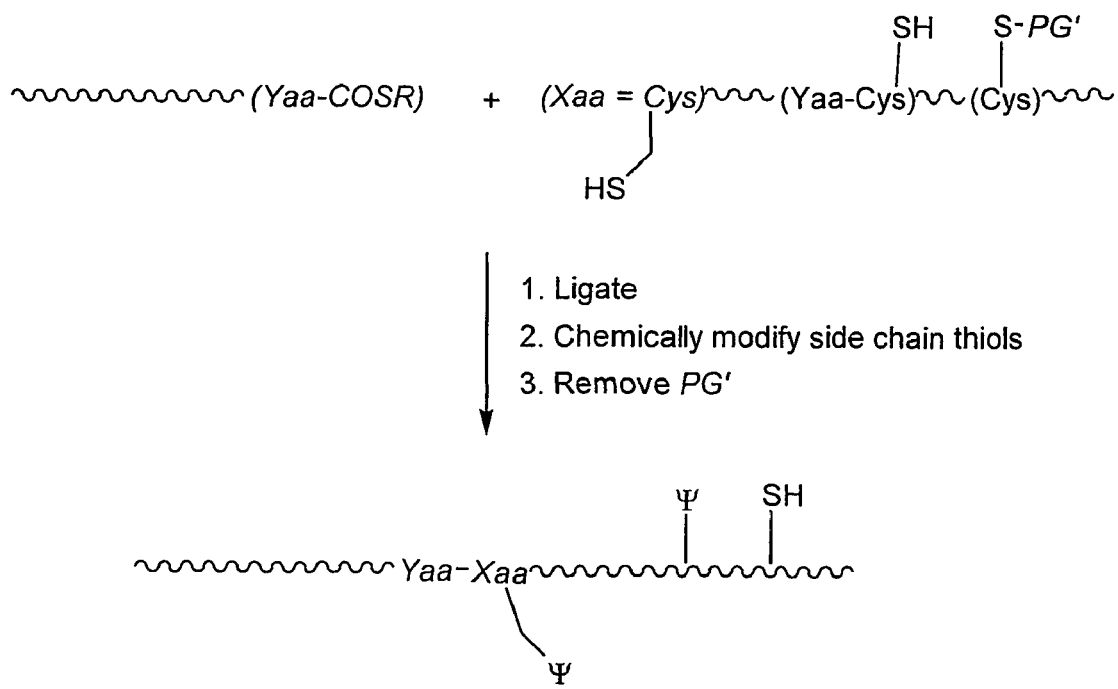
Figure 4C:
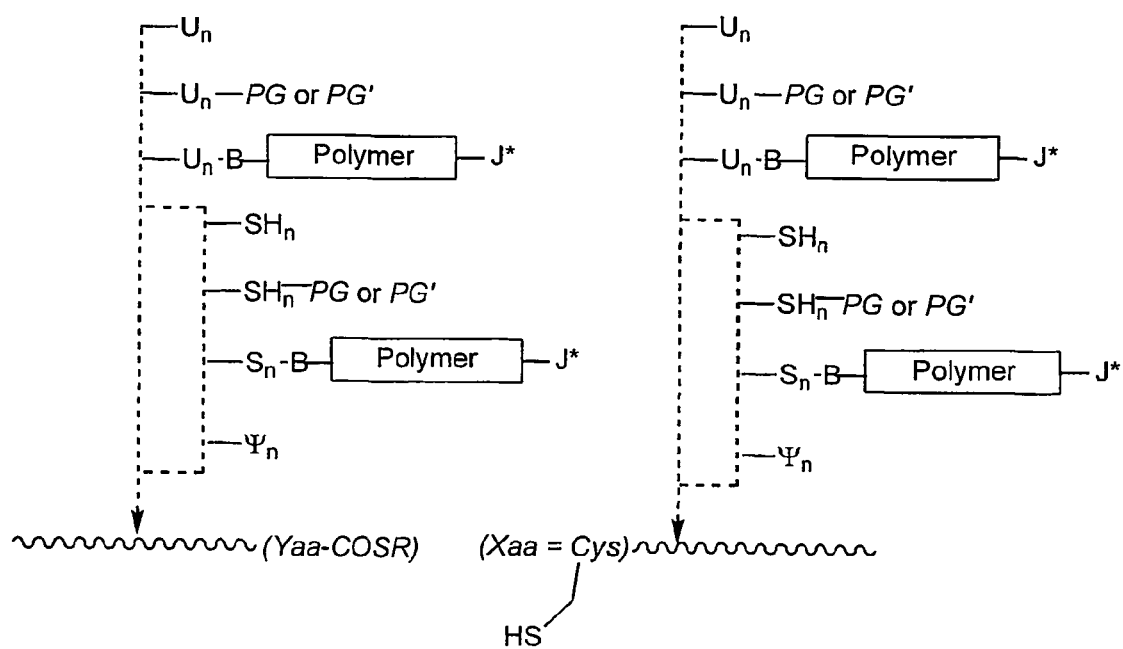

FIGS. 4A–4C illustrate how native chemical ligation and chemical modification of the resulting side-chain thiol may be accomplished in accordance with the principles of the present invention. In particular, FIGS. 4A–4B depict the use of native chemical ligation and chemical modification of the resulting cysteine side-chain thiol at the ligation site(s) to form a "pseudo amino acid" (depicted by ψXaa) via thio- alkylation and generation of chemically modified side chain (depicted by ψ) comprising a thioether bond. In an alternative embodiment not depicted, the side chain thiol can be converted to an alanine in a desulfurization reaction (Liang et al, *J. Amer. Chem. Soc.* (2001) 123(4):526–533). An significant aspect for both reactions is that any other side-chain thiols that one does not wish to convert or modify be protected with a suitable protecting group (PG) or for multi-segment ligations and orthogonal protecting group (PG') where the segment bearing the carboxy terminal Yaa group comprises a protected amino terminal Xaa group, i.e., PG-Xaa-peptide, which is provided by way of example in FIG. 4B. FIG. 4C illustrates the diversity of groups that may be present or absent in the peptide segments employed in ligation and polymer modification according to FIGS. 4A–4B, as well as FIGS. 1A–1E, FIGS. 2A–2C, and FIGS. 3A–3B.

In designing the polymer-modified synthetic bioactive proteins of the invention, an initial polypeptide backbone amino acid sequence for a target protein is obtained, typically from any number of various sources including databases such as gene and/or protein databases, or obtained de novo for instance through proteomic identification of a novel protein target of interest. As noted above, examples of such databases include, but are not limited to, GeneBank (Benson, et al., *Nucleic Acids Res* (1998) 26(1):1–7; USA National Center for Biotechnology Information, National Library of Medicine, National Institutes of Health, Bethesda, Md., USA), TIGR Database (The Institute for Genomic Research, Rockville, Md., USA), Protein Data Bank (Brookhaven National Laboratory, USA), and the ExPASy and Swiss-Protein database (Swiss Institute of Bioinformatics, Geneve, Switzerland). Publicly available patent databases also may be used for this purpose. The polypeptide backbone employed for the design can represent a portion (e.g., a domain) or all of a target sequence (e.g., a mature form of the polypeptide chain).

With the initial polypeptide backbone sequence, the desired full-length polymer-modified polypeptide structure is designed for a given target synthetic protein or panel of analogs thereof. This involves design of the polypeptide backbone, structure of the water-soluble polymer(s), and the ligation and water-soluble polymer attachment strategy for a given synthetic protein construct of interest. In particular, the polypeptide amino acid sequence on which a design is based is reviewed for the presence of one or more glycosylation sites, one or more immunogenic sites, or one or more protease sensitive site (i.e., regions substantially devoid of helix or beta-sheet secondary structure; typically loop and turn regions). Other sites can be gleaned as well, including aggregation sites and glycosaminoglycan (GAG) binding sites, the latter of which is common to all chemokines. Moreover, the three dimensional structures of many proteins are known and can be used to aid design.

The glycosylation sites include N-linked and O-linked glycosylation sites, which typically occur at disordered regions found in loops and turns. The immunogenic sites include hydrophilic sites at turns that are on the surface of the protein. The protease sensitive sites of interest include amino acid sequences that are recognized by proteases and on the surface of the protein, typically disordered regions. Aggregation and GAG sites for many proteins and methods for their identification, particularly chemokines are well known (See e.g., "The Cytokine Handbook", 3$^{rd}$ Edition, Ed. A. Thomas, Associated Press, 1998; "Cytokines", Ed. A. Mire-Sluis & R. Thorpe, Academic Press, 1998; and "Cytokine Reference", Vol. 1, Ligands, A compendium of cytokines and other mediators of host defense, Eds. J. J. Oppendheim and M. Feldmann, Acedemic Press, 2001)).

For instance, immunogenicity or protease stability of a given protein target can be reduced or eliminated by site-specific attachment of one or more polymers to the immunogenic epitope or protease recognition sequence to generate a protease resistant or non-immunogenic water-soluble polymer-modified bioactive protein of the invention. Other sites amenable to polymer attachment include the amino and/or carboxy terminus for a given protein target.

Glycosylation sites, including natural as well as sites engineered to contain them are particularly preferred sites for attachment of water-soluble polymers. This is based on a finding of the present invention that synthetic bioactive proteins can be produced that are modified exclusively at one or more of such sites with water-soluble polymers so as to replace and mimic the positive biological effect of one or more of the carbohydrate chains of a naturally occurring glycoprotein at that position.

Such water-soluble polymer attachment sites can be determined using by modeling and/or biological or chemical analysis approaches. Modeling includes bioinformatic approaches, such as the use of homology modeling software algorithms or programs that compare portions up to all of a given nucleic acid or amino acid sequence of a target protein, two-dimensional structure information for a polypeptide of interest, and three-dimensional structure information for a protein of interest, or a combination thereof. Any number of software programs and databases are well known and available for this purpose. (See, e.g., GeneBank (Benson, et al., *Nucleic Acids Res* (1998) 26(1): 1–7; USA National Center for Biotechnology Information, National Library of Medicine, National Institutes of Health, Bethesda, Md., USA), TIGR Database (The Institute for Genomic Research, Rockville, Md., USA), Protein Data Bank (Brookhaven National Laboratory, USA), and the ExPASy and Swiss-Protein database (Swiss Institute of Bioinformatics, Genève, Switzerland). An example of a software program that integrates these methods is "MAX-VECTOR" (Oxford Molecular Group), which contains multiple protein analysis tools for predicting secondary structure (Chou-Fasman and Robson-Garnier methods); hydrophilicity (Hopp-Woods, Kyte-Doolittle, Goldman-Engelman-Steitz (GES), and von-Heijne methods); hydrophobicity (Fauchere-Pliska, Janin, Manavalan, Sweet-Eisenberg methods); antigenicity (Hopp-Woods, Parker, Protrusion Index (Thornton), Welling methods); surface probability (Karplus & Schultz's methods); Flexibility (Janin and Emini methods); amphiphilicity (Eisenberg method); PROSITE based subsequence database and user-defined subsequences; customized subsequence sets; and protease site and proteolytic digestion predictions.

For example, when scanning a protein target for the presence of one or more glycosylation sites, part or all of the native amino acid sequence typically are reviewed for N-linked glycosylation sites (which typically occur at Asn-Xaa-Thr or Asn-Xaa-Ser sequences in loops or turns) and O-linked sites (which typically occur at Ser-Xaa-Xaa-Pro or Thr-Xaa-Xaa-Pro sequences in loops or turns). Various algorithms and modeling programs are suitable for this purpose (See, e.g., ExPASy and Swiss-Protein database (Swiss Institute of Bioinformatics, Geneve, Switzerland; Gupta et al., Glycobiology (1999) 9(10):1009–1022; "DICTYOGLYC", Hansen et al., Biochemical Journal (1995) 308:801–813; "O-GLYCBASE" Hansen et al., Nucleic Acids Research (1997) 25:278–282; NETOGLYX" Hansen et al., Glycoconjugate J. (1998) 15:115–130).

To predict immunogenic sites in proteins, the following approach can be used. A secondary structure prediction is run on the protein sequence. Chou-Fasman parameters are particularly useful for this purpose (Chou et al., Advanced Enzymology (1978) 47:45–148; Maclin et al., "Refining algorithms with knowledge-based neural networks: Improving the Chou-Fasman algorithm for protein folding", Working Paper 91–2, Computer Sciences Dept., Univ. of Wisconsin—Madison, 1991; and Qian et al., J. Molecular Biology (1988) 202:865–884; "PEPEPLOT" program from Genetics Computer Group, Inc.). Disordered regions, and particularly turns are identified. The protein sequence also is scanned for hydrophobicity, typically using a running average of six residues following standard methods (e.g., Fauchere-Pliska or Hopp-Woods hydrophobicity prediction methods or Bull-Breese), and the more hydrophilic regions are identified with particular attention to those that are turns. In conjunction, glycosylation sites, including N-linked sites and O-linked sites are identified. The most hydrophilic site in the protein, if it is in a turn and not predicted to be glycosylated, will have a high probability of immunogenicity and therefor serve as a site for polymer modification. The same basic rules can be applied to successively less hydrophilic regions to identify secondary sites for polymer modification.

Biological and chemical analysis also may be used to identify specific sites for polymer attachment in generating the synthetic bioactive proteins of the invention. For instance, an isolated glycoprotein that is to be used a basis of design and synthesis of a synthetic bioactive protein of the invention can be subjected to enzymatic digestion and analysis e.g. by HPLC peptide mapping and mass spectrometry, to experimentally identify sites of O- and N-linked glycosylation. For identifying immunogenic sites, or protease sensitive sites, more highly disordered 'loop' regions on the surface of the protein molecule that contain such regions may be identified in a number of biological or chemical ways. For instance, an isolated protein that is to be used a basis of design and synthesis of a synthetic bioactive protein of the invention can be subjected to limited proteolytic digestion with a variety of proteases, followed by mass spectrometric analysis of the resulting peptide fragments to map the sites of greatest susceptibility to proteases following standard protocols (See, e.g., Coligan J E, Dunn B M, Ploegh H L, Speicher D W, Wingfield P T, editors. Current Protocols in Protein Structure, vol II. New York: John Wiley & Sons, 1997; Chait, B T, Structure (1994) 2:465–467; Kriwacki et al., J Chromatogr A (1997) 777: 23–30; Hillenkamp et al., Anal Chem (1991) 63:A1193–1201; Fenn et al., Mass Spectr Rev (1990) 9:37–70; and Siuzdak G. Mass Spectrometry for Biotechnology. San Diego: Academic Press, 1996). And there are many proteases commonly used for such purposes (Konigsberg W H, Methods Enzymol (1995) 262:331–346; Carrey, E A, In: Creighton T, editor. Protein Structure, a Practical Approach. New York: IRL Press, (1989) pp: 117–144; and Coligan, J E, Dunn B M, Ploegh H L, Speicher D W, Wingfield P T, editors. Current Protocols in Protein Structure, vol II. New York: John Wiley & Sons, 1997). Surface loop regions of the folded protein's polypeptide chain are usually associated with increased susceptibility to proteolytic digestion. A similar approach using limited 'random' chemical modification followed by digestion and peptide mapping by mass spectrometry can also be used to identify exposed surface regions of a protein of unknown three-dimensional structure.

For identifying immunogenic sites, protease sensitive sites or other sites suitable for polymer modification, alanine scanning also can be performed to identify specific residues in the polypeptide backbone that are amenable as water-soluble polymer attachment sites. This is particularly useful for identifying invariant residues required for biological activity, and when a water-soluble polymer attachment site is positioned at an immunogenic or protease sensitive site of the target molecule. Alanine scanning is particularly useful when used in combination with other protein analysis tools, such as described above. Another approach is to systematically prepare a library of synthetic proteins of interest with the modifying water-soluble polymer moiety being located at a different site in the polypeptide chain of each molecule. After folding the library of polymer-modified polypeptide chains, a functional selection/assay can be performed to separate, for example, folded from non-folded molecules, or receptor-binding from non-binding molecules. Then the location of the sites of polymer modification can be determined for the functional molecules. Such an approach can make use of the principles of the 'protein signature analysis' method to facilitate identification of non-interfering sites of polymer modification (Muir et al., Chemistry & Biology (1996) 3:817–825).

In conjunction with the design, the peptides or polypeptide segments utilized for synthesizing the polypeptide backbone are constructed. This involves selection of suitable ligation sites that are chosen based on the ligation chemistry selected for assembling the various polypeptide backbone segments, the polymer attachment chemistry chosen for a given target protein, and the particular polymer attachment sites. When native chemical ligation is employed, cysteine ligation sites are determined by scanning the target polypeptide backbone amino acid sequence for suitable naturally occurring cysteine residue. When Extended Native Chemical Ligation" is employed, as described herein, ligation sites can be selected by scanning the target polypeptide backbone amino acid sequence for suitable naturally occurring ligation site junctions that permit robust ligations, such as Xaa-Gly sites. Because extended native chemical ligation is not limited to ligation at cysteine residues, any number of residues may serve as the ligation site junction. In some instances, a combination of native and extended native chemical ligation may be part of the design.

In a preferred embodiment, native chemical ligation is used to generate part or all of the full-length polypeptide chain. Cysteines present in the naturally occurring protein on which the synthetic bioactive protein in based can be used as the chemical ligation sites. However, where a preferred ligation junction is devoid of a suitable cysteine, the non-cysteine amino acid at that position can be replaced with a cysteine so as to permit native chemical ligation at that site. If desired, the newly introduced cysteine can be converted to a pseudo amino acid residue corresponding to the original amino acid at that position, as described herein. Alternatively, when the cysteine is introduced at a site for polymer modification, the side chain thiol can be exploited for the attachment of a thiol-reactive water-soluble polymer construct, provided that all other cysteines in the target polypeptide that one does not wish to modify are protected.

In another preferred embodiment, extended native chemical ligation, as described herein, can be utilized to generate part or all of the full-length polypeptide. For this method, N-terminal Nα-substituted 2 or 3 carbon chain alkyl or aryl thiol amino acids may be employed. Such residues (where present at the N-terminus of a peptide or polypeptide segment used for ligation) can be advantageously used to ligate that polypeptide to a polypeptide having a C-terminal α-carboxy thioester moiety, in accordance with the methods of extended native chemical ligation described herein.

Typically, the synthesis of peptides employs stepwise standard Boc and/or Fmoc solid phase peptide synthesis using standard automated peptide synthesizers, or manually following standard protocols, or ordered and purchased from commercial vendors. ("Synthetic Peptides, A User's Guide," G. A. Grant, Ed., W. H. Freeman & Company, New York, N.Y.,1992; "Priciples of Peptide Synthesis, 2nd ed.," M. Bodanszky, Ed., Springer-Verlag, 1993; "The Practice of Peptide Synthesis, 2nd ed.," M. Bodanszlky and A. Bodanszky, Eds., Springer-Verlag, 1994; and "Protecting Groups," P. J. Kocienski, Ed., Georg Thieme Verlag, Stuttgart, Germany, 1994; "Fmoc Solid Phase Peptide Synthesis, A Practical Approach, Eds. W. C. Chan and P. D. White, Oxford University Press, 2000). For peptides utilized for thioester-mediated ligation, such as for native chemical ligation, they can be made following standard protocols as well. (see, e.g., Dawson et al., Science (1994) 266:776–779; Canne et al. Tetrahedron Lett. (1995) 36:1217–1220; Kent, et al., WO 96/34878; Kent, et al., WO 98/28434; Ingenito et al., JACS (1999) 121(49):11369–11374; and Hackeng et al., Proc. Natl. Acad. Sci. U.S.A. (1999) 96:10068–10073); Amiato et al., supra.).

For ligation and site-specific attachment of water-soluble polymers, chemically orthogonal strategies are employed in the synthesis of the peptides (See, e.g., FIGS. 1–4, and Examples) so as to avoid side reactions that result in unwanted attachment. For instance, depending on ligation design and the polymer attachment approach, a variety of orthogonal synthesis strategies can be exploited. In particular, the nature of the water-soluble polymer to be attached, and in particular the functional group for joining it to the polypeptide are considered, for instance as discussed below for the preferred glyco-mimetic polymers of the invention.

In particular, the water-soluble polymer is made to comprise a unique functional group U that is selectively reactive with a unique functional group on a target peptide employed for ligation, full-length material or even the folded polypeptide. As chemical synthesis is employed, the peptide is made to contain a mutually reactive chemoselective group at a precise, user-defined site. This aspect of the invention embodies the principles of peptide synthesis (protecting group strategies) and chemical ligation (partial or no protecting group strategies). For the protecting group strategy, all potentially reactive functional groups except for the desired functional group on the water-soluble polymer and its mutually reactive functional group present on the target molecule are blocked with suitable protecting groups. Many protecting groups are known and suitable for this purpose (See, e.g., "Protecting Groups in Organic Synthesis", 3rd Edition, T. W. Greene and P. G. M. Wuts, Eds., John Wiley & Sons, Inc., 1999; NovaBiochem Catalog 2000; "Synthetic Peptides, A User's Guide," G. A. Grant, Ed., W. H. Freeman & Company, New York, N.Y., 1992; "Advanced Chemtech Handbook of Combinatorial & Solid Phase Organic Chemistry," W. D. Bennet, J. W. Christensen, L. K. Hamaker, M. L. Peterson, M. R.Rhodes, and H. H. Saneii, Eds., Advanced Chemtech, 1998; "Principles of Peptide Synthesis, 2nd ed.," M. Bodanszky, Ed., Springer-Verlag, 1993; "The Practice of Peptide Synthesis, 2nd ed.," M. Bodanszky and A. Bodanszky, Eds., Springer-Verlag, 1994; and "Protecting Groups," P. J. Kocienski, Ed., Georg Thieme Verlag, Stuttgart, Germany, 1994).

Thus, the water-soluble polymer can represent be made to posses a wide range of functional groups, such as those described above. For the partial or no protecting group strategy, the functional group on the polymer and its mutually reactive functional group present on the target peptide or polypeptide employ a chemoselective reaction pair in which other functional groups may be present in the reaction system but are unreactive. This includes groups amenable to amine capture strategies (e.g., ligation by hemiaminal formation, by imine formation, and by Michael addition), thiol capture strategies (e.g., ligation by mercaptide formation, by disulfide exchange), native chemical ligation strategies (e.g., ligation by thioester exchange involving cysteine or thiol contain side-chain amino acid derivative), and orthogonal ligation coupling strategies (e.g., ligation by thiazolidine formation, by thioester exchange, by thioester formation, by disulfide exchange, and by amide formation)(See, e.g., Coltart, D M., *Tetrahedron* (2000) 56:3449–3491).

A preferred chemoselective U group for this embodiment will comprise a residue of a unique functional group employed in an aqueous compatible ligation chemistry such as native chemical ligation (Dawson, et al., *Science* (1994) 266:776–779; Kent, et al., WO 96/34878), extended general chemical ligation (Kent, et al., WO 98/28434), oxime-forming chemical ligation (Rose, et al., *J. Amer. Chem. Soc.* (1994) 116:30–33), thioester forming ligation (Schnölzer, et al., *Science* (1992) 256:221–225), thioether forming ligation (Englebretsen, et al., *Tet. Letts.* (1995) 36(48):8871–8874), hydrazone forming ligation (Gaertner, et al., *Bioconj. Chem.* (1994) 5(4):333–338), and thiazolidine forming ligation and oxazolidine forming ligation (Zhang, et al., *Proc. Natl. Acad. Sci.* (1998) 95(16):9184–9189; Tam, et al., WO 95/00846) or by other methods (Yan, L. Z. and Dawson, P. E., "Synthesis of Peptides and Proteins without Cysteine Residues by Native Chemical Ligation Combined with Desulfurization," *J. Am. Chem. Soc.* 2001, 123, 526–533, herein incorporated by reference; Gieselnan et al., Org. Lett. 2001 3(9):1331–1334; Saxon, E. et al., "Traceless" Staudinger Ligation for the Chemoselective Synthesis of Amide Bonds. Org. Lett. 2000, 2, 2141–2143).

Given the various attachment chemistries described above, the bond formed between the water-soluble polymer and a target peptide or polypeptide can comprise a residue of a bond selected from carbonate, ester, urethane, orthoester, amide, amine, oxime, imide, urea, thiourea, thioether, thiourethane, thioester, ether, thaizolidine, hydrazone, oxazolidine and the like. The most preferred bonds are oxime and amide bonds.

Figure 8:
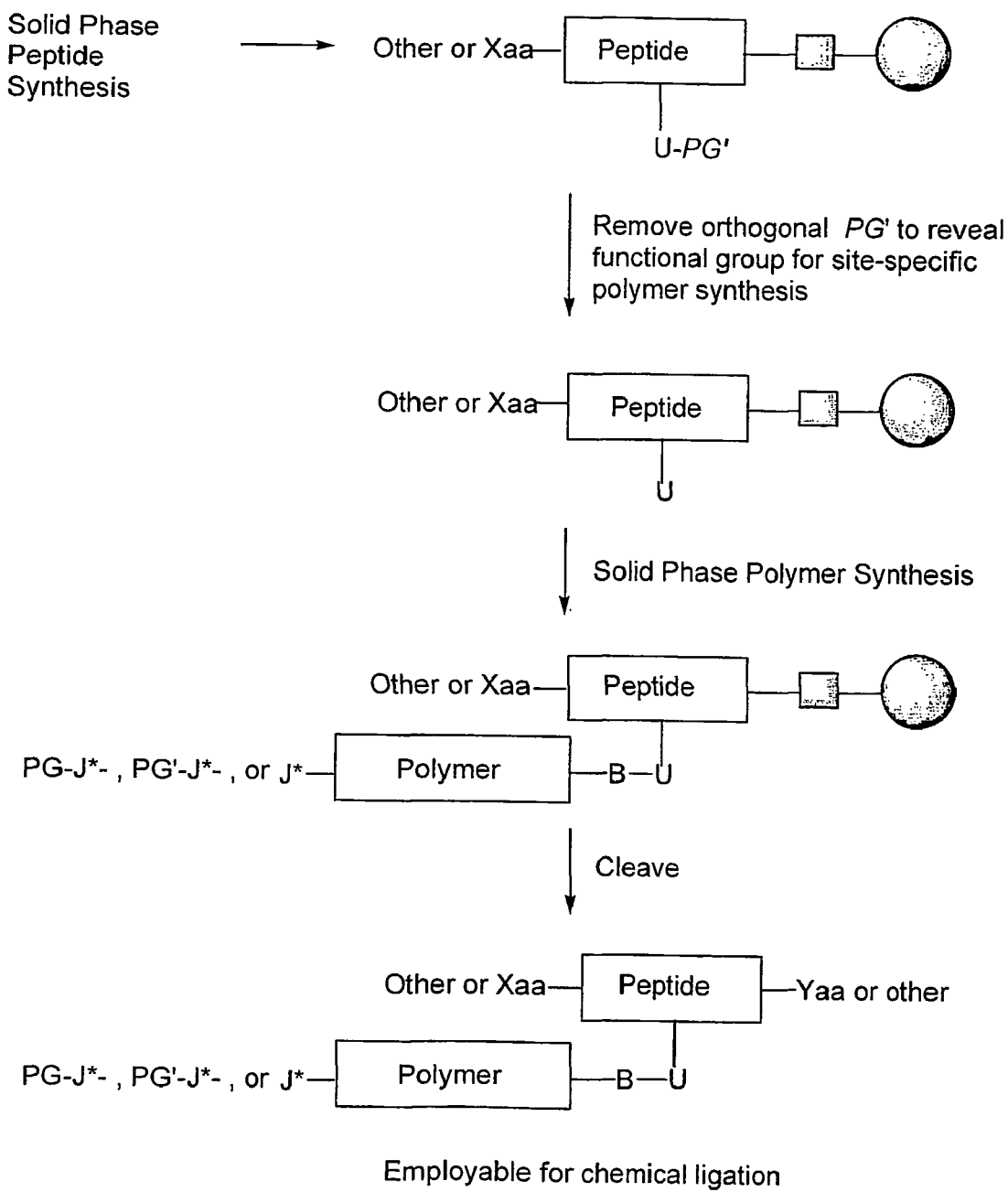
FIG. 8 depicts an alternative route for precision attachment of a water-soluble polymer to a peptide segment employable for ligation and production of bioactive synthetic proteins of the invention.
Figure 9:
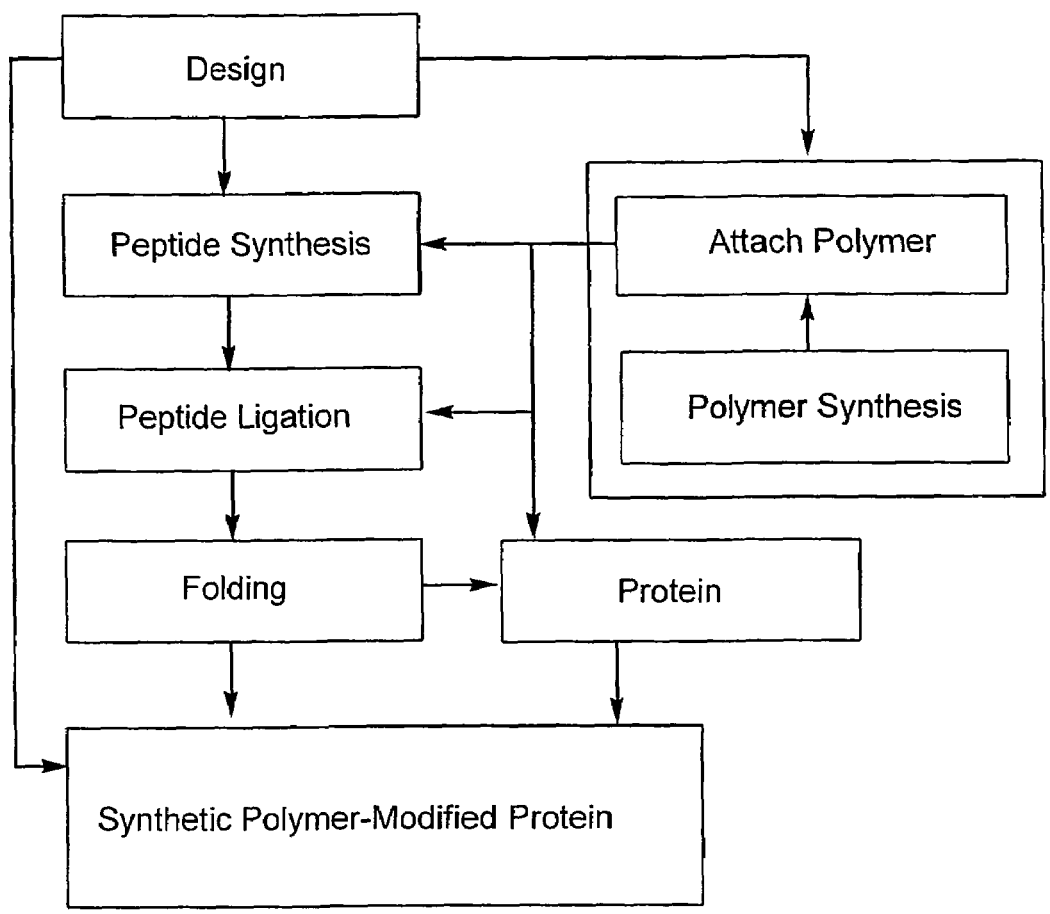
FIG. 9 illustrates the overall process of preparing the synthetic bioactive proteins of the present invention.

The peptide ligation step, for example as shown in FIGS. 1–4, may employ solid or solution phase ligation strategies. FIG. 8 depicts another route for precision attachment of a water-soluble polymer to a peptide segment employable for ligation and production of polymer-modified synthetic bioactive proteins of the invention. The first step employs solid phase peptide synthesis ("SPPS") (e.g., Fmoc or Boc SPPS), in which an amino acid side chain targeted for polymer attachment is protected with an orthogonal protecting group (e.g., if using Fmoc SPPS, a Boc group can be used to protect the site of polymer attachment, or if using Boc SPPS, an Fmoc group can be employed as the orthogonal protecting group). Following peptide synthesis, the orthogonal protecting group is selectively removed while the rest of the peptide remains protected. This affords a single attachment site for the next step—solid phase polymer synthesis. Once the orthogonal protecting group is removed, the polymer chain is attached as a precursor. More preferably, the polymer chain is built through successive rounds of polymer synthesis using a process depicted in FIGS. 6A–6D. Although a single polymer attachment site is shown, more than one can be provided.

As noted above, chemical ligation involves the formation of a selective covalent linkage between a first chemical component and a second chemical component. Unique, mutually reactive, functional groups present on the first and second components can be used to render the ligation reaction chemoselective. For example, the chemical ligation of peptides and polypeptides involves the chemoselective reaction of peptide or polypeptide segments bearing compatible unique, mutually reactive, C-terminal and N-terminal amino acid residues. Several different chemistries have been utilized for this purpose, examples of which include native chemical ligation (Dawson, et al., *Science* (1994) 266:776–779; Kent, et al., WO 96/34878; Kent, et al., WO 98/28434), oxime forming chemical ligation (Rose, et al., *J. Amer. Chem. Soc.* (1994) 116:30–34), thioester forming ligation (Schnölzer, et al., Science (1992) 256:221–225), thioether forming ligation (Englebretsen, et al., *Tet. Letts.* (1995) 36(48):8871–8874), hydrazone forming ligation (Gaertner, et al., *Bioconj. Chem.* (1994) 5(4):333–338), and thiazolidine forming ligation and oxazolidine forming ligation (Zhang, et al., *Proc. Natl. Acad. Sci.* (1998) 95(16):9184–9189; Tam, et al., WO 95/00846; U.S. Pat. No. 5,589, 356); Gieselman et al., Selenocysteine-mediated native chemical ligation (*Org. Lett.* (2001) 3(9):1331–1334); and Staudinger amide forming chemical ligation (Saxon et al., *Org. Lett.* (2000) 2:2141–2143). Thus, as will be appreciated, any chemoselective reaction chemistry that can be applied to the ligation of unprotected peptide segments that is amenable for such purpose.

Reaction conditions for a given ligation chemistry are selected to maintain the desired interaction of the peptide or polypeptide segments employed for ligation. For example, pH and temperature, water-solubility of the ligation label, ratio of the first segment to the second segment, water content and composition of the reaction mixture can be varied to optimize ligation. Addition or exclusion of reagents that solubilize the ligation segments to different extents may further be used to control the specificity and rate of the desired ligation reaction, i.e., control exposure and presentation of reactive groups by manipulating solubility of the peptide or polypeptide segments. Reaction conditions are readily determined by assaying for the desired chemoselective reaction product compared to one or more internal and/or external controls.

Where the ligation involves the joining of a polypeptide that possesses an N-terminal cysteine residue, the procedure of native chemical ligation is preferably employed (Dawson, et al., *Science* (1994) 266:776–779; Kent, et al., WO 96/34878; Kent, et al., WO 98/28434)). This methodology has proven a robust methodology for generating a native amide bond at the ligation site. Native chemical ligation involves a chemoselective reaction between a first peptide or polypeptide segment having a C-terminal α-carboxythioester moiety and a second peptide or polypeptide having an N-terminal cysteine residue. A thiol exchange reaction yields an initial thioester-linked intermediate, which spontaneously rearranges to give a native amide bond at the ligation site while regenerating the cysteine side chain thiol. In many instances, the sequence of the natural protein will comprise suitably placed cysteine residues such that polypeptide fragments having an N-terminal cysteine residue may be synthesized and used in a native chemical ligation reaction. In other instances, the peptide synthesis can be conducted so as to introduce cysteine residues into a polypeptide for this purpose. Thus in its standard form, native chemical ligation involves thioester-mediated chemoselective reaction at a cysteine residue in a target polypeptide sequence; a peptide bond is formed at the ligation site and the side chain of the Cys is regenerated in native form.

Alternatively, the proteins of the present invention may be synthesized through the use of "Pseudo-Native Chemical Ligation," or "Extended Native Chemical Ligation. Pseudo-Native Chemical Ligation involves the use of non-naturally occurring pseudo-amino acid residues at preselected positions in the peptides employed in the protein synthesis (e.g., See FIG. 4). The structures of such pseudo-amino acids mimic both the structures of cysteine and the structures of the amino acids that are naturally found at such preselected positions in the protein being synthesized. Pseudo-native chemical ligation is thus directed to the thioalkylation of cysteine side chains generated at ligation sites from native chemical ligation. A preferred aspect is thioallcylation of cysteine ligation sites wherein at least one peptide contains a native cysteine having its thiol side chain protected with a suitable protecting group.

In a preferred embodiment of the invention, the thiol moiety of a cysteine group is modified into a desired side chain, for example, into the side chain of a ribosomally specified amino acid, an analog of such an amino acid, or into a non-ribosomally specified amino acid. As used herein, a ribosomally specified amino acid is an amino acid that is recognized by ribosomes in the process of protein translation and can be incorporated into a ribosomally produced protein. Considerable published literature exists describing chemical modifications of the cysteine side chain thiol moiety (see, e.g., "Current Protocols in Protein Science," Edited by: John E. Coligan et al., John Wiley & Sons, NY (2000)). Kaiser, E. T. has described the conversion of cysteine residue side chains to mimic the chemical properties of a naturally occurring amino acid side chain (see, e.g., Kaiser, E. T. et al., "Chemical Mutation Of Enzyme Active Sites," Science. 1984 November 2;226(4674):505–11). Additionally, the use of a cysteine side chain to introduce a label into a peptide or protein has been described. Cysteine side chain modifications are reviewed in Chemistry of Protein Conjugation and Crosslinking, S. S. Wong, (1991, CRC Press); Chemical Modification of Proteins, Gary E. Means et al., (1971, Holden-Day), Chemical Modification of Proteins: Selected methods and analytical procedures, Glazer, A. N. et al. (1975, Elsevier); Chemical Reagents for Protein Modification, R L Lundblad (1991, CRC Press). Tam et al. (Biopolymers (1998) 46:319–327) have disclosed the use of homocysteine ($-CH_2-CH_2-SH$) for non-cys native chemical ligation, followed by thioalkylation using methyl p-nitrobenzenesulfonate (methylating reagent) to convert the homocysteine side chain to a native methionine side chain ($-CH_2-CH_2-S-CH_3$). The present invention also can be used for converting homocysteines to pseudo amino acids as well, i.e., to amino acids other than methionine. However, as with the conversion of cysteines described herein, in accordance with the present invention it is necessary to use protecting groups to avoid destruction of native cysteines involved in disulfide pairing for peptides that contain at least one native cysteine that one does not wish to convert. Suitable protecting groups are described below.

While the method of pseudo-native chemical ligation does not facilitate the mimicking of the side chains of certain ribosomally-specified amino acids (e.g., the side chains of glycine, alanine, valine, and proline) (alanine's side chain can, however, be formed through a desulfurization reaction (Liang, Z. Y. and Dawson, P. E., "Synthesis of Peptides and Proteins without Cysteine Residues by Native Chemical Ligation Combined with Desulfurization," J. Am. Chem. Soc. 2001, 123, 526–533, herein incorporated by reference), it may be used to form side chains that mimic many ribosomally-specified or non-encoded amino acids. Amino acids produced in accordance with the pseudo-native chemical ligation method of the present invention will contain a thioether linkage, and will have no beta-branching (in that they will all include a methyl group at the beta position, i.e., aa-$CH_2-S-$. Thus, the pseudo-amino acid versions of the beta-branched amino acids, isoleucine and threonine can be made to have the pendant side chain structure, without having the beta geometry and its attendant constraints.

Significantly, the methods of the present invention may be used to form amino acid side chains that are the same length as that of ribosomally specified amino acids, or are longer or shorter than such length. Such alteration in side chain length can be used to stabilize (or destabilize) the three-dimensional conformation to increase protein stability (or to enhance the ability of the protein to alter its conformation and thereby accept a different range of substrates, inhibitors, receptors, ligands, etc. relative to those accepted by the naturally occurring protein. For example, Cys-$CH_2-SH+$Br-$CH_2-COOH$ yields Cys-$CH_2-S-CH_2-COOH$ (such "pseudo-glutamic acid" has one additional side chain atom, namely the $-S-$ group; alternatively, if used in the place of aspartic acid, it will possess two additional side chain atoms, namely a $-CH_2-S-$ group). Other side chains have the same number of atoms in the side chain, but differ by inclusion of the thioether linkage ($-S-$). For example, Cys-$CH_2-SH+$Br-$CH_2-CH_2-NH$-PG, followed by removal of PG yields Cys-$CH_2-S-CH_2-CH_2-NH_2$. The resulting structure has no additional atoms in the side chain, but one $-CH_2-$ group is replaced with $-S-$. Methionine is another example here, Cys-$CH_2-SH+I-CH_2-CH_3$ yields Cys-$CH_2-S-CH_2-CH_3$ (versus native met structure of Met-$CH_2-CH_2-S-CH_3$); thus the thioether is relocated. Arginine also: Cys-$CH_2-SH+$Br-$CH_2-NH-CH((-NH_2)(=NH_2^+))$ yields Cys-$CH_2-S-CH_2-NH-CH((-NH_2)(=NH_2^+))$. Preferably, protection of reactive amino groups, particularly for the constructing pseudo lysine can be employed to avoid unwanted side reactions. Once the thioalkylation reaction is performed, the protecting group can be removed.

In general, where the desire is to mimic a naturally occurring protein as closely as possible, it is most preferred to employ a pseudo amino acid molecule having a side chain length that is the same length as that of the ribosomally-specified amino acid normally present at such position in the protein; it is less preferred to employ a pseudo amino acid molecule having a side chain length that is one atom longer than that of the ribosomally-specified amino acid, and still less preferred to employ a pseudo amino acid molecule having a side chain length that is two atoms longer than that of the ribosomally-specified amino acid. Moreover, its is preferred to select a cysteine ligation site that is in a location where genetic changes are not likely to disrupt function or where amino acids at that site in related proteins are conserved. Such sites can be identified by alanine scanning, homology modeling, and other methods.

In pseudo-native chemical ligation, a peptide containing an amino terminal cysteine residue is ligated to a peptide having a carboxy terminal thioester, as in native chemical ligation. The thiol side chain of the cysteine is then reacted with a compound of the formula $R_{aa}-X$, where X is a good leaving group, and $R_{aa}$ is a group whose structure mimics the terminal portion of the side chain of an ribosomally-specified or synthetic amino acid.

Significantly, the reactions of pseudo-native chemical ligation work with either the natural L-configuration of cysteine side chain, or the D-configuration. Use of the D-configuration can impart protease resistance at that ligation site, and thus may be desired when increased stability to proteolysis is desired. However, in using the D-cysteine, the backbone structure at that site will be altered. Such alteration, in addition to protease resistance, may be desired to alter bioactivity. However, to minimize impact on bioactivity, it is preferred to locate the D-cysteine at a site of high flexibility, such as a disorded region, such as at a disorded loop that will be located on the surface of the resulting folded molecule, on at a disorded terminus of the molecule. Desirably, the reactions of pseudo-native chemical ligation may be used to place large, charged side chains (e.g., the side chains of Lys, Arg, Asp or Glu) on the surface of the synthesized molecule.

Examples of suitable good leaving groups, X, include halogens, especially Iodine and Bromine. Examples of $R_{aa}$ groups include $PO_4$, COOH, COO, $CONH_2$, guanidinium, amine, alkyl, substituted alkyl, aryl, substituted aryl, imidazole, alkylated imidazole, indole, or alkylated indole groups.

The selection of which $R_{aa}$ to employ will depend upon the amino acid side chain desired to be present at a particular position. Thus, for example, a desired polypeptide or protein having the amino acid sequence:

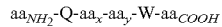
$aa_{NH_2}$-Q-$aa_x$-$aa_y$-W-$aa_{COOH}$ where Q and W each denote the optional presence or absence of additional amino acid residues, and $aa_x$ and $aa_y$ denote internal adjacent residues (having side chains x and y, respectively), and $aa_{NH_2}$ and respectively denote the amino (N—) terminal residue and the carboxy (C—) terminal residue of the polypeptide or protein an be synthesized by preparing two peptide fragments:

$aa_{NH_2}$-Q-$aa_x$-COSR and Cys-W-$aa_{COOH}$ where Cys denote the replacement of $aa_y$ with cysteine, and R is any group compatible with the thioester group, including, but not limited to, aryl, benzyl, and alkyl groups. Examples of R include 3-carboxy-4-nitrophenyl thioesters, benzyl esters, and mercaptoproprionic acid leucine esters (See, e.g., Dawson et al., Science (1994) 266:776–779; Canne et al. Tetrahedron Lett. (1995) 36:1217–1220; Kent, et al., WO 96/34878; Kent, et al., WO 98/28434; Ingenito et al., JACS (1999) 121(49):11369–11374; and Hackeng et al., Proc. Natl. Acad. Sci. U.S.A. (1999) 96:10068–10073). Other examples include dithiothreitol, or alkyl or aryl thioesters, which can be produced by intein-mediated biological techniques, which also are well known (See, e.g., Chong et al., Gene (1997) 192:277–281; Chong et al., Nucl. Acids Res. (1998) 26:5109–5115; Evans et al., Protein Science (1998) 7:2256–2264; and Cotton et al., Chemistry & Biology (1999) 6(9):247–256); and then ligating the fragments together to form:

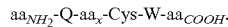
$aa_{NH_2}$-Q-$aa_x$-Cys-W-$aa_{COOH}$.

The ligated fragment is then reacted with $R_y$—X, where $R_y$ is a side group that mimics the structure of the y side chain). The reaction is conducted under conditions sufficient to convert the thiol group of the cysteine into a "pseudo-y" side chain. For example, if $R_{aa}$ is selected to be $CH_2$—COOH or $(CH_2)_2$—COOH, then the reaction will lead to the formation an amino acid residue that mimics the structure and function of aspartic acid ("pseudo-Asp") or glutamic acid ("pseudo-Glu"). As will be appreciated, in light of the above description, more complicated synthesis can be conducted employing more than two peptide fragments.

A significant feature of this approach is that cysteine residues that one does not wish to modify in the reacting segments be side chain protected, e.g. as Cys(Acm), to prevent chemical modification of Cys residues other than the one(s) at the ligation site(s), or that any other Cys residues in the reacting segments be intended for the simultaneous formation of identical 'pseudo amino acids' by the chemical modification reaction after ligation.

As used herein, the symbol φ denotes a benzyl group; IM denotes an imidazole group, and IN denotes an indole group; PG denotes a protecting group. Below is a summary of $R_{aa}$ side groups that may be used to synthesize peptides containing pseudo-amino acid residues in accordance with the present invention (where X is a halogen (I, Br, Cl, F, with I and Br preferred for most, and F preferred for φ attachment):

Basic Amino Acids:
Lys (no extra atoms)
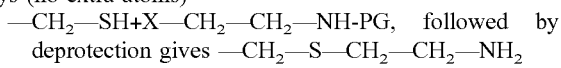
—$CH_2$—SH+X—$CH_2$—$CH_2$—NH-PG, followed by deprotection gives —$CH_2$—S—$CH_2$—$CH_2$—$NH_2$
Arg (no extra atoms)
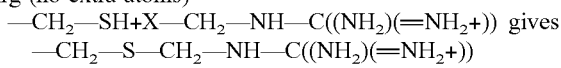
—$CH_2$—SH+X—$CH_2$—NH—C(($NH_2$)(=$NH_2$+)) gives —$CH_2$—S—$CH_2$—NH—C(($NH_2$)(=$NH_2$+))
His (2 extra atoms)
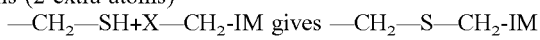
—$CH_2$—SH+X—$CH_2$-IM gives —$CH_2$—S—$CH_2$-IM Acidic Amino Acids:
Asp (2 extra atoms)
—$CH_2$—SH+X—$CH_2$—COOH gives —$CH_2$—S—$CH_2$—COOH
Glu (1 extra atoms)
—$CH_2$—SH+X—$CH_2$—COOH gives —$CH_2$—S—$CH_2$—COOH Uncharged Polar Amino Acids:
Tyr (no or 1 extra atom)
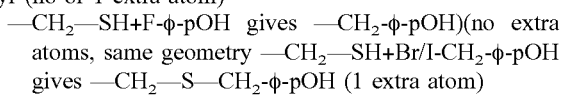
—$CH_2$—SH+F-φ-pOH gives —$CH_2$-φ-pOH)(no extra atoms, same geometry —$CH_2$—SH+Br/I-$CH_2$-φ-pOH gives —$CH_2$—S—$CH_2$-φ-pOH (1 extra atom)
Gln (1 extra atom)
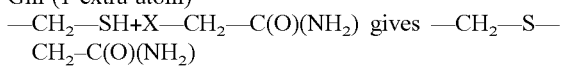
—$CH_2$—SH+X—$CH_2$—C(O)($NH_2$) gives —$CH_2$—S—$CH_2$—C(O)($NH_2$)
Asn (2 extra atoms)
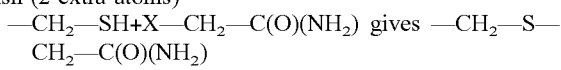
—$CH_2$—SH+X—$CH_2$—C(O)($NH_2$) gives —$CH_2$—S—$CH_2$—C(O)($NH_2$)
Ser (2 or 3 extra atoms)
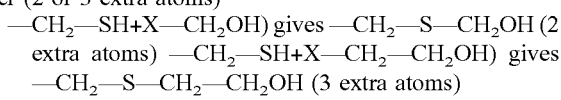
—$CH_2$—SH+X—$CH_2OH$) gives —$CH_2$—S—$CH_2OH$ (2 extra atoms) —$CH_2$—SH+X—$CH_2$—$CH_2OH$) gives —$CH_2$—S—$CH_2$—$CH_2OH$ (3 extra atoms)
Thr (2 or 3 extra atoms, missing beta branching)
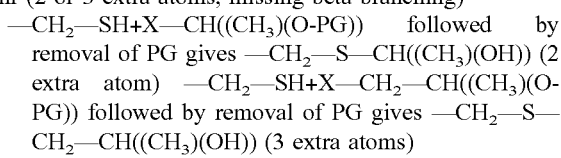
—$CH_2$—SH+X—CH(($CH_3$)(O-PG)) followed by removal of PG gives —$CH_2$—S—CH(($CH_3$)(OH)) (2 extra atom) —$CH_2$—SH+X—$CH_2$—CH(($CH_3$)(O-PG)) followed by removal of PG gives —$CH_2$—S—$CH_2$—CH(($CH_3$)(OH)) (3 extra atoms)

Non-Polar Amino Acids:
Leu (1 or 2 extra atoms)
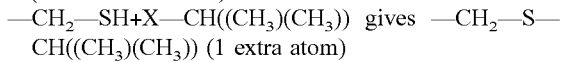
—$CH_2$—SH+X—CH(($CH_3$)($CH_3$)) gives —$CH_2$—S—CH(($CH_3$)($CH_3$)) (1 extra atom)
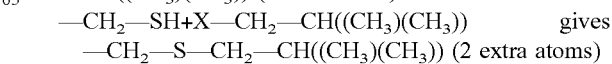
—$CH_2$—SH+X—$CH_2$—CH(($CH_3$)($CH_3$)) gives —$CH_2$—S—$CH_2$—CH(($CH_3$)($CH_3$)) (2 extra atoms)

Ile (2 or 3 extra atoms, missing beta branching)

—$CH_2$—SH+X—$CH(CH_3)$—$CH_2$—$CH_3$ gives —$CH_2$—S—$CH(CH_3)$—$CH_2$—$CH_3$ (2 extra atoms)

—$CH_2$—SH+X—$CH_2$—$CH(CH_3)$—$CH_2$—$CH_3$ gives —$CH_2$—S—$CH_2$—$CH(CH_3)$—$CH_2$—$CH_3$ (3 extra atoms)

Phe (1 or 2 extra atoms)

—$CH_2$—SH+F-φ gives —$CH_2$—S-φ (1 extra atom)

—$CH_2$—SH+Br/I—$CH_2$-φ gives —$CH_2$—S—$CH_2$-φ (2 extra atoms)

Met (no extra atoms)

—$CH_2$—SH+I—$CH_2$—$CH_3$ gives —$CH_2$—S—$CH_2$—$CH_3$

Trp (1 extra atom)

—$CH_2$—SH+F-IN gives —$CH_2$—S-IN

However, where it is either inconvenient or undesirable to modify a protein sequence so as to introduce a cysteine or homocysteine residue at a given N-terminus of a polypeptide utilized for ligation, or utilize a pseudo amino acid at the ligation site, the method of native chemical ligation may be extended using polypeptides whose N-terminus has been modified to contain an N-substituted, and preferably, Nα-substituted, 2 or 3 carbon chain amino alkyl or aryl thiol, and thereby permit the principles of native chemical ligation to be employed with polypeptides lacking cysteine residues (see, U.S. patent application Ser. No. 60/231,339, herein incorporated by reference).

The method of "Extended Native Chemical Ligation" involves ligating a first component comprising a carboxyl thioester, and more preferably, an α-carboxyl thioester with a second component comprising an acid stable N-substituted, and preferably, Nα-substituted, 2 or 3 carbon chain amino alkyl or aryl thiol. Chemoselective reaction between the carboxythioester of the first component and the thiol of the N-substituted 2 or 3 carbon chain alkyl or aryl thiol of the second component proceeds through a thioester-linked intermediate, and resolves into an initial ligation product. More specifically, the thiol exchange occurring between the COSR thioester component and the amino alkyl thiol component generates a thioester-linked intermediate ligation product that after spontaneous rearrangement generates an amide-linked first ligation product through a 5-membered or 6-membered ring intermediate depending upon whether the amino alkyl thiol component has formula I or II, respectively:

J1-C(O)—N(C1(R1)—C2-SH)-J2    I

J1-C(O)—N(C1(R1)—C2(R2)—C3(R3)—SH)-J2    II where J1 is a peptide or polypeptide having one or more optionally protected amino acid side chains, or a moiety of such peptide or polypeptide, a polymer, a dye, a suitably functionalized surface, a linker or detectable marker, or any other chemical moiety compatible with chemical peptide synthesis or extended native chemical ligation; R1, R2 and R3 are independently H or an electron donating group conjugated to C1; with the proviso that at least one of R1, R2 and R3 comprises an electron donating group conjugated to C1; and J2 is a peptide or polypeptide having one or more optionally protected amino acid side chains, or a moiety of such peptide or polypeptide, a polymer, a dye, a suitably functionalized surface, a linker or detectable marker; or any other chemical moiety compatible with chemical peptide synthesis or extended native chemical ligation.

The N-substituted 2 or 3 carbon chain alkyl or aryl thiol [HS—C2—C1(R1)—] or [HS—(C3(R3)—C2(R2)—C1(R1)—] at the ligation site is amenable to being removed, under peptide-compatible conditions, without damage to the product, to generate a final ligation product of formula III, having a native amide bond at the ligation site:

J1-C(O)—HN-J2    III where J1, J2, R1, R2, and R3 are as defined above.

The R1, R2 and R3 groups are selected to facilitate cleavage of the N—C1 bond under peptide compatible cleavage conditions. For example, electron donating groups, particularly if conjugated to C1, can be used to form a resonance stabilized cation at C1 that facilitates cleavage. The chemical ligation reaction preferably includes as an excipient a thiol catalyst, and is carried out around neutral pH conditions in aqueous or mixed organic-aqueous conditions. Chemical ligation of the first and second components may proceed through a five or six member ring that undergoes spontaneous rearrangement to yield an N-substituted amide linked ligation product. Where the first and second components are peptides or polypeptides, the N-substituted amide linked ligation product has formula IV or V:

J1-C(O)—Nα(C1(R1)—C2—HS)—CH(Z2)—C(O)-J2    IV

J1-C(O)—Nα(C1(R1)—C2(R2)—C3(R3)—HS)—CH(Z2)—C(O)-J2    V where J1, J2 and R1, R2, R3 and Z2 are as defined above The conjugated electron donating groups R1, R2 or R3 of the N-substituted amide bonded ligation product facilitate cleavage of the N-C1 bond and removal of the 2 or 3 carbon chain alkyl or aryl thiol from the N-substituted amide-linked ligation product. Removal of the alkyl or aryl thiol chain of the N under peptide-compatible cleavage conditions generates a ligation product having a native amide bond at the ligation site. Where the first and second components are peptides or polypeptides, the ligation product will have the formula:

J1-CONαH—CH(Z2)—C(O)-J2    X

Exemplary R1 substituents for Formula I are depicted in Table I.

TABLE I

Formula I

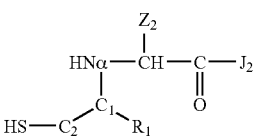

R1 Substituent Groups for Formula I (C1 included for reference)

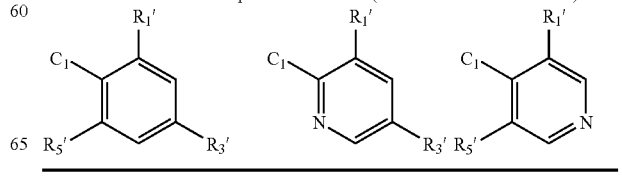

Exemplary R1, R2 and R3 substituents for Formula II are depicted in Table II.

TABLE II

Formula II

R1, R2 and R3 Substituents (C1 included for reference)

As with the N-substituted 2 carbon chain compounds, positioning of the benzyl and picolyl electron-donating substituents R1', R3' and R5' in the ortho or para positions is necessary to maintain electronic conjugation to the C1 carbon for robust cleavage of the Nα-C1 bond following ligation. However, when R2 and R3 form a benzyl group with C2 and C3, at least one of R1' and R3' comprises a strong electron donating group, where R1' or R3' is selected from methoxy (—OCH3), thiol (—SH), hydroxyl (—OH), and thiomethyl (—SCH3). For the N-substituted 3 carbon chain thiols in which R2 and R3 are hydrogens, R1 comprises a benzyl or picolyl group in which R1', R3' and R5' include either strong or moderate electron-donating groups, or a combination thereof. As with the N-substituted 2 carbon chain alkyl or aryl thiols, the strong electron-donating groups enhance the sensitivity of the 3 carbon chain alkyl or aryl thiol to cleavage following ligation. Thus a particular electron-donating group or combination thereof can be selected accordingly.

Similar to the N-substituted 2 carbon chain compounds, the N-substituted 3 carbon chain compounds of the present invention may include a thiol as a substituent of R1 in the R1' and R5' positions when available for substitution in a construct of interest. Here again the electron-donating thiol group is conjugated to C1 and its introduction at these locations enables the compounds to have two routes for the 6-member ring forming ligation event. It also increases the local concentration of available thiols for reacting with the α-carboxy thioester, and provides for additional conformations in terms of structural constraints that can improve ligation.

Synthesis of the N-terminal N-substituted 2 or 3 carbon chain alkyl or aryl thiol amino acids of the invention can carried out as described herein, for example, in Scheme I and Scheme II, and in accordance with standard organic chemistry techniques known in the art. See, e.g., "Advanced Organic Chemistry, Reactions, Mechanisms, and Structure," 4$^{th}$ Edition, J. March (Ed.), John Wiley & Sons, New York, N.Y., 1992; "Comprehensive Organic Transformations, A Guide to Functional Group Preparations," R. Larock (Ed.), VCH Publishers, New York, N.Y., 1989. They may be synthesized in solution, by polymer-supported synthesis, or a combination thereof. The preferred approach employs N alpha protected N alkylated S-protected amino alkyl- or aryl-thiol amino acid precursors. The reagents utilized for synthesis can be obtained from any number of commercial sources. Also, it will be well understood that the starting components and various intermediates, such as the individual amino acid derivatives can be stored for later use, provided in kits and the like.

In preparing the N-terminal Nα-substituted 2 or 3 carbon chain alkyl or aryl thiol amino acids of the invention, protecting group strategies are employed. The preferred protecting groups (PG) utilized in the various synthesis strategies in general are compatible with Solid Phase Peptide Synthesis ("SPPS"). In some instances, it also is necessary to utilize orthogonal protecting groups that are removable under different conditions. Many such protecting groups are known and suitable for this purpose (See, e.g., "Protecting Groups in Organic Synthesis", 3rd Edition, T. W. Greene and P. G. M. Wuts, Eds., John Wiley & Sons, Inc., 1999; NovaBiochem Catalog 2000; "Synthetic Peptides, A User's Guide," G. A. Grant, Ed., W.H. Freeman & Company, New York, N.Y.,1992; "Advanced Chemtech Handbook of Combinatorial & Solid Phase Organic Chemistry," W. D. Bennet, J. W. Christensen, L. K. Hamaker, M. L. Peterson, M. R.Rhodes, and H. H. Saneii, Eds., Advanced Chemtech, 1998; "Priciples of Peptide Synthesis, 2nd ed.," M. Bodanszky, Ed., Springer-Verlag, 1993; "The Practice of Peptide Synthesis, 2nd ed.," M. Bodanszky and A. Bodanszky, Eds., Springer-Verlag, 1994; and "Protecting Groups," P. J. Kocienski, Ed., Georg Thieme Verlag, Stuttgart, Germany, 1994). Examples include benzyloxycarbonyl (Z), Boc, Bpoc, Trt, Nps, FmocCl-Z, Br-Z; NSC; MSC, Dde, etc. For sulfur moieties, examples of suitable protecting groups include, but are not limited to, benzyl, 4-methylbenzyl, 4-methoxybenzyl, trityl, ACM, TACAM, xanthyl, disulfide derivatives, picolyl, and phenacyl.

More particularly, the Nα-substituted 2 or 3 carbon chain alkyl or aryl thiols can be prepared in accordance with Scheme I (Solid-Phase preparation of the Nα-substituted precursor), Scheme II (Solution-Phase preparation of the Nα-substituted precursor). In Scheme I, Nα-substituted 2 or 3 carbon chain alkyl or aryl thiols are assembled directly on the solid phase using standard methods of polymer-supported organic synthesis, while the Nα-protected, N-alkylated, S-protected, aminoalkyl or arylthiol amino acid precursor of Scheme II are coupled to the resin using standard coupling protocols. Where racemic or diastereomeric products are produced, it may be necessary to separate these by standard methods before use in extended native chemical ligation.

Scheme I
Solid-phase synthesis of ECL auxilliary deriviatized molecules

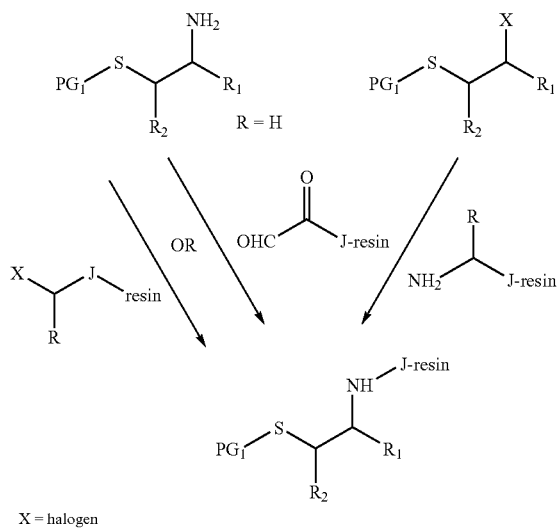

X = halogen

The α-carboxythioesters can be generated by chemical or biological methods following standard techniques known in the art, such as those described herein, including the Examples. For chemical synthesis, α-carboxythioester peptides can be synthesized in solution or from thioester-generating resins, which techniques are well known (See, e.g., Dawson et al., Science (1994) 266:776–779; Canne et al. Tetrahedron Lett. (1995) 36:1217–1220; Kent, et al., WO 96/34878; Kent, et al., WO 98/28434; Ingenito et al., JACS (1999) 121(49):11369–11374; and Hackeng et al., Proc. Natl. Acad. Sci. U.S.A. (1999) 96:10068–10073); Amiato et al., supra.). For instance, chemically synthesized thioester peptides can be made from the corresponding peptide α-thioacids, which in turn, can be synthesized on a thioester-resin or in solution, although the resin approach is preferred. The peptide-α-thioacids can be converted to the corresponding 3-carboxy-4-nitrophenyl thioesters, to the corresponding benzyl ester, or to any of a variety of alkyl thioesters. All of these thioesters provide satisfactory leaving groups for the ligation reactions, with the 3-carboxy-4-nitrophenyl thioesters demonstrating a somewhat faster reaction rate than the corresponding benzyl thioesters, which in turn may be more reactive than the alkyl thioesters. As another example, a trityl-associated mercaptoproprionic acid leucine thioester-generating resin can be utilized for constructing C-terminal thioesters (Hackeng et al., supra). C-terminal thioester synthesis also can be accomplished using a 3-car

Scheme II

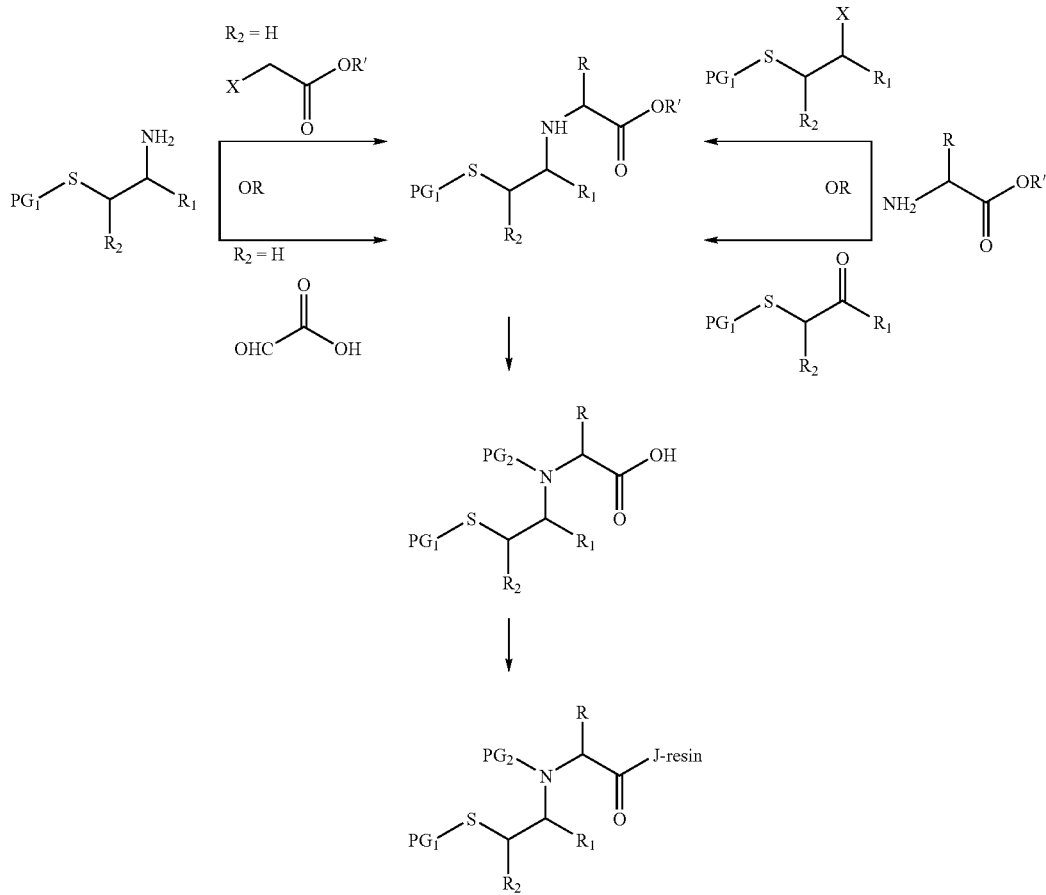

boxypropanesulfonamide safety-catch linker by activation with diazomethane or iodoacetonitrile followed by displacement with a suitable thiol (Ingenito et al., supra; Bertozzi et al.).

C-terminal α-carboxythioester peptides also can be made using biological processes, such as intein-mediated biological techniques (See, e.g., Chong et al., Gene (1997) 192: 277–281; Chong et al., Nucl. Acids Res. (1998) 26:5109–5115; Evans et al., Protein Science (1998) 7:2256–2264; and Cotton et al., Chemistry & Biology (1999) 6(9):247–256). For instance, intein expression systems, with or without labels such as affinity tags can be utilized to exploit the inducible self-cleavage activity of an 'intein' protein-splicing element to generate a C-terminal dithiothreitol (DTT) ester peptide or polypeptide segment. In particular, the intein undergoes specific self-cleavage in the presence of thiols such as DTT, b-mercaptoethanol or cysteine, which generates a peptide segment bearing a C-terminal thioester. See, e.g., Chong et al., (1997) supra; Chong et al, (1998) supra; Evans et al., supra; and Cotton et al., supra. However, when using a recombinantly produced segment, the chemically synthesized portion of the final construct will typically contain the polymer modification where included.

Ligation of the N-substituted 2 or 3 carbon chain alkyl or aryl thiol components of the invention with the first carboxythioester component generates a ligation product having an N-substituted amide bond at the ligation site. The ligation conditions of the reaction are chosen to maintain the selective reactivity of the thioester with the N-substituted 2 or 3 carbon chain alkyl or aryl thiol moiety. In a preferred embodiment, the ligation reaction is carried out in a buffer solution having pH 6–8, with the preferred pH range being 6.5–7.5. The buffer solution may be aqueous, organic or a mixture thereof. The ligation reaction also may include one or more catalysts and/or one or more reducing agents, lipids, detergents, other denaturants or solubilizing reagents and the like. Examples of preferred catalysts are thiol and phosphine containing moieties, such as thiophenol, benzylmercaptan, TCEP and alkyl phosphines. Examples of denaturing and/or solubilizing agents include guanidinium, urea in water or organic solvents such as TFE, HFIP, DMF, NMP, acetonitrile admixed with water, or with guanidinium and urea in water. The temperature also may be utilized to regulate the rate of the ligation reaction, which is usually between 5° C. and 55° C., with the preferred temperature being between 15° C. and 40° C. As an example, the ligation reactions proceed well in a reaction system having 2% thiophenol in 6M guanidinium at a pH between 6.8 and 7.8.

For the N-substituted 2 carbon chain alkyl or aryl thiols, the ligation event results from a thiol exchange that occurs between the COSR thioester component and the amino alkyl thiol component. The exchange generates a thioester-linked intermediate ligation product that after spontaneous rearrangement through a 5-membered ring intermediate generates a first ligation product of the formula J1-HN—CH(Z1)—C(O)—Nα(C1(R1)—C2—SH)—CH(Z2)-J2 having a removable N-substituted 2 carbon chain alkyl or aryl thiol [HS—C2—C1(R1)—] at the ligation site, where the substituents are as defined above. The N-substituted 2 carbon chain alkyl or aryl thiol [HS—C2—C1(R1)—] at the ligation site is amenable to being removed, under peptide-compatible conditions, to generate a final ligation product of the formula J1-HN—CH(Z1)—CO—NH—CH(Z2)—CO-J2 having a native amide bond at the ligation site.

For the N-substituted 3 carbon chain aryl or alkyl thiols, the thiol exchange between the COSR thioester component and the amino alkyl thiol component generates a thioester-linked intermediate ligation product that after spontaneous rearrangement through a 6-membered ring intermediate generates a first ligation product of the formula J1-HN—CH(Z1)—C(O)—Nα(C1-C2(R2)—C3(R3)—SH)—CH(Z2)-J2 having a removable N-substituted 3 carbon chain alkyl or aryl thiol [HS—C3(R3)—C2(R2)—C1(R1)—] at the ligation site. The N-substituted 3 carbon chain aryl thiol [HS—C3(R3)—C2(R2)—C1(R1)—] at the ligation site is amenable to being removed, under peptide-compatible conditions, to generate a final ligation product of the formula J1—HN—CH(Z1)—CO—NH—CH(Z2)—CO-J2 having a native amide bond at the ligation site.

Removal of the N-substituted alkyl or aryl thiol group is preferably performed in acidic conditions to facilitate cleavage of the N—C1 bond, yielding a stabilized, unsubstituted amide bond at the ligation site. By "peptide-compatible cleavage conditions" is intended physical-chemical conditions compatible with peptides and suitable for cleavage of the alkyl or aryl thiol moiety from the ligation product. Peptide-compatible cleavage conditions in general are selected depending on the α-substituted compound employed, which can be readily deduced through routine and well known approaches (See, e.g., "Protecting Groups in Organic Synthesis", 3rd Edition, T. W. Greene and P. G. M. Wuts, Eds., John Wiley & Sons, Inc., 1999; NovaBiochem Catalog 2000; "Synthetic Peptides, A User's Guide," G. A. Grant, Ed., W.H. Freeman & Company, New York, N.Y., 1992; "Advanced Chemtech Handbook of Combinatorial & Solid Phase Organic Chemistry," W. D. Bennet, J. W. Christensen, L. K. Hamaker, M. L. Peterson, M. R.Rhodes, and H. H. Saneii, Eds., Advanced Chemtech, 1998; "Priciples of Peptide Synthesis, 2nd ed.," M. Bodanszky, Ed., Springer-Verlag, 1993; "The Practice of Peptide Synthesis, 2nd ed.," M. Bodanszky and A. Bodanszky, Eds., Springer-Verlag, 1994; and "Protecting Groups," P. J. Kocienski, Ed., Georg Thieme Verlag, Stuttgart, Germany, 1994).

For example, where the R1, R2 or R3 substituents comprises a methoxy, hydroxyl, thiol or thiomethyl, methyl and the like, the more universal method for removal involves acidic cleavage conditions typical for peptide synthesis chemistries. This includes cleavage of the N—C1 bond under strong acidic conditions or water-acidic conditions, with or without reducing reagents and/or scavenger systems (e.g., acid such as anhydrous hydrogen fluoride (HF), triflouroacetic acid (TFA), or trimethylsulfonyl flouroacetic acid (TMSFA) and the like). More specific acidic cleavage systems can be chosen to optimize cleavage of the Nα-C1 bond to remove the aryl or alkyl thiol moiety for a given construct. Such conditions are well known and compatible with maintaining the integrity of peptides. A thiol scavenger may be included, particularly where tryptophans are present in a peptide or polypeptide sequence to avoid reaction of the tryptophan side chain with the liberated aryl or alkyl thiol moiety. Examples of thiol scavengers include ethanediol, cysteine, beta-mercaptoethanol and thiocresol.

Other specialized cleavage conditions include light or reductive-cleavage conditions when the picolyl group is the substituent. As an example, when the R1, or R2 and R3 substituents comprise a picolyl moiety, photolysis (e.g., ultraviolet light), zinc/acetic acid or electrolytic reduction may be used for cleavage following standard protocols. Where R1 of the N-substituted 2 carbon chain thiol comprises a thiomethane at R1, the mercury or HF cleavages can be used. The cleavage system also can be used for simultaneous cleavage from a solid support and/or as a deprotection reagent when the first or second ligation components comprise other protecting groups.

In one embodiment of the present invention Nα-substituted 2 or 3 chain alkyl or aryl thiols are employed in the peptide synthesis step (particularly in automated peptide synthesis and orthogonal and convergent ligation strategies) to yield properly N-terminally derivatized polypeptides that can be used as substrates for extended chemical ligation to yield synthetic bioactive proteins. Such compounds comprise a fully protected, partially protected or fully unprotected acid stable Nα-substituted 2 or 3 carbon chain amino alkyl or aryl thiol of the formula (PG1)S—C2—C1(R1)—Nα(PG2)—CH(Z2)—C(O)-J2 or (PG1)S—C3(R3)—C2(R2)—C1(R1)—Nα(PG2)—CH(Z2)—C(O)-J2, which are depicted below in Table III and Table IV. In particular, one or more of R1, R2 and R3 comprises an electron donating group conjugated to C1 that, following conversion of the Nα-substituted amino alkyl or aryl thiol to an Nα-substituted amide alkyl or aryl thiol, is capable of forming a resonance stabilized cation at C1 that facilitates cleavage of the Nα-C1 bond under peptide compatible cleavage conditions. PG1 and PG2 are protecting groups that are present individually or in combination or are absent and can be the same or different, where Z2 is any chemical moiety compatible with chemical peptide synthesis or extended native chemical ligation, and where J2 is any chemical moiety compatible with chemical peptide synthesis or extended native chemical ligation. PG1 (or X1) is a group for protecting the amine. PG2 (or X2) is a group for protecting the thiol. Many such protecting groups are known and suitable for this purpose (See, e.g., "Protecting Groups in Organic Synthesis", 3rd Edition, T. W. Greene and P. G. M. Wuts, Eds., John Wiley & Sons, Inc., 1999; NovaBiochem Catalog 2000; "Synthetic Peptides, A User's Guide," G. A. Grant, Ed., W.H. Freeman & Company, New York, N.Y., 1992; "Advanced Chemtech Handbook of Combinatorial & Solid Phase Organic Chemistry," W. D. Bennet, J. W. Christensen, L. K. Hamaker, M. L. Peterson, M. R.Rhodes, and H. H. Saneii, Eds., Advanced Chemtech, 1998; "Priciples of Peptide Synthesis, 2nd ed.," M. Bodanszky, Ed., Springer-Verlag, 1993; "The Practice of Peptide Synthesis, 2nd ed.," M. Bodanszky and A. Bodanszky, Eds., Springer-Verlag, 1994; and "Protecting Groups," P. J. Kocienski, Ed., Georg Thieme Verlag, Stuttgart, Germany, 1994).

TABLE III

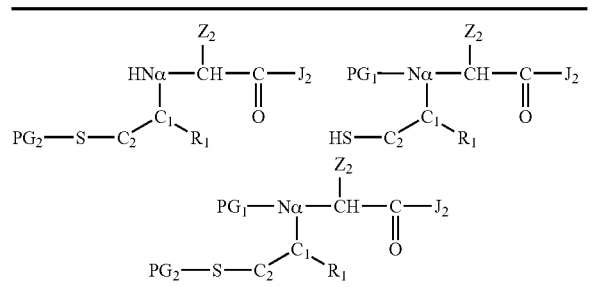

Examples of preferred protecting groups for PG1 and X1 include, but are not limited to [Boc(t-Butylcarbamate), Troc (2,2,2,-Trichloroethylcarbamate), Fmoc(9-Fluorenylmethylcarbamate), Br—Z or Cl—Z(Br— or Cl-Benzylcarbamate), Dde(4,4,-dimethyl-2,6-dioxocycloexl-ylidene), MsZ(4-Methylsulfinylbenzylcarbamate), Msc(2-Methylsulfoethylcarbamate) Nsc(4-nitrophenylethylsulfonylethyloxy-carbonyl]. Preferred PG1 and X1 protecting groups are selected from "Protective Groups in Organic Synthesis," Green and Wuts, Third Edition,Wiley-Interscience, (1999) with the most preferred being Fmoc and Nsc. Examples of preferred protecting groups for PG2 include, but are not limited to [Acm (acetamidomethyl), MeoBzl or Mob(p-Methoxybenzyl), Meb(p-Methylbenzyl), Trt(Trityl), Xan(Xanthenyl), tButhio (s-t-butyl), Mmt(p-Methoxytrityl), 2 or 4 Picolyl(2 or 4 pyridyl)), Fm(9-Fluorenylmethyl), tbut(t-Butyl), Tacam(Trimethylacetamidomethyl)] Preferred protecting groups PG2 and X2 are selected from "Protective Groups in Organic Synthesis," Green and Wuts, Third Edition,Wiley-Interscience, (1999), with the most preferred being Acm, Mob, MeB, Picolyl.

TABLE IV

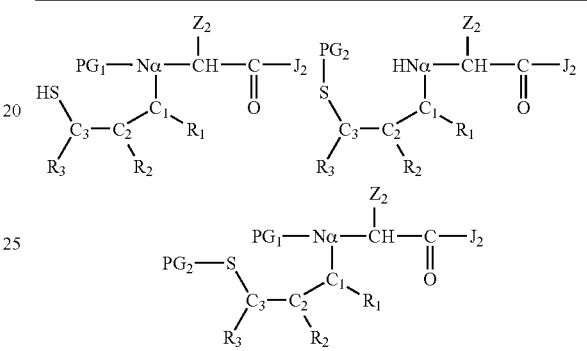

The protected forms of the Nα-substituted 2 or 3 chain alkyl or aryl thiols of the invention can be prepared as in Schemes I and II above.

The compounds of the present invention may be produced by any of a variety of means, including halogen-mediated amino alkylation, reductive amination, and by the preparation of Nα-protected, N-alkylated, S-protected, amino alkyl- or aryl-thiol amino acid precursors compatible with solid phase amino acid synthesis methods. When desirable, resolution of the racemates or diastereomers produced to give compounds of acceptable chiral purity can be carried out by standard methods.

III. Preferred Water-soluble Polymers of the Invention and Production

As used herein, the term "molecular heterogeneity" is intended to refer to a variation in the number of polymer molecules attached to each protein of a protein preparation. The term "molecular diversity" is intended to refer to (a) a variation in the site(s) of the protein that are modified by the polymer, (b) a variation in the length of the polymer adducts of different sites of the same protein, or of the same site(s) in different proteins of a protein preparation, or (c) a variation in the extent and/or nature of any branching of the polymer adducts of different sites of the same protein, or of the same site(s) in different proteins of a protein preparation. As used herein, the term "molecularly homogeneous" is intended to refer to a preparation of a protein in which all of the protein molecules contain the amino acid sequence and the same polymer modifications at the same positions. A mixture of two or more "molecularly homogeneous" protein preparations is referred to herein as a "molecularly defined" preparation.

In accordance with this aspect of the invention, a solution to the above-identified problems of polymer heterogeneity, diversity, and unsuitability involves the production of a new class of biocompatible polymers which combine the advantages of both polypeptides (precise length, convenient synthesis) and "pPEG" ("precision PEG"), a flexible, amphiphilic, non-immunogenic, polymer not susceptible to proteases) Rose, K. et al. (U.S. patent application Ser. No. 09/379,297, herein incorporated by reference). This new class of biocompatible polymer has the formula:

—[CO—X—CO—NH—Y—NH]$_n$— n is an integer, preferably from 1–100 and more preferably from 2–100, where X and Y are biocompatible repeat elements of precise structure linked by an amide bond. Preferably, X and Y will be divalent organic radicals lacking reactive functional groups or are absent and are the same or different, and can vary independently with each repeating unit (n). Preferably, when n=2, at least one of X or Y will be selected from the group consisting of a substituted, unsubstituted, branched and linear aliphatic and aromatic group. More preferably, one of X or Y will be selected from the group consisting of phenyl, a $C_1$–$C_{10}$ alkylene moiety, a $C_1$–$C_{10}$ alkyl group, a heteroatom-containing phenyl, a heteroatom-containing $C_1$–$C_{10}$ alkylene moiety, a heteroatom-containing $C_1$–$C_{10}$ alkyl group, and a combination thereof.

Particularly preferred pPEG moieties have the formulae:

—{CO—(CH$_2$)$_2$—CO—NH—(CH$_2$)$_3$—
(OCH$_2$CH$_2$)$_3$—CH$_2$—NH}$_n$— where n preferably varies from 1–100 and more preferably from 2–100; or —{CO—(CH$_2$)$_2$—CO—NH—(CH$_2$)$_6$—NH—CO—(CH$_2$)$_2$—CO—NH—(CH$_2$)$_3$—(OCH$_2$CH$_2$)$_3$—CH$_2$—NH—}$_n$—, where n preferably varies from 1–50 and more preferably from 2–50.

Such pPEG moieties can be synthesized in any of a variety of ways. Such moieties are, however, preferably produced using a solid phase stepwise chain assembly of units, rather than a polymerization process. The use of such an assembly process permits the moieties of a preparation to have a defined and homogeneous structure, as to their length, the nature of their X and Y substituents, the position(s) (if any) of branch points, and the length, X and Y substituents, and position(s) of any branches.

Preferably, such moieties will be synthesized by steps such as:

(a) acylating the amino or hydroxyl group of a compound of the formula Z—Q-support with a molar excess of a derivative of a diacid having the formula, HOOC—X—COOH, where Z is H$_2$N— or HO—; Q is a linker or a target molecule; and the support is a solid phase, matrix or surface;

(b) activating the free carboxyl group of the product of step(a);

(c) aminolysing the product of step (b) with a molar excess of a diamine having the formula, NH$_2$—Y—NH$_2$; and (d) optionally repeating steps (a)–(c) using HOOC—X—COOH and NH2-Y—NH2, where said X and Y are divalent organic radicals or are absent and are the same or different, and can vary independently with each of said optionally repeated units, and are the same or different from the X and Y substituents used in any of the previous acylating and aminolysing steps.

In preferred embodiments, 6-mers, 12-mers, 18-mers and 32-mers of above repeat unit are employed. Where desired, the repeat unit can be used, for example, in conjunction with the amino group of lysine to form branched pPEG structures. The pPEG may be attached to the synthetic proteins of the present invention by a variety of chemistries, including thioether, oxime and amide linkage formation. In one embodiment, the solid phase stepwise chain assembly of units comprises:

Step 1: Couple protected or unprotected diacid to amino on resin to generate amide bond at linkage site (where PG is a protecting group that is present or absent depending on diacid employed):

PG-OOC—X—COOH+NH$_2$—Y—NH-Resin

Step 2: Remove protecting group (PG) on resin, if present
HOOC—X—CO—NH—Y—NH-Resin Step 3: Couple protected or unprotected diamino to carboxy on resin to generate amide bond at linkage site (where PG is present or absent depending on diamino employed)

PG-NH—Y—NH+HOOC—X—CO—NH—Y—NH-Resin

Step 4: Remove protecting group (PG) on resin, if present
—NH—Y—NH—OC—X—CO—NH—Y—NH-Resin Step 5: Repeat steps 1–4 'n' times to add 'n' units then cleave from resin —[CO—X—CO—NH—Y—NH]—[CO—X—CO—NH—Y—NH]—[CO—X—CO—NH—Y—NH]—[CO—X—CO—NH—Y—NH]—

As discussed, linear and branched pPEG constructs are preferred water-soluble polymers for attachment to the synthetic bioactive molecules of the invention. The pPEGs employed bear pendant groups that are charged or neutral under physiological conditions, and can be made to vary in attachment chemistry, length, branching and solubility depending on the pPEG structure one employs. As noted above, preferred pPEGs of the invention comprise a water-soluble polyamide having the repeat unit —CO—X—CO—NH—Y—NH—, where one or both of X and Y comprises a water-soluble repeat unit, and most preferably a 'PEG'-based repeat unit. Although oligoureas are in principle accessible using a simple two-step solid phase procedure, as shown below for the case of an amino resin, NH$_2$-Resin, and a symmetrical diamine, NH$_2$—Y—NH$_2$:

Activation with carbonyldiimidazole→im-CO—NH-Resin

Aminolysis with diamine NH$_2$—Y—NH$_2$→NH$_2$—Y—NH—CO—NH-Resin where these two steps may be repeated a number of times to give an oligourea with repeat unit —NH—Y—NH—CO—, this approach is less preferred. This is because the yields of the above steps may be non-quantitative at room temperature, even with very large excesses of reagents and long reaction times. Accordingly, it is preferable to use a three-step solid phase procedure, shown below for the case of an amino resin, NH$_2$-Resin, to form a polyamide. The Reagents HO$_2$C—X—CO$_2$H and NH$_2$—Y—NH$_2$ should be symmetrical in order to avoid isomeric products.

Acylation with diacid HO$_2$C—X—CO$_2$H→HO—CO—X—CO—NH-Resin

Activation with carbonyldiimidazole→im-CO—OCO—X—CO—NH-Resin

Aminolysis with diamine NH$_2$—Y—NH$_2$→NH$_2$—Y—NH—CO—X—CO—NH-Resin

These three steps may be repeated in sequence a number of times to give a polyamide with repeat unit —NH—Y—NH—CO—X—CO—. The polymer contains a precise number of monomer units, X and Y can be varied independently at each step, and end-groups can be chosen at will. For example, by using succinic anhydride ("Succ") for the acylation step and 4,7,10-trioxa-1,13-tridecanediamine (also referred to as "EDA" or "TTD") for the aminolysis step, 'PEG'-based polyamides are formed wherein X is —CH$_2$CH$_2$—, Y is —NH—CH$_2$CH$_2$CH$_2$—(OCH$_2$CH$_2$)$_3$—

CH$_2$—NH— and the repeat unit is —NH—CH$_2$CH$_2$CH$_2$—(OCH$_2$CH$_2$)$_3$—CH$_2$—NH—COCH$_2$CH$_2$CO—. In spite of the fact that the procedure involves divalent reagents with no protecting groups, cross-linking is not a problem when standard commercial peptide synthesis resins are used (Rose et al., (U.S. Pat. No. 6,552,167); and Rose et al., J. Am. Chem. Soc. (1999) 121:7034), except as noted below for the case of branched Lys cores for making branched constructs.

For example, branched pPEG constructs can be made in a similar manner as for the "chemobody" constructs described in Rose et al., (U.S. Pat. No. 6,552,167) and Rose, K. and Vizzavona, J. (J. Am. Chem. Soc. (1999) 121:7034). Thus, branched pPEG constructs can be made to have a branching core such as a lysine branching core, which is coupled through oxime linkers to a preferred water-soluble polyamide such as —(COCH$_2$CH$_2$CO—NH—CH$_2$CH$_2$CH$_2$—(OCH$_2$CH$_2$)$_3$—CH$_2$—NH)$_n$—. For instance, oxime bonds can be readily formed between an aminooxyacetyl group on a Lys side chain at the other extremity of the polyamide, and glyoxylyl groups on a lysine core, for example the tetrameric core (O=CHCO)$_4$Lys$_2$Lys-. Thus an oxime linker off of each lysine branch point can be prepared as the structure -Lys(COCH$_2$ON=CHCO—)amide-.

An alternative construction can place the oxime bond between the polyamide and the free pendant group of the polyamide, preferably using a monoprotected diamine and deprotection after coupling the polyamide, to generate a tetravalent branched constructed depicted below:

[O=CHCO—(NH—CH$_2$CH$_2$CH$_2$—[OCH$_2$CH$_2$]$_3$—CH$_2$—NH—COCH$_2$CH$_2$CO—)$_n$]$_4$Lys$_2$Lys-

Figure 15:
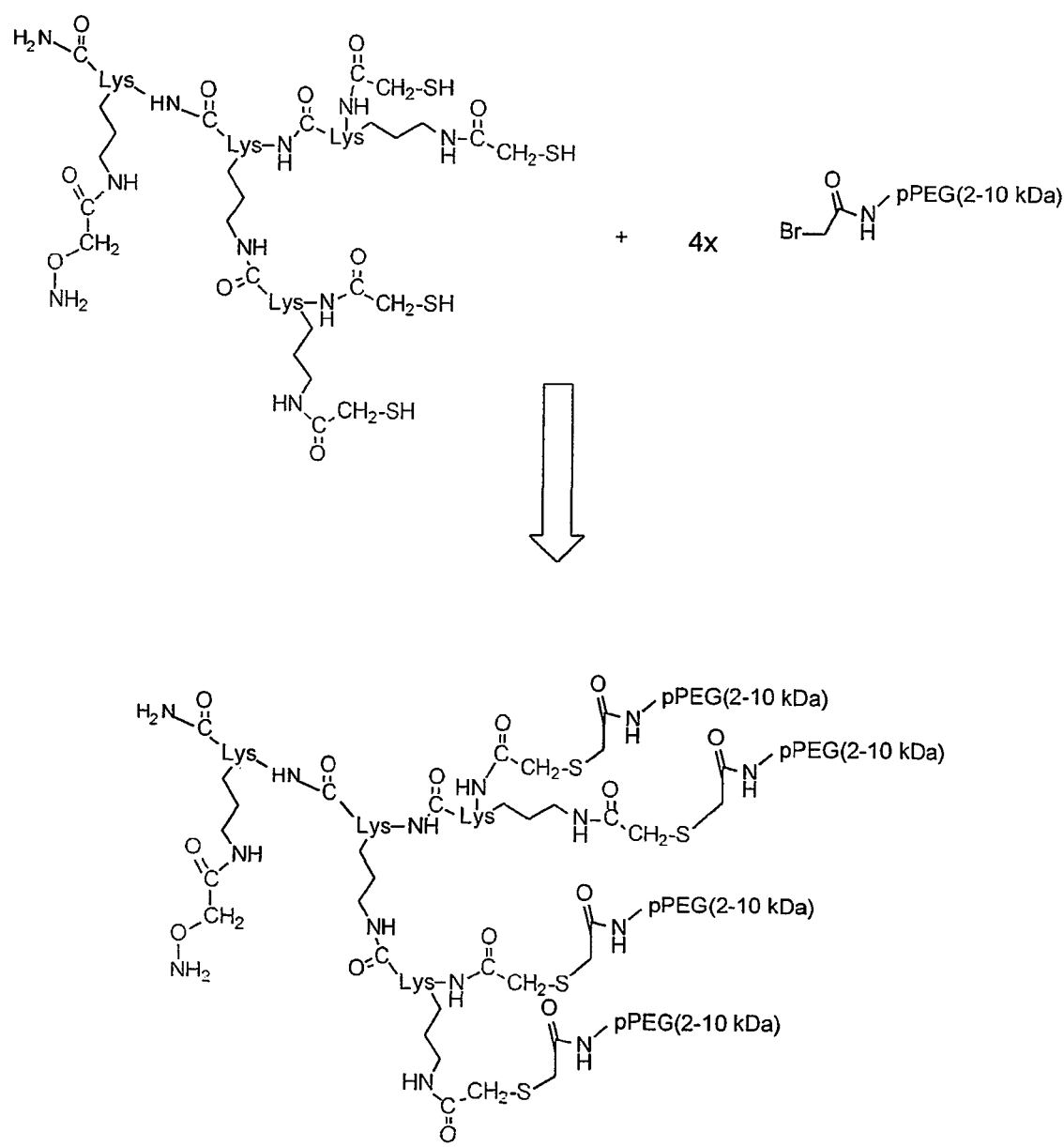
FIG. 15 depicts schematically the formation of branched-chain pPEG polymers.
Figure 16A:
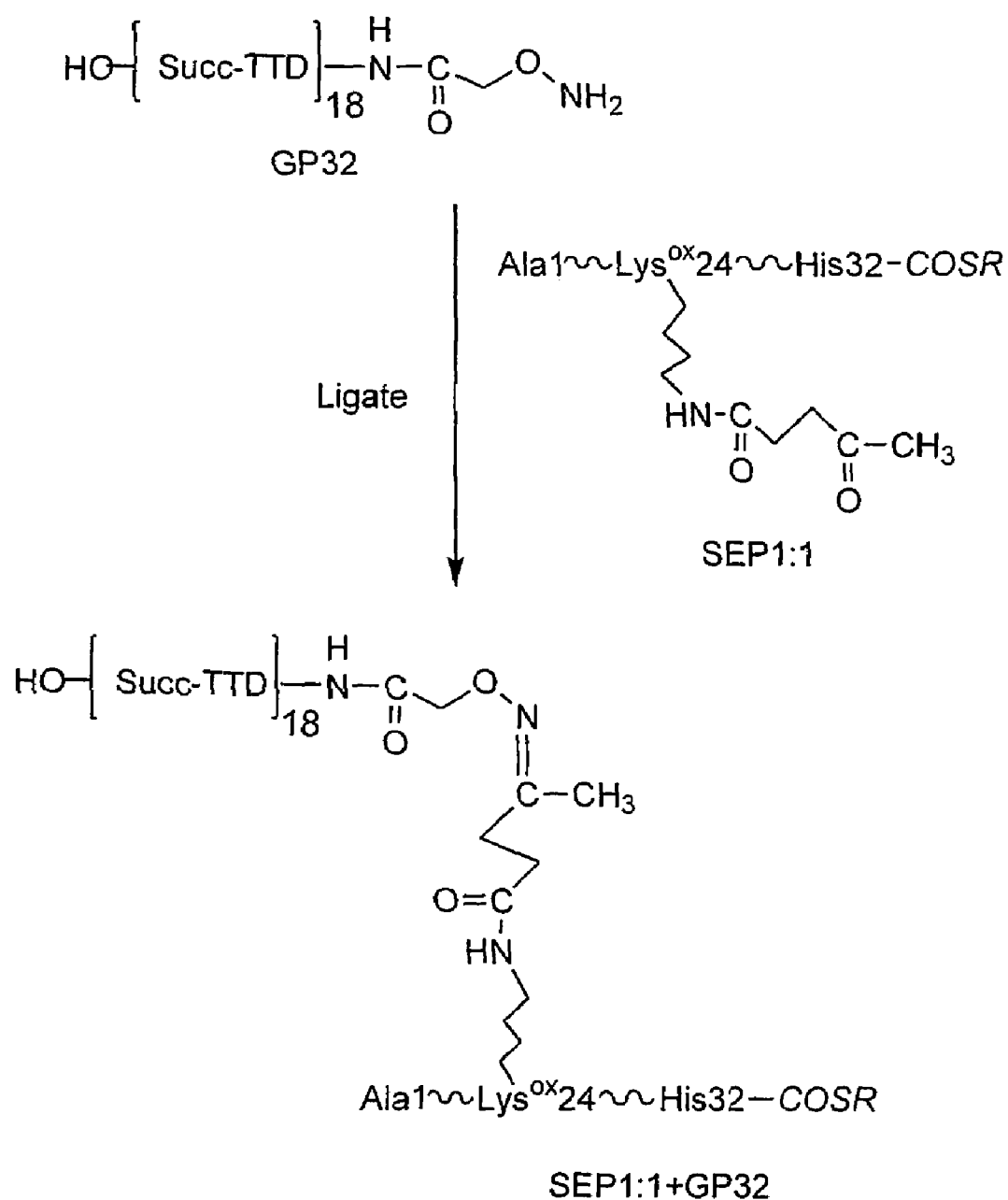
FIG. 16 depicts the synthesis of a synthetic cytokine designated SEP1-L30, which is a precision polymer-modified synthetic analog of human EPO prepared as described in Example 2.
Figure 16B:
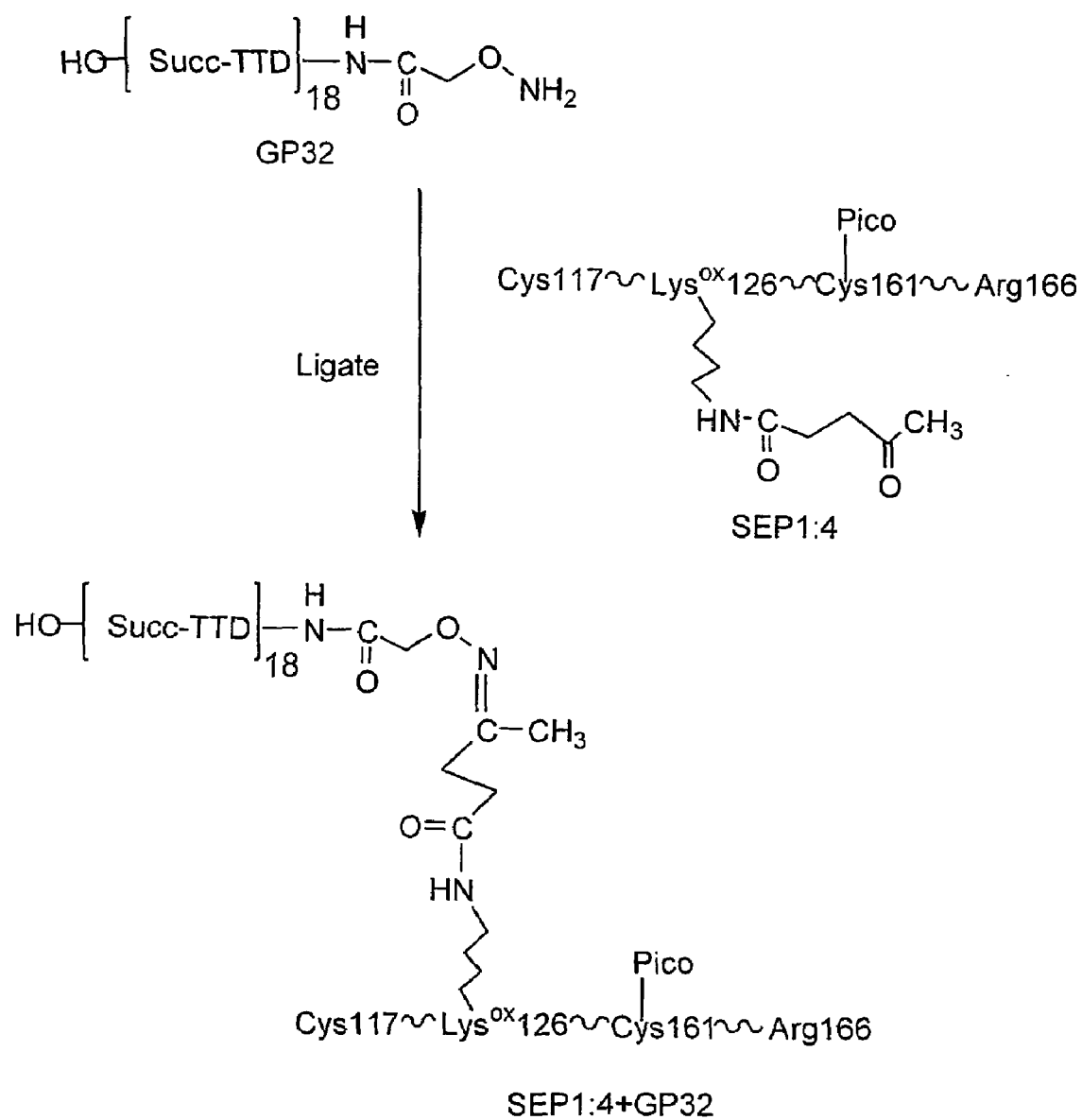
Figure 16C:
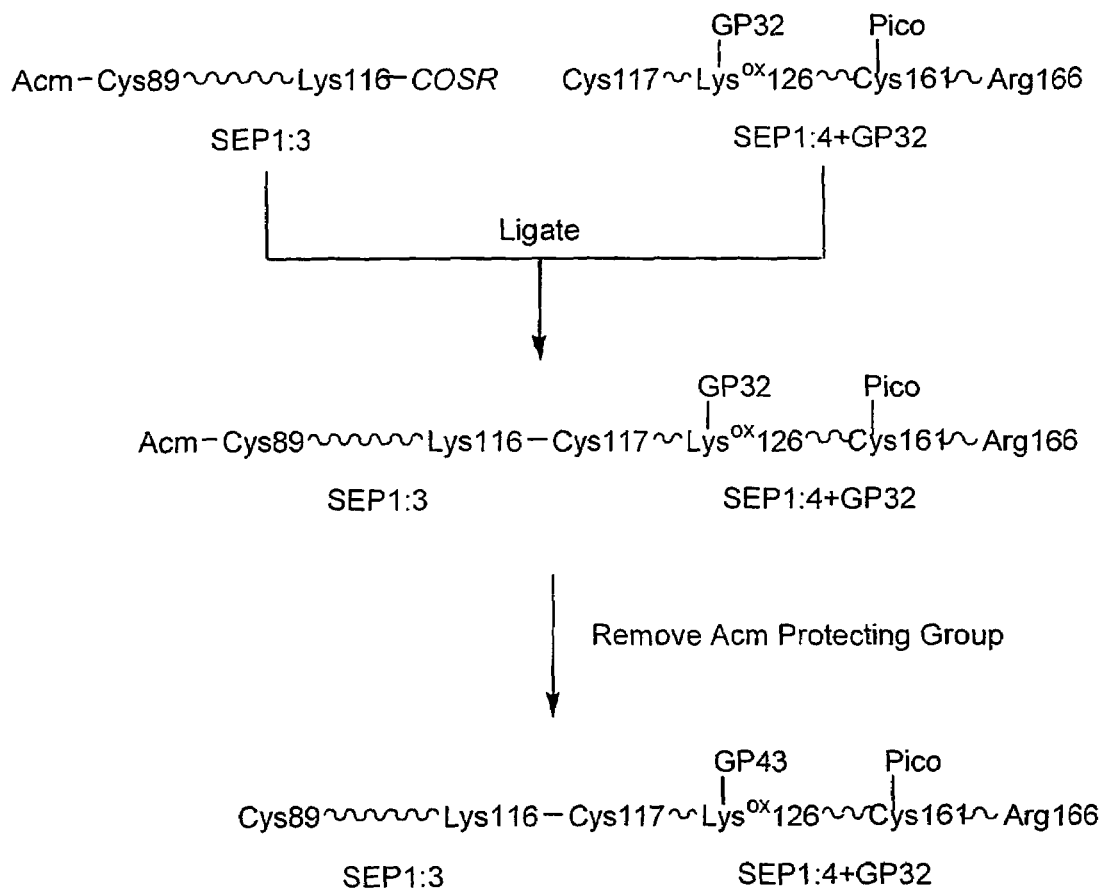
Figure 16D:
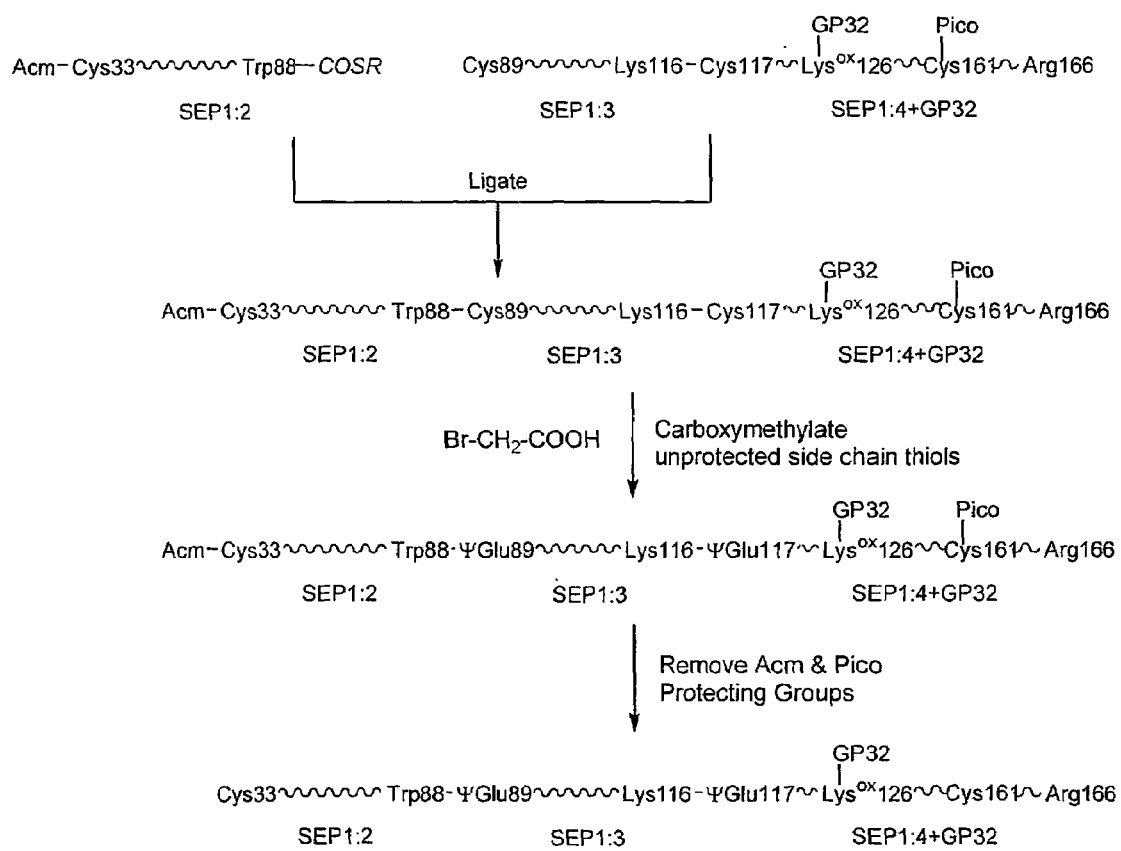
Figure 16E:
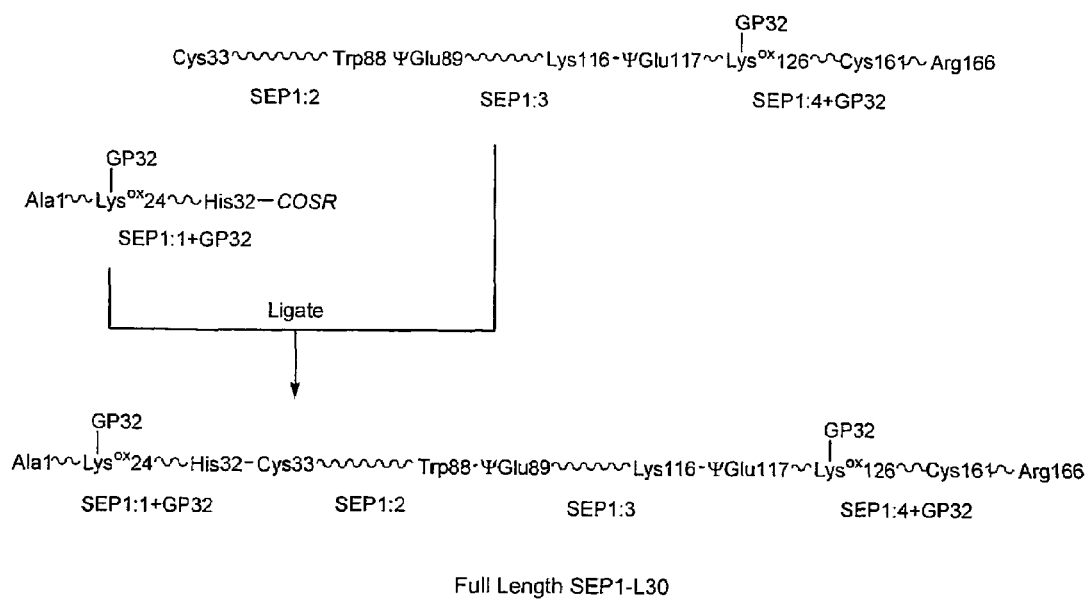

Oxime chemistry can be used in making not only dimeric and tetrameric branched constructs, but it also suitable for assembling octameric branched constructs (Rose, K., J. Am. Chem. Soc. (1994) 116:30; Rose, K. et al., Bioconj. Chem. (1996) 7:552). It is, of course, possible to use other chemistries for such purposes when using such pPEG polyamides (See, e.g., FIG. 15). Moreover, polyamide formation may be incorporated into a synthetic scheme for peptide synthesis involving Boc or Fmoc chemistry, but when elaborating such schemes it must be borne in mind that the aminolysis step will remove the Fmoc group, and will remove formyl protection of indole if Boc chemistry is to be used.

Accordingly, such pPEGs can be made to have various branching cores (e.g., Lysine branching core etc.) linked through a bond of choice (e.g., amide, thioether, oxime etc.) to a linear water-soluble polyamide (e.g., -(Succ-TTD)$_n$-, etc.), where the free end of each linear water-soluble polyamide can each be capped with a desired pendant group (e.g., carboxylate, amino, amide etc.) to provide a desired charge. Moreover the linear and branched pPEGs of the present invention can be made to comprise a unique functional group for attachment to a synthetic protein bearing one or more unique and mutually reactive functional groups, and the pendant groups of the pPEGs will preferably be non-antigenic (See, e.g., FIG. 15).

In a particularly preferred embodiment, the invention is directed to molecularly homogeneous glyco-mimetic water-soluble polymers of the formula:

U-s1-B-s2-Polymer-s3-J* where U is a residue of a unique functional group, B is a branching core having three or more arms that may be the same or different and may be present or absent, Polymer is a polyamide having a molecular weight greater than about 5,000 Da of the formula —[C(O)—X—C(O)—NH—Y—NH]$_n$- or —[H—Y—NH—C(O)—X—C(O)]$_n$-, where X and Y are divalent radicals that may be the same or different and may be branched or linear, and n is a discrete integer from 2 to 50, and where either or both of X and Y comprises a substantially non-antigenic water-soluble repeat unit that may be linear or branched, J* is a residue of a substantially non-antigenic pendant group having a net charge under physiological conditions selected from the group consisting of negative, positive and neutral, and where s1, s2, and s3 are spacer or linker moieties that may be the same or different, and may be individually present or absent. Such polymers include those described in U.S. patent application Ser. No. 60/236,377, which is incorporated herein in its entirety. Formula U-s1-B-s2-Polymer-s3-J* also can be represented by the formula U-B-Polymer-J*, where spacer or linker groups s1, s2, s3 may be present or absent.

Figure 5A:
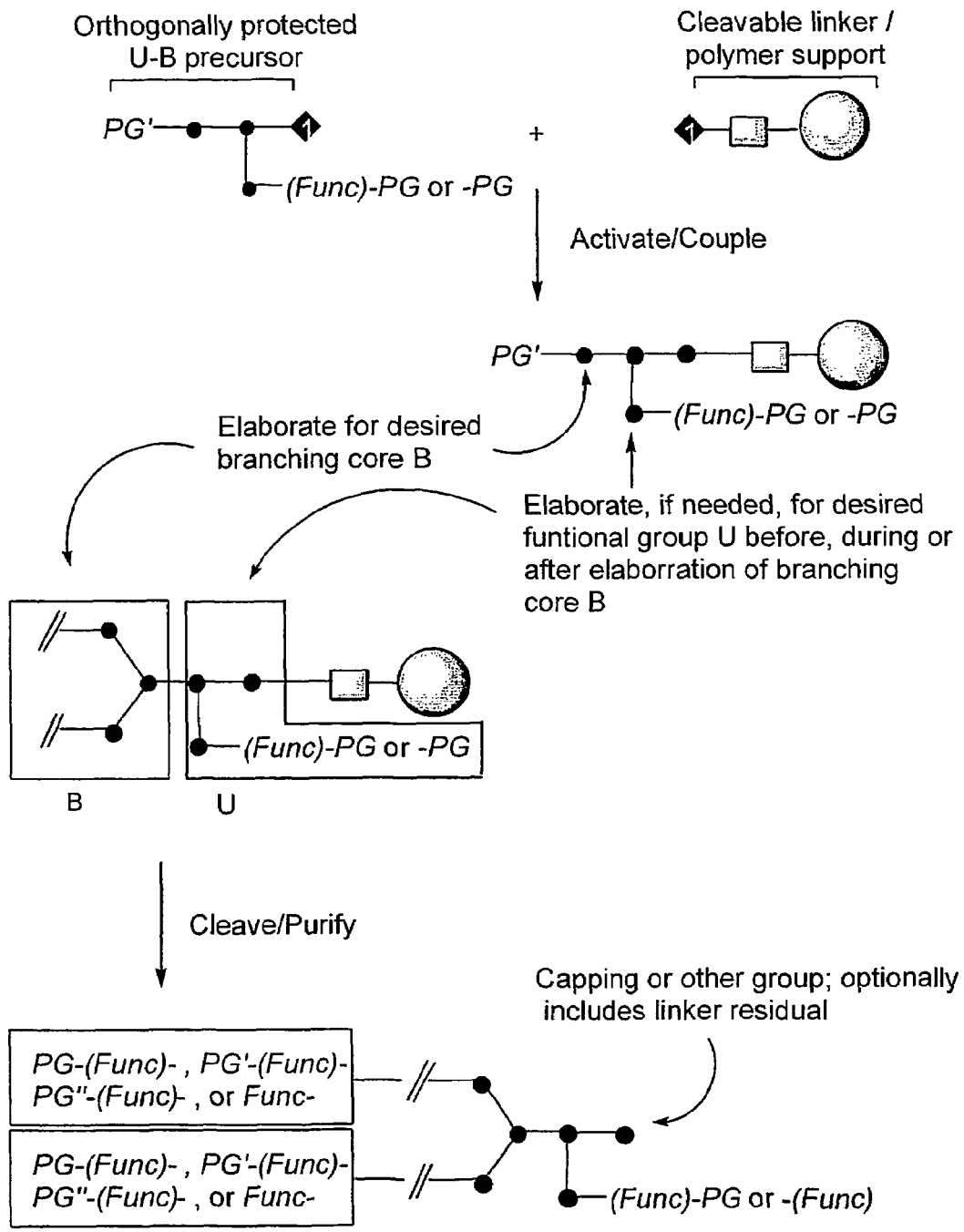
FIGS. 5A–5B depict solid phase process for generating the branching core (B) and unique chemoselective functional group (U) of the water-soluble polymer U-B-Polymer-J* of the invention.
Figure 5B:
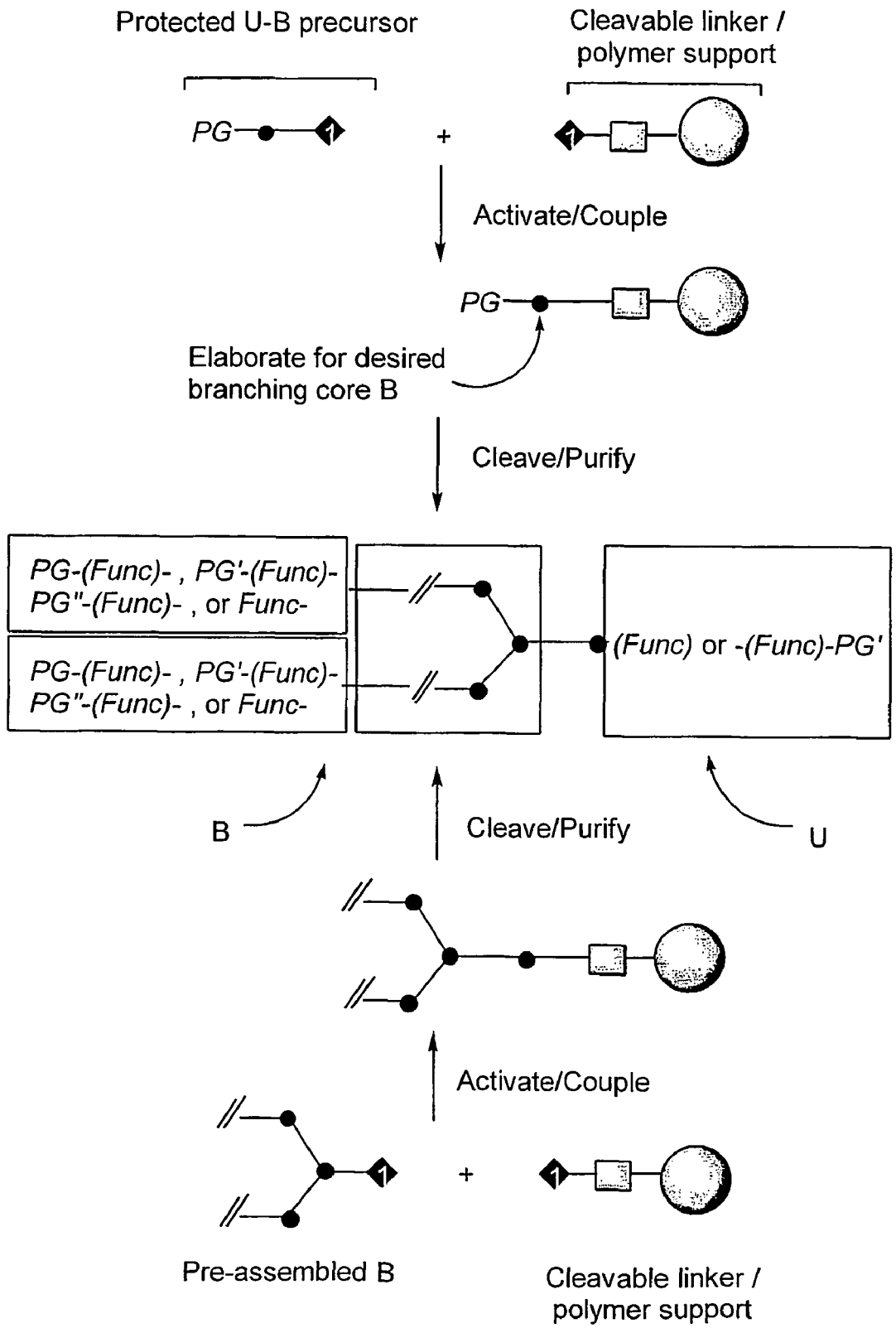
Figure 6A:
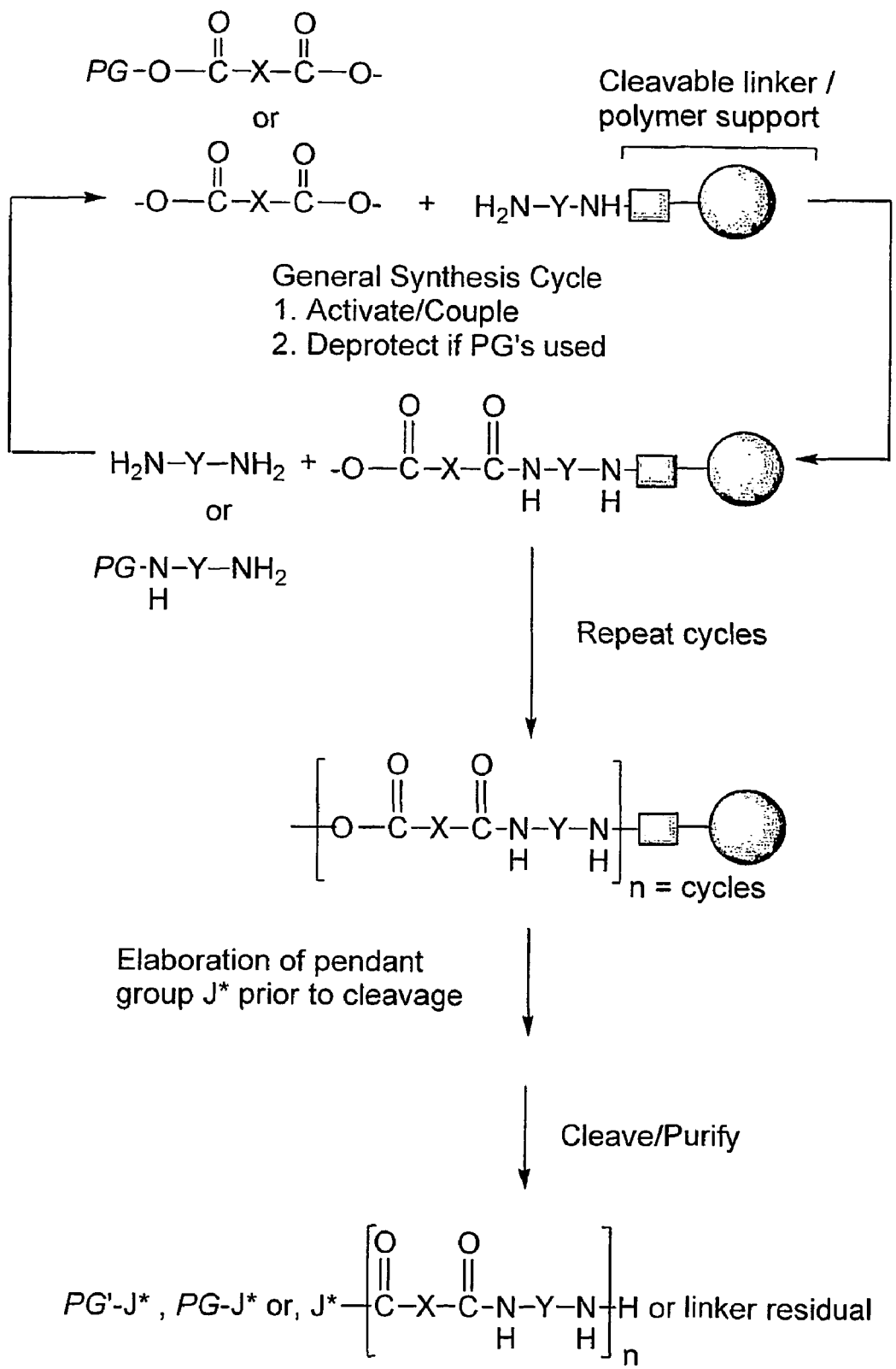
FIGS. 6A–6D depict a solid phase process for generating preferred substantially non-antigenic water-soluble polyamide Polymer-J* components of the invention for subsequent attachment to the U-B core.
Figure 6B:
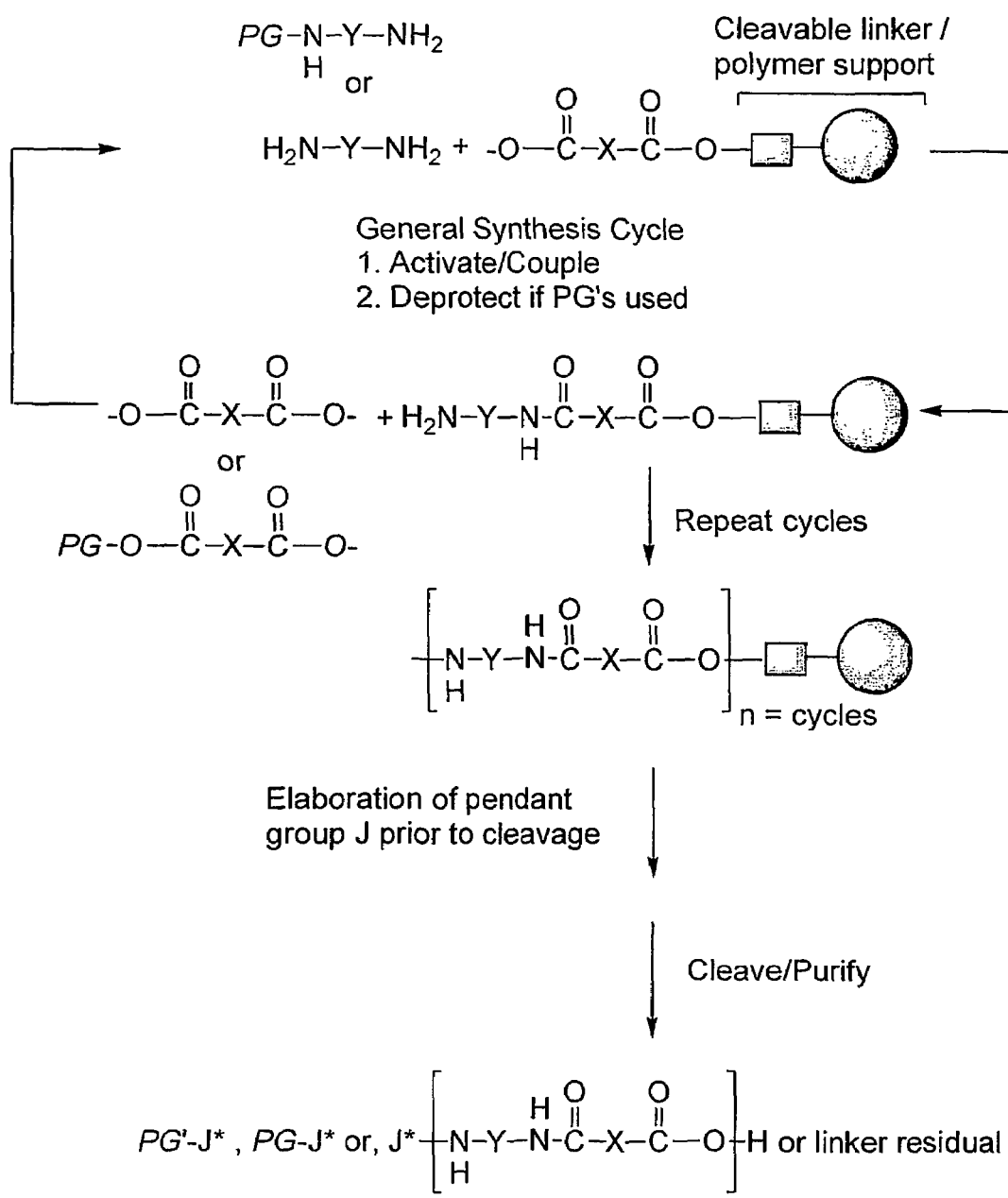
Figure 6C:
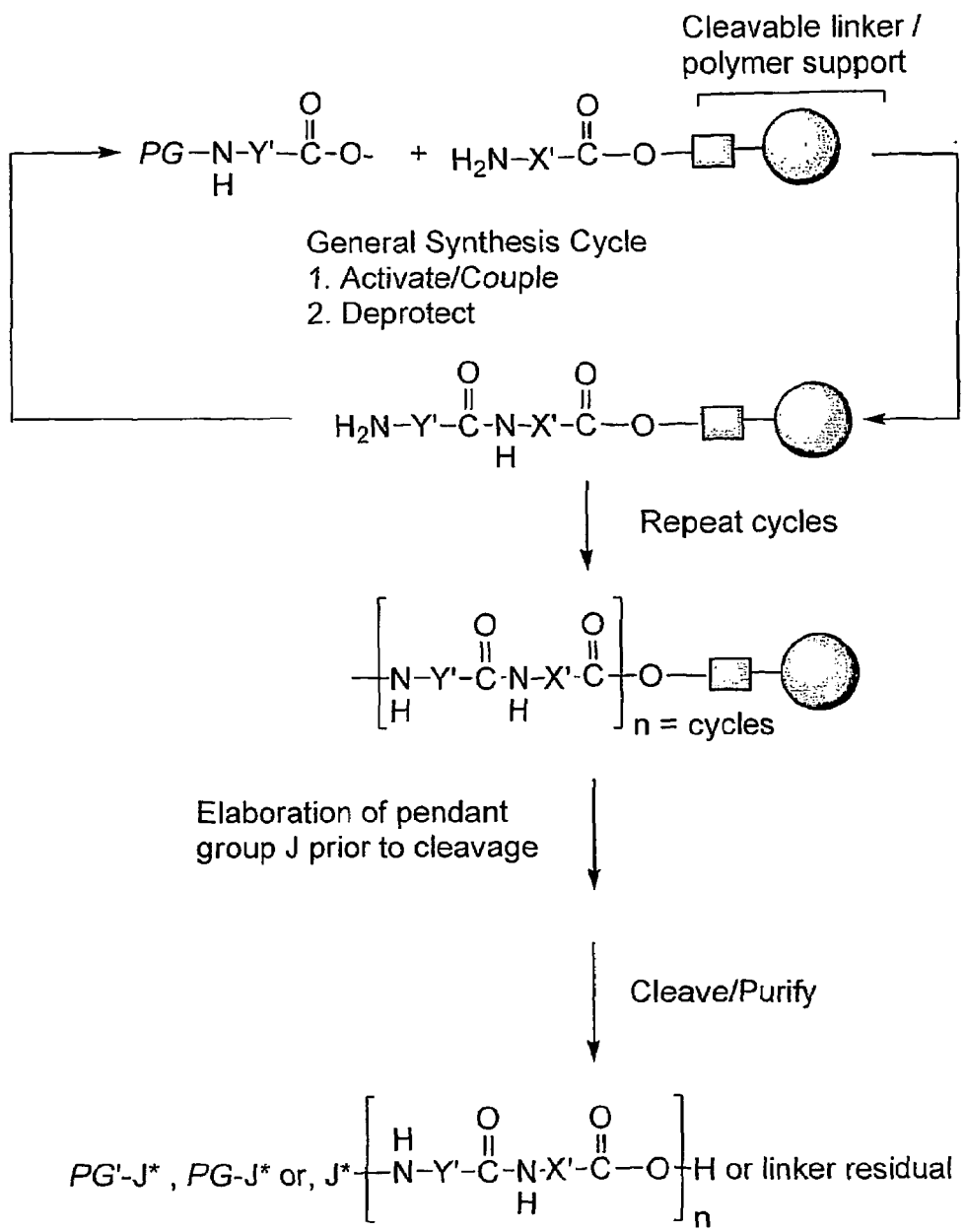
Figure 6D:
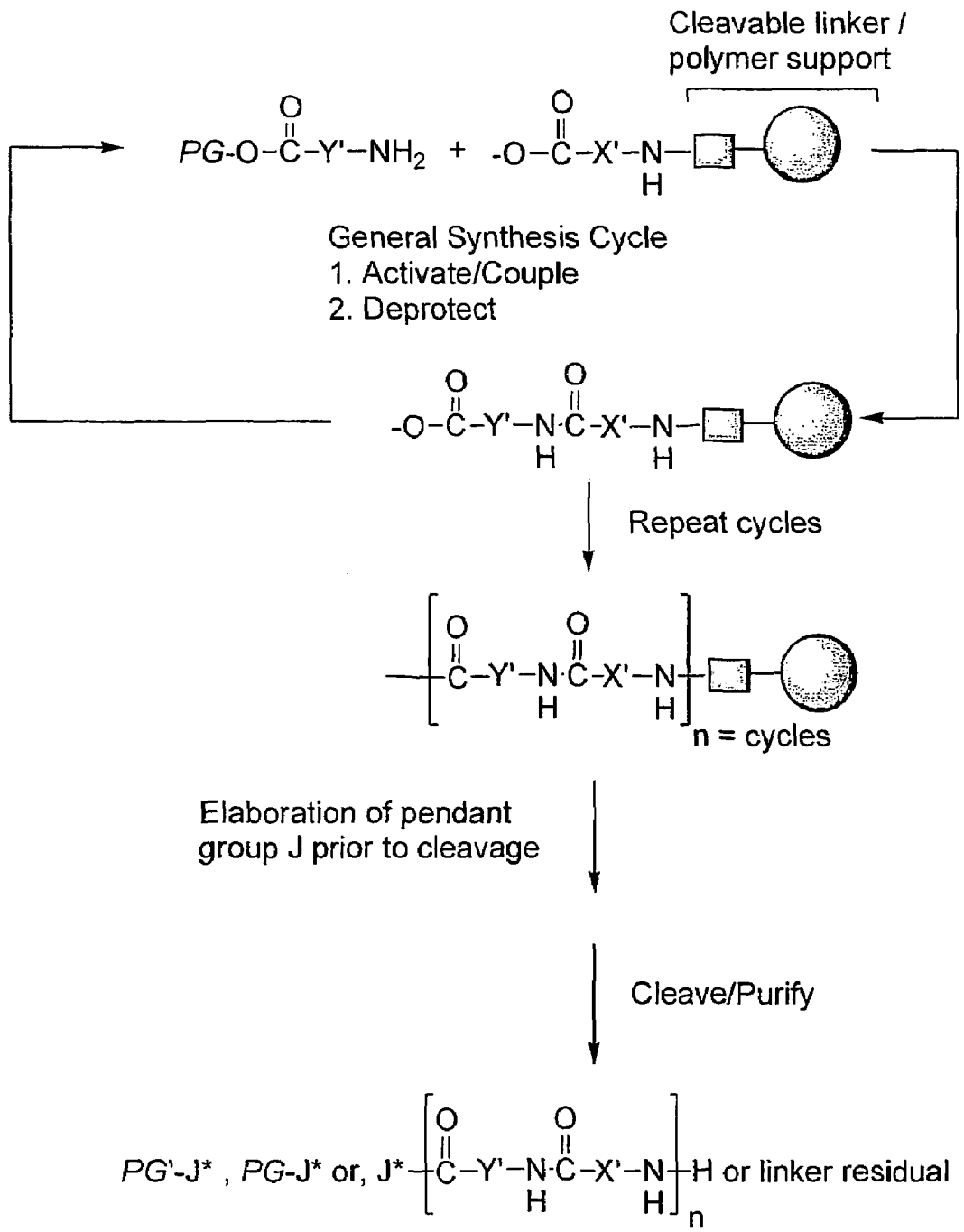
Figure 7:
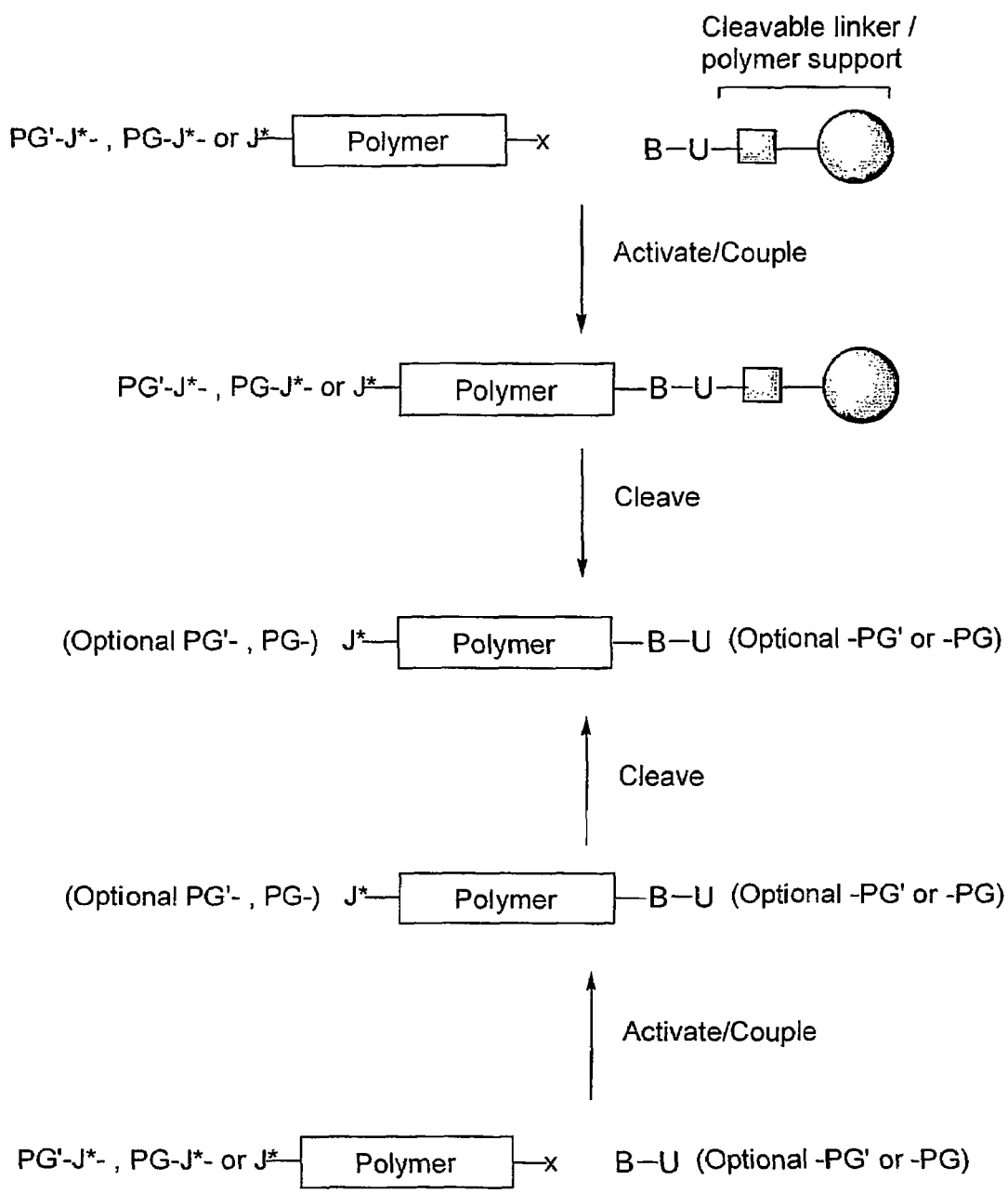
FIG. 7 depicts process for coupling the U-B component to Polymer-J* component to generate the preferred synthetic polymer constructs of the invention of the formula U-B-Polymer-J*.

The preferred process of forming the preferred glycomimetic polymers of the invention are illustrated in FIGS. 5–7. FIGS. 5A–5B depict solid phase process for generating the branching core (B) and unique chemoselective functional group (U) of the water-soluble polymer U-B-Polymer-J* of the invention. The process may be carried out in solution, although the solid phase approach as shown is preferred. In particular, FIG. 5A shows orthogonally protected U-B precursor moiety with reactive group (—◆) and the basic geometric structure of such construct is depicted by dots linked with bonds (●—●); this basic geometric structure is not intended to limit that types of chemical linkages or groups employed, but merely illustrative of the relative points of geometry for building structures and chemical elaboration points suitable for generation of U-B moieties of the invention. The orthogonally protected U-B precursor is coupled to a polymer support/resin comprising a suitable cleavable linker and co-reactive group (—◆) following activation that is capable of covalent linkage to the U-B precursor:

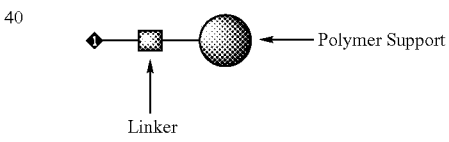

This system employs the principles of polymer-supported organic chemistry. Following coupling the branching core is elaborated (only a first branch point shown, and additional branch points may be present or absent) as illustrated to generate a branching core that is suitable for subsequent attachment of a desired Polymer component, such as a substantially non-antigenic, water-soluble linear polymer. Also shown is the U group, which can be provided at the outset of synthesis as part of the orthogonally protected U-B precursor, or elaborated during or after elaboration of the branching core B. While attachment of the Polymer component can be achieved on-resin, i.e., prior to cleavage, a preferred route is cleavage of the U-B moiety from the polymer support/resin so as to generate a U-B core that can be purified for subsequent attachment the Polymer component.

As illustrated, the pendant branch points of core group B are built to comprise a functional group (Func), which can be the same or different, and may be reversibly protected (PG, PG' or PG") or unprotected. In each case, the final step for attachment of the Polymer component involves the generation of a functional group (Func) at the pendant branch points, and generation of group U (See FIG. 7). FIG. 5B depicts an alternative process in which a protected U-B precursor is employed in combination with a polymer support bearing a linker, which upon cleavage generates the desired protected or unprotected U-group. FIG. 5B also depicts attachment of a pre-assembled branching core B to a polymer support, and use of a U-group generating resin to make the U-B moiety for subsequent attachment of the Polymer component.

FIGS. 6A–6D depict a solid phase process for generating preferred substantially non-antigenic water-soluble polyamide Polymer-J* components of the invention for subsequent attachment to the U-B core. Although the solid phase process is illustrated, which is the preferred process, a solution phase process can be adapted to achieve the same end result. In FIGS. 6A and 6B, diacid and diamino units are coupled using the principles of solid phase organic chemistry. Optionally, protected amino-X'-acid and /or amino-Y'-acid units can be incorporated for additional diversity of the groups X and Y in the final cleavage product having a polyamide structure of the formula —[NH—Y—NHCO—X—CO]—. FIG. 6A depicts synthesis in the N- to C-terminal direction, whereas FIG. 6B depicts synthesis in the C- to N-terminal direction. In FIGS. 6C and 6D, protected amino-X'-acid and/or amino-Y'-acid units are coupled using the principles of solid phase organic chemistry. FIG. 6C depicts synthesis in the N- to C-terminal direction, whereas FIG. 6D depicts synthesis in the C- to N-terminal direction. As apparent from FIGS. 6A–6D, the nature of the final polyamide products can be precisely controlled, which depends on the number of cycles one carries out for synthesis. Moreover, the pendant group J* can be built to virtually any user-defined specification. Where mono-disperse repeat units X, Y, X' and Y' are employed, the exact molecular structure of the final polyamide product can be precisely controlled.

A preferred process for coupling the U-B component to Polymer-J* component to generate the preferred synthetic polymer constructs of the invention of the formula U-B-Polymer-J* is depicted in FIG. 7. As illustrated, various protecting groups can be provided, and are optional depending on the intended end use of a given construct. Also illustrated different routes to produce the desired U-B-Polymer-J* constructs, including a solid phase approach and a solution phase approach.

As noted above, preferred water-soluble repeat units comprise a polyalkylene oxide, polyamide alkylene oxide, or derivatives thereof. The most preferred water-soluble repeat unit comprises an ethylene oxide of the formula —($CH_2$—$CH_2$—O)— or —($CH_2$—$CH_2$—O)—. The number of such water-soluble repeat units can vary significantly, but the more preferred number of such units is from 2 to 500, 2 to 400, 2 to 300, 2 to 200, 2 to 100, 2 to 50, and more preferably 2 to 32, with 3 to 8 being the most preferred. An example of a more preferred embodiment is where one or both of X and Y is selected from: —(($CH_2$)$_{n1}$—($CH_2$—$CH_2$—O)$_{n2}$—($CH_2$)$_{n1}$—)— or —(($CH_2$)$_{n1}$—(O—$CH_2$—$CH_2$)$_{n2}$—($CH_2$)$_{n1}$—), where n1 is 1 to 6, 1 to 5, 1 to 4 and most preferably 1 to 3, and where n2 is 2 to 50, 2 to 25, 2 to 15, 2 to 10, 2 to 8, and most preferably 2 to 5. An example of a highly preferred embodiment is where X is —($CH_2$—$CH_2$)—, and where Y is —($CH_2$—($CH_2$—$CH_2$—O)$_3$—$CH_2$—$CH_2$—$CH_2$)— or —($CH_2$—$CH_2$—$CH_2$—(O—$CH_2$—$CH_2$)$_3$—$CH_2$)—. Even more preferred are mono-disperse compositions where each n of is a discrete integer. In a highly preferred embodiment, X is —($CH_2$—$CH_2$)— and Y is —($CH_2$—($CH_2$—$CH_2$—O)$_3$—$CH_2$—$CH_2$—$CH_2$)n- or —($CH_2$—$CH_2$—$CH_2$—(O—$CH_2$—$CH_2$)$_3$—$CH_2$)-n where n is 12 to 36.

In particular, the Polymer will preferably have when the water-soluble polymer contains polymer chains having polyalkylene oxide repeat units, such as ethylene oxide repeat units, it is preferred that each chain have a molecular weight of between about 1500 and about 42,000 Da and preferably between about 2,000 to about 20,000 Da being the most preferred.

A preferred U group comprises a moiety capable of chemical ligation. Preferred polymers are branched where group B comprises three or more arms. A preferred component J* comprises a group that is ionizable under physiological conditions, and most preferably one that is negatively charged. Either or both of U and J may comprise a protecting group that is capable of being removed without damaging the integrity of the construct.

Preferred spacers or linkers include linear or branched moieties comprising one or more repeat units employed in a water-soluble polymer, diamino and or diacid units, natural or unnatural amino acids or derivatives thereof, as well as aliphatic moieties, including alkyl, aryl, heteroalkyl, heteroaryl, alkoxy, and the like, which preferably contain up to 18 carbon atoms or even an additional polymer chain.

As noted above, component U is a residue of a functional group that is capable of being attached or is attached to a target molecule, such as a peptide or polypeptide, or other surface of interest. When U is a residue of a functional group for conjugation to a target molecule, U comprises a nucleophilic group or electrophilic group, and the target molecule comprises a mutually reactive electrophilic group or nucleophilic group, respectively.

Many such mutually reactive functional groups are known and are capable of attachment to side chain functional groups common to peptides and polypeptides, or derivatized side chain functional groups (Zalipsky et al., *Bioconjugate Chemistry* (1995) 6:150–165; "Perspectives in Bioconjugate Chemistry", C. F. Meares, Ed., ACS, 1993; "Chemistry of Protein Conjugation and Cross-Linking", S. S. Wong, Ed., CRC Press, Inc. (1993)). Examples of functional groups include groups capable of reacting with an amino group such as (a) carbonates such as the p-nitrophenyl, or succinimidyl; (b) carbonyl imidazole; (c) aziactones; (d) cyclic imide thiones; and (e) isocyanates or isothiocyanates. Examples of functional groups capable of reacting with carboxylic acid groups and reactive carbonyl groups include (a) primary amines; or (b) hydrazine and hydrazide functional groups such as the acyl hydrazides, carbazates, semicarbamates, thiocarbazates, aminooxy etc. Functional groups capable of reacting with mercapto or sulfhydryl groups include phenyl glyoxals, maleimides, and halogens. Examples of functional groups capable of reacting with hydroxyl groups such as (carboxylic) acids, or other nucleophiles capable of reacting with an electrophilic center, include hydroxyl, amino, carboxyl, thiol groups, active methylene and the like.

For instance, the above polymer can be prepared to carry component U as a functional group for attachment to a target molecule, where the functional group is acrylate, aldehyde, ketone, aminooxy, amine, carboxylic acid, ester, thioester, halogen, thiol, cyanoacetate, dipalmitoyl phosphatidylethanolamine, distearoyl phosphatidylethanolamine, epoxide, hydrazide, azide, isocyanate, maleimide, methacrylate, nitrophenyl carbonate, orthopyridyl disulfide, silane, sulfhydryl, vinyl sulfones, succinimidyl glutarate, succinimidyl succinate, succinic acid, tresylate and the like. U also may be provided in an activatable form, e.g., a carboxylic acid that can be converted to an active ester thereof that is capable of reacting with a nucleophile such as an amine.

In a preferred embodiment, U is a residue of a unique functional group that is selectively reactive with a unique functional group on the target molecule. This aspect of the invention embodies the principles of peptide synthesis (protecting group strategies) and chemical ligation (partial or no protecting group strategies) as discussed above in Section II. Thus, U can represent a residue of a wide range of functional groups, such as those described above. Preferred U groups are amenable to amine capture strategies (e.g., ligation by hemiaminal formation, by imine formation, and by Michael addition), thiol capture strategies (e.g., ligation by mercaptide formation, by disulfide exchange), native chemical ligation strategies (e.g., ligation by thioester exchange involving cysteine or thiol contain side-chain amino acid derivative), and orthogonal ligation coupling strategies (e.g., ligation by thiazolidine formation, by thioester exchange, by thioester formation, by disulfide exchange, and by amide formation)(See, e.g., Coltart, D M., Tetrahedron (2000) 56:3449–3491). A particularly preferred U comprises a residue of a unique functional group employed in an aqueous compatible chemical ligation chemistry such as described above in Section II. Accordingly, U can be a functional group capable of forming a bond selected from the group consisting of carbonate, ester, urethane, orthoester, amide, amine, oxime, imide, urea, thiourea, thioether, thiourethane, thioester, ether, thaizolidine, hydrazone, oxazolidine and the like. Preferred bonds are oxime and amide bonds.

As noted above, B is a branching core moiety having three or more arms, and may be present or absent. When B is present, one arm is joined to U or a spacer or linker attached to U, and each other arm is joined to a Polymer or a spacer or linker attached to a Polymer. Examples of branching cores B include, but are not limited to, amino, amide, carboxylic, and combinations thereof. These include oligoamides of lysine and the like, or oligomers prepared from alkanediamines and acrylic acid ("polyamidoamines"), the later providing a net positive charge in the branching core. (See, e.g., Zeng et al., J. Pept. Sci. (1996) 2:66–72; Rose et al., Bioconjugate Chem., (1996) 7(5):552–556; NovoBiochem Catalog and Peptide Synthesis Handbook, Laufelfingen, 2001; Wells et al., Biopolymers (1998) 47:381–396; Mahajan et al., (1999) 40:4909–49–12; Judson et al. (1998) 39:1299–1302; Swali et al., (1997) 62:4902–4903; U.S. Pat. Nos. 5,932,462, 5,919,455, 5,643,575, 5,681,567). Many other different branching cores can be used and are suitable for this purpose, including substituted diamines, substituted diacids, alkyl acids such as glycerol and other moieties having three or more functional or activatable groups including multivalent alkyl, aryl, heteroalkyl, heteroaryl, and alkoxy moities and the like, and oligosaccharides (e.g., Nierengarten et al., Tetrahedron Lett. (1999) 40:5681–5684; Matthews et al., Prog. Polym. Sci. (1998) 1–56; Suner et al., Macromolecules (2000) 33:253; Fischer et al., Angew. Chem. Int. Ed. (1999) 38:884; Sunder et al., Adv. Mater. (2000) 12:235; Mulders et al., Tetrahedron Lett. (1997) 38:631–634; Mulders et al., Tetrahedron Lett. (1997) 38:30–3088; and Turnbull et al., Chembiocehm (2000) 1(1): 70–74). The most preferred branching core linked to the Polymer component is joined by amide bonds.

Preferred branching cores emanate from amino, carboxylic or mixed amino and carboxylic functionalities. Examples of preferred branching cores are lysine amino cores, aspartic or glutamic acid branching cores, and gamma-glutamic acid branching cores, respectively. Moreover, preferred branched polymer constructs are those in which branching emanates from a single branching core, such as an oligoamide or polyamidoamine core. However, other classes of branched constructs can be employed, such as worm-like structures in which the branching emanates from a sequence of multiple branching cores distributed along a polymer backbone (Schlüter et al., Chem. Int. Ed. (2000) 39:864). Depending on the chemical composition and/or the bulkiness of polymer backbone and repeat units, the resulting worm-like structures can be designed to be water soluble or prone to induce liquid crystalline organization (Ouali et al., Macromolecules (2000) 33:6185), which can be advantageous for delivery applications, stability and duration of action. As with the other branched polymer constructs of the invention, the worm-like constructs are made to contain a pendant functional group comprising U.

The Polymer component, or one or more of the spacers or linkers, may include polymer chains or interspaced linkers or bonds that are biostable or biodegradable, for example as discussed above in Section I. As also noted above in Section I, component J* is a residue of pendant group having a net charge under physiological conditions selected from the group consisting of negative, positive and neutral. The most preferred is where J* comprises an ionizable carboxylate moiety and has a net negative charge under physiological conditions. The components s1, s2, and s3 are spacer or linker moieties that may be the same or different, and may be individually present or absent, such as those discussed in Section I. Most preferably the spacer or linker comprises a polymer chain, where the spacer or linker comprises one or more repeat units of the formula —[CO—X—CO—NH—Y—NH]$_n$-.

IV. Preferred Polymer-Modified Synthetic Bioactive Proteins of the Invention

As noted above, polymer-modified synthetic cytokines and chemotactic cytokines comprise particularly preferred examples the invention. More preferred cytokines are glycoproteins. Many such cytokines are glycoproteins and include, for example, many of the interleukins, interferons, growth factors, chemokines and the like. By way of example, cytokines such as EPO, TPO, GCSF, GM-CSF, IL-1, IL-2, IL-3, IL-4, IL-5, IL-6, IL-7, IL-9, IL-10, IL-12, IL-13, IL-14, IL-15, IFα-II, IF-γ, LIL, IF-beta, nerve growth factor, and Rantes and many other chemokines are glycoproteins, and the glycosylation sites of these and other such proteins are known.

EPO is a particularly preferred example of a protein whose amino acid sequence can be used to aid in the design of a polymer-modified synthetic bioactive protein having erythropoiesis-stimulating activity. Colony-stimulating factors and RANTES also comprise particularly preferred examples of proteins whose amino acid sequence can be used to aid in the design of a synthetic bioactive protein within the ambit of the present invention.

EPO is the principal factor responsible for the regulation of red blood cell production during steady-state conditions and for accelerating recovery of red blood cell mass following hemorrhage (Jelkmann, W. (1992) Physiol. Reviews 72:449; Krantz, S. B. (1991) Blood 77:419; Porter, D. L. and M. A. Goldberg (1993) Exp. Hematol. 21:399; Nissenson, A. R. (1994) Blood Purif. 12:6). The circulating form of human EPO is a 165 amino acid (aa) glycoprotein with a molecular weight of approximately 30,000 (Sawyer, S. T. et al. (1994) Hematol. Oncol. Clinics NA 8:895; Jacobs, K. J. et al. Nature (1985) 313:806; Lin, F-K. et al. Proc. Natl. Acad. Sci. USA (1985) 82:7580). Although the cDNA for EPO predicts a molecule with 166 amino acid residues, the carboxy-terminal arginine is removed in a post-translational modification. There are three potential sites for N-linked glycosylation and all are filled. One O-linked carbohydrate moiety is also present. The effects of glycosylation are complex. Although unglycosylated *E. coli*-derived EPO shows full biological activity in vitro, glycosylation is apparently necessary for full activity in vivo. Thus, *E. coli*-produced and deglycosylated, naturally derived EPO show very low activity in animal studies (Krantz, S. B. (1991) Blood 77:419; Sasaki, H. et al. (1987) J. Biol. Chem. 262:12059; Losy, P. H. et al. (1960) Nature 185:102; Wojchowski, D. M. et al. Biochem. Biophys. Acta 910:224; Dordal, M. S. et al. (1985) Endocrinology 116:2293), Consistent with the above, variable glycosylation patterns show variable effects. For example, desialyated EPO exhibits both enhanced in vitro and decreased in vivo activity, an effect attributed to the exposure of galactose residues which are recognized, bound, and cleared by hepatocytes (Spivak, J. L. and B. B. Hogans (1989) Blood 73v:90; Goldwasser, E. et al. (1974) J. Biol. Chem. 249:4202). The branching pattern of fully sialyated EPO also makes a difference in biological activity. Predominantly tetra-antennary branched EPO shows activity equivalent to "standard" EPO, while predominantly bi-anternnary branched EPO shows threefold more activity in vitro but only 15% of normal activity in vivo (Takeuchi, M. et al. (1989) Proc. Natl. Acad. Sci. USA 86:7819). Studies have indicated that only N-linked, and not O-linked sugars, are important in EPO functioning (Higuchi, M. et al. (1992) J. Biol. Chem. 267:770319).

In a particularly preferred embodiment, the synthetic bioactive proteins of the present invention comprise a polymer-modified synthetic erythropoiesis stimulating protein. As used herein, an erythropoiesis stimulating protein is a protein that mediates the production of red blood cells. The erythropoiesis stimulating bioactivity of a protein may be determined by any of a variety of means, such as by following erythropoiesis after in vivo administration, by assaying the capacity of the protein to mediate the proliferation of EPO-dependent cell lines, etc.

A preferred erythropoiesis stimulating protein is mammalian, most preferably human, EPO and its analogs. (See. e.g., U.S. Pat. Nos. 5,856,298; 5,955,422; 8,888,772; 5,858,347; 5,614,184; 5,457,089; and 6,077,939; and WO00/32772). Erythropoietin is predominantly synthesized and secreted by tubular and juxtatubular capillary endothelial and interstitial cells of the kidney. Chronic kidney disease causes the destruction of EPO-producing cells in the kidney. The resulting lack of EPO frequently induces anemias. The main clinical use of EPO is therefore the treatment of patients with severe kidney insufficiency (hematocrit below 0.3) who usually also receive transfusions as well as the treatment of anemic patients following chemotherapy. Typically, EPO is synthesized recombinantly in hamster ovary cells for clinical use. EPO is a relative heat- and pH-stable acidic (pI=4.5) protein of 165 amino acid residues in its mature form. EPO conveys its activity through the EPO-receptor. Approximately 40 percent of the molecular mass of EPO is due to its glycosylation. Glycosylation is an important factor determining the pharmacokinetic behavior of EPO in vivo. Non-glycosylated EPO has an extremely short biological half-life. It still binds to its receptor and may even have a higher specific activity in vitro. However, recent experiments have shown that PEGylation of EPO significantly enhances its lifetime, but significantly decreases EPO activity in a cell-based assay system.

The synthetic erythropoiesis stimulating proteins ("SEPs") of the present invention are preferably polymer-modified synthetic analogs of human urinary EPO. In a preferred embodiment, they contain one or more polymer moieties (most preferably pPEG moieties) attached to one or more peptide residue(s) through a thioether, oxime, amide or other linkage. In a highly preferred embodiment, such linkages will be at one or more of the positions that are naturally glycosylated in human urinary EPO (i.e., positions 24, 38, 83 and 126). Most preferably, the SEP molecules will have pPEG moieties at two or more of such positions. In an alternative embodiment, other protein residues may be modified by polymer moieties. The positions of modification for the synthetic bioactive proteins of the present invention include residues located in a disordered loop, region or domain of the protein, or at or near sites of potential protease cleavage. For example, polymer modifications may be introduced at one or more positions of 9, 69 and/or 125 of EPO. The total molecular weight of the SEP molecules of the present invention may vary from about 25 to about 150 kDa, and more preferably from about 30 to about 80 kDa. The molecular weight can be controlled by increasing or decreasing the number and structure of the polymer (such as pPEG) utilized for modification of a given analog. The pPEG mediated hydrodynamic MW for the larger constructs is greater than about 100 kDa. In vitro assays in cells expressing the human EPO receptor indicate that SEPs of the present invention have an ED50 that is equivalent to that of recombinantly produced glycosylated human EPO.

Figure 10:
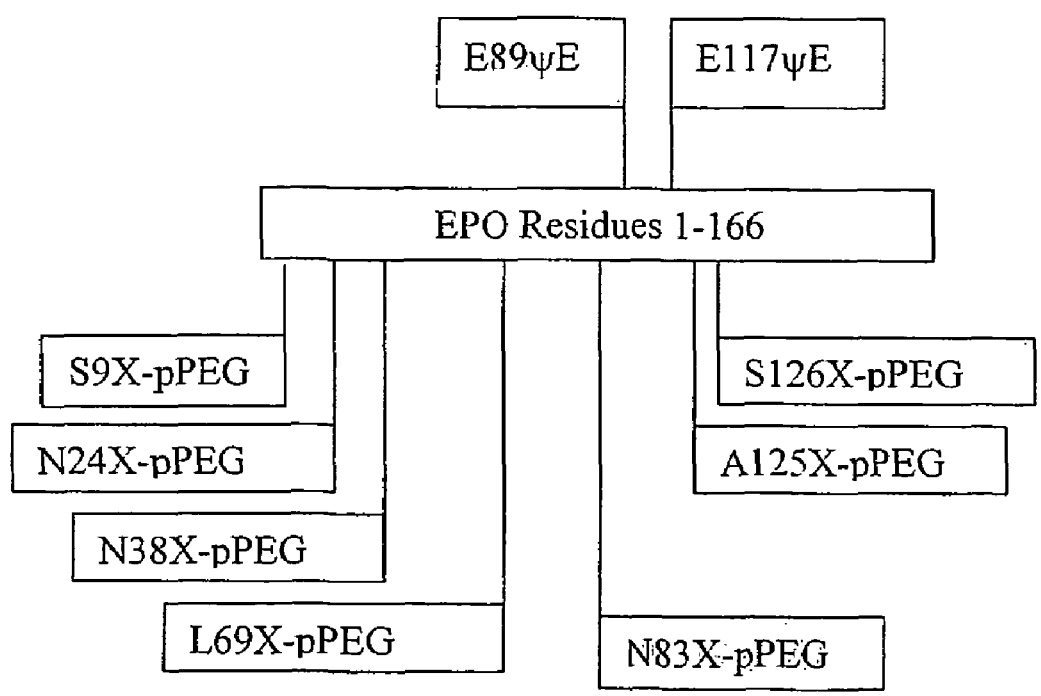
FIG. 10 depicts the basic structure of a preferred type of synthetic erythropoiesis stimulating proteins. pPEG="precision PEG"

Oxime-linked pPEG analogs are preferably constructed by attaching an aminooxy, ketone or aldehyde functionalized pPEG to the SEP protein at a non-naturally encoded amino acid bearing a side chain aminooxy, ketone or aldehyde functionality. For example, positions S9 and 117 of SEP-0 and 1 contain pseudo glutamates (a non-naturally encoded amino acid bearing a side chain of the formula —CHα—CH$_2$—S—COOH (as compared to glutamate side chain —CHα—CH$_2$—CH$_2$—COOH)). SEP analogs utilizing thioether linkages are preferably constructed to contain a thiol functionality provided by a cysteine or unnatural amino acid with a side chain bearing the thiol. FIG. 10 depicts the basic structure of one type of preferred synthetic erythropoiesis stimulating protein.

In an alternative embodiment, the SEP molecules of the present invention may comprise "circularly permuted" EPO analogs in which the natural amino and carboxy terminus of EPO have been relocated. Most preferably, such relocation will move the amino and carboxy termini to positions of low structural constraint, such as to disordered loops, etc. The disordered loop around positions 125 and 126 (relative to the native EPO residue numbering system) is an example of such a relocation site. Most preferably, such SEPs will be disulfide free, and will be chemically modified to contain polymer moieties at preselected residues.

Alternatively, the SEP molecules may have amino and carboxy termini relocated to a naturally occurring glycosylation site, or to other sites amenable to glycosylation, such as position 126 and 125. The SEP molecules may also include modifications of the amino and carboxy termini to eliminate or modify charge (such as by carboxy amidation, etc.). In a preferred example of such circularly permuted molecules, new N- and C-termini are provided by positions 126 and 125, respectively. The natural disulfide-forming cysteines at positions 7, 29, 33 and 161 are preferably replaced by the non-naturally encoded amino acid, L-α-N-butyric acid (Aba), which cannot form disulfide bridges. Residues R166, E37 and V82 are preferably replaced with alanines to improve production. Also, an additional cysteine is preferably inserted between positions 1 and 166 relative to the native EPO number scheme, which is numbered below as '0'. The resulting molecule contains four cysteines (at positions 126, 0, 38, and 83 (as read in the N- to C-terminal direction)), which are utilized as (1) ligation sites and (2) thioether-forming pPEG attachment sites. Optionally, a cysteine may replace A125 to provide an additional pPEG attachment site.

Figure 11:
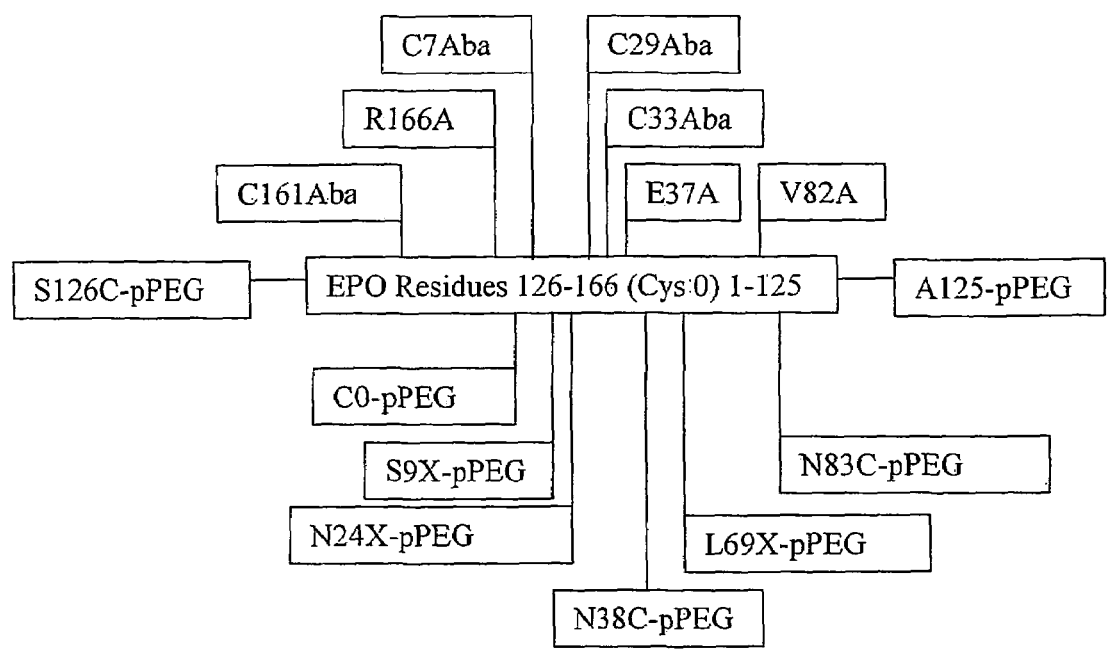
FIG. 11 shows the general structure of circularly permuted SEP analogs having a relocated amino and carboxy terminus.
Figure 14A:
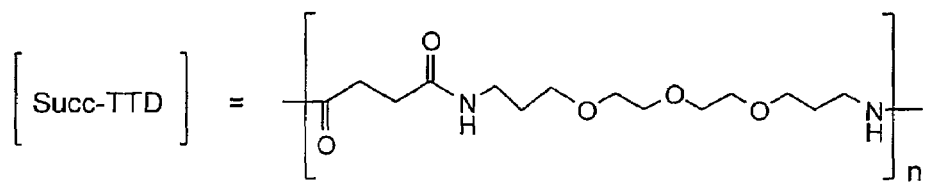
FIG. 14 shows a structure of a preferred water-soluble polymer, and various linear and branched constructs thereof.
Figure 14B:
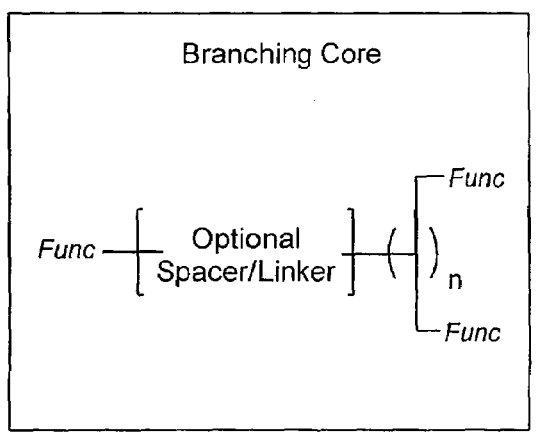
Figure 14C:
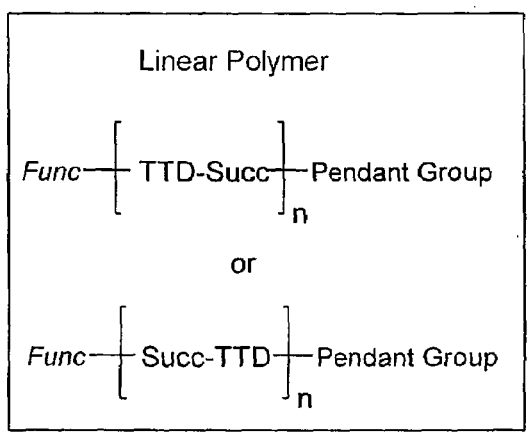
Figure 14D:
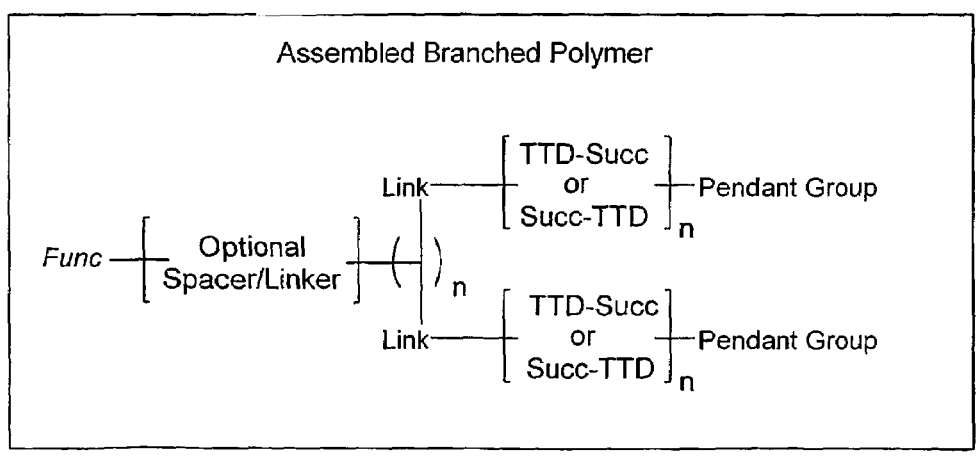

The total molecular weight of such SEP molecules of the present invention may vary from about 25 to about 150 kDa, and more preferably from about 30 to about 80 kDa. The molecular weight can be controlled by increasing or decreasing the number and structure of the polymer (such as pPEG) utilized for modification of a given analog. The pPEG mediated hydrodynamic MW for the larger constructs is greater than 100 kDa. Optional pPEG attachment sites are located at positions 125, 9, and 24 (as read in the N- to C-terminal direction). Additional SEP analog designs have alternative N- and C-termini in the disordered loop region, and/or truncate residues from the new N- and/or C-termini. The basic structure of preferred circularly permuted molecules is shown in FIG. 11.

Figure 38:
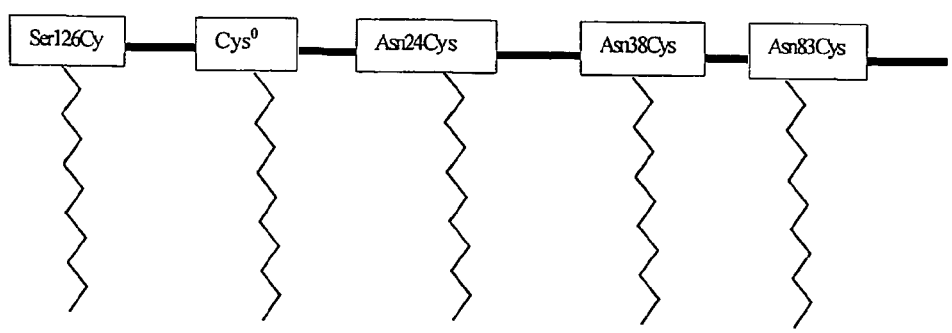
FIG. 38 shows a circularly-permuted, polymer-modified SEP construct.

For example, a sequence was designed by circularly permuting the native sequence of human EPO in the following manner: the natural N-terminal Ala$^1$ and the C-terminal Arg$^{166}$ were joined by an additional Cys residue, thus giving a polypeptide of 167 amino acids; new N- and C-terminals were created by disjoining the chain at residues125–126 of the native sequence; all the native Cys residues were replaced with L-□amino-n-butyric acid residues; and the following substitutions were made: Glu37Ala; Asn38Cys; Val82Ala; Asn83Cys; Ser126Cys; Arg166Ala (all residue numbers based on the native sequence of human EPO). Together, these design elements result in the amino acid sequence of SEP-5 as shown. The SEP-5-L28 protein was polymer-modified at Cys residues 126, 0, 24, 38, and 83 (numbering based on the human EPO sequence) with a maleimide-modified linear (TTD-Succ)$_6$ carboxylate polymer construct, by a Michael addition reaction. These changes were designed to improve synthesis and handling of the SEP-5-L28 protein. The designed sequence was made from four peptide segments, each with an N-terminal Cys residue. The chemical ligation sites were Cys$^0$, Cys$^{38}$, Cys$^{83}$. Peptides were synthesized where the C-terminal peptide was an □-carboxylate; the other three peptides were □-thioesters, and the N-terminal Cys residues were thus side chain Acm protected. Cys$^{24}$ was side chain unprotected. The segments were joined sequentially by native chemical ligation, starting with the C-terminal two segments. After the ligation, the free Cys side chain at the ligation site was reacted with the maleimide-modified linear (TTD-Succ)$_6$ carboxylate polymer construct, by a Michael addition reaction, then the Cys side chain Acm protecting group was removed, and ligation of the next segment and polymer modification performed in similar fashion. After removal of the Acm group, ligation of the next (fourth) segment was performed, the final Acm group was removed and polymer modification was performed in similar fashion giving the circularly-permuted, polymer-modified SEP construct described above and shown in FIG. 38.

In an alternative embodiment, the synthetic bioactive proteins of the present invention are a mammalian, most preferably human C-GSF. G-CSF induces the rapid proliferation and release of neutrophilic granulocytes to the blood stream, and thereby provides therapeutic effect in fighting infection. The human GCSF protein is 174 amino acids in length (Patent: EP 0459630 (Camble,R. et al.), and variants of its sequence have been isolated. (See, e.g., U.S. Pat. Nos. 6,004,548; 4,810,643; 5,218,092; 5,214,132; 5,416,195; and 5,580,755) The protein has four cysteine residues and an O-glycosylation site at threonine position 133.

In one embodiment of such a synthetic GCSF molecules, the amino acid sequence of the molecule can be altered, relative to the sequence of native GCSF, so as to contain natural, or more preferably, non-naturally encoded, hydrophobic residues at one or more of positions 1, 2 or 3. Optionally, such molecules will be further modified to contain an additional natural, or more preferably, non-naturally encoded, hydrophobic residues at position 5 of GCSF, and/or at positions 173 and/or 174.

In a further preferred embodiment the synthetic GCSF molecules will be polymer-modified (preferably pPEG) at one or more of positions 63, 64 and/or 133 and/or at one or more of positions 1 and 174. The pPEG polymers may be linear or branched, charged, uncharged, or mixed; and may have a molecular weight range of from about 5 to about 80 kDa, and more preferably, from about 40 to about 70 kDa pPEG total MW contribution depending on the number and structure of pPEGs utilized for modification. The hydrodynamic radius exhibits a larger MW effect in vivo (for example, a 10 kDa branched pPEG exhibits an effective MW of about 55 kDa). The estimated pPEG mediated hydrodynamic MW is greater than 100 kDa.

For analogs utilizing oxime linkage, the pPEG is preferably attached to non-naturally encoded residues bearing a side chain aminooxy, ketone or aldehyde functionality. For analogs utilizing thioether linkage, the pPEG is preferably attached to a cysteine or unnatural amino acid with a side chain bearing a thiol. For analogs utilizing amide linkage, the pPEG is attached to a natural or unnatural amino acid bearing a reactive side chain amine.

The basic structure of the synthetic bioactive GCSF proteins is shown in FIG. 12. In the figure, "J" designates a non-naturally encoded residue having a hydrophobic side chain.

The bioactivity of such polymer-modified synthetic bioactive GCSF proteins may be assayed by conventional means, such as by assaying for their capacity to mediate the proliferation of a factor-dependent human or mouse cell line (e.g., NFS60 cell line), or by measuring neutrophil stimulation, half-life, and immunogenicity in vivo, either with or without a delivery system targeting >20 day half-life/release).

In an alternative embodiment, the synthetic bioactive proteins of the present invention are a mammalian, most preferably human chemokine, RANTES. RANTES blocks entry of M-tropic HIV strains through the primary receptor CCR5, and also down-modulates inflammation pathways involved in asthma, transplant rejection and wound healing (Kalinkovich A, et al., Immunol Lett. (1999) 68:281–287). The synthetic RANTES molecules of the present invention preferably differ from the RANTES chemokine in being chemically modified such that: (1) the N-terminal serine found at position 1 of RANTES 1–68 is substituted with an n-nonanoyl ("NNY") group; and (2) the tyrosine at position 3 is substituted with a non-naturally encoded amino acid having a hydrophobic side chain. Such compounds have been found to be extremely potent, possessing ED50 in the pM range, compared to the mM range for recombinant "Met-RANTES 1–68".

Potent RANTES analogs have been created having one or more additional changes to those noted above, such as replacement of the proline at position 2 with a non-naturally encoded amino acid having a hydrophobic side chain, and by the attachment of a fatty acid to the C-terminus of the molecule. Receptor specificity has been improved in combination with potency by modifications to the N-loop region corresponding to RANTES residues 12–20. In a further preferred embodiment, the synthetic RANTES molecules of the invention incorporate a polymer moiety (such as pPEG, or nonanoy ("NNY") or Y3X at their N- or C-terminus to improve inter alia in vivo half-life. The pPEG moiety is preferably attached through an oxime linkage to a non-naturally encoded amino acid that is introduced at position 66, 67, 68 or linker at position 68, with preference to position 67, which is a region responsible for aggregation region. The fatty acid is preferably attached through an oxime linkage (preferably through a linker) to residue 68, such as an amino-oxy modified amino acid di- or tri-peptide linker. Other attachment chemistries may alternatively be employed. The molecular weight of the larger constructs of such synthetic RANTES analogs ranges from about 25 kDa to about 45 kDa depending upon the nature and structure of the pPEG attachment, and for the larger constructs have a pPEG mediated hydrodynamic MW of greater than 60 kDa. The structure of preferred synthetic RANTES analogs is shown in FIG. 13.

V. Pharmaceutics

The polymer-modified synthetic bioactive proteins of the present invention may be employed as pharmaceutical agents to effect the treatment of diseases and conditions. Most preferably, when administered to a patient or individual in need of therapy, such synthetic bioactive polypeptides and/or proteins will be administered using a drug delivery system. The uses such a system enables a drug to be presented to the patient in a manner that makes it acceptable for them and enhances the effectiveness of the desired bioactivity. The purposes of the present invention, preferred drug delivery systems include systems capable of administering polypeptides or proteins buyout oral, nasal, or inhalation routes, or intramuscularly, subcutaneously, transdermally, intravenously, intraurally or intraocularly.

Such drug delivery systems may include formulations that provide site-specific release, or that enhance protection for the intestinal mucosa. Suitable formulations include: dry powder formulations, delivery via viral particle encapsulation, liposome encapsulation, transdermal patches, electrically aided transport (electroporation therapy) and polymer/niazone conjugation.

In a preferred embodiment, such drug delivery devices will respond to changes in the biological environment and deliver—or cease to deliver—drugs based on these changes. A range of materials have been employed to control the release of drugs and other active agents.: poly(urethanes), poly(siloxanes), poly(methyl methacrylate), poly(vinyl alcohol) for hydrophilicity and strength, poly(ethylene), poly(vinyl pyrrolidone), poly(2-hydroxy ethyl methacrylate), poly(n-vinyl pyrrolidone), poly(methyl methacrylate), poly(vinyl alcohol), poly(acrylic acid), polyacrylamide, poly(ethylene-co-vinyl acetate), poly(ethylene glycol), poly(methacrylic acid), etc. In a further preferred embodiment, biodegradeable polymers will be employed to facilitate drug delivery. Such polymers include polylactides (PLA), polyglycolides (PGA), poly(lactide-co-glycolides) (PLGA), polyanhydrides, and polyorthoesters. Drug delivery devices, and methods for their use are described in U.S. Pat. Nos. 6,072,041; 6,041,253; 6,018,678; 6,017,318; 6,002,961; 5,879,712; 5,849,331; 5,792,451; 5,783,212; 5,766,633; 5,759,566; 5,690,954; 5,681,811; 5,654,000; 5,641,511; 5,438,040; 4,810,499; and 4,659,558.

Accordingly, another aspect of the invention relates to pharmaceutical compositions and methods of treating a mammal in need thereof by administering therapeutically effective amounts of compounds comprising the polymer-modified synthetic bioactive proteins of the invention, or pharmaceutically acceptable salts thereof. By "pharmaceutically acceptable salt" is intended to mean a salt that retains the biological effectiveness and properties of the polypeptides of the invention and which are not biologically or otherwise undesirable. Salts may be derived from acids or bases. Acid addition salts are derived from inorganic acids, such as hydrochloric acid, hydrobromic acid, sulfuric acid (giving the sulfate and bisulfate salts), nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, salicylic acid, p-toluenesulfonic acid, and the like. Base addition salts may be derived from inorganic bases, and include sodium, potassium, lithium, ammonium, calcium, magnesium salts, and the like. Salts derived from organic bases include those formed from primary, secondary and tertiary amines, substituted amines including naturally-occurring substituted amines, and cyclic amines, including isopropylamine, trimethylamine, diethylamine, triethylamine, tripropylamine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, N-ethylpiperidine, and the like. Preferred organic bases are isopropylamine, diethylamine, ethanolamine, piperidine, tromethamine, and choline.

The term "treatment" as used herein covers any treatment of a disease in a mammal, particularly a human, and includes: (i) preventing the disease from occurring in a subject which may be predisposed to the disease but has not yet been diagnosed as having it; (ii) inhibiting the disease, i.e. arresting its development; or (iii) relieving the disease, i.e. causing regression of the disease.

By the term "a disease state in mammals that is prevented or alleviated by treatment with a protein antagonist or agonist" as used herein is intended to cover all disease states which are generally acknowledged in the art to be usefully treated with protein inhibitors in general, and those disease states which have been found to be usefully prevented or alleviated by treatment with the specific compounds of the invention. These include, by way of illustration and not limitation, asthma, allergic rhinitis, atopic dermatitis, viral diseases, atheroma/atheroschleosis, rheumatoid arthritis and organ transplant rejection.

As used herein, the term "therapeutically effective amount" refers to that amount of a polymer-modified synthetic bioactive protein which, when administered to a mammal in need thereof, is sufficient to effect treatment (as defined above), for example, as an anti-inflammatory agent, anti-asthmatic agent, an immunosuppressive agent, or anti-autoimmune disease agent to inhibit viral infection in mammals. The amount that constitutes a "therapeutically effective amount" will vary depending on the protein derivative, the condition or disease and its severity, and the mammal to be treated, its weight, age, etc., but may be determined routinely by one of ordinary skill in the art with regard to contemporary knowledge and to this disclosure. As used herein, the term "q.s." means adding a quantity sufficient to achieve a stated function, e.g., to bring a solution to a desired volume (e.g., 100 mL).

The polymer-modified synthetic bioactive proteins of this invention and their pharmaceutically acceptable salts, i.e., the active ingredient, are administered at a therapeutically effective dosage, i.e., that amount which, when administered to a mammal in need thereof, is sufficient to effect treatment, as described above. Administration of the synthetic bioactive proteins described herein can be via any of the accepted modes of administration for agents that serve similar utilities. As used herein, the terms "polymer-modified synthetic bioactive proteins of this invention", "pharmaceutically acceptable salts of the polypeptides of the invention" and "active ingredient" are used interchangeably.

The level of the polymer-modified synthetic bioactive proteins in a formulation can vary within the full range employed by those skilled in the art, e.g., from about 0.01 percent weight (% w) to about 99.99% w of the protein antagonist or agonist based on the total formulation and about 0.01% w to 99.99% w excipient. More typically, the polymer-modified synthetic bioactive proteins will be present at a level of about 0.5% w to about 80% w.

While human dosage levels have yet to be optimized for the polymer-modified synthetic bioactive proteins of the invention, generally, the amount of compound administered will, of course, be dependent on the subject and the disease state targeted for prevention or alleviation, the nature or severity of the affliction, the manner and schedule of administration and the judgment of the prescribing physician. Such use optimization is well within the ambit of those of ordinary skill in the art.

Administration can be via any accepted systemic or local route, for example, via parenteral, oral (particularly for infant formulations), intravenous, nasal, bronchial inhalation (i.e., aerosol formulation), transdermal or topical routes, in the form of solid, semi-solid or liquid or aerosol dosage forms, such as, for example, tablets, pills, capsules, powders, liquids, solutions, emulsion, injectables, suspensions, suppositories, aerosols or the like. The polymer-modified synthetic bioactive proteins of the invention can also be administered in sustained or controlled release dosage forms, including depot injections, osmotic pumps, pills, transdermal (including electrotransport) patches, and the like, for the prolonged administration of the polypeptide at a predetermined rate, preferably in unit dosage forms suitable for single administration of precise dosages. The compositions will include a conventional pharmaceutical carrier or excipient and a protein antagonist or agonist of the invention and, in addition, may include other medicinal agents, pharmaceutical agents, carriers, adjuvants, etc. Carriers can be selected from the various oils, including those of petroleum, animal, vegetable or synthetic origin, for example, peanut oil, soybean oil, mineral oil, sesame oil, and the like. Water, saline, aqueous dextrose, and glycols are preferred liquid carriers, particularly for injectable solutions. Suitable pharmaceutical carriers include starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like. Other suitable pharmaceutical carriers and their formulations are described in "Remington's Pharmaceutical Sciences" by E. W. Martin.

If desired, the pharmaceutical composition to be administered may also contain minor amounts of non-toxic auxiliary substances such as wetting or emulsifying agents, pH buffering agents and the like, such as for example, sodium acetate, sorbitan monolaurate, triethanolamine oleate, etc.

Although more of the active ingredient may be required, oral administration can be used to deliver the polymer-modified synthetic bioactive proteins of the invention using a convenient daily dosage regimen, which can be adjusted according to the degree of prevention desired or in the alleviation of the affliction. For such oral administration, a pharmaceutically acceptable, non-toxic composition is formed by the incorporation of any of the normally employed excipients, such as, for example, pharmaceutical grades of mannitol, lactose, starch, povidone, magnesium stearate, sodium saccharine, talcum, cellulose, croscarmellose sodium, glucose, gelatin, sucrose, magnesium carbonate, and the like. Such compositions take the form of solutions, suspensions, dispersible tablets, pills, capsules, powders, sustained release formulations and the like. Oral formulations are particularly suited for treatment of gastrointestinal disorders. Oral bioavailablity for general systemic purposes can be adjusted by utilizing excipients that improve uptake to systemic circulation, such as formulation comprising acetylated amino acids. See, e.g., U.S. Pat. Nos. 5,935,601 and 5,629,020.

The compositions may take the form of a capsule, pill or tablet and thus the composition will contain, along with the active ingredient, a diluent such as lactose, sucrose, dicalcium phosphate, and the like; a disintegrant such as croscarmellose sodium, starch or derivatives thereof; a lubricant such as magnesium stearate and the like; and a binder such as a starch, polyvinylpyrrolidone, gum acacia, gelatin, cellulose and derivatives thereof, and the like.

Liquid pharmaceutically administrable compositions can, for example, be prepared by dissolving, dispersing, etc. a polymer-modified synthetic bioactive proteins of the invention (about 0.5% to about 20%) and optional pharmaceutical adjuvants in a carrier, such as, for example, water, saline, aqueous dextrose, glycerol, glycols, ethanol, preservatives and the like, to thereby form a solution or suspension. If desired, the pharmaceutical composition to be administered may also contain minor amounts of nontoxic auxiliary substances such as wetting agents, suspending agents, emulsifying agents, or solubilizing agents, pH buffering agents and the like, for example, sodium acetate, sodium citrate, cyclodextrine derivatives, polyoxyethylene, sorbitan monolaurate or stearate, etc. Actual methods of preparing such dosage forms are known, or will be apparent, to those skilled in this art; for example, see Remington's Pharmaceutical Sciences, Mack Publishing Company, Easton, Pa. The composition or formulation to be administered will, in any event, contain a quantity of the active ingredient in an amount effective to prevent or alleviate the symptoms of the subject being treated. For oral administration to infants, a liquid formulation (such as a syrup or suspension) is preferred.

For a solid dosage form containing liquid, the solution or suspension, in for example propylene carbonate, vegetable oils or triglycerides, is preferably encapsulated in a gelatin capsule. For a liquid dosage form, the solution, e.g. in a polyethylene glycol, may be diluted with a sufficient quantity of a pharmaceutically acceptable liquid carrier, e.g. water, to be easily measured for administration.

Alternatively, liquid or semi-solid oral formulations may be prepared by dissolving or dispersing the active ingredient in vegetable oils, glycols, triglycerides, propylene glycol esters (e.g. propylene carbonate) and the like, and encapsulating these solutions or suspensions in hard or soft gelatin capsule shells.

In applying the polymer-modified synthetic bioactive proteins of this invention to treatment of the above conditions, administration of the active ingredients described herein are preferably administered parenterally. Parenteral administration is generally characterized by injection, either subcutaneously, intramuscularly or intravenously, and can include intradermal or intraperitoneal injections as well as intrasternal injection or infusion techniques. Injectables can be prepared in conventional forms, either as liquid solutions or suspensions, solid forms suitable for solution or suspension in liquid prior to injection, as emulsions or in biocompatible polymer-based microspheres (e.g., liposomes, polyethylene glycol derivatives, poly(D,C)lactide and the like). Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents, solubility enhancers, protein carriers and the like, such as for example, sodium acetate, polyoxyethylene, sorbitan monolaurate, triethanolamine oleate, cyclodextrins, serum albumin etc.

The polymer-modified synthetic bioactive proteins of the present invention can be administered parenterally, for example, by dissolving the compound in a suitable solvent (such as water or saline) or incorporation in a liposomal formulation followed, by dispersal into an acceptable infusion fluid. A typical daily dose of a polypeptide of the invention can be administered by one infusion, or by a series of infusions spaced over periodic intervals. For parenteral administration there are especially suitable aqueous solutions of an active ingredient in water-soluble form, for example in the form of a water-soluble salt, or aqueous injection suspensions that contain viscosity-increasing substances, for example sodium carboxymethylcellulose, sorbitol and/or dextran, and, if desired, stabilizers. The active ingredient, optionally together with excipients, can also be in the form of a lyophilisate and can be made into a solution prior to parenteral administration by the addition of suitable solvents.

A more recently devised approach for parenteral administration employs the implantation of a slow-release or sustained-release system, such that a constant level of dosage is maintained. See, e.g., U.S. Pat. Nos. 3,710,795, 5,714,166 and 5,041,292, which are hereby incorporated by reference.

The percentage of the active ingredient contained in such parental compositions is highly dependent on the specific nature thereof, as well as the activity of the polypeptide and the needs of the subject. However, percentages of active ingredient of 0.01% to 10% in solution are employable, and will be higher if the composition is a solid which will be subsequently diluted to the above percentages. Preferably the composition will comprise 0.02–8% of the active ingredient in solution.

Another method of administering the polymer-modified synthetic bioactive proteins of the invention utilizes both a bolus injection and a continuous infusion.

Aerosol administration is an effective means for delivering the polymer-modified synthetic bioactive proteins of the invention directly to the respiratory tract. Some of the advantages of this method are: 1) it circumvents the effects of enzymatic degradation, poor absorption from the gastrointestinal tract, or loss of the therapeutic agent due to the hepatic first-pass effect; 2) it administers active ingredients which would otherwise fail to reach their target sites in the respiratory tract due to their molecular size, charge or affinity to extra-pulmonary sites; 3) it provides for fast absorption into the body via the alveoli of the lungs; and 4) it avoids exposing other organ systems to the active ingredient, which is important where exposure might cause undesirable side effects. For these reasons, aerosol administration is particularly advantageous for treatment of asthma, local infections of the lung, and other diseases or disease conditions of the lung and respiratory tract.

There are three types of pharmaceutical inhalation devices, nebulizers inhalers, metered-dose inhalers and dry powder inhalers. Nebulizer devices produce a stream of high velocity air that causes the protein derivative (which has been formulated in a liquid form) to spray as a mist that is carried into the patient's respiratory tract. Metered-dose inhalers typically have the formulation packaged with a compressed gas and, upon actuation, discharge a measured amount of the polypeptide by compressed gas, thus affording a reliable method of administering a set amount of agent. Dry powder inhalers administer the polypeptide in the form of a free flowing powder that can be dispersed in the patient's air-stream during breathing by the device. In order to achieve a free flowing powder, the protein derivative is formulated with an excipient, such as lactose. A measured amount of the protein derivative is stored in a capsule form and is dispensed to the patient with each actuation. All of the above methods can be used for administering the present invention.

Pharmaceutical formulations based on liposomes are also suitable for use with the polymer-modified synthetic bioactive proteins of this invention. See, e.g., U.S. Pat. Nos. 5,631,018, 5,723,147, and 5,766,627. The benefits of liposomes are believed to be related to favorable changes in tissue distribution and pharmacokinetic parameters that result from liposome entrapment of drugs, and may be applied to the polypeptides of the present invention by those skilled in the art. Controlled release liposomal liquid pharmaceutical formulations for injection or oral administration can also be used.

For systemic administration via suppository, traditional binders and carriers include, for example, polyethylene glycols or triglycerides, for example PEG 1000 (96%) and PEG 4000 (4%). Such suppositories may be formed from mixtures containing the active ingredient in the range of from about 0.5 w/w % to about 10 w/w %; preferably from about 1 w/w % to about 2 w/w %.

All publications and patent applications mentioned in this specification are herein incorporated by reference to the same extent as if each individual publication or patent application was specifically and individually indicated to be incorporated by reference. The discussion of the background to the invention herein is included to explain the context of the invention. This is not to be taken as an admission that any of the material referred to was published, known, or part of the prior art or common general knowledge anywhere in the world as of the priority date of any of the claims. Having now generally described the invention, the same will be more readily understood through reference to the following examples, which are provided by way of illustration, and are not intended to be limiting of the present invention, unless specified.

EXAMPLES

Abbreviations

Acm=acetamidomethyl thiol-protecting group [i.e. —CH$_2$NHCOCH$_3$]

AoA=aminooxyacetyl
Arg(Tos)=L-arginine(side chain N^G toluenesulfonyl-protected)
ART=absolute reticulocyte count
Asp(cHex)=L-aspartic acid(side chain cyclohexyl ester-protected)
AUC=area under the curve
Boc=tert.butoxycarbonyl
CD=circular dichroism
CDI=carbonyldiimidiazole
CHO=chinese hamster ovary
CL=clearance (mL/hr/kg)
Cmax=maximum concentration
Cys(4MeBzl)=L-cysteine(side chain (4-methyl)benzyl-protected)
Cys(Acm)=L-cysteine(side chain acetamidomethyl [i.e. —$CH_2NHCOCH_3$]— protected)
DCM=dichloromethane
DIC=diisopropylcarbodiimide
DIEA=diisopropylethylamine
DMF=dimethylformamide
DMSO=dimethylsulfoxide
DPC=dodecylphosphocholine
Dpr=L-1,2diaminopropionic acid
ED50=effective dose required to reach 50% maximum effect
EDA=(4,7,10)-trioxatridecane-1,13diamine
ELISA=enzyme-linked immunoassay
EPO=erythropoietin
ES-MS=electrospray ionization mass spectrometry
FBS=fetal bovine serum
Glu(cHex)=L-glutamic acid(side chain cyclohexyl ester-protected)
GM-CSF=granulocyte-macrophage colony stimulating factor
HATU=O-(7-azabenzotriazol-1-yl)-1,1,3,3-tetramethylammonium hexafluorophosphate
HCT=hematocrit
HGB=hemoglobin
His(Dnp)=L-histidine(side chain N^{Im} dinitrophenyl-protected)
HOBT=N-hydroxybenzotriazole
HPLC=high pressure liquid chromatography
IMDM=Iscove's modified Dulbecco's medium
IPA=isopropanol.
Lev=levulinic acid
Lys(CIZ)=L-lysine(side chain 2-chlorobenzyloxycarbonyl)-protected
MBHA=4-methylbenzhydrylamine
MRT=mean residence time
MTT=4-methylTrityl
MTT=thiazolyl blue
NHS=N-hydroxysuccinimide
—$OCH_2$-Pam-resin=—O—$CH_2$—Bz—$CH_2CONHCH_2$ (copolystyrene-divinylbenzene)-resin
Pbo=4—($CH_3S(O)$—)benzyl
PBS=phosphate buffered saline
PCV=packed cell volume
RBC=red blood cell
RET=reticulocyte
rhEPO=recombinant human EPO
RSA=rat serum albumin
SDS=sodium docyl sulfate
SDS-PAGE=SDS-polyacrylamide gel electrophoresis
Ser(Bzl)=L-serine(side chain benzyl-protected)
Single letter code for amino acids: A=alanine; C=cysteine; D=aspartic acid; E=glutamic acid; F=phenylalanine; G=glycine; H=histidine; I=isolecuine; K=lysine; L=leucine; M=methionine; N=asparagine; P=proline; Q=glutamine; R=arginine; S=serine; T=threonine; V=valine; W=tryptophan; Y=tyrosine
SPPS=stepwise solid phase peptide synthesis
Succ=succinly [i.e. —$COCH_2CH_2CO$—]
TCEP=tris(2-carboxyethyl)phosphine hydrochloride
TFE=2,2,2-trifluoroethanol
Thr(Bzyl)=L-threonine(side chain benzyl-protected)
Three letter code for the amino acids: Ala=alanine; Arg=arginine; Asn=asparagine; Asp=aspartic acid; Chg=cyclohexylglycine; Cys=cysteine; Gln=glutamine; Glu=glutamic acid; Gly=glycine; His=histidine; Ile=isoleucine; Leu=leucine; Lys=lysine; Met=methionine; Phe=phenylalanine; Pro=proline; Ser=serine; Thr=threonine; Thz=4-thioproline; Trp=tryptophan; Tyr=tyrosine; Val=valine
Trp(formyl)=L-tryptophan(side chain N^{Im} formyl-protected)
TTD=(4,7,10)-trioxatridecane-1,13diamine
Tyr(BrZ)=L-tyrosine(side chain 2-bromobenyzloxycarbonyl-protected)
Vc=volume of distribution of the central compartment Example 1

Synthesis of Synthetic Erythropoiesis Stimulating Protein SEP-0

A synthetic erythropoiesis stimulating protein (SEP) was synthesized. The sequence of the full-length synthesized protein (designated "SEP-0 (1-166)") is:

```
                                         (SEQ ID NO:1)
APPRLICDSR VLERYLLEAK EAEKITTGCA EHCSLNEKIT

VPDTKVNFYA WKRMEVGQQA VEVWQGLALL SEAVLRGQAL

LVKSSQPWψP LQLHVDKAVS GLRSLTTLLR ALGAQKψAIS

PPDAASAAPL RTITADTFRK LFRVYSNFLR GKLKLYTGEA

CRTGDR
``` where Ψ denotes a non-native amino acid residue consisting of a cysteine that is carboxymethylated at the sulfhydryl group. The SEP-0 protein was synthesized in solution from four polypeptide segments:

Segment SEP-0:1 (GRFN 1711; composed of residues 1–32 of SEQ ID NO:1):
  APPRLICDSR VLERYLLEAK EAEKITTGCA EH-thioester
Segment SEP-0:2 (GRFN 1712, composed of residues 33–88 of SEQ ID NO:1):
  CSLNEKITVP DTKVNFYAWK RMEVGQQAVE VWQGLALLSE AVLRGQALLV KSSQPW-thioester (where $Cys^{33}$ is Acm protected)
Segment SEP-0:3 (GRFN 1713, composed of residues 89–116 of SEQ ID NO:1):
  CPLQLHVDKA VSGLRSLTTL LRALGAQK-thioester (where $Cys^{89}$ is Acm protected)
Segment SEP-0:4 (GRFN 1714, composed of residues 117–166 of SEQ ID NO:1):
  CAISPPDAAS AAPLRTITAD TFRKLFRVYS NFLRGKLKLY TGEACRTGDR-carboxylate (where the C-terminal cysteine ($Cys^{161}$) carries a picolyl (pico) protecting group)

The peptides SEP-0:1 and SEP-0:2 and SEP-0:3 were synthesized on a thioester-generating resin by the in situ neutralization protocol for Boc (tert-butoxycarbonyl) chemistry and stepwise solid phase peptide synthesis (SPPS) using established SPPS, side-chain protection and thioester-resin strategies (Hackeng, et al., PNAS (1999) 96: 10068–10073; and Schnolzer, et al., Int. J. Pept. Prot. Res., (1992) 40: 180–193)) on an ABI433A automated peptide synthesizer or by manual chain assembly, or ordered and acquired from commercial vendors. For instance, a standard set of Boc SPPS protecting groups was used, namely: Arg(Tos); Asp(cHex); Cys(4MeBzl) & Cys(Acm); Glu (cHex); His(DNP); Lys(CIZ); Ser(Bzl); Thr(Bzl); Trp (formyl); Tyr(BrZ); Met, Asn, Gln were side-chain unprotected. Segment SEP-0:4 was synthesized analogously on a —OCH$_2$-Pam-resin. The peptides were deprotected and simultaneously cleaved from the resin support using HF/p-cresol according to standard Boc chemistry procedure; however, for those peptides containing protecting groups not removed in HF/p-cresol, the protecting groups were retained. The peptides were purified by preparative C4 reverse-phase-high pressure liquid chromatography (HPLC). Fractions containing pure peptide were identified using ES-MS (electrospray ionization mass spectrometry), pooled and lyophilized for subsequent ligation.

Step 1: Ligation #1 Segment SEP-0:4 and segment SEP-0:3 were dissolved in TFE at 15 mM concentration. Saturated phosphate buffer (pH 7.9) containing 6 M guanidinium chloride and 1% thiophenol was added, resulting in a clear solution of the peptide segments. After ligation, the ligation mix was added to a solution of 2 ml TFE (trifluoroethanol), 6 ml 6M guanidinium chloride, 100 mM phosphate containing 25% β-mercaptoethanol and incubated for 20 minutes. The solution was acidified with a solution of 15 mg/ml TCEP (tris(2-carboxyethyl)phosphine.HCl) in glacial acetic acid and loaded onto a preparative C4 reverse-phase HPLC column (1 inch diameter). The peptides were then purified by preparative gradient reverse-phase HPLC. Fractions containing the desired ligated product SEP-0:Acm+SEP-0:3+SEP-0:4 were identified by ES-MS and pooled.

Step 2. Acm-removal #1 For Acm removal, the aqueous acetonitrile solution containing the pooled fractions of SEP-0:Acm+SEP-0:3+SEP-0:4 was diluted 1× with HPLC grade water, and solid urea was added for a final concentration of 2 molar. A threefold molar excess (relative to the total expected cysteine concentration) of a 30 mg/ml Hg(acetate)$_2$ solution in 3% aqueous acetic acid was added and the solution is stirred for one hour. The solution was then made 20% in β-mercaptoethanol, loaded onto a semi-preparative reverse-phase HPLC column and purified with a step gradient. Fractions containing the desired product SEP-0:3+SEP-0:4 were identified by ES-MS and lyophilized overnight.

Step 3: Ligation #2 Equal amounts of SEP-0:3+SEP-0:4 and SEP-0:2 were jointly dissolved in neat TFE at 15 mM concentration. 250 mM Phosphate buffer (pH 7.5) containing 6 M guanidinium chloride and 1% thiophenol was added, resulting in a clear solution of the peptide segments. After one day of ligation, the ligation mix was added to a solution of 10 ml TFE, 10 ml β-mercaptoethanol, 10 ml piperidine and 20 ml 6M guanidinium chloride, pH 4, and incubated for 20 minutes to remove any remaining protecting groups. The solution was acidified with a solution of 15 mg/ml TCEP in 20% aqueous acetic acid, loaded onto a preparative reverse-phase HPLC column and purified with a linear gradient. Fractions containing the desired ligated product SEP-0:Acm+SEP-0:2+SEP-0:3+SEP-0:4 were identified by ES-MS and lyophilized overnight.

Step 4: Carboxymethylation SEP-0:Acm+SEP-0:2+SEP-0:3+SEP-0:4 was dissolved in TFE at 15 mM concentration. A two-fold excess (v/v) of 200 mM Phosphate buffer (pH 7.9) containing 6 M guanidinium chloride was added, resulting in a clear solution of the peptide segment. A 25-fold excess of bromo-acetic acid dissolved in a minimum amount of methanol was added, and the solution was allowed to react for two hours. The solution was acidified with a solution of 15 mg/ml TCEP in 20% aqueous acetic acid, loaded onto a preparative reverse-phase HPLC column and purified with a step gradient. Fractions containing the desired carboymethylated product SEP-0:Acm+SEP-0:2+SEP-0:3+SEP-0:4+Et were identified by ES-MS and pooled.

Step 5: Picolyl Removal Zinc dust was activated in 2M HCl for 30 minutes. Peptide SEP-0:Acm+SEP-0:2+SEP-0:3+SEP-0:4+Et was dissolved in neat TFE at about 10 mg/ml concentration. The solution was diluted with 4× (v/v relative to TFE) 6M guanidinium chloride, 100 mM acetate, pH 4, containing (freshly added) 35 mg/ml L-methionine and 35 mg/ml dodecylsarcosine (i.e. sodium N-dodecanoylsarcosine). The solution was added to the activated Zn powder. The reaction was monitored at ~1 hr intervals and is complete after five hours. After completion, the supernatant was removed and the remaining Zn powder washed twice for five minutes with 6M guanidinium chloride, pH 4, 100 mM acetate containing 35 mg/ml L-methionine and 35 mg/ml dodecylsarcosine containing 20% TFE as well as once with the same solution containing 20% β-mercaptoethanol. The combined product was acidified with a solution of 15 mg/ml TCEP in 20% aqueous acetic acid, loaded onto a preparative reverse-phase HPLC column and purified with a step gradient. Fractions containing the desired modified product SEP-0:Acm+SEP-0:2+SEP-0:3+SEP-0:4+Et-Pico were identified by ES-MS and pooled.

Step 6: Acm-removal #2 The pooled solution of SEP-0:Acm+SEP-0:2+SEP-0:3+SEP-0:4+Et-Pico was diluted 3× with HPLC grade water, and solid urea was added for a final concentration of 2 molar. A threefold molar excess (relative to the total expected cysteine concentration) of a 30 mg/ml Hg(acetate)$_2$ solution in 3% aqueous acetic acid was added and the solution stirred for one hour. The solution was then made 20% in β-mercaptoethanol, loaded onto a semi-preparative reverse-phase HPLC column and purified with a step gradient. Fractions containing the desired product SEP-0:2+SEP-0:3+SEP-0:4+Et-Pico were identified by ES-MS, diluted 2× (v/v) with water containing 2× (w/w relative to peptide mass) DPC (dodecylphosphocholine) and lyophilized overnight.

Step 7: Ligation #3 Equal amounts of SEP-0:2+SEP-0:3+SEP-0:4+Et-Pico and SEP-0:1 were jointly dissolved in neat TFE at 15 mM concentration and 250 mM Phosphate buffer (pH 7.5) containing 6 M guanidinium chloride is added. To the solution 1% thiophenol was added. After one day of ligation, the ligation mix was added to a solution of 10 ml TFE, 10 ml β-mercaptoethanol, 10 ml piperidine and 20 ml 6M guanidinium chloride, pH 4, and incubated for 20 minutes to remove any remaining protecting groups. The solution was acidified with a solution of 15 mg/ml TCEP in 20% aqueous acetic acid, loaded onto a preparative reverse-phase HPLC column and purified with a linear gradient. Fractions containing the desired ligated product SEP-0 (1–166): (SEQ ID NO:1) were identified by electrospray mass spectrometry, diluted 2× (v/v) with water containing 2× (w/v relative to peptide mass) dodecylsarcosine and lyophilized.

Step 8 Folding: Full-length ligated peptide SEP-0 (1–166) was dissolved in 200 mM Tris buffer (pH 8.7) containing 6 M guanidinium chloride and 20% TFE and a ten-fold molar excess (relative to Cys residues in protein) of cysteine. This solution was dialyzed overnight against a solution of 200 mM Tris buffer (pH 8.7) containing 3 M guanidinium chloride at room temperature. The solution was then dialyzed against a solution of 200 mM Tris buffer (pH 8.7) containing 1 M guanidinium chloride at room temperature for 4 hours at 4° C. and finally against 10 mM phosphate buffer (pH 7.0) for 4 hours at 4° C. to yield the final folded product. Folding was verified by electrospray ES-MS and CD (circular dichroism) spectrometry.

Step 9 Purification. The folded polypeptide was concentrated 5× in centricon concentrator vials and loaded on to Resource S cation exchange column equilibrated at 10 mM phosphate, pH 7.0. The folded protein was eluted in a linear salt gradient to 500 mM NaCl in 10 minutes. Fractions containing the desired folded product SEP-0 (1–166) were identified by SDS-polyacrylamide gel electrophoresis (SDS-PAGE), and frozen and stored at −80° C. An analytical reverse-phase HPLC chromatogram and an ES-MS spectrum of the folded protein product as well as a CD spectrum demonstrated the presence of folded protein.

Example 2

Synthesis of Synthetic Erythropoiesis Stimulating Protein SEP-1-L30

A second synthetic erythropoiesis stimulating protein (designated SEP-1-L30) was synthesized to contain oxime-forming groups at positions 24 and 126 of SEP-0. These groups were then used to form SEP-1-L30, in which linear (EDA-Succ-)$_{18}$ carboxylate (EDA=(4,7,10)-trioxatridecane-1,13diamine, also called TTD; Succ=—CO—CH$_2$CH$_2$CO—) polymers have been joined to the protein backbone. The sequence of the full-length SEP-1 (1–166) is:

```
                                          (SEQ ID NO:2)
APPRLICDSR   VLERYLLEAK   EAEKᵒˣITTGCA   EHCSLNEKIT

VPDTKVNFYA   WKRMEVGQQA   VEVWQGLALL    SEAVLRGQAL

LVKSSQPWψP   LQLHVDKAVS   GLRSLTTLLR    ALGAQKψAIS

PPDAAKᵒˣAAPL  RTITADTFRK   LFRVYSNFLR    GKLKLYTGEA

Figure 17:
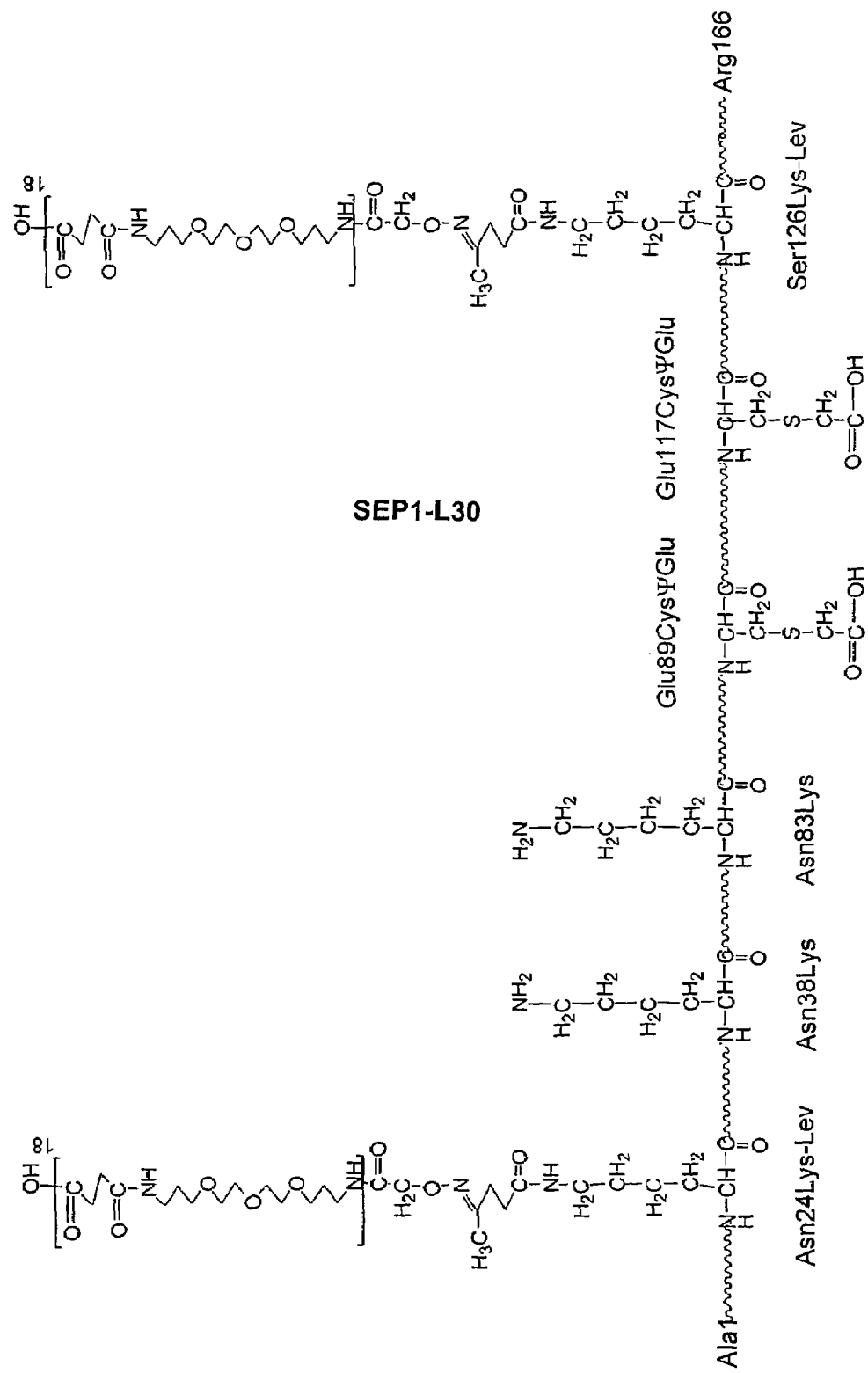
FIG. 17 depicts a synthetic cytokine designated SEP1-L30, which is a precision polymer-modified synthetic analog of human EPO prepared as described in Example 2.

CRTGDR
``` where Ψ denotes an non-native amino acid residue consisting of a cysteine that is carboxymethylated at the sulfhydryl group, and where $K^{ox}$ denotes a non-native lysine that is chemically modified at the ε-amino group with an oxime linker group coupled to a designated water-soluble polymer through an oxime bond. The structure of SEP-1-L30 also is shown in FIG. 17.

A schematic illustrating the chemical synthesis of SEP1-L30 described below is shown in FIG. 16. Briefly, in FIGS. 16A and 16B, water-soluble polymer GRFN32 (GP32) is attached to peptides SEP-1:1 and SEP-1:4 through an oxime bond-forming chemical ligation reaction. As shown, peptide SEP-1:1 bears a C-terminal Yaa group at position 32 comprising a histidine alpha-carboxyl thioester for subsequent native chemical ligation, and a non-native lysine residue at position 24 (a glycosylation site of natural human EPO) the side chain of which has been chemically modified to bear a $U_{n=1}$ group comprising an aminooxy acyl moiety. The N-terminal alanine corresponding to position 1 of the final full-length product is shown for reference. Peptide SEP-1:4 has an unprotected N-terminal Xaa group at position 117 comprising a cysteine, a $U_{n=1}$ group comprising an aminooxy acyl modified Lysine at position 126 (a glycosylation site of natural human EPO), and cysteine at position 161 (a disulfide forming cysteine) that has its side-chain thiol protected with a picolyl group. $Cys^{161}$ is protected to prevent its thioalkylation in a subsequent conversion of cysteines introduced for native chemical ligation sites (See FIG. 16D); also, a picolyl protecting group is used since its removal is orthogonal to the conditions required for removing an Acm (acetamidomethyl) protected cysteine in a first native chemical ligation reaction (See FIG. 16C). Site-specific, and exclusive attachment of the GP32 polymer constructs at positions 24 and 126 is achieved through oxime-forming chemical ligation to produce the precision polymer-modified peptides SEP-1:1+GP32 and SEP-1:4+GP32. FIG. 16C shows native chemical ligation of SEP-1:4+GP32 to a middle peptide segment SEP-1:3 and generation of SEP-1:3-SEP+1:4+GP32, the ligation site of which is at $Lys^{116}$ and $Cys^{117}$. As shown peptide SEP-1:3 comprises an N-terminal Xaa group at position 89 comprising an Acm protected cysteine, and a C-terminal Yaa group at position 116 comprising a lysine alpha-carboxyl thioester. Following native chemical ligation, the Acm protecting group is removed to prepare this ligation product for the next ligation reaction. FIG. 16D shows native chemical ligation of SEP-1:3+SEP-1:4+GP32 to a middle peptide segment SEP-1:2 and generation of SEP-1:2+SEP-1:3+SEP-1:4+GP32, the ligation site of which is at $Trp^{88}$ and $Cys^{89}$. As shown peptide SEP-1:2 comprises an N-terminal Xaa group at position 33 comprising an Acm cysteine, and a C-terminal Yaa group at position 89 comprising a tryptophan alpha-carboxyl thioester. Following native chemical ligation, the ligation product is exposed to bromoacetic acid for carboxymethylation of the side chain thiols of ligation site cysteines 89 and 117, and thus their conversion to pseudo glutamic acids. Following carboxymethylation, the Acm and Picolyl protecting groups are removed to prepare this unprotected, polymer-modified ligation product for the next ligation reaction. FIG. 16E shows native chemical ligation of SEP-1:3-SEP1:4+GP32 to peptide segment SEP-1:1+GP32 (corresponding the N-terminal segment of the full length product) and generation of the full length SEP-1-L30 product SEP-1:1+GP32+SEP-1:2+SEP-1:3+SEP-1:4+GP32, the final ligation site of which is at $His^{32}$ and $Cys^{33}$. As shown the full-length SEP-1-L30 product comprises two water-soluble polymers (G32) attached exclusively at user-defined sites, i.e., glycosylation sites corresponding to position 24 and position 126 of natural human EPO. The details of the synthesis are described below.

A. Oximation of GRFN1776 and GRFN1711 with GRFNP32

Oxime formation was performed to attach water-soluble polymers bearing an aminooxyacetyl group to peptides carrying a ketone carbonyl group. To accomplish this, the following peptide segments were synthesized:

Segment SEP-1:4 (GRFN 1776; composed of residues 117–166 of SEQ ID NO:2):
CAISPPDAAK AAPLRTITAD TFRKLFRVYS NFL-RGKLKLY TGEACRTGDR-carboxylate (where $Lys^{126}$ is modified with a levulinic acid residue at the ε-amino group, and where $Cys^{117}$ is Acm protected)

Segment SEP-1:1 (GRFN 1711, composed of residues 1–32 of SEQ ID NO:2):
APPRLICDSR VLERYLLEAK EAEKITTGCA EH-thioester (where Lys24 is modified with a levulinic acid residue)

Segment SEP-1:1 (GRFN 1711) was synthesized on a thioester-generating resin, and Segment SEP-1:4 (GRFN 1776) on a —OCH$_2$-Pam-resin as in Example 1. Lysines 24 and 126 of these two peptide segments were initially protected with an Fmoc group at the ε-amino group. After completion of the chain assembly, the Fmoc-bearing amino groups were deprotected following standard Fmoc deprotection procedures and modified by attachment of levulinic acid to each peptide resin, respectively. The peptides were then deprotected and simultaneously cleaved from the resin support as described in Example 1. The peptides were purified by preparative C4 reverse phase HPLC. Fractions containing pure peptide were identified using ES-MS, pooled and lyophilized for subsequent ligation. GRFNP32 [-(EDA-Succ)$_{18}$ carboxylate] was assembled on a Sasrin carboxyl-generating resin following standard protocols (Rose, K. et al., U.S. patent application Ser. No. 09/379,297; Rose, et al., *J Am Chem Soc.*(1999) 121: 7034). An aminooxyacetyl (AoA) moiety was attached to the N-terminal amino group of the polymer by coupling a fivefold excess of activated Boc-aminooxyacetic acid. The polymer chain was cleaved from the resin support using classic Fmoc-chemistry procedures. The polymer chain was purified by preparative C4 reverse-phase HPLC. Fractions containing pure polymer were identified using ES-MS, pooled and lyophilized for subsequent ligation.

Segment SEP-1:4 and GRFNP32 were jointly dissolved at an equimolar ratio in 50% aqueous acetonitrile containing 0.1% TFA. The solution was then lyophilized. The dried powder was dissolved and the polymer-modified peptide separated from unmodified peptide and unreacted polymer by preparative gradient C4 reverse-phase HPLC. Fractions containing the desired oximated product SEP-1:4+GP32 were identified by ES-MS and pooled and lyophilized.

Segment SEP-1:1 and GRFNP32 were jointly dissolved at an equimolar ratio in 50% aqueous acetonitrile containing 0.1% TFA. The solution was then lyophilized. The dried powder was dissolved and the polymer-modified peptide separated from unreacted polymer by preparative gradient C4 reverse-phase HPLC. Fractions containing the desired oximated product SEP-1:1+GP32 were identified by ES-MS and pooled and lyophilized.

B. Synthesis of Synthetic Erythropoiesis Stimulating Protein SEP-1-L30

SEP-1-L30 was synthesized in solution from four polypeptide segments:

Segment SEP-1:1+GP32 (GRFN 1711+GRFNP32, corresponding to residues 1–32 of SEQ ID NO:2):
  APPRLICDSR VLERYLLEAK EAEK$^{ox}$ITTGCA EH-thioester (where Lys$^{24}$ is modified at the ε-amino group with a levulinic oxime linker group that is coupled to GRFNP32 through a levulinic-aminooxyacetyl (Lev-AoA) oxime bond denoted K$^{ox}$)

Segment SEP-1:2 (GRFN 1712, corresponding to residues 33–88 of SEQ ID NO:2):
  CSLNEKIT VPDTKVNFYA WKRMEVGQQA VEVWQGLALL SEAVLRGQAL LVKSSQPW-thioester(where Cys$^{33}$ is Acm protected)

Segment SEP-1:3 (GRFN 1713, corresponding to residues 89–116 of SEQ ID NO:2):
  CP LQLHVDKAVS GLRSLTTLLR ALGAQK-thioester (where Cys$^{89}$ is Acm protected)

Segment SEP:1:4+GP32 (GRFN 1776+GRFNP32, corresponding to residues 117–166 of SEQ ID NO:2):
  CAIS PPDAAK$^{ox}$AAPL RTITADTFRK LFRVYSNFLR GKLKLYTGEA CRTGDR-carboxylate (where Lys$^{126}$ is modified at the ε-amino group with a levulinic oxime linker group that is coupled to GRFNP32 through a levulinic-aminooxycetyl (Lev-AoA) oxime bond denoted K$^{ox}$, and where the C-terminal cysteine carries a picolyl (pico) protecting group)

Synthesis of additional peptides, ligation reactions, carboxymethylation, protecting group removal reactions, folding and purification were performed as described in Example 1 to yield full-length, folded SEP-1-L30. An analytical reverse-phase HPLC chromatogram and an ES-MS spectrum of the folded protein product as well as a CD spectrum demonstrated the presence of folded protein Example 3

Synthesis of Synthetic Erythropoiesis Stimulating Protein SEP-1-L26

A third synthetic erythropoiesis stimulating protein (designated SEP-1-L26) was synthesized to contain oxime-forming groups at positions 24 and 126 of SEP-0. These groups were then used to form SEP-1-L26, in which the linear polymers (EDA-Succ)$_{18}$ carboxylate and (EDA-Succ)$_6$-amide have been joined to the protein backbone through oxime linkages at positions 24 and 126, respectively. The sequence of the full-length SEP-1 (1–166) is:

(SEQ ID No:2)
APPRLICDSR VLERYLLEAK EAEK$^{ox}$ITTGCA EHCSLNEKIT

VPDTKVNFYA WKRMEVGQQA VEVWQGLALL SEAVLRGQAL

LVKSSQPWψP LQLHVDKAVS GLRSLTTLLR ALGAQKψAIS

PPDAAK$^{ox}$AAPL RTITADTFRK LFRVYSNFLR GKLKLYTGEA

CRTGDR where Ψ denotes an non-native amino acid residue consisting of a cysteine that is carboxymethylated at the sulhydryl group, and where K$^{ox}$ denotes a non-native lysine that is chemically modified at the c-amino group with an oxime linker group coupled to a designated water-soluble polymer through an oxime bond.

Figure 18:
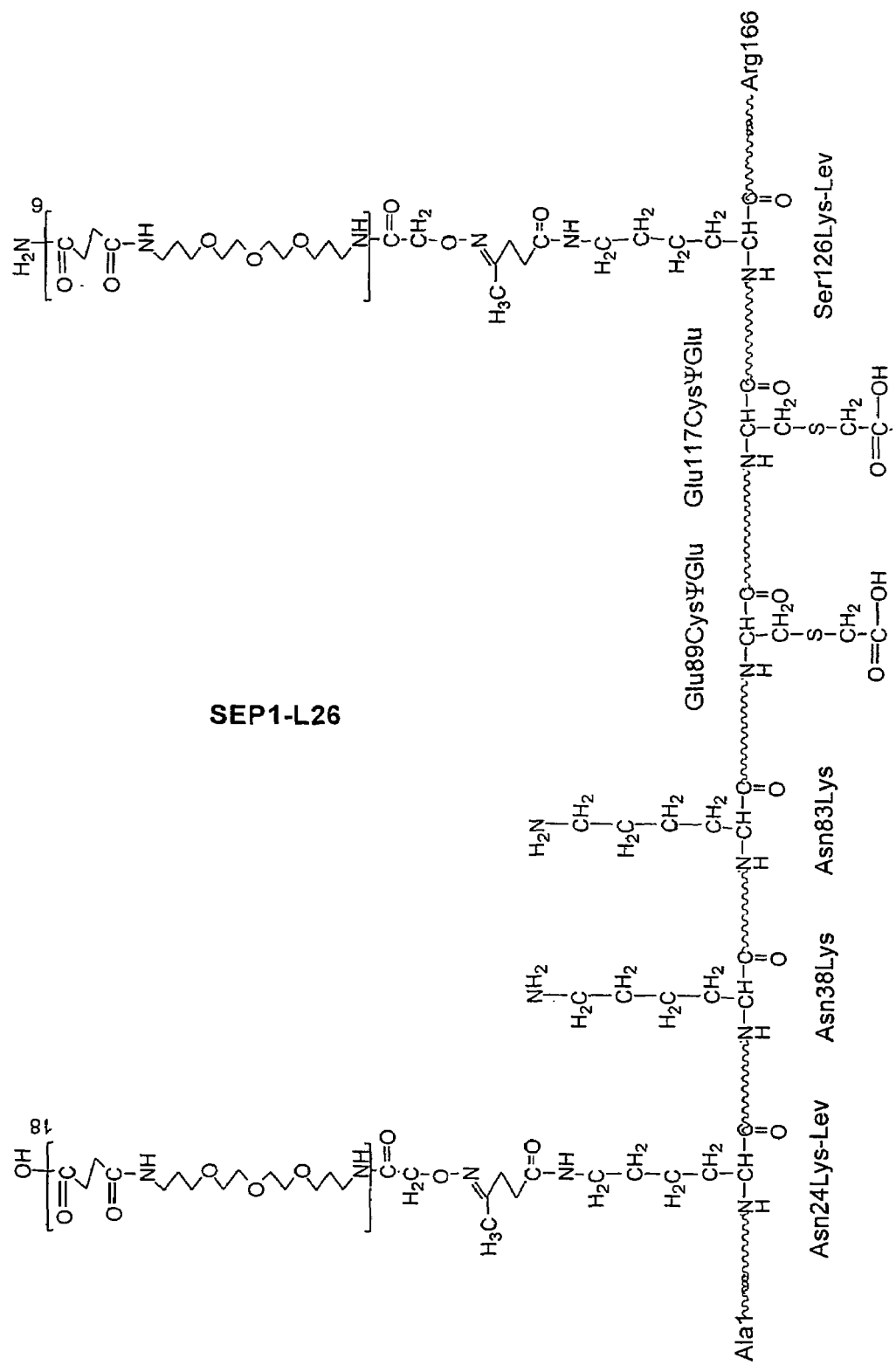
FIG. 18 depicts a synthetic cytokine designated SEP1-L26, which is a precision polymer-modified synthetic analog of human EPO prepared as described in Example 3.

In contrast to SEP-1-L30, the SEP-1-L26 construct was designed to bear a smaller and uncharged water-soluble polymer attached at position 126. The polymer attached at position 24 was the same as in SEP-1-L30. Assembly of the full-length product was as described in Example 2. The structure of SEP-1-L26 is shown in FIG. 18.

A. Oximation of GRFN1776 With GRFNP6 and Oximation of GRFN1711 With GRFNP32

Oxime formation was performed to attach water-soluble polymers bearing an aminooxyacetyl group to peptides carrying a ketone carbonyl group. To accomplish this, the following peptide segments were synthesized:

Segment SEP-1:4 (GRFN 1776; composed of residues 117–166 of SEQ ID NO:2):
  CAISPPDAAK AAPLRTITAD TFRKLFRVYS NFL$_{126}$-RGKLKLY TGEACRTGDR-carboxylate (where Lys$^{126}$ is modified with a levulinic acid residue at the ε-amino group, and where Cys$^{117}$ is Acm protected)

Segment SEP-1:1 (GRFN 1711, composed of residues 1–32 of SEQ ID NO:2):
  APPRLICDSR VLERYLLEAK EAEKITTGCA EH-thioester (where Lys$^{24}$ is modified with a levulinic acid residue)

Segment SEP-1:1 (GRFN 1711) was synthesized on a thioester-generating resin, and Segment SEP-1:4 (GRFN 1776) on a —OCH$_2$-Pam-resin as in Example 1. Lysines 24 and 126 of these two peptide segments were initially protected with an Fmoc group at the E-amino group. After completion of the chain assembly, the Fmoc-bearing amino groups were deprotected following standard Fmoc deprotection procedures and modified by attachment of levulinic acid to each peptide resin, respectively, following standard coupling protocols. The peptides were then deprotected and simultaneously cleaved from the resin support according to standard Boc-chemistry procedures as in Example 1. The peptides were separately purified by preparative C4 reverse-phase HPLC. For each peptide, fractions containing pure peptide were identified using ES-MS, pooled and lyophilized for subsequent ligation.

The water soluble polymer (EDA-Succ)$_{18}$ carboxylate (GRFNP32) was assembled on a Sasrin carboxy-generating resin following standard protocols (Rose, K. et al., U.S. patent application Ser. No. 09/379,297; Rose, et al., *J Am Chem Soc.*(1999) 121: 7034). The water soluble polymer (EDA-Succ)$_6$-amide (GRFNP6) was assembled on a Sieber amide-generating resin following standard protocols (Rose, K. et al., U.S. patent application Ser. No. 09/379,297; Rose, et al., *J Am Chem Soc.*(1999) 121: 7034). An aminooxyacetyl (AoA) moiety was attached to the N-terminal amino group of each resin-bound polymer by coupling a fivefold excess of activated Boc-aminooxyacetic acid. The two polymer chains were separately cleaved from the respective resin supports using classic Fmoc–chemistry procedures. Each polymer chain was purified by preparative reverse phase HPLC. For each polymer, fractions containing pure polymer were identified using ES-MS, pooled and lyophilized for subsequent ligation.

Segment SEP-1:4 and GRFNP6 were jointly dissolved at an equimolar ratio in 50% aqueous acetonitrile containing 0.1% TFA. The solution was then lyophilized. The dried powder was dissolved and the polymer-modified peptide separated from unmodified peptide and unreacted polymer by preparative gradient C4 reverse-phase HPLC. Fractions containing the desired oximated product SEP-1:4+GP6 were identified by ES-MS and pooled and lyophilized.

Segment SEP-1:1 and GRFNP32 were jointly dissolved at an equimolar ratio in 50% aqueous acetonitrile containing 0.1% TFA. The solution was then lyophilized. The dried powder was dissolved and the polymer-modified peptide separated from unreacted polymer by preparative gradient C4 reverse-phase HPLC. Fractions containing the desired oximated product SEP-1:1+GP32 were identified by ES-MS and pooled and lyophilized.

B. Synthesis of Synthetic Erythropoiesis Stimulating Protein SEP-1-L26

SEP-1-L26 was synthesized in solution from four polypeptide segments:

Segment SEP:1:1+GP32 (GRFN 1711+GRFNP32, corresponding to residues 1–32 of SEQ ID NO:2):
APPRLICDSR VLERYLLEAK EAEK$^{ox}$ITTGCA EHthioester (where Lys$^{24}$ is modified at the ε-amino group with a levulinic oxime linker group that is coupled to GRFNP32 through a levulinic-aminooxyacetyl (Lev-AoA) oxime bond denoted K$^{ox}$)

Segment SEP-1:2 (GRFN 1712, corresponding to residues 33–88 of SEQ ID NO:2):
CSLNEKIT VPDTKVNFYA WKRMEVGQQA VEVWQGLALL SEAVLRGQAL LVKSSQPW-thioester (where Cys$^{33}$ is Acm protected)

Segment SEP-1:3 (GRFN 1713, corresponding to residues 89–116 of SEQ ID NO:2):
CP LQLHVDKAVS GLRSLTTLLR ALGAQK-thioester (where Cys$^{89}$ is Acm protected)

Segment SEP:1:4+GP6 (GRFN 1776+GRFNP6, corresponding to residues 117–166 of SEQ ID NO:2):
CAIS PPDAAK$^{ox}$AAPL RTITADTFRK LFRVYSNFLR GKLKLYTGEA CRTGDR-carboxylate (where Lys$^{126}$ is modified at the ε-amino group with a levulinic oxime linker group that is coupled to GRFNP6 through a levulinic-aminooxyacetyl (Lev-AoA) oxime bond denoted K$^{ox}$ and where the C-terminal cysteine [i.e. Cys$^{161}$] carries a picolyl (pico) protecting group)

Synthesis of additional peptides, ligation reactions, carboxymethylation, protecting group removal reactions, folding and purification were performed as described in Examples 1 and 2 to yield full-length, folded SEP-1-L26. An analytical C4 reverse-phase HPLC chromatogram and an ES-MS spectrum of the folded protein product as well as a CD spectrum demonstrated the presence of folded protein.

Example 4

Synthesis Of Synthetic Erythropoiesis Stimulating Protein SEP-1-B50

A fourth synthetic etythropoiesis stimulating protein (designated SEP-1-B50) was synthesized. The amino acid sequence of the full-length SEP-1-B50 is the same as that of SEP-1-L30:

(SEQ ID NO:2)
```
APPRLICDSR   VLERYLLEAK  EAEK^oxITTGCA  EHCSLNEKIT

VPDTKVNFYA   WKRMEVGQQA  VEVWQGLALL    SEAVLRGQAL

LVKSSQPWψP   LQLHVDKAVS  GLRSLTTLLR    ALGAQKψAIS

PPDAAK^oxAAPL RTITADTFRK LFRVYSNFLR    GKLKLYTGEA

CRTGDR
``` where Ψ denotes an non-native amino acid residue consisting of a cysteine that is carboxymethylated at the sulfhydryl group, and where K$^{ox}$ denotes a non-native lysine that is chemically modified at the ε-amino group with an oxime linker group coupled to a designated water-soluble polymer through an oxime bond.

However, the protein was derivatized with a branched polymer construct having four linear (Succ-EDA)$_{12}$ moieties rather than the linear (Succ-EDA)$_{18}$ polymer of SEP-1-L30. Derivatization was accomplished via oxime linkages.

Figure 19A:
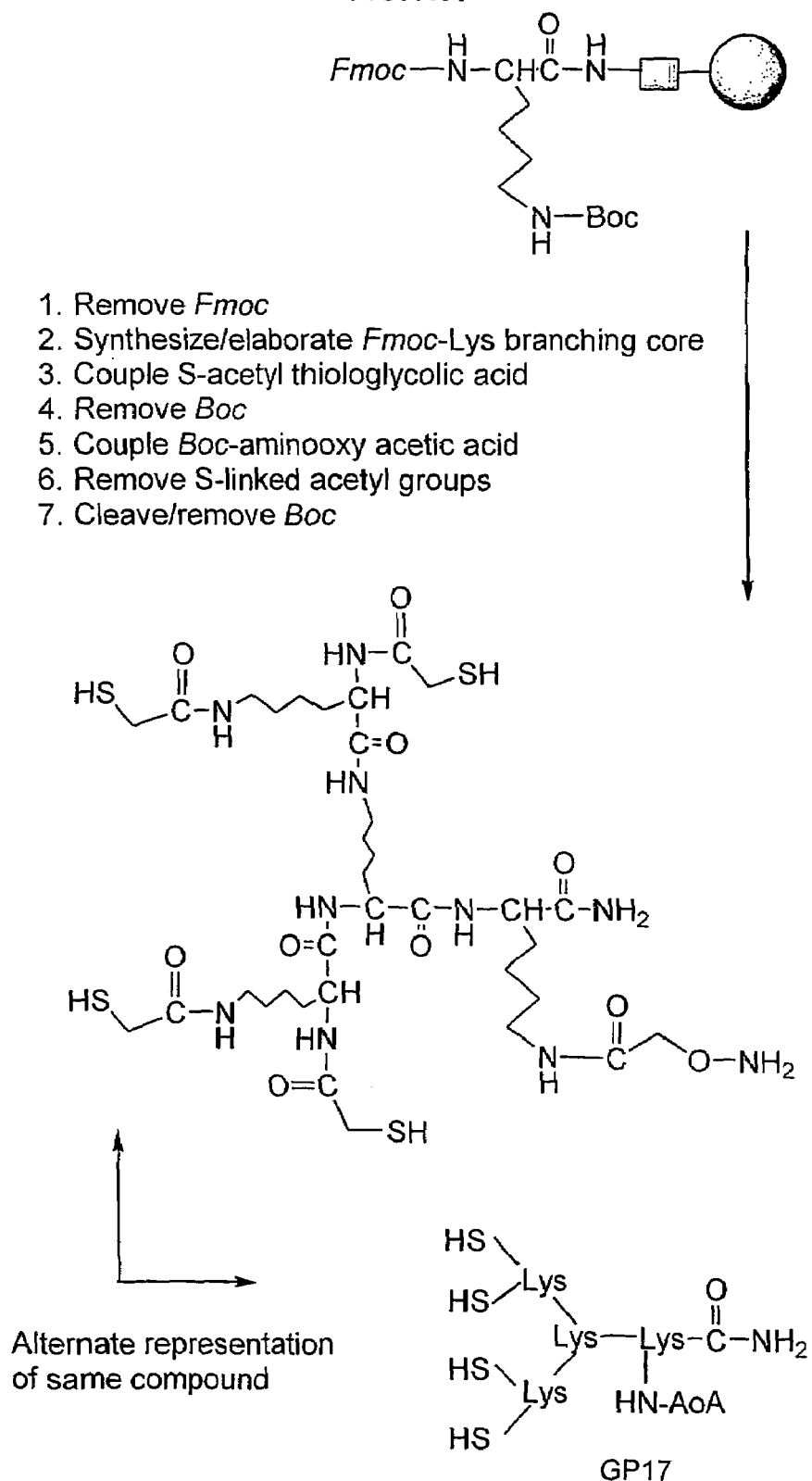
FIG. 19 depicts schematically the formation of a preferred branched-chain water-soluble polymer that is attached to a synthetic cytokine designated SEP1-B50, which is a precision polymer-modified synthetic analog of human EPO prepared as described in Example 4.
Figure 19B:
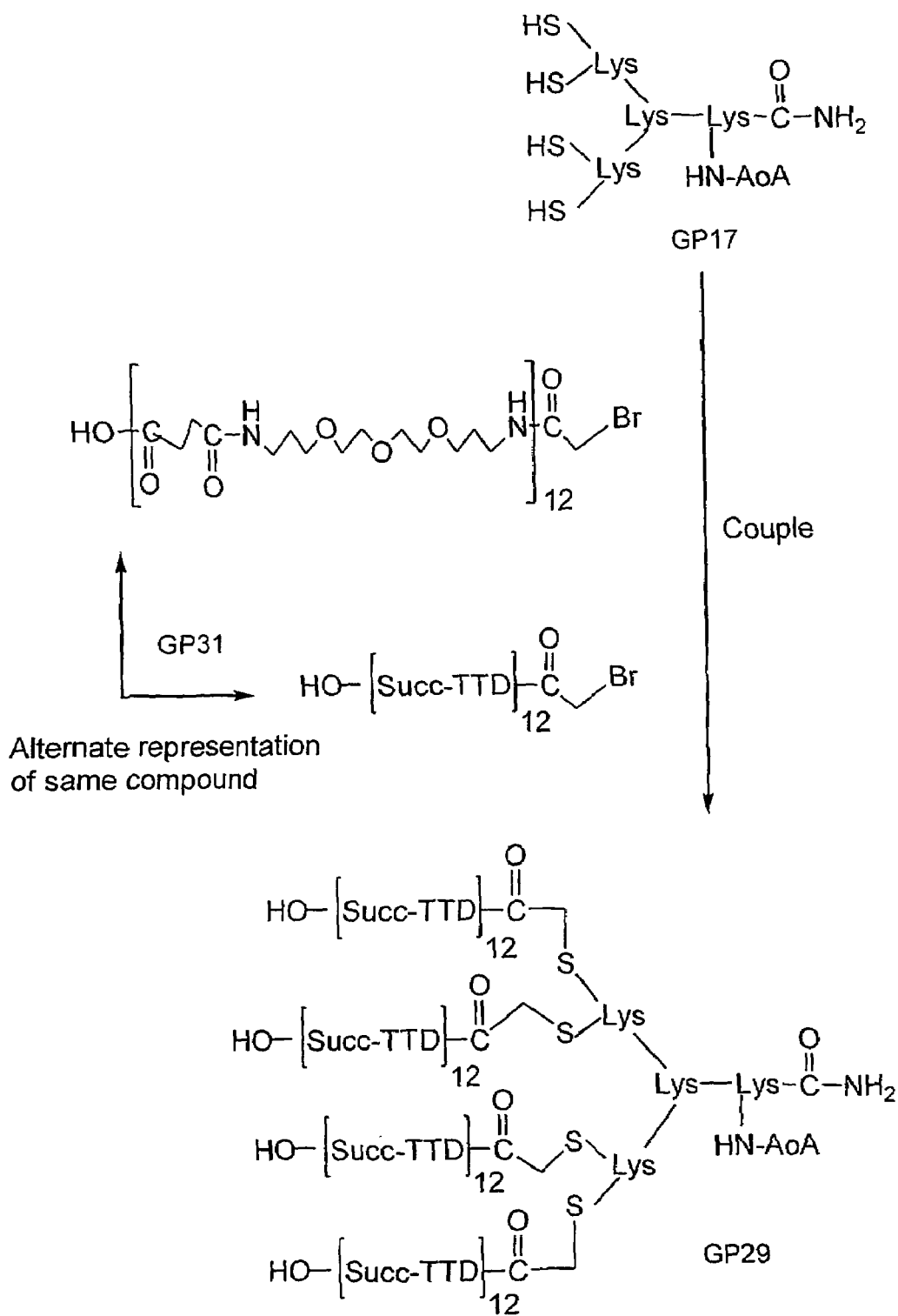
Figure 20:
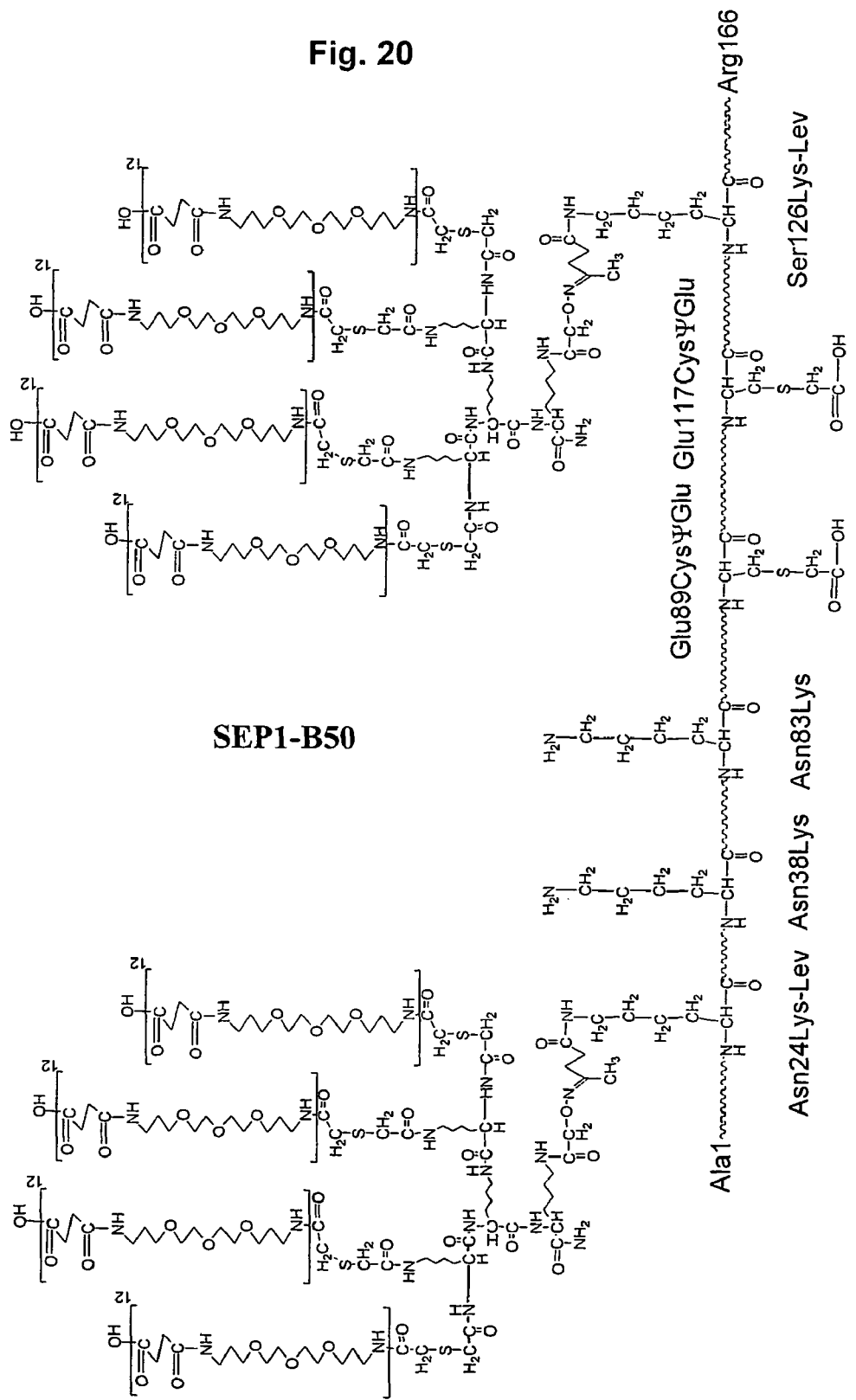
FIG. 20 depicts a synthetic cytokine designated SEP1-B50, which is a precision polymer-modified synthetic analog of human EPO prepared as described in Example 4.

FIG. 19 is a schematic illustrating the chemical synthesis of the branched water-soluble polymer GRFNP29 (GP29) that was joined to the SEP-1-B50 through oxime forming ligation as described in detail below. As shown in FIG. 19, an orthogonally protected lysine U-B precursor was used to generate U-B component GRFN17 (GP17) bearing an aminooxy acyl as the U group, and having a 3× lysine branching core B bearing four pendant thiol groups for subsequent coupling through thioether linkages to a linear water-soluble polyamide ethylene oxide construct designated GP29, which bears a pendant carboxylate donated by a succinic acid residue. Assembly of the full-length product was as described in Example 2. The structure of SEP-1-B50 is shown in FIG. 20.

A. Synthesis of Template GRFNP17 Carrying Multiple Thiol Groups

The template GRFNP17 was synthesized manually on an amide generating (4-methyl)benzhydrylamine(MBHA)-resin on a 0.4 mmol scale. Fmoc-Lys(Boc)-OH was coupled using standard coupling protocols (Schnölzer, M., *Int J Pept*

*Protein Res.* (1992) 40:180–93). 2.1 mmol amino acid, 10% DIEA in 3.8 ml 0.5M HBTU was used; i.e. 5-fold excess of amino acid. After removal of the Fmoc protecting group, Fmoc-Lys(Fmoc)-OH was coupled using standard amino acid coupling protocols (2.1 mmol amino acid, 10% DIEA in 3.8 ml 0.5M HBTU; i.e. 5-fold excess amino acid). After a second Fmoc removal step, Fmoc-Lys(Fmoc)-OH was coupled using standard amino acid coupling protocols (4.2 mmol amino acid, 10% DIEA in 7.6 ml 0.5M HBTU; i.e. 5-fold excess amino acid relative to free amine). After a final Fmoc deprotection step, a five-fold excess (relative to free amines) of S-acetyl thioglycolic acid pentafluorophenyl ester (SAMA-oPfp) in DMF was coupled for 30 minutes. The Boc protecting group of the side chain of the C-terminal lysyl residue was removed by two times one minute batch washes with neat TFA, followed by neutralization of the resin by washing with 10% DIEA in DMF. 2 mmol Boc-aminooxyacetic acid and 2 mmol N-hydroxysuccinimide (NHS) were dissolved in 3 ml DMF. After addition of 2 mmol DIC (diisopropylcarbodiimide), the acid was activated for 30–60 minutes. The solution was added to the neutralized resin and coupled 1 hr. Finally, the S-linked acetyl groups were removed with 20% piperidine in DMF for 30 minutes. The template was deprotected and simultaneously cleaved from the resin support using HF/p-cresol according to standard Boc-chemistry procedures in the presence of cysteine as a scavenger for free aldehyde (Schnolzer, M., *Int J Pept Protein Res.* (1992) 40:180–93). The recovered polyamide in 50% B [i.e. 50% aqueous acetonitrile containing 0.1% TFA] (aldehyde free) was frozen and lyophilized. For purification, the template crude product was dissolved in 2 ml 50% B, and 100 ml 100% A [i.e. 0.1% TFA in water] was added to dilute the sample (Avoid guanidinium chloride or acetate addition, since the addition of aldehyde is guaranteed). The template was loaded onto a C4 preparative reverse-phase HPLC column equilibrated at T=40° C. at 3% B. Salts were eluted isocratically and the desired template, GRFNP17 purified in a linear gradient. Fractions containing the desired product were identified by ES-MS, pooled and lyophilized.

B. Synthesis of Branched Water-Soluble Polymer GRNP29

GRFNP29, a branched (EDA-Succ)$_{12}$ polymer of 15 kDa molecular weight was synthesized by thioether-generating ligation of purified thiol-containing template GRFNP17 and a linear polymer GRFNP31, Br-acetyl-(EDA-Succ)$_{12}$ carboxylate, where GRFNP31 was synthesized on a Sasrin carboxy-generating resin following standard protocols (Rose, K. et al., U.S. patent application Ser. No. 09/379,297; Rose, et al., *J Am Chem Soc.*(1999) 121: 7034).

A 1.3× molar excess (over total thiols) of the purified GRFNP31, Br-acetylated (EDA-Succ)$_{12}$, and purified thiol-containing template GRFNP17 were jointly dissolved 0.1 M Tris -HCl/6 M guanidinium chloride, pH 8.7 at ~10 mM concentration. After dissolution, the solution was diluted threefold (v/v) with 0.1 M Tris -HCl, pH 8.7 buffer. The ligation mixture was stirred at room temperature and the reaction monitored by reversed-phase HPLC and ES/MS. Additional GRFNP31 reactant was added on an as-needed basis until the desired reaction product was the major product. For workup, 3× (v/v to ligation mix) 0.1M acetate/6 M guanidinium chloride, pH 4 was added, and the solution was loaded onto a preparative C4 reverse-phase HPLC column, and purified with a linear gradient. Fractions containing pure GRFNP29 construct were identified using ES-MS, pooled and lyophilized.

C. Oximation of GRFN1776 and GRFN1711 with GRFNP29

Segments SEP-1:4, and Segment SEP-1:1 were synthesized as described in Example 2. Segment SEP-1:4 and GRFNP29 were jointly dissolved at an equimolar ratio in 50% aqueous acetonitrile containing 0.1% TFA. The solution was lyophilized. The dried powder was loaded onto a preparative reverse-phase HPLC column (1 inch diameter). The polymer-modified peptide was separated from unmodified peptide and unreacted polymer by preparative gradient C4 reverse-phase HPLC. Fractions containing the desired oximated product SEP:1:4+GP29 were identified by ES-MS and pooled.

Segment SEP-1:1 and GRFNP29 were jointly dissolved at an equimolar ratio in 50% aqueous acetonitrile containing 0.1% TFA. The solution was frozen and lyophilized. The dried powder was dissolved in 50% aqueous acetonitrile containing 0.1% TFA and loaded onto a preparative GPC (gel permeation chromatography) column (1 inch diameter). The polymer-modified peptide was separated from unmodified peptide and unreacted polymer by isocratic elution. Fractions containing the desired oximated product SEP-1:1+GP29 were identified by ES-MS and pooled.

D. Synthesis Of Synthetic Erythropoiesis Stimulating Protein SEP-1-B50

SEP-1-B50 (SEQ ID NO:2) was synthesized in solution from four polypeptide segments:

Segment SEP-1:1+GP29 (GRFN 1711+GRFNP29, corresponding to residues 1–32 of SEQ ID NO:2):
APPRLICDSR VLERYLLEAK EAEK$^{ox}$ITTGCA EH-thioester (where Lys$^{24}$ is modified at the ε-amino group with a levulinic oxime linker group that is coupled to GRFNP29 through a levulinic-aminooxyacetyl (Lev-AoA) oxime bond denoted K$^{ox}$)

Segment SEP-1:2 (GRFN 1712, corresponding to residues 33–88 of SEQ ID NO:2):
CSLNEKIT VPDTKVNFYA WKRMEVGQQA VEVWQGLALL SEAVLRGQAL LVKSSQPW-thioester (where Cys$^{33}$ is Acm protected)

Segment SEP-1:3 (GRFN 1713, corresponding to residues 89–116 of SEQ ID NO:2):
CP LQLHVDKAVS GLRSLTTLLR ALGAQK-thioester (where Cys$^{89}$ is Acm protected)

Segment SEP11:4+GP29 (GRFN 1776+GRFNP29, corresponding to residues 117–166 of SEQ ID NO:2):
CAIS PPDAAK$^{ox}$AAPL RTITADTFRK LFRVYSNFLR GKLKLYTGEA CRTGDR-carboxylate (where Lys$^{126}$ is modified at the ε-amino group with a levulinic oxime linker group that is coupled to GRFNP29 through a levulinic-aminooxyacetyl (Lev-AoA) oxime bond denoted K$^{ox}$, and where the C-terminal cysteine carries a picolyl (pico) protecting group)

Synthesis of additional peptides, ligation reactions, carboxymethylation, protecting group removal reactions, folding and purification were performed as described in Examples 1 and 2, except that purification was on a Resource Q column, to yield full-length, folded SEP-1-B50 (SEQ ID NO: 2). An analytical C4 reverse-phase HPLC chromatogram and an ES-MS spectrum of the folded protein product SEP-1-B50 as well as a CD spectrum demonstrated the presence of folded protein.

Example 5

Synthesis Of Synthetic Erythropoiesis Stimulating Protein SEP-3-L42

A fifth synthetic erythropoiesis stimulating protein (designated SEP-3-L42) was synthesized. The amino acid sequence of the full-length SEP-3 protein is:

```
                                        (SEQ ID NO:3)
APPRLICDSR VLERYLLEAK EAECITTGCA EHCSLNECIT

VPDTKVNFYA WKRMEVGQQA VEVWQGLALL SEAVLRGQAL

LACSSQPWEP LQLHVDKAVS GLRSLTTLLR ALGAQKEAIS

PPDAACAAPL RTITADTFRK LFRVYSNFLR GKLKLYTGEA

CRTGDR
```

Figure 22:
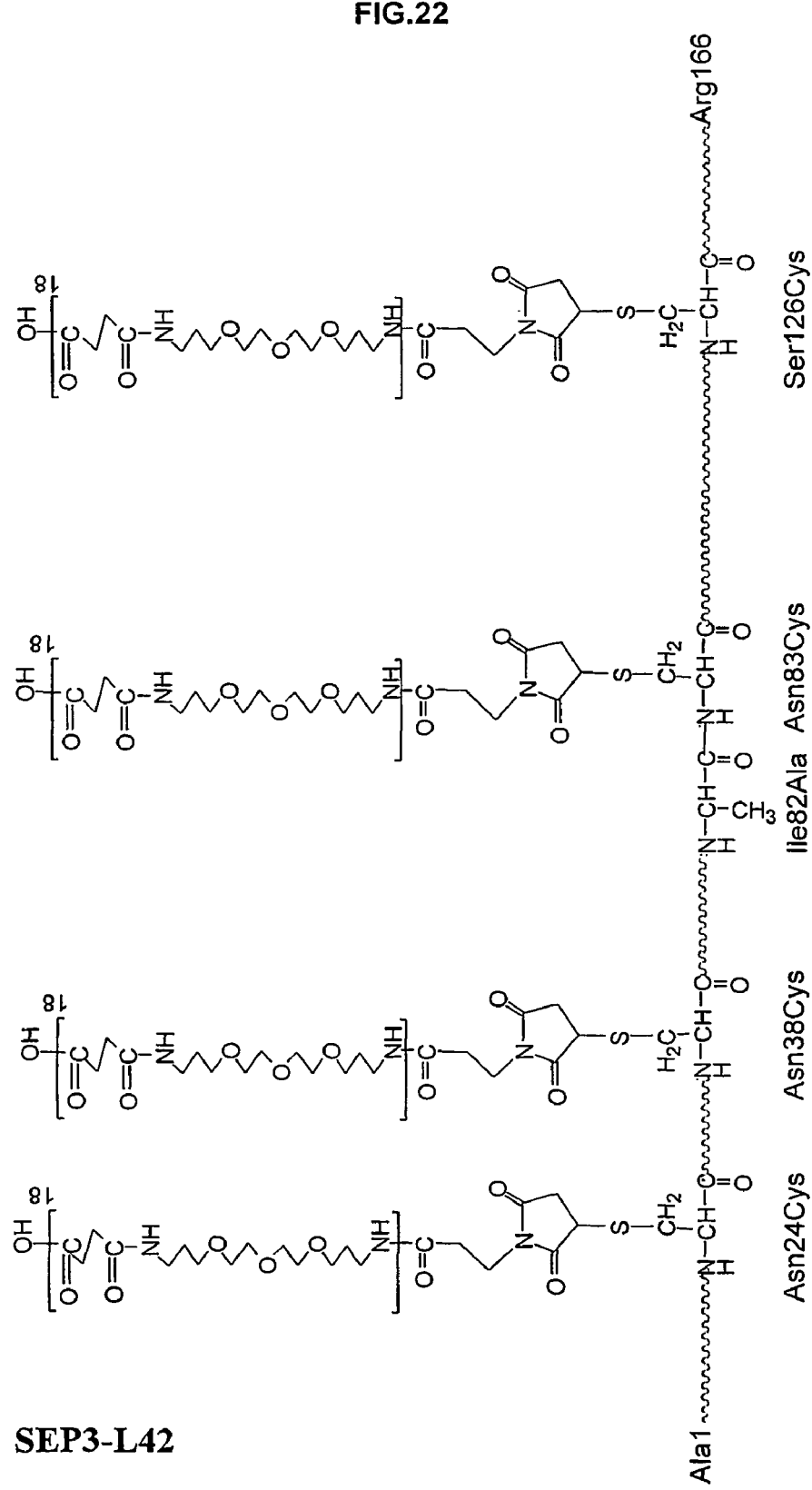
FIG. 22 depicts synthetic cytokine designated SEP3-L42, which is a precision polymer-modified synthetic analog of human EPO prepared as described in Example 5.

The cysteine residues in positions: 24, 38, 83, and 126 were modified with maleimide-functionalized (EDA-Succ)$_{18}$ (GRFNP32) polymer units (via a Michael addition reaction) to form SEP-3-L42. The structure of SEP-3-L42 is shown in FIG. 22.

Figure 21A:
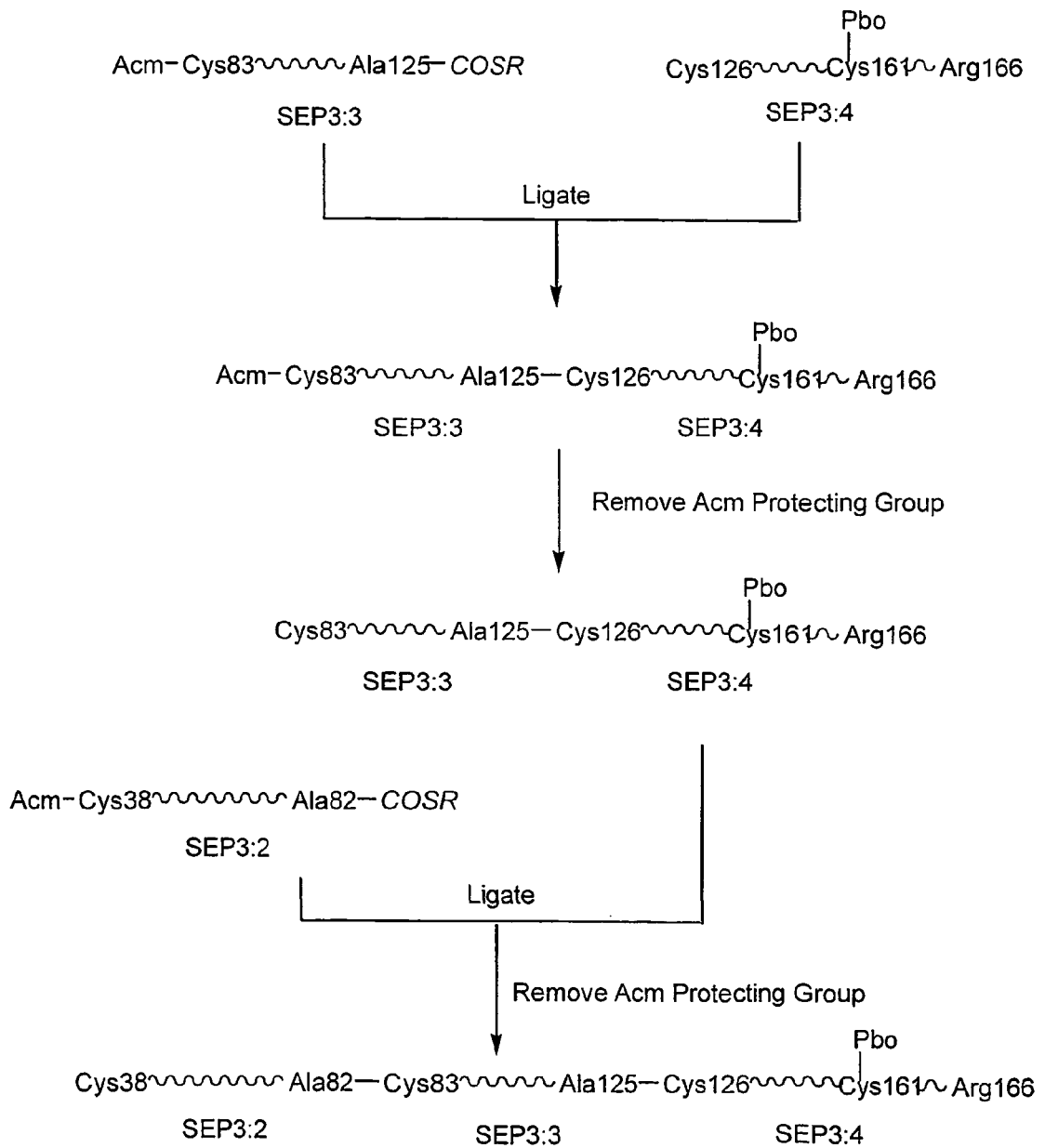
FIG. 21 depicts the synthesis of a synthetic cytokine designated SEP3-L42, which is a precision polymer-modified synthetic analog of human EPO prepared as described in Example 5.
Figure 21B:
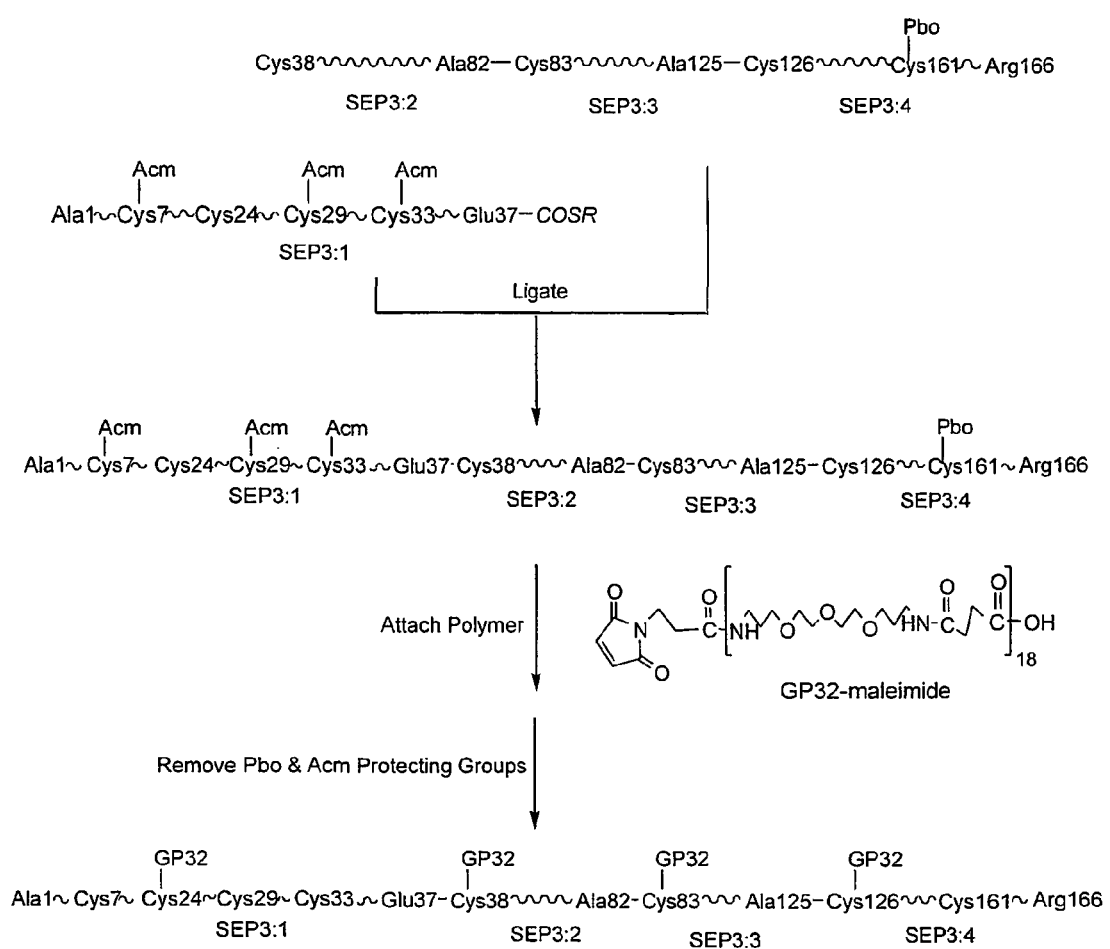

A schematic illustrating the chemical synthesis of SEP-3-L42 described below is shown in FIG. 21. Briefly, FIGS. 21A and 21B show the native chemical ligation of the four SEP-3-L42 peptide segments SEP-3:1 through SEP-3:4, which generates cysteines at the ligation sites corresponding to all four native glycosylation sites in human EPO. In particular, FIG. 21B shows full-length polypeptide having all disulfide-forming cysteines protected, permitting the site-specific attachment of four charged linear water soluble polymers (designated GRFN32-maleimide (GP32-maleimide)) at the cysteine ligation sites through a Michael addition reaction. FIG. 21B also shows the final deprotection step of the disulfide-forming cysteines, and generation of the full-length, polymer-modified product.

In detail, SEP-3 was synthesized in solution from four polypeptide segments:
Segment SEP-3:1 (GRFN 1747, corresponding to residues 1–37 of SEQ ID NO:3):
  APPRLICDSR VLERYLLEAK EAECITTGCA EHC-SLNE-thioester (where $Cys^7$, $Cys^{29}$, and $Cys^{33}$ are Acm protected)
Segment SEP-3:2 (GRFN 1774, corresponding to residues 38–82 of SEQ ED NO:3):
  CIT VPDTKVNFYA WKRMEVGQQA VEVWQGLALL SEAVLRGQAL LA-thioester (where $Cys^{38}$ is side chain protected with the Acm group)
Segment SEP-3:3 (GRFN 1749, corresponding to residues 83–125 of SEQ ID NO:3):
  CSSQPWEP LQLHVDKAVS GLRSLTTLLR ALGAQKEAIS PPDAA-thioester (where $Cys^{83}$ is side chain protected with the Acm group)
Segment SEP-3:4 (GRFN 1750, corresponding to residues 126–166 of SEQ ID NO:3):
  CAAPL RTITADTFRK LFRVYSNFLR GKLKLYTGEA CRTGDR-carboxylate (where $Cys^{161}$ is Pbo [i.e., 4-($CH_3$S(O)-)benzyl-] protected)

Peptide synthesis. The peptides SEP-3:1 and SEP-3:2 and SEP-3:3 were synthesized on a thioester-generating resin by the in situ neutralization protocol for Boc chemistry SPPS, using established side-chain protection strategies as described in Example 1, with changes in protecting group strategy as noted in the specific peptides above. Segment SEP-3:4 was synthesized analogously on a —$OCH_2$-Pam-resin. The peptides were deprotected and simultaneously cleaved from the resin support as described in Example 1. The resulting peptides described above were purified by preparative RP-HPLC. Fractions containing pure peptide were identified using ES-MS, pooled and lyophilized for subsequent ligation.

Step 1: Ligation #1. Segment SEP-3:4 and segment SEP-3:3 were dissolved in TFE at 15 mM concentration. Saturated phosphate buffer (pH 7.5) containing 6 M guanidinium chloride and 1% thiophenol was added, resulting in a clear solution of the peptide segments. After ligation, the ligation mix (defined as 1 volume) was added to 2 volumes of a solution of {2 ml TFE, 6 ml 6 M guanidinium chloride, 100 mM phosphate containing 25% β-mercaptoethanol} and incubated for 20 minutes. The solution was acidified with a solution of 15 mg/ml TCEP in glacial acetic acid, loaded onto a preparative C4 reverse-phase HPLC column and purified with a linear gradient. Fractions containing the desired ligated product SEP-3:Acm+SEP-3:3+SEP-3:4 were identified by ES-MS and pooled.

Step 2: Acm-removal #1 For Acm removal, the aqueous acetonitrile solution containing the pooled fractions of SEP-3:Acm+SEP-3:3+SEP-3:4 was diluted 1× with HPLC grade water, and solid urea was added for a final concentration of 2 molar. A threefold molar excess (relative to the total expected cysteine concentration) of a 30 mg/ml Hg(acetate)$_2$ solution in 3% aqueous acetic acid was added and the solution was stirred for one hour. The solution was then made 20% in β-mercaptoethanol, loaded onto a semi-preparative C4 reverse-phase HPLC column and purified with a step gradient. Fractions containing the desired ligated product SEP-3:3+SEP-3:4 were identified by ES-MS and lyophilized overnight.

Step 3: Ligation #2 Equal amounts of SEP-3:3+SEP-3:4 and SEP-3.2 were jointly dissolved in neat TFE trifluoroethanol at 15 mM concentration. 250 mM Phosphate buffer (pH 7.5) containing 6 M guanidinium and 1% thiophenol was added, resulting in a clear solution of the peptide segments. After one day of ligation, the ligation mix (defined as 1 volume) was added to 2 volumes of a solution of 10 ml TFE, 10 ml β-mercaptoethanol, 10 ml piperidine and 20 ml 6M guanidinium, pH 4, and incubated for 20 minutes to remove any remaining protecting groups. The solution was acidified with a solution of 15 mg/ml TCEP in 20% aqueous acetic acid, loaded onto a preparative C4 reverse-phase HPLC column and purified with a linear gradient. Fractions containing the desired ligated product SEP-3:Acm+SEP-3:2+SEP-3:3+SEP-3:4 were identified by ES-MS and lyophilized overnight.

Step 4 Acm removal For Acm removal, the aqueous acetonitrile solution containing the pooled fractions of SEP-3:Acm+SEP-3:2+SEP-3:3+SEP-3:4 was diluted 1× with HPLC grade water, and solid urea added for a final concentration of 2 molar. A threefold molar excess (relative to the total expected cysteine concentration) of a 30 mg/ml Hg(acetate)$_2$ solution in 3% aqueous acetic acid was added and the solution stirred for one hour. The solution was then made 20% in β-mercaptoethanol, loaded onto a C4 semi-preparative reverse-phase HPLC column and purified with a step gradient. Fractions containing the desired ligated product SEP-3:2+SEP-3:3+SEP-3:4 were identified by ES-MS and lyophilized overnight.

Step 5: Ligation #3 Equal amounts of SEP-3:2+SEP-3:3+SEP-3:4 and SEP:3:1 were jointly dissolved in neat TFE at 15 mM concentration. 250 mM Phosphate buffer (pH 7.5) containing 6 M guanidinium and 1% thiophenol was added, resulting in a clear solution of the peptide segments. After one day of ligation, the ligation mix (defined as 1 volume) was added to 2 volumes of a solution of 10 ml TFE, 10 ml β-mercaptoethanol, 10 ml piperidine and 20 ml 6M guanidinium, pH 4, and incubated for 20 minutes to remove any remaining protecting groups. The solution was acidified with a solution of 15 mg/ml TCEP in 20% aqueous acetic acid, loaded onto a preparative C4 reverse-phase HPLC column and purified with a linear gradient. Fractions containing the desired ligated product SEP-3:1+SEP-3:2+SEP-3:3+SEP-3:4 were identified by ES-MS and lyophilized overnight.

Step 6: Attachment of the Polymer GRFNP32. A maleimide-functionalized linear (EDA-Succ)$_{18}$ polymer called GRFNP32-maleimide was prepared by functionalizing GRFNP32 with BMPS (3-maleimido propionic acid NHS ester, Pierce, USA) following the manufacturers protocols to form a maleimide-functionalized (EDA-Succ)$_{18}$ polymer [i.e., maleimide-(EDA-Succ)$_{18}$]. SEP-3:1+SEP-3:2+SEP-3:3+SEP-3:4 was dissolved in the minimum amount of TFE required. A threefold excess of GRFNP32-maleimide was dissolved in 6M guanidinium chloride, 100 mM phosphate, pH 7.5 and added to the TFE solution. The progress of the Michael addition reaction was followed by analytical reverse-phase HPLC. After the reaction was complete, the solution was loaded onto a preparative C4 reverse-phase HPLC column and purified with a linear gradient. Fractions containing the desired polymer-modified product SEP3:Acm+SEP-3:1+SEP-3:2+SEP-3:3+SEP-3:4+pPEG [i.e. the ligated full-length 166 residue polypeptide chain with four copies of GRFNP32 attached to the side chain thiols of $Cys^{24}$, $Cys^{38}$, $Cys^{83}$ and $Cys^{126}$, and thus also called SEP3:Acm+SEP-3:1+SEP-3:2+SEP-3:3+SEP-3:4+GP32], were identified by ES-MS and lyophilized overnight.

Step 7: Pbo removal For Pbo reduction, the lyophilized powder of SEP3:Acm+SEP-3:1+SEP-3:2+SEP-3:3+SEP-3:4+GP32 was dissolved in neat TFA containing 5% ethanedithiol. The Pbo group was then cleaved by addition of 10% thioanisole and 15% bromotrimethylsilane for 30 minutes. The solution was dried in a rotator-evaporator and taken up in aqueous acetonitrile containing 0.1% TFA. The resulting solution was loaded onto a semi-preparative reverse-phase HPLC column and purified with a step gradient. Fractions containing the desired $Cys^{161}$-deprotected product SEP3:Acm+SEP-3:1+SEP-3:2+SEP-3:3+SEP-3:4+GP32-Pbo were identified by ES-MS and lyophilized overnight.

Step 8: Acm removal For final Acm removal from the side chains of $Cys^7$, $Cys^{29}$, and $Cys^{33}$, the aqueous acetonitrile solution containing the pooled fractions of SEP3:Acm+SEP-3:1+SEP-3:2+SEP-3:3+SEP-3:4+GP32-Pbo was diluted 1× with HPLC grade water, and solid urea was added for a final concentration of 2 molar. A threefold molar excess (relative to the total expected cysteine concentration) of a 30 mg/ml Hg(acetate)$_2$ solution in 3% aqueous acetic acid was added and the solution was stirred for one hour. The solution was then made 20% in β-mercaptoethanol, loaded onto a semi-preparative C4 reverse-phase HPLC column and purified with a step gradient. Fractions containing the desired ligated, polymer-modified product SEP-3 (1–166) were identified by ES-MS and lyophilized overnight.

Step 9 Folding: Full-length ligated, polymer-modified peptide SEP-3 (1–166) was dissolved in 200 mM Tris buffer (pH 8.7) containing 6 M guanidinium chloride and 20% TFE and a ten-fold molar excess (relative to Cys residues in SEP-3) of cysteine. This solution was dialyzed overnight against a solution of 200 mM Tris buffer (pH 8.7) containing 3 M guanidinium chloride at room temperature. The solution was then dialyzed against a solution of 200 mM Tris buffer (pH 8.7) containing 1 M guanidinium chloride for 4 hours at 4° C. and finally against 10 mM phosphate buffer (pH 7.0) for 4 hours at 4° C. to yield the final folded product. Folding was verified by electrospray ES-MS and CD spectrometry.

Step 10 Purification: The folded polypeptide was concentrated 5× in centricon concentrator vials and loaded on to Resource S cation exchange column equilibrated at 10 mM phosphate, pH 7.0. The folded protein was eluted in a linear salt gradient to 500 mM NaCl in 10 minutes. Fractions containing the desired folded product SEP-3-L42 were identified by SDS-PAGE, and frozen and stored at −80° C.

Example 6

Bioactivity Assay of Synthetic Erythropoiesis Stimulating Proteins

The bioactivity of folded synthetic erythropoiesis stimulating proteins, SEP-0, SEP-1-L26, SEP-1-L30, SEP-1-B50, and SEP-3-L42 was determined using UT/7 and 32D 103197 cell lines, in factor-dependent cell-line proliferation assays using commercial recombinant erythropoietin as a control standard. UT-7 is a human megakaryoblastic leukemia cell line with absolute dependence on one of interleukin-3, granulocyte-macrophage colony-stimulating factor (GM-CSF), or erythropoietin (EPO) for growth and survival (Miura Y, et al., Acta Haematol (1998) 99:180–184); Komatsu N, et al., Cancer Res. (1991) 51:341–8). 32D 103197 is a murine hemopoietic cell line (Metcalf, D. Int J Cell Cloning (1992) 10:116–25).

Stock-solutions of the SEP constructs were made in Iscove's modified Dulbecco's medium (IMDM), 10% FBS (Fetal bovine serum), glutamine and Penstrep, and serial 2× dilutions of these stock solutions were added to multi-well plates to which human UT17 EPO cells at a concentration of 5000 cells/50 µl were added. The plates were incubated at 37° C. in the presence of 5% $CO_2$ and monitored daily for growth. After four days, 20 µl 2,5 mg/ml MTT (methylthiazol tetrazolium) in PBS (phosphate buffered saline) was added and the plates were incubated for four hours. 150 µl IPA was added and the absorbance of each well was read at 562 nm. The ED50 (effective dose to reach 50% of maximum effect) values for the SEP compounds was determined and compared to that of CHO (Chinese hamster ovary)-cell produced rhEPO (recombinant human erythropoietin). The results from these experiments demonstrated that all of the synthetic erythropoiesis stimulating proteins exhibited bioactivity. ED50 results for SEP-0, SEP-1-L26, SEP-1-L30, and SEP-1-B50 are shown in Table V.

TABLE V

| Erythropoiesis Stimulating Protein | In Vitro ED50 Values (pM) | |
| --- | --- | --- |
| | UT-7 (Human) Cells | 32D 103197 (Mouse) Cells |
| SEP-0 | 1,570 | 863 |
| SEP-1-L26 | 46.5 | 100.8 |
| SEP-1-L30 | 71.5 | 182.5 |
| SEP-1-B50 | 182 | 6200 |
| rh EPO | 32.5 | 136.3 |

Additional results from these experiments when normalized for peptide content only using an extinction coefficient for calculating protein concentration by absorbance for polymer-modified SEP-1-L30 are shown in Table VI and FIG. 28 for SEP-0, SEP-1-L26, SEP-1-L30, SEP-1-B50, SEP-3-L42, and SEP-1-B51 (synthesis of the SEP-1-B51 compound is described in Example 7 below). Collectively, these in vitro assays demonstrate the differential effect of varying the polymer structures and sites of attachment on in vitro bioactivity, where these compounds have the following relative order of potency when tested for (1) human EPO receptor activity (from most potent to least potent): SEP-1-L26≈SEP-1-L30>SEP-1-B50≈SEP-1-B51>SEP-3-L42>SEP-0; and (2) mouse EPO receptor activity (from most potent to least potent): SEP-1-L26>SEP-1-L30>SEP-0>SEP-3-L42>SEP-1-B50≈SEP-1-B51.

TABLE VI

|  | In Vitro ED50 Values (ng/ml) | |
|---|---|---|
| Erythropoiesis Stimulating Protein | UT-7 Cells (Human EPO R) | 32D 103197 Cells (Mouse EPO R) |
| SEP-0 | 11 | 20 |
| SEP-1-L26 | 0.8 | 1 |
| SEP-1-L30 | 0.8 | 4 |
| SEP-3-L42 | 7 | 70 |
| SEP-1-B50 | 2.5 | 125 |
| SEP-1-B51 | 2 | 125 |

Figure 28:
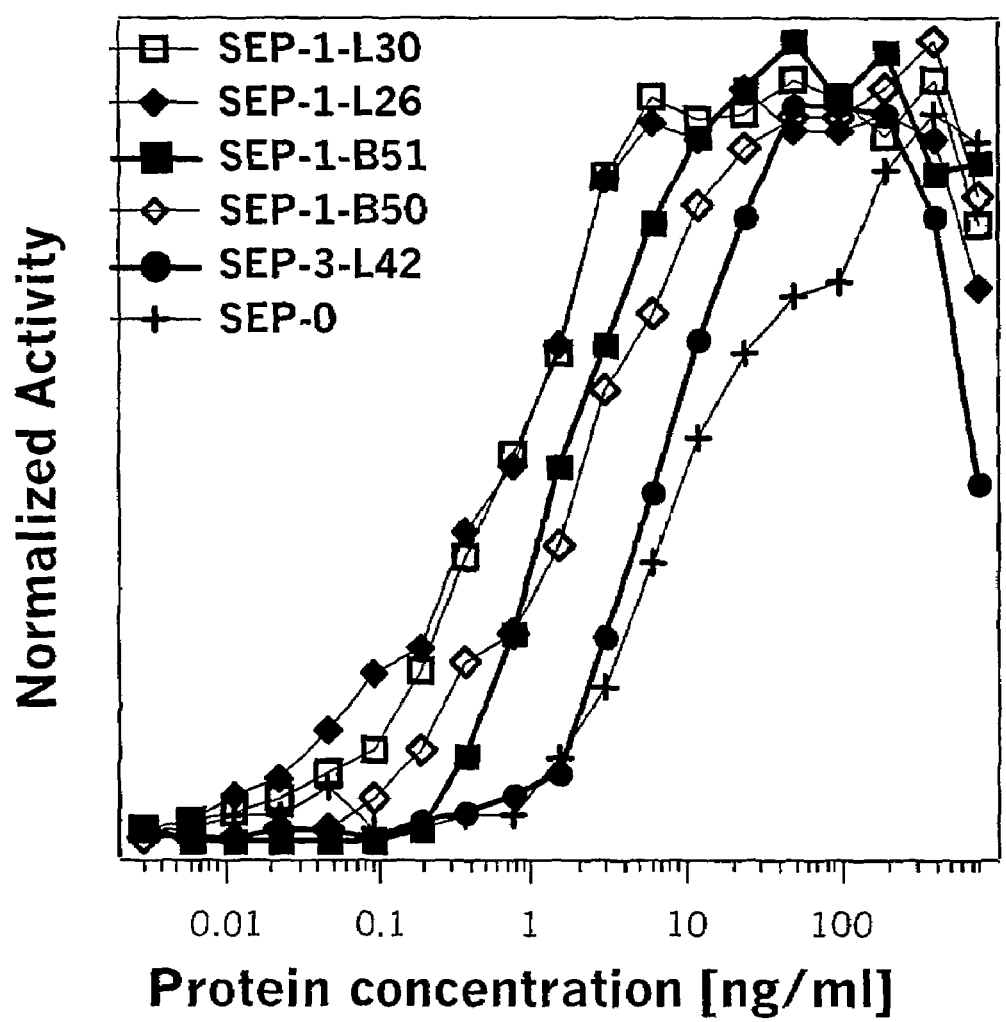
FIG. 28 shows the in vitro activity in a factor-dependent cell line of SEP compounds SEP0, SEP1-L26, SEP1-L30, SEP1-B50, SEP1-B51 and SEP3-L42.

The results in Table VI and FIG. 28 also show a significant difference in receptor preference for the polymer-modified SEP constructs compared to the non-polymer modified construct SEP-0. In particular, SEP-1-L26 is modified with different linear polymers attached at corresponding human EPO glycosylation site position 24 (a 5.5 kDa linear polymer with a pendant negative charge attached at this site) and position 126 (a 1.8 kDa linear polymer with a pendant neutral charge attached at this site); this construct had a similar activity against both human and mouse receptors. SEP-1-L30 is modified with a 5.5 kDa linear polymer having a pendant negative charge at corresponding human EPO glycosylation site positions 24 and 126; this construct was about 5× more active against the human receptor compared to the mouse receptor. SEP-3-L42, which is modified with a 5.5 kDa linear polymer having a pendant negative charge at corresponding human EPO glycosylation site positions 24, 38, 83 and 126 was about 10× more active against the human receptor compared to the mouse receptor.

The largest differential was observed for SEP-1-B850 and SEP-1-BS 1, which are modified with branched, negatively charged 15 kDa polymers attached at corresponding human EPO glycosylation site positions 24 and 126, and have a pI of approximately 5 (similar to human EPO); these two constructs were ~60× more active against the human receptor compared to the mouse receptor.

As mouse EPO is missing a glycosylation site at a position corresponding to human EPO position 126 (mouse EPO has non-glycosylated proline instead of the O-glycosylated serine found in human EPO), the altered receptor activity may be due in part to this difference, and thus preference of the mouse receptor for an EPO that is missing O-linked glycosylation at corresponding position 126. This is in line with the comparison of SEP-1-L26 and SEP-1-L30 to SEP-1-B50 and SEP-1-B52. For example, SEP-1-L26 has a 1.8 kDa uncharged polymer at position 126 whereas SEP-1-L30 has a 5.5 kDa negatively charged polymer at position 126. Although equivalent activity was observed against the human EPO receptor, a 4-fold difference was found against the mouse EPO receptor. The largest difference was observed for the SEP-1-B50 and SEP-1-B51 constructs, with negatively charged 15 kDa polymers attached at corresponding human EPO glycosylation site position 126. Addition of the 5.5 kDa negatively charged polymers at sites corresponding to all four native glycosylation positions in human EPO, i.e., 24, 38, 83 and 126 as with the SEP-3-L42 construct reduced preference for mouse even further, but less than the SEP-1-B50 and SEP-1-B51 constructs. These results demonstrate that receptor-specificity can be modulated by precision modification of sites corresponding to glycosylation sites in a biologically produced, glycosylated protein, and by adjusting the size, the nature of branching and charge of the polymer.

Example 7

Synthesis Of Synthetic Erythropoiesis Stimulating Protein SEP-1-B51

A. Composition of SEP-1-B51. A sixth synthetic erythropoiesis stimulating protein (designated SEP-1-B51) was synthesized. The amino acid sequence of the full-length SEP-1-B51 is the same as that of SEP-1-B50:

```
                                           (SEQ ID NO:2)
APPRLICDSR    VLERYLLEAK    EAEK^ox ITTGCA   EHCSLNEKIT

VPDTKVNFYA    WKRMEVGQQA    VEVWQGLALL       SEAVLRGQAL

LVKSSQPWψP    LQLHVDKAVS    GLRSLTTLLR       ALGAQKψAIS

PPDAAK^ox AAPL  RTITADTFRK    LFRVYSNFLR       GKLKLYTGEA

CRTGDR
``` where Ψ denotes an non-native amino acid residue consisting of a cysteine that is carboxymethylated at the sulfhydryl group, and where $K^{ox}$ denotes a non-native lysine that is chemically modified at the ε-amino group with an oxime linker group coupled to a designated water-soluble polymer through an oxime bond.

However, in contrast to SEP-1-B50, the protein was derivatized with a branched polymer construct having four linear $(Succ-TTD)_{12}$-Succ-Alanine-OH [i.e., $(Succ-TTD)_{12}$-Succ-Ala-OH, or $(Succ-TTD)_{12}$Succ-Ala] polymers coupled through amide bonds to the lysine branching core. Coupling of the linear polymers to the branching core through amide bonds was designed to improve stability. The four linear polymers also are designed to carry an alanine moiety and pendant negative charges, with the negative charges mimicking sialic acids and the alanine a hydrophobic character similar to pendant sugar moieties of carbohydrate chains. The branched polymers also were designed to have a water-soluble spacer between the branching core and the protein backbone attachment site to improve synthesis and handling properties of the branching core template, and to mimic the spacing found in natural carbohydrate chains between the site of sugar attachment to the protein backbone and the first branch point of the carbohydrate.

Figure 23B:
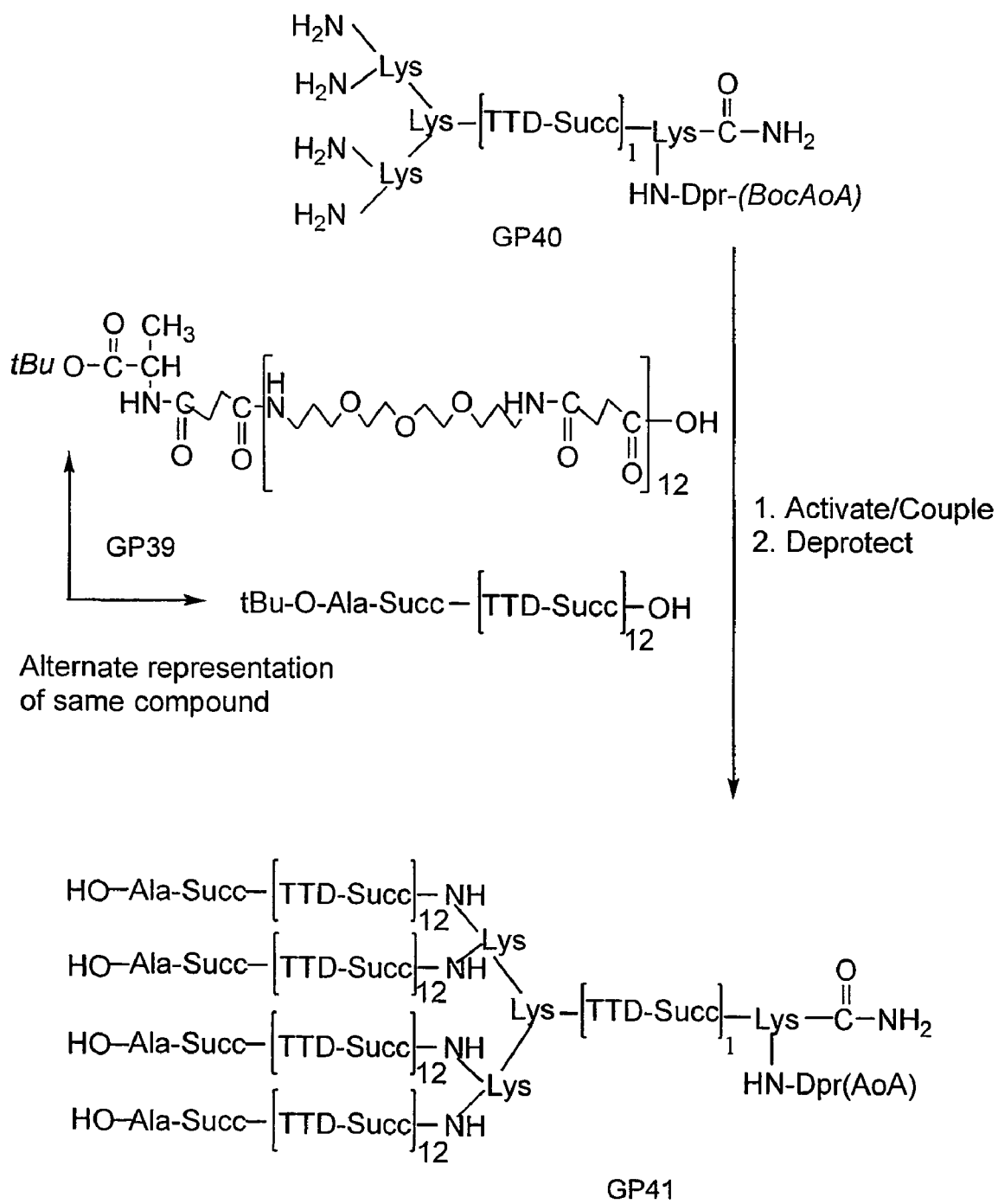
FIG. 23 depicts the synthesis of a preferred water-soluble polymer for attaching to a synthetic cytokine designated SEP1-B51, which is a precision polymer-modified synthetic analog of human EPO prepared as described in Example 7.
Figure 24:
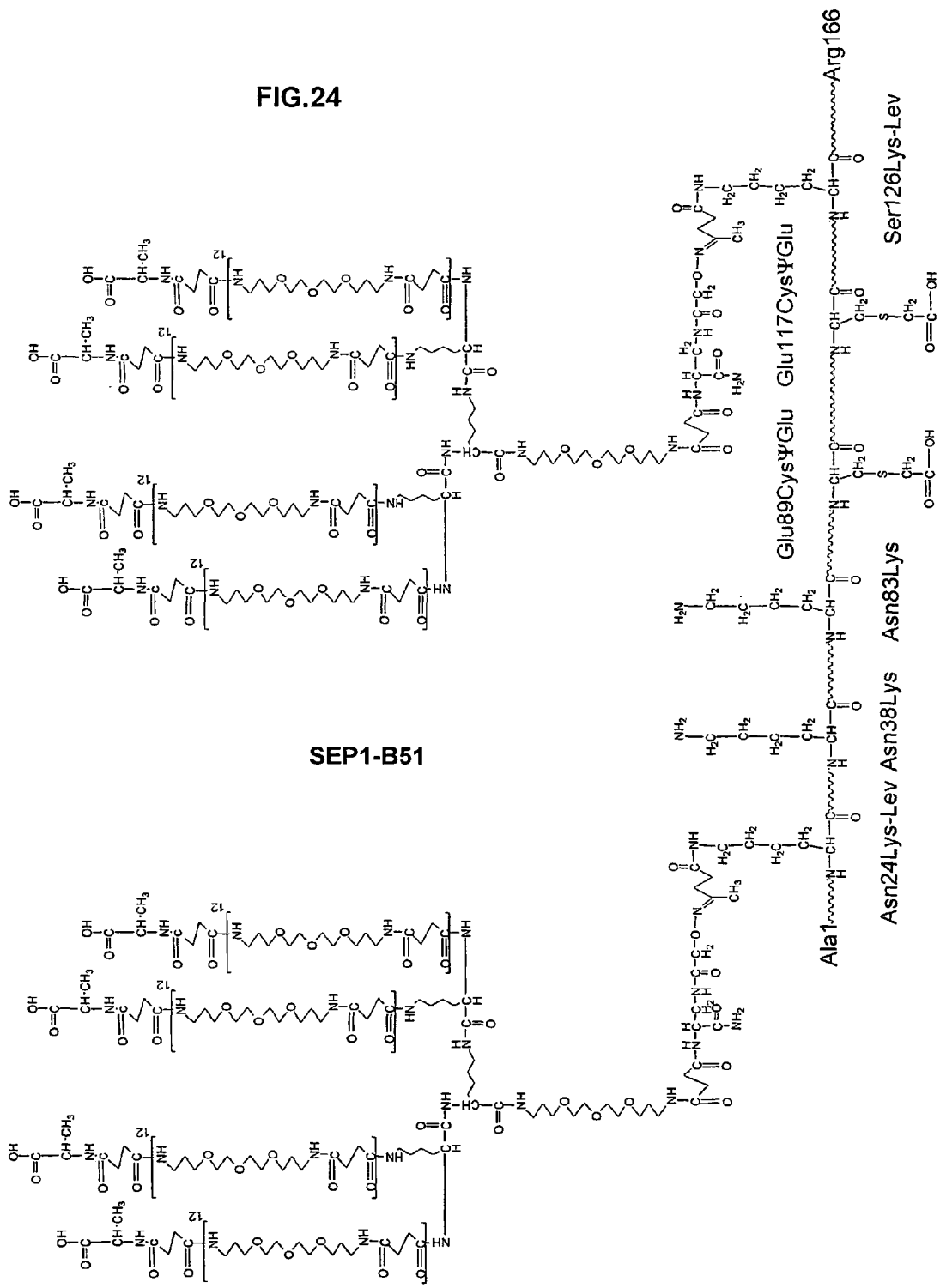
FIG. 24 depicts a synthetic cytokine designated SEP1-B51, which is a precision polymer-modified synthetic analog of human EPO prepared as described in Example 7.

FIG. 23 is a schematic illustrating the chemical synthesis of the branched water-soluble polymer GRFNP41 (GP41) that was joined to the SEP-1-B51 through oxime-forming ligation as described below. Assembly of the full-length product was as described in Example 2. The structure of SEP-1-B51 is shown in FIG. 24.

B. Synthesis of (Succ-TTD)$_{12}$Succ-AlaOtBu (GRFNP39) for Coupling to the Branching Template (GRFNP40)

Linear polymer (Succ-TTD)$_{12}$Succ-AlaOtBu (GRFNP39) was synthesized on a 0.5 mmol scale on Sasrin acid labile, carboxylic acid-generating resin. 0.5 mmole (~0.5 grams) Sasrin acid labile, carboxylic acid-generating polystyrene resin (hydroxyl substitution 1.02 mmole/g;) was swelled in DMF for 15 minutes, and then drained. To this hydroxyl-functionalized resin was added 450 mg (4.5 mmole) succinic anhydride and 488 mg (4 mmole) 4-(dimethylamino)pyridine dissolved in 8 ml of DMF containing 500 microliter (3.9 mmole) DIEA (diisopropylethylamine) and allowed to react for 30 minutes with vortex agitation, and drained. The coupling was repeated and excess reactants and soluble coproducts were removed by a 1 minute vortexing flow wash with DMF (~50 ml) and then drained. The HOOC—CH$_2$CH$_2$CO—O-resin (0.5 mmole) was activated by addition of 8 ml of fresh 1.0 M (8 mmole) CDI (carbonyldiimidazole) solution in DMF and allowed to react for 40 minutes, and then drained. Excess reactants and soluble coproducts were removed by a 1 minute vortexing flow wash with DMF (~50 ml), then drained. 4 ml (4 grams, 18.2 mmole) (4,7,10)-trioxatridecane-1,13diamine (TTD) dissolved in 4 ml 0.5M (2 mmol) HOBT solution in DMF was added and allowed to react with vortex agitation for 30 minutes, then drained. Excess reactants and soluble coproducts were removed by a 1 minute vortexing flow wash with DMF (~50 ml), then drained. Succinic anhydride (450 mg, 4.5 mmole) dissolved in 8 ml of 0.5M (4 mmole) HOBT (N-hydroxybenzotriazole) solution containing 500 microliter (3.9 mmole) DIEA was added to the resin and allowed to react with vortex agitation for 15 minutes, then drained. The three steps (CDI activation; TTD coupling; succinic anhydride reaction) were repeated eleven times [i.e. a total of twelve times]. Excess reactants and soluble coproducts were removed by a 1 minute vortexing flow wash with DMF (~50 ml), and drained. The HOOC—CH$_2$CH$_2$CO(TTD-succinyl)$_{12}$-O-resin (0.5 mmole) was activated with 8 ml of fresh 1.0 M (8 mmole) CDI solution in DMF and allowed to react for 40 minutes, and then drained. Excess reactants and soluble coproducts were removed by a 1-minute vortexing flow wash with DMF (~50 ml), then drained. 2.5 mmole H-AlaOtBu.HCl was dissolved in 4.75 ml 0.5 M (2.375 mmole) HOBT in DMF containing 150 microliter (111 mg, 0.825 mmole) DIEA, and allowed to react with the CDI-activated HOOC—CH$_2$CH$_2$CO(TTD-succinyl)$_{12}$-O-resin (0.5 mmole) for 1 hour with vortex agitation, then drained. Excess reactants and soluble coproducts were removed by a 1-minute vortexing flow wash with DMF (~50 ml), and then drained. The product tertBuOOC—CH(CH3)—NH—OC—CH$_2$CH$_2$CO(TTD-succinyl)$_{12}$-O-resin was washed extensively with DCM (dichlormethane), drained and then the resin was dried under vacuum to constant weight. Typical weight of product-resin was around 2 grams.

The linear (Succ-TTD)$_{12}$Succ-AlaOtBu polymer was cleaved from the resin support according to standard Fmoc-chemistry procedures using 4% TFA in DCM. The precipitated crude product was dissolved in 50% aqueous acetonitrile containing 0.1% TFA and lyophilized. The lyophilized polymer was dissolved in a small amount of 50% aqueous acetonitrile containing 0.1% TFA and diluted to reduce the concentration of organic below 1%. The crude product was loaded onto a C4 preparative reverse-phase column equilibrated at T=40° C. at 3% B. Salts were eluted isocratically and the desired template was purified with a linear gradient of 20–35% Buffer B (acetonitrile containing 0.1% TFA) versus 0.1% aqueous TFA over 60 minutes. Fractions containing the desired (Succ-TTD)$_{12}$-Succ-AlaOtBu material (GRFNP39) were identified by ES-MS, frozen and lyophilized.

C. Synthesis of a Template Carrying Multiple Amine Groups for Branching and a Protected Aminooxy Group for (Later) Attachment to the Protein (GRFNP40)

The template GRFNP40 was synthesized manually on a Sieber amide-generating resin on a 0.4 mmol scale. There was a one-minute flow-washing step with DMF between every coupling, deprotection and activation step. 2 mmol N$^\alpha$-Fmoc-N$^\beta$(Boc-aminooxyacetyl)-L-diaminopropionic acid was coupled to the resin, using 30 minute NHS-ester pre-activation with 2 mmol DIC and 2 mmol NHS in DCM/DMF (dimethylformamide), for 1 hour. After removal of the Fmoc protecting group (2×3 minutes 20%v/v piperidine in DMF) and washing, 4 mmol succinic anhydride dissolved in 8 ml of 0.5M HOBT (N-hydroxybenzotriazole) solution containing 2.2 mmol DIEA was coupled to the resin for 10 minutes. After this step, the carboxyl group was activated with 8 ml of fresh 0.5 M (4 mmole) CDI solution in DMF. 4 ml (18.2 mmole) TTD was added in 4 ml 0.5M HOBT solution in DMF and coupled for 30 minutes.

Fmoc-Lys(Fmoc)-0H (2 mmol) was coupled to the resulting amino-TTD-Succ-Dpr(BocAoA)-resin (where Dpr=diaminopropionic acid) using 30 minutes pre-activation with 2 mmol DIC and 2 mmol NHS in DMF and coupling for 1 hour. This coupling was repeated once. After an Fmoc removal step (2×3 minutes 20%v/v piperidine in DMF), 4 mmol Fmoc-Lys(Fmoc)-0H was coupled as described above, including recoupling. After a final Fmoc protection step (2×3 minutes 20%v/v piperidine in DMF), the template was cleaved from the resin support according to standard Fmoc-chemistry procedures using 4% TFA in DCM. The precipitated product was dissolved in 50% aqueous acetonitrile containing 0.1% TFA and lyophilized. The lyophilized crude product was dissolved in a small amount of 50% aqueous acetonitrile containing 0.1% TFA and diluted to reduce the concentration of organic below 1%. The template was loaded onto a C4 preparative reverse-phase HPLC column equilibrated at T=40° C. at 3% Buffer B (0.1%TFA in acetonitrile). Salts and other non-amide material were eluted isocratically, and the desired template was purified with a linear gradient of 5–12 % Buffer B (acetonitrile containing 0.1% TFA) versus 0.1% aqueous TFA over 60 minutes. Fractions containing the desired Lys-Lys(Lys)-TTD-Succ-Dpr(BocAOA).amide material (GRFNP40) were identified by ES-MS, frozen and lyophilized.

D. Assembly and Deprotection of the Amide-coupled Branched Polymer (GRFNP41)

GRFNP41, a branched (TTD-Succ)$_{49}$-polymer of 16 kDa molecular weight was synthesized by coupling of GRFNP39 [(Succ-TTD)$_{12}$-Succ-AlaOtBu] to the purified template GRFNP40. Purified (Succ-TTD)$_{12}$-Succ-AlaOtBu (GRFNP39) (1.0 mmole) dissolved in DMSO (dimethylsulfoxide) at 60° C. to a concentration of 20 mg/ml was activated with 0.95 mole of HATU {O-(7-azabenzotriazol-1-yl)-1,1,3,3-tetramethyluronium hexafluorophosphate} in DMSO at a concentration of 10 mg/ml in the presence of a twenty-fold (molar) excess of DIEA. Purified template GRFNP40 (0.24 mole) dissolved in DMSO at a concentration of 3.9 mg/ml was added immediately. Progress of the reaction was monitored by C4 analytical reverse-phase HPLC and ES-MS. Typically, the coupling was complete within minutes. For work-up, 4 volumes (relative to ligation mix) 0.1M sodium acetate/6 M guanidinium chloride, pH 4 was added, and the solution was loaded onto a preparative (C4) reverse-phase HPLC column. Salts and other non-amide containing material were eluted isocratically and the desired branched polymer product was purified with a linear gradient of 20–35% Buffer B (acetonitrile containing 0.1% TFA) versus 0.1% aqueous TFA in 80 minutes. Fractions containing the desired material were identified by ES-MS, frozen and lyophilized.

The resulting purified polymer was dissolved in neat TFA at a concentration of 1 mg/ml for 1 hour to remove the Boc group from the aminooxyacetyl moiety and to remove the tertButyl ester groups from the -Ala-OtBu moieties. The solution was rotated to dryness in a rotator evaporator and the dried polymer was dissolved in 50% Buffer B (acetonitrile containing 0.1% TFA). Aminooxyacetic acid (a.k.a. 'Carboxymethoxylamine') was added to a final concentration of 0.5M to scavenge adduct-forming impurities. After 20 minutes, the solution was diluted out with 3.3 volumes of Buffer A (0.1%TFA in water), and loaded onto a preparative C4 reverse phase HPLC column and pumped at 10% Buffer B until all the aminooxyacetic acid was removed, then the polymer was purified with a step gradient from 15% to 45% Buffer B versus 0.1% aqueous TFA over 80 minutes. Pooled fractions containing the desired branched polymer material (GRFNP41) were frozen and lyophilized.

E. Oxime-forming Ligation (Oximation) of the Peptide Segments GRFN1776 and GRFN1711 With the Branched Polymer GRFNP41

Segments SEP-1:4 (GRFN1776, composed of residues 117–166 of SEQ ID NO:2 and Segment SEP-1:1 (GRFN1711, composed of residues 1–32 of SEQ ID NO:2 were synthesized as described above in Example 1 using standard in situ neutralization Boc chemistry SPPS. Peptide GRFN1776 was synthesized on an —OCH$_2$-Pam-Resin following standard protocols also as described above. Peptide GRFN1711 was synthesized on a thioester-generating resin following standard protocols as described above. Segment GRFN1776 containing a levulinic acyl moiety on Lys$^{126}$ and the AoA-containing GRFNP41 were jointly dissolved at an equimolar ratio in 50% aqueous acetonitrile containing 0.1% TFA. The solution was lyophilized. The dried powder crude product was redissolved in 50% aqueous acetonitrile containing 0.1% TFA and loaded onto a preparative reverse-phase (C4) HPLC column. The polymer-modified peptide was separated from unmodified peptide and unreacted polymer by preparative gradient reverse phase HPLC. Fractions containing the desired oxime-linked (oximated) product SEP-1:4+GP41 were identified by ES-MS and pooled and lyophilized.

Segment GRFN1711 containing a levulinic acyl moiety on Lys$^{24}$ and the AoA-containing GRFNP41 were jointly dissolved at an equimolar ratio in 50% aqueous acetonitrile containing 0.1% TFA. The solution was frozen and lyophilized. The dried powder was dissolved in 50% aqueous acetonitrile containing 0.1% TFA and loaded onto a C4 preparative reverse-phase HPLC column. The polymer-modified peptide was separated from unmodified peptide and unreacted polymer by preparative gradient elution C4 reverse-phase HPLC. Fractions containing the desired oxime-linked (oximated) product SEP-1:1+GP41 were identified by ES-MS, and pooled and lyophilized.

F. Synthesis Of Synthetic Erythropoiesis Stimulating Protein SEP-1-B51

SEP-1-B51, having (SEQ ID NO:2), was synthesized in solution from four polypeptide segments:

Segment SEP-1:1+GP41 (GRFN 1711+GRFNP41; corresponding to residues 1–32 of SEQ ID NO:2):
APPRLICDSR VLERYLLEAK EAEK$^{ox}$ITTGCA EH-thioester (where Lys$^{24}$ has a levulinic acyl pendant moiety oxime-linked to the branched polymer GRFNP41, as denoted by K$^{ox}$; and where His$^{32}$ is Dnp protected)

Segment SEP-1:2 (GRFN 1712; corresponding to residues 33–88 of SEQ ID NO:2):
CSLNEKIT VPDTKVNFYA WKRMEVGQQA VEVWQGLALL SEAVLRGQAL LVKSSQPW-thioester (where Cys$^{33}$ is Acm protected; and where the three Trp residues are formyl protected)

Segment SEP-1:3 (GRFN 1713, corresponding to residues 89–116 of SEQ ID NO:2):
CP LQLHVDKAVS GLRSLTTLLR ALGAQK-thioester (where Cys$^{89}$ is Acm protected; and where His$^{94}$ is Dnp protected)

Segment SEP-1:4+GP41 (GRFN 1776+GRFNP41, corresponding to residues 117–166 of SEQ ID NO:2):
CAIS PPDAAK$^{ox}$AAPL RTITADTFRK LFRVYSTIFLR GKLKLYTGEA CRTGDR-carboxylate (where the C-terminal cysteine (i.e. Cys$^{161}$) carries a picolyl (pico) protecting group, and where Lys$^{126}$ has a levulinic acyl pendant moiety oxime-linked to the branched polymer GRFNP41, as denoted by K$^{ox}$)

Synthesis of additional peptides, ligation reactions, carboxymethylation, protecting group removal reactions, folding and purification to yield full-length, folded SEP-1-B51 (SEQ ID NO:2) were performed as described in Examples 1–4, with the following modifications:

Step 1. Ligation #1 Segment SEP-1:4+GP41 was dissolved in TFE (1 volume) at 3 mM concentration. Segment SEP-1:3 was dissolved in 2 volumes of 300 mM Na phosphate buffer (pH 7.9) containing 6 M guanidinium chloride to a concentration of 2.25 mM. The two solutions were mixed, giving final segment concentrations of 1 mM SEP-1:4+GP41 and 1.5 mM SEP-1:3, and 1% thiophenol was added, resulting in a solution ('3 volumes') of the peptide segments at a pH of 6.8–7.2. Reaction was allowed to proceed overnight at room temperature. After ligation, β-mercaptoethanol (3 volumes) was added to the ligation mix, followed by 3 volumes of 6 M guanidinium chloride 300 mM Na phosphate pH7.9 buffer, and TCEP was added (0.25 by weight of the total weight of peptide segments), and the solution stirred for 20 minutes. The solution was acidified to pH4.0+/−0.1 with 0.6 volumes of glacial acetic acid to give a clear solution to which was added 30 volumes of pH4.0, 100 mM Na acetate dilution buffer, 6M in guanidinium chloride. The resulting solution was pumped onto a preparative reverse-phase (C4) HPLC column. Buffer was pumped at 5% B [thus the remainder is 95% Buffer A (0.1%TFA in water)] until all non-peptide materials had eluted from the column, then the ligation product was purified by a gradient of 25–45% Buffer B over 80 minutes. Fractions containing the desired ligated product (Cys$^{89}$(Acm)){SEP-1:3+SEP-1:4+GP41} were identified by electrospray mass spectrometry and pooled.

Step2: Acm-removal #1 For Acm removal, the aqueous acetonitrile solution containing the pooled fractions of (Cys$^{89}$(Acm)) {SEP-1:3+SEP-1:4+GP41} was diluted 1× with HPLC grade water, and solid urea was added for a final concentration of 2 M. A threefold molar excess (relative to the total cysteine concentration) of a 30 mg/ml Hg(acetate)$_2$ solution in 3% aqueous acetic acid was added and the solution was stirred for one hour. The solution was then made 20% in β-mercaptoethanol, loaded onto a semi-preparative reverse-phase HPLC column and pumped at 25% Buffer B until all non-peptide material had eluted, and the product was then purified with a step gradient to 50% Buffer B. Fractions containing the desired ligated product {SEP-1:3+SEP-1:4+GP41} were identified by electrospray mass spectrometry, pooled and lyophilized.

Step 3: Ligation #2 The {SEP-1:3+SEP-1:4+GP41} product [i.e. 1713-1776-GP41] from Step 2 was dissolved in TFE (1 volume) at 3 mM concentration. Segment SEP-1:2 (segment GRFN1712) was dissolved in 2 volumes of 300 mM Na phosphate buffer (pH 7.9) containing 6 M guanidinium chloride to a concentration of 2.25 mM. The two solutions were mixed, giving final segment concentrations of 1 mM {SEP-1:3+SEP-1:4+GP41} and 1.5 mM SEP-1:2, and 1% thiophenol was added, resulting in a solution ('3 volumes') of the peptide segments at a pH of 6.8–7.2. Reaction was allowed to proceed overnight at room temperature. Then the ligation mix was diluted with 3 volumes (i.e. relative to the volume of TFE used above) of dilution buffer: 100 mM sodium acetate pH4.0 containing 6M guanidinium chloride, and was then added to a solution, cooled to 4° C., consisting of 3 volumes TFE, 3 volumes β-mercaptoethanol, 3 volumes piperidine and 6 volumes of 6M guanidinium chloride, 100 mM Na acetate pH 4.0 and was stirred for 20 minutes at room temperature to remove any remaining protecting groups. The solution was acidified with 1.8 volumes of frozen glacial acetic acid to give a clear solution to which was added TCEP (0.25 by weight of the total weight of peptide segments), and the solution was incubated for 20 minutes. Then 30 volumes of pH4.0, 100 mM Na acetate dilution buffer, 6 m in guanidinium chloride was added and the solution was mixed. The resulting solution was pumped onto a preparative reverse-phase (C4) HPLC column. Buffer was pumped at 30% C (Buffer C: 0.1% TFA in 60% isopropanol/30% acetonitrile/10%water) until all non-peptide materials had eluted from the column, then the ligation product was purified by a gradient of 37–57%% Buffer C over 80 minutes. Fractions containing the desired ligated product $(Cys^{33}(Acm))${SEP-1:2+SEP-1:3+SEP-1:4+GP41} were identified by ES-MS and pooled and lyophilized.

Step 4: Carboxymethylation of residues $Cys^{89}$ and $Cys^{117}$ The $(Cys^{33}(Acm))$ {SEP-1:2+SEP-1:3+SEP-1:4+GP41} [i.e. $(Cys^{33}(Acm))$-1712-1713-1776-GP41] was dissolved in TFE at 1 mM concentration. 10 volumes of 300 mM Na phosphate buffer (pH 7.9) containing 6 M guanidinium chloride was added. A 25-fold excess (over sulfhydryl groups) of bromoacetic acid dissolved in methanol at 75 mg/ml was added, and the solution was allowed to react with stirring for two hours at room temperature The reaction mixture was then diluted with 11 volumes of 100 mM Na acetate pH4.0, 6M guanidinium chloride, and loaded onto a preparative reverse-phase (C4) HPLC column and pumped at 20% Buffer C until all non-peptide components had eluted, then the ligation product was purified with a step gradient to 55% Buffer C. Fractions containing the desired modified product $(Cys^{33}(Acm); \Psi^{89,117})$ {SEP-1:2+SEP-1:3+SEP-1:4+GP41} were identified by ES-MS and pooled and lyophilized.

Step 5: Picolyl Removal Zinc dust (71 milligrams per milligram of peptide) was activated in 2M HCl for 5 minutes, the activation was repeated once, then the zinc was washed for 10 minutes with 6M guanidinium chloride, 50 mM glycine pH2.2 containing (freshly added) 35 mg/ml L-methionine and 35 mg/ml Na dodecanoylsarcosine and 10%v/v TFE. to remove excess acid. The wash was repeated once. The $Cys^{161}$(Pico)-containing peptide $(Cys^{33}(Acm); \Psi^{89,117})$ {SEP-1:2+SEP-1:3+SEP-1:4+GP41} was dissolved in neat TFE at about 30 mg/ml concentration. The solution was diluted with 4 volumes (relative to TFE) 6M guanidinium chloride, 50 mM glycine pH2.2 containing (freshly added) 35 mg/ml L-methionine and 35 mg/ml Na dodecanoylsarcosine and 10%v/v TFE. The solution was added to the activated zinc powder and stirred for 50 minutes at room temperature. The reaction was monitored by analytical C4 reverse-phase HPLC of aliquots (treated with an equal volume of β-mercaptoethanol and a few grains of TCEP, then diluted with 2 volumes of 6M guanidinium chloride, 100 mM Na acetate pH4.0 for analysis) at ~1 hr intervals and was complete after 2 to 5 hours. After picolyl group removal was complete, as shown by ES-MS analysis of the analytical HPLC peaks (i.e. loss of 91Da mass), the supernatant was removed by filtration and the remaining Zn powder was washed 3 times with 6M guanidinium chloride, pH 4, 100 mM acetate containing 35 mg/ml L-methionine and 35 mg/ml dodecylsarcosine containing 20% TFE. Bio-Rad SM-2 beads (approximately one-third the volume of the solution) were added to the combined supernatant and washes and stirred at room temperature for 30 minutes, then filtered. β-mercaptoethanol was added to 10%v/v, then 0.25×(combined weight of peptides) of TCEP was added and the solution stirred for 5 minutes at room temperature. The solution was diluted 1:1 with an equal volume of 100 mM Na acetate pH4.0, 6M guanidinium chloride and loaded onto a preparative (C4) reverse-phase HPLC column and 35% Buffer C pumped until all the non-peptide material was eluted, and the desired product was purified with a step gradient to 55% Buffer C. Fractions containing the desired $Cys^{161}$-deprotected product $(Cys^{33}(Acm); \Psi^{89,117})$ {SEP-1:2+SEP-1:3+SEP-1:4+GP41-Pico} were identified by electrospray mass spectrometry and pooled.

Step 6: Acm-removal #2 The pooled solution of $(Cys^{33}(Acm); \Psi^{89,117})$ {SEP-1:2+SEP-1:3+SEP-1:4+GP41-Pico} [i.e. $(Cys^{33}(Acm); \Psi^{89,117})$-1712-1713-1776-GP41] was diluted 3× with HPLC grade water, and solid urea was added for a final concentration of 2M. A threefold molar ratio (relative to the total cysteine concentration) of a 30 mg/ml $Hg(acetate)_2$ solution in 3% aqueous acetic acid was added and the solution was stirred for one hour at room temperature. The solution was then made 20% in β-mercaptoethanol, and was loaded onto a semi-preparative (C4) reverse-phase HPLC column. Buffer C (20%) was pumped until all non-peptide material had been eluted, and then the desired product was purified with a step gradient to 55% Buffer C. Fractions containing the desired product $(Cys^{33}; \Psi^{89,117})$ {SEP-1:2+SEP-1:3+SEP-1:4+GP41-Pico} were identified by ES-MS, diluted 2× (v/v) with water containing 2× (w/w relative to peptide mass) DPC (dodecylphosphocholine) and were lyophilized overnight.

Step 7: Ligation #3 $(Cys^{33}; \Psi^{89,117})$ {SEP-1:2+SEP-1:3+SEP-1:4+GP41-Pico} [i.e. $(Cys^{33}; \Psi^{89,117})$-1712-1713-1776-GP41] was dissolved in neat TFE (1 volume) at 3 mM concentration. SEP-1:1 [i.e. 1711-GP41] was dissolved in 2 volumes 300 mM Na phosphate buffer (pH 7.9) containing 6 M guanidinium chloride. The solutions were combined, and 1%v/v thiophenol was added. The ligation mix was stirred overnight at room temperature. To the solution was added 3 volumes (relative to TFE volume above) of β-mercaptoethanol, and 9 volumes of ligation buffer (300 mM Na phosphate buffer pH 7.9, containing 6 M guanidinium chloride). To the solution was added 0.25×(combined weight of peptides) TCEP and the solution was stirred at room temperature for 20 minutes. Glacial acetic acid (0.6 volumes) was added to acidify the solution to pH4.0, and the solution was then diluted with 30 volumes of 100 mM Na acetate pH4.0 containing 6M guanidinium chloride, and loaded onto a preparative (C4) reverse-phase HPLC column. Buffer C (25%) was pumped until all non-peptide material was eluted, then the ligation product was purified with a linear gradient of Buffer C from 35–55% over 80 minutes. Fractions containing the desired ligated product SEP-1 (1–166) ($\Psi^{89,117}$) {SEP-1:1(+GP41)+SEP-1:2+SEP-1:3+SEP-1:4+GP41}: (SEQ ID NO:2) were identified by electrospray mass spectrometry, and pooled.

Step 8 Folding: To the combined fractions containing full-length ligated peptide SEP-1 (1–166) ($\Psi^{89,117}$) {SEP-1:1(+GP41)+SEP-1:2+SEP-1:3+SEP-1:4+GP41} [i.e. 1711 (GP41)-1712-1713-1776-GP41] was added solid guanidinium chloride, 1M Tris buffer (pH 8.7) and distilled water to make the final solution 0.1 milligrams per ml ligated peptide SEP-1 (1–166), 6M guanidinium chloride, 100 mM Tris, This ligated peptide ('protein') solution was loaded into 15 ml dialysis cassettes and dialyzed overnight at 4° C. against a solution of 100 mM Tris buffer (pH 8.5) containing 3 M guanidinium chloride, 5 micromolar cysteine and 2 micromolar cystine. The protein solution was then dialyzed against a solution of 100 mM Tris buffer (pH 8.5) containing 1 M guanidinium chloride for 8 hours at 4° C. and finally dialyzed against 10 mM Tris buffer (pH 7.0) for 14 hours at 4° C. to yield the final folded product. The folded protein-containing solutions from the dialysis cassettes were combined. Folding was verified by ES-MS, analytical RP-HPLC, and by CD spectrometry.

Figure 27:
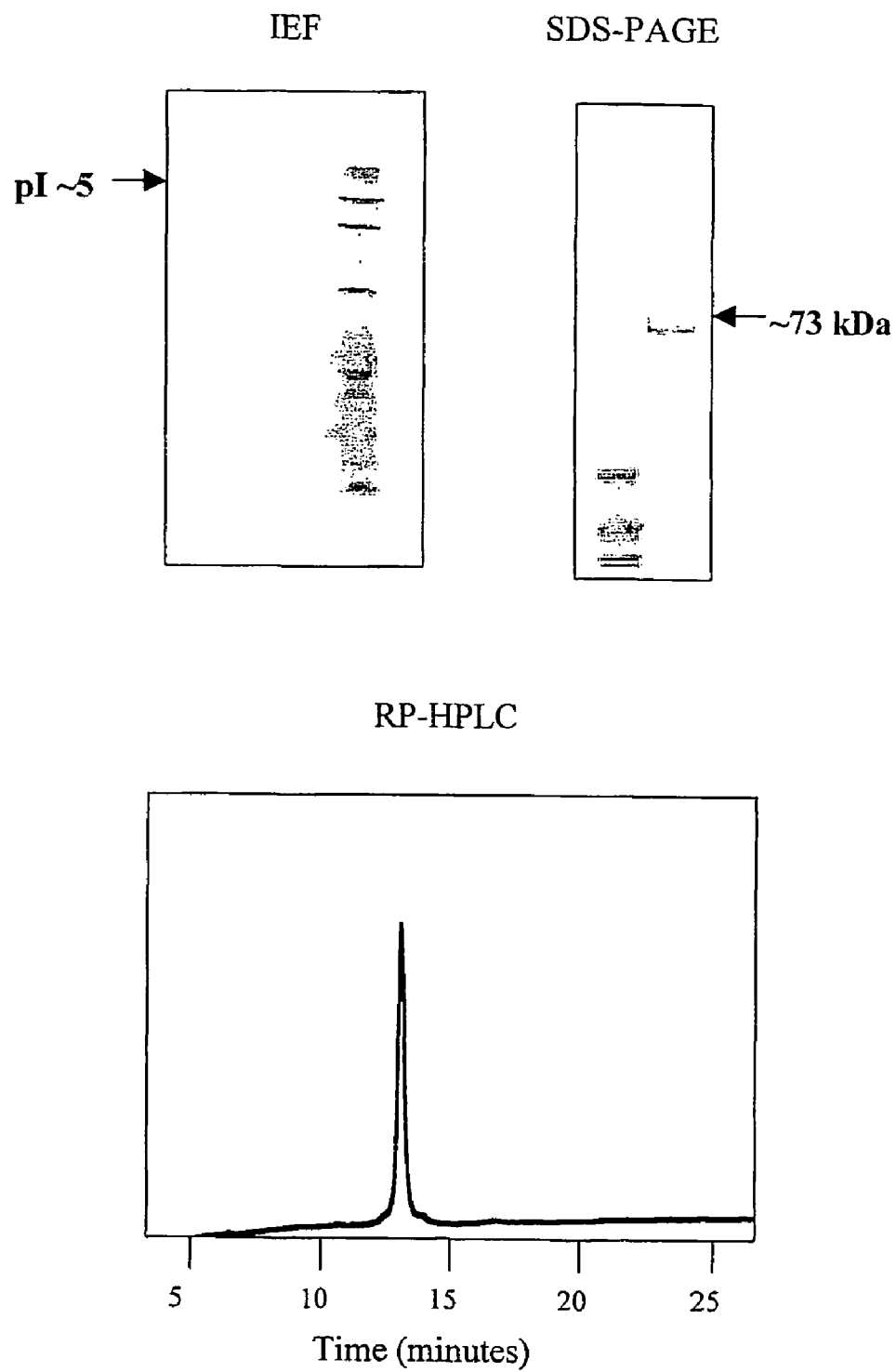
FIG. 27 shows representative analytical data for the precision polymer-modified synthetic analogs of human EPO prepared as described in Examples 2–5 and 7–8. As shown, a representative Isoelectric Focusing Gel (IEF) and non-reducing SDS-PAGE gel demonstrate the relative monomer molecular weight of the folded, purified SEP1-B51.

Step 9 Purification: The folded protein-containing solution was loaded on to Q-Sepharaose ion exchange column equilibrated at 10 mM Tris, pH 7.0. The folded protein was eluted using a linear salt gradient to 125 mM NaCl. Fractions containing the desired folded product SEP-1-B51 were identified by non-reducing SDS-PAGE, and pooled. The combined fractions were concentrated by ultrafiltration to a concentration of approximately 2 milligrams per milliliter, then the protein solution was loaded onto a 2.6×100 cm S-300 gel filtration column. The purified SEP-1-B51 was eluted with 10 mM Tris pH7.0, 137 mM sodium chloride. Fractions containing high purity SEP-1-B51 were identified by non-reducing SDS-PAGE, and were pooled, frozen and stored at −80° C. The final, purified folded protein SEP-1-B51 was characterized by analytical (C4) reverse-phase HPLC, ES-MS, by non-reducing SDS-PAGE, and CD spectrometry. FIG. 27 shows a representative Isoelectric Focusing Gel (IEF) and non-reducing SDS-PAGE gel showing the relative molecular weight of the folded, purified SEP1-B51. A molecular weight standard run on the same gels are shown for comparison. As shown, the relative molecular weight of SEP1-B51 by determined by non-reducing SDS-PAGE is approximately 73 kDa. The relative pI is approximately 5.0. Also shown is a representative RP-HPLC chromatogram of the folded, purified SEP-1-B51 product. This illustrates the purity and increased relative molecular weight of the precision polymer-modified proteins of the present invention.

Example 8

Synthesis Of Synthetic Erythropoiesis Stimulating Protein SEP-1-B52

A. Composition of SEP-1-B52. A seventh synthetic erythropoiesis stimulating protein (designated SEP-1-B52) was synthesized. The amino acid sequence of the full-length SEP-1-B52 is the same as that of SEP-1-B51:

(SEQ ID NO:2)
APPRLICDSR    VLERYLLEAK  EAEK$^{ox}$ITTGCA  EHCSLNEKIT

-continued

VPDTKVNFYA    WKRMEVGQQA  VEVWQGLALL    SEAVLRGQAL

LVKSSQPW$\psi$P   LQLHVDKAVS  GLRSLTTLLR    ALGAQK$\psi$AIS

PPDAAK$^{ox}$AAPL  RTITADTFRK  LFRVYSNFLR    GKLKLYTGEA

CRTGDR where $\Psi$ denotes an non-native amino acid residue consisting of a cysteine that is carboxymethylated at the sulfhydryl group, and where K$^{ox}$ denotes a non-native lysine that is chemically modified at the $\epsilon$-amino group with an oxime linker group coupled to a designated water-soluble polymer through an oxime bond.

The SEP-1-B52 protein was derivatized at residues 24 and 126 with a branched (Succ-TTD)$_{12}$-Succ-Ala polymer construct similar to SEP-1-B51, but for this analog the polymer was attached via an oxime bond between pyruvic acid and aminooxyacetic acid. Moreover, the $\epsilon$-amino group of lysine residues 24 and 126 were modified to bear an aminooxyacetyl functional group instead of a levulinic acyl moiety, and the branched (Succ-TTD)$_{12}$-Succ-Ala polymer construct was made to bear a pedant pyruvic acyl moiety. These changes were designed to improve synthesis and handling, and to further increase stability of the oxime linkages.

Figure 25B:
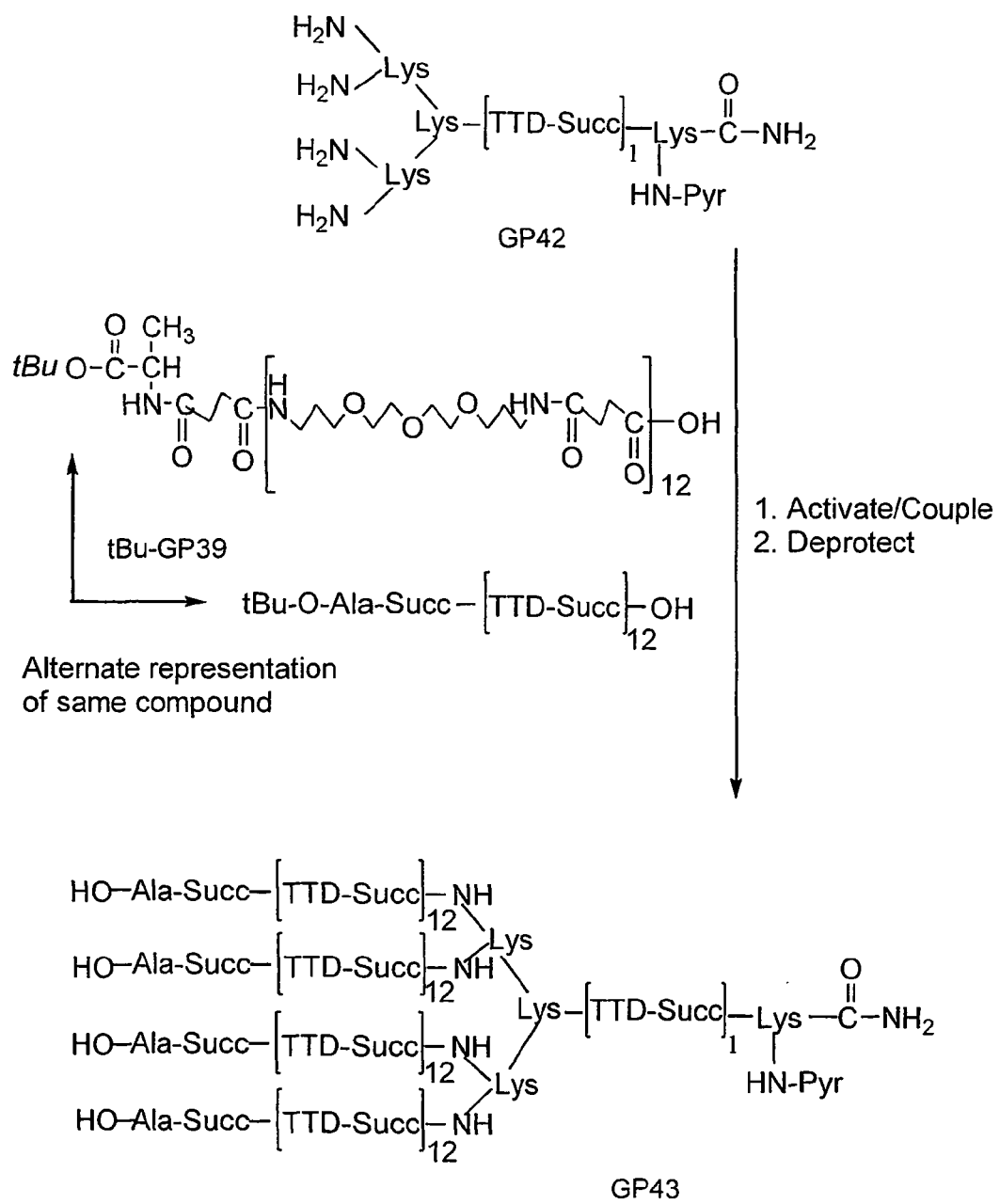
FIG. 25 depicts the synthesis of a preferred water-soluble polymer for attaching to a synthetic cytokine designated SEP1-B52, which is a precision polymer-modified synthetic analog of human EPO prepared as described in Example 8.
Figure 26:
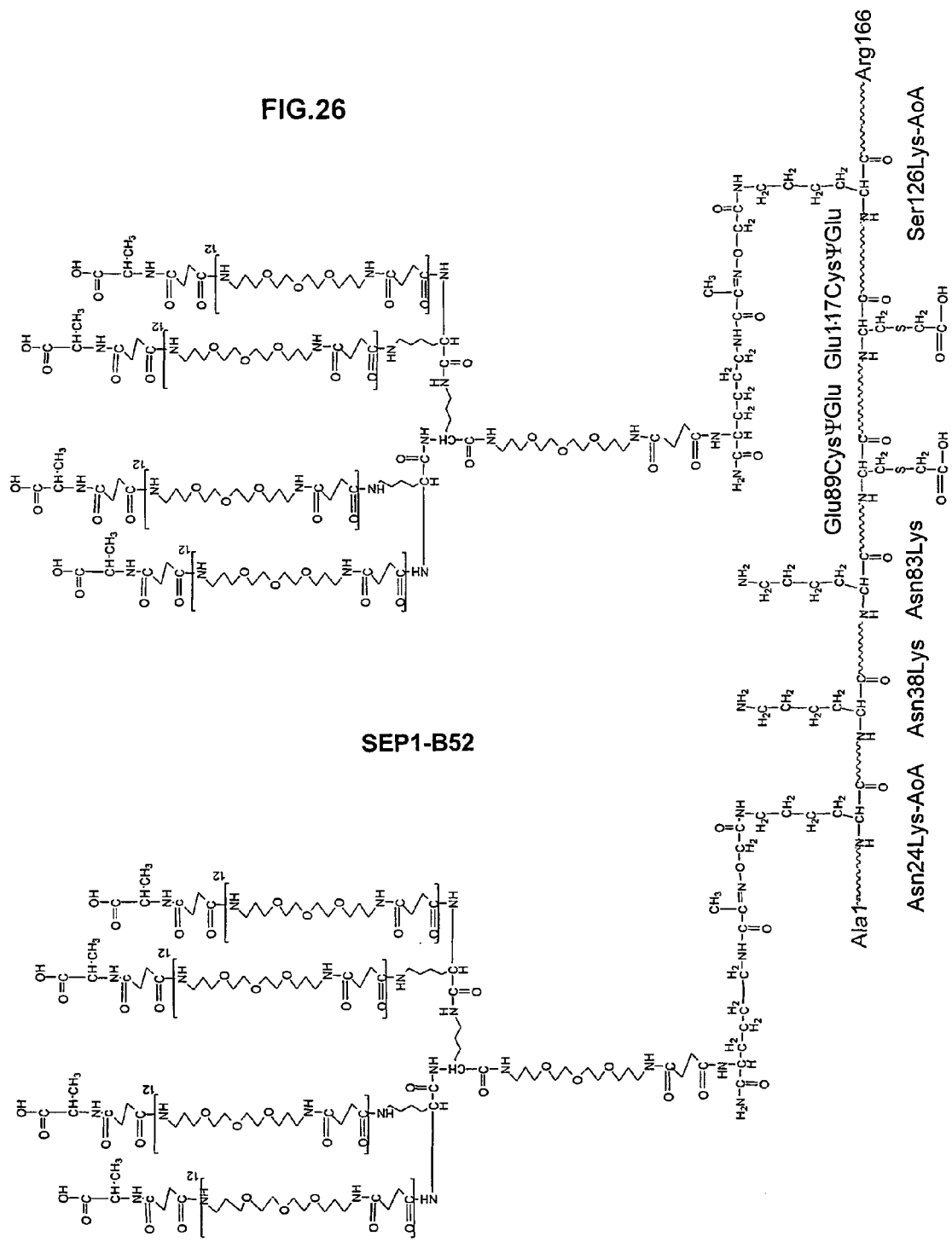
FIG. 26 depicts a synthetic cytokine designated SEP1-B52, which is a precision polymer-modified synthetic analog of human EPO prepared as described in Example 8.

FIG. 25 is a schematic illustrating the chemical synthesis of the branched water-soluble polymer GRFNP43 (GP43) that was joined to the SEP-1-B52 through oxime-forming ligation as described below. Assembly of the full-length product was as described in Example 2. The structure of SEP-1-B52 is shown in FIG. 26.

B. Synthesis of (Succ-TTD)$_{12}$-Succ-AlaOtBu (GRFNP39) for Coupling to the Branching Template (GRFNP42)

(Succ-TTD)$_{12}$-Succ-AlaOtBu (GRFNP39) was synthesized on a 0.5 mmol scale. 0.5 mmole (~0.5 grams) Sasrin acid labile, carboxylic acid-generating polystyrene resin (hydroxyl substitution 1.02 mmole/g;) was swelled in DMF for 15 minutes and then drained. To this hydroxyl-functionalized resin was added 450 mg (4.5 mmole) succinic anhydride and 488 mg (4 mmole) 4-(dimethylamino)pyridine dissolved in 8 ml of DMF containing 500 microliter (3.9 mmole) DIEA (diisopropylethylamine) and allowed to react for 30 minutes with vortex agitation, then drained. The coupling was repeated and excess reactants and soluble coproducts were removed by a 1 minute vortexing flow wash with DMF (~50 ml), then drained. The HOOC—CH$_2$CH$_2$CO—O-resin (0.5 mmole) was activated by addition of 8 ml of fresh 1.0 M (8 mmole) CDI solution in DMF and allowed to react for 40 minutes, then drained. Excess reactants and soluble coproducts were removed by a 1 minute vortexing flow wash with DMF (~50 ml), and drained. 4 ml (4 grams, 18.2 mmole) TTD dissolved in 4 ml 0.5M (2 mmole) HOBT solution in DMF was added and allowed to react with vortex agitation for 30 minutes and drained. Excess reactants and soluble coproducts were removed by a 1 minute vortexing flow wash with DMF (~50 ml) and drained. Succinic anhydride (450 mg, 4.5 mmole) dissolved in 8 ml of 0.5M (4 mmole) HOBT (N-hydroxybenzotriazole) solution containing 500 microliter (3.9 mmole) DIEA was added to the resin and allowed to react with vortex agitation for 15 minutes, then drained. The three steps (CDI activation; TTD coupling; succinic anhydride reaction) were repeated eleven times [i.e. a total of twelve times]. Excess reactants and soluble coproducts were removed by a 1 minute vortexing flow wash with DMF (~50 ml), and drained. The HOOC—CH$_2$CH$_2$CO(TTD-succinyl)$_{12}$-O-resin (0.5 mmole) was activated with 8 ml of fresh 1.0 M (8 mmole) CDI solution in DMF, allowed to react for 40 minute, and drained. Excess reactants and soluble coproducts were removed by a 1-minute voltexing flow wash with DMF (~50 ml), and drained. 2.5 mmole H-AlaOtBu.HCl was dissolved in 4.75 ml 0.5 M (2.375 mmole) HOBT in DMF containing 150 microliter (111 mg, 0.825 mmole) DIEA, and allowed to react with the CDI-activated HOOC—CH$_2$CH$_2$CO(TTD-succinyl)$_{12}$-O-resin (0.5 mmole) for 1 hour with vortex agitation, then drained. Excess reactants and soluble coproducts were removed by a 1-minute vortexing flow wash with DMF (~50 ml), and then drained. The product tertBuOOC—CH(CH3)—NH—OC—CH$_2$CH$_2$CO(TTD-succinyl)$_{12}$-O-resin was washed extensively with DCM, drained and then the resin was dried under vacuum to constant weight. Typical weight of product-resin was around 2 grams.

The linear GRFNP39 was cleaved from the resin support according to standard Fmoc-chemistry procedures using 4% TFA in DCM. The precipitated crude product was dissolved in 50% aqueous acetonitrile containing 0.1% TFA and lyophilized. The lyophilized polymer was dissolved in a small amount of 50% aqueous acetonitrile containing 0.1% TFA and diluted to reduce the concentration of organic below 1%. The crude product was loaded onto a C4 preparative reverse-phase HPLC column equilibrated at T=40° C. at 3% B. Salts were eluted isocratically and the desired template was purified with a linear gradient of 20–35% Buffer B (acetonitrile containing 0.1% TFA) versus 0.1% aqueous TFA over 60 minutes. Fractions containing the desired (Succ-TTD)$_{12}$-Succ-AlaOtBu material (GRFNP39) were identified by ES-MS, frozen and lyophilized.

C. Synthesis of a Template Carrying Multiple Amine Groups for Branching and a Pendant Pyruvic Acyl Moiety for (Later) Attachment to the Protein (GRFNP42)

The template was synthesized manually on a Boc-Leu-OCH$_2$-Pam-resin on a 0.4 mmol scale. A one-minute flow-washing step with DMF was used between every coupling, deprotection and activation step. The Boc group was removed by treatment with neat (i.e. 100%) TFA. After DMF washing, 2 mmol Fmoc-(Rink-linker)-OH was coupled to the resin after activation with 1.8 mmol HBTU in 3.8 ml DMF containing 1 ml DIEA. After removal of the Fmoc protecting group (2×3 minutes 20% piperidine in DMF), 2 mmol Fmoc-Lys(MTT)-OH [MTT=4-methyltrityl] was coupled to the resin using NHS-ester activation with 2 mmol DIC and 2 mmol NHS in DMF. After removal of the Fmoc protecting group (2×1 minute 0.5% DBU in DMF), 4 mmol succinic anhydride dissolved in 8 ml of 0.5M HOBT solution containing 2.2 mmol DIEA was coupled to the resin for 10 minutes. After this step, the resin-bound carboxyl group was activated with 8 ml of fresh 0.5 M CDI solution in DMF. 4 ml TTD was added in 4 ml 0.5M HOBT solution and coupled for 30 minutes.

2 mmol Fmoc-Lys(Fmoc)-OH was coupled to the resin using NHS-ester activation with 2 mmol DIC and 2 mmol NHS in DMF. After an Fmoc removal step (2×1 minute 0.5% DBU in DMF), 4 mmol Boc-Lys(Boc)-NHS is coupled in 3 ml DMF.

The MTT protecting group was removed by multiple washes with 2% TFA in DCM. Deprotection was complete when the supernatant lost its yellow color. The resin was neutralized with 10% DEEA in DMF for one minute. 2 mmol pyruvic acid was coupled to the resin using NHS-ester activation with 2 mmol DIC and 2 mmol NHS in DMF for 45 minutes. The template was deprotected and cleaved from the resin support using neat TFA containing 5% water. The cleavage solution was evaporated to dryness in a rotator evaporator. The residue was dissolved in 50% aqueous acetonitrile containing 0.1% TFA and lyophilized. The lyophilized template was dissolved in a small amount of 50% aqueous acetonitrile containing 0.1% TFA and diluted to reduce the concentration of organic below 1%. The pyruvate-containing template was loaded onto a C4 Prep column equilibrated at T=40° C. at 0% Buffer B [i.e. 100% Buffer A=0.1%TFA in water]. Salts were eluted isocratically and the desired template was purified with a linear gradient of 5–12% Buffer B versus 0.1% aqueous TFA in 60 minutes. Fractions containing the desired material (GRFNP42) were identified by ESI-MS, frozen and lyophilized.

D. Assembly and Deprotection of the Amide-coupled Branched Polymer (GRFNP43)

GRFNP43, a branched (TTD-Succ)$_{49}$-polymer of 16 kDa molecular weight was synthesized by coupling GRFNP39 to the purified template GRFNP42. Purified (Succ-TTD)$_{12}$-Succ-AlaOtBu (GRFNP39) (1.0 mmole) dissolved in DMSO at 60° C. to a concentration of 20 mg/ml was activated with 0.95 mole of HATU in DMSO at a concentration of 10 mg/ml in the presence of a twenty-fold (molar) excess of DIEA. Purified template (0.24 mole)GRFNP42 dissolved in DMSO at a concentration of 3.9 mg/ml was added immediately. Progress of the reaction was monitored by analytical C4 reversed-phase HPLC and ES-MS. Typically, the coupling was complete within minutes. For work-up, 4 volumes (relative to ligation mix) 0.1M acetate/6 M guanidinium chloride, pH 4 was added, and the solution was loaded onto a preparative (C4) reverse-phase HPLC column. Salts and other non-amide containing material were eluted isocratically and the desired product branched polymer was purified with a linear gradient of 20–35% Buffer B (acetonitrile containing 0.1% TFA) versus 0.1% aqueous TFA over 80 minutes. Fractions containing the desired material were identified by ES-MS, frozen and lyophilized.

The resulting purified branched polymer construct GRFNP43 was dissolved in neat TFA at a concentration of 1 mg/ml for 1 hour to remove the Ala-OtBu tertButyl ester protection. The solution was evaporated to dryness in a rotary evaporator and the dried polymer was dissolved in 50% Buffer B (acetonitrile containing 0.1% TFA). The polymer was desalted on a preparative reverse phase HPLC with a step gradient from 15% to 45% Buffer B versus 0.1% aqueous TFA in 80 minutes. Pooled fractions containing the desired material (GRFNP43) were frozen and lyophilized, and the dried powder used for the oximation-forming ligation step.

E. Oxime-forming Ligation (Oximation) of GRFN1776 and GRFN1711 With the Branched Polymer GRFNP43

Segments SEP-1:4, and Segment SEP-1:1 were synthesized as described above in Examples 2, 3, 4, and 7, only that instead of levulinic acid an aminooxyacetyl (AoA) moiety was appended to Lys[24] and Lys[126] in the respective peptide segments following standard coupling protocols. Thus, after assembly of the peptide-resins, the side chain Fmoc group was removed from each peptide-resin and 2 mmol Boc-aminooxyacetic acid was added to the resin using NHS-ester activation with 2 mmol DIC and 2 mmol NHS in DMF. The two peptides were deprotected and cleaved from the resin with HF and purified by C4 reverse-phase HPLC. Suitable precautions were taken to avoid exposure to carbonyl compounds. Segment SEP-1:4 and GRFNP43 were jointly dissolved at an equimolar ratio in 50% aqueous acetonitrile containing 0.1% TFA (trifluoroacetic acid). The solution was lyophilized. The dried powder was re-dissolved in 50% aqueous acetonitrile containing 0.1% TFA and loaded onto a preparative C4 reverse-phase HPLC column. The polymer-modified peptide was separated from unmodified peptide and unreacted polymer by preparative gradient reverse-phase HPLC. Fractions containing the desired oximated product SEP-1:4+GP43 were identified by ES-MS and pooled.

Segment SEP-1:1 and GRFNP43 were jointly dissolved at an equimolar ratio in 50% aqueous acetonitrile containing 0.1% TFA. The solution was frozen and lyophilized. The dried powder was dissolved in 50% aqueous acetonitrile containing 0.1% TFA and loaded onto a preparative gradient C4 reverse-phase HPLC column. The polymer-modified peptide was separated from unmodified peptide and unreacted polymer by preparative reverse-phase gradient elution. Fractions containing the desired oximated product SEP-1:1+GP43 were identified by ES-MS and pooled.

F. Synthesis Of Synthetic Erythropoiesis Stimulating Protein SEP-1-B52

SEP-1-B52 (SEQ ID NO:2) was synthesized in solution from four polypeptide segments:
Segment SEP:1:1+GP43 (GRFN 1711+GRFNP43; corresponding to residues 1–32 of SEQ ID NO:2):
  APPRLICDSR VLERYLLEAK EAEK$^{ox}$ITTGCA EH-thioester (where Lys$^{24}$ has an AoA pendant moiety oxime-linked to the branched polymer GRFNP43, as denoted by K$^{ox}$; and where His$^{32}$ is Dnp protected)
Segment SEP-1:2 (GRFN 1712; corresponding to residues 33–88 of SEQ ID NO:2):
  CSLNEKIT VPDTKVNFYA WKRMEVGQQA VEVWQGLALL SEAVLRGQAL LVKSSQPW-thioester (where Cys$^{33}$ is Acm protected; and where the three Trp residues are formyl protected)
Segment SEP-1:3 (GRFN 1713, corresponding to residues 89–116 of SEQ ID NO:2):
  CP LQLHVDKAVS GLRSLTTLLR ALGAQK-thioester (where Cys$^{89}$ is Acm protected; and where His$^{94}$ is Dnp protected)
Segment SEP-1:4+GP43 (GRFN 1776+GRFNP43, corresponding to residues 117–166 of SEQ ID NO:2):
  CAIS PPDAAK$^{ox}$AAPL RTITADTFRK LFRVYSNFLR GKLKLYTGEA CRTGDR-carboxylate (where the C-terminal cysteine (i.e. Cys$^{161}$) carries a picolyl (pico) protecting group, and where Lys$^{q126}$ has an AoA pendant moiety oxime-linked to the branched polymer GRFNP43, as denoted by K$^{ox}$).

Synthesis of additional peptides, ligation reactions, carboxymethylation, protecting group removal reactions, folding and purification are performed as described above in Examples 1, 2, 3, 4, and 7, to yield full-length, folded SEP-1-B52 (SEQ ID NO:2), which was characterized by analytical (C4) reverse-phase HPLC, ES-MS, and non-reducing SDS-PAGE. Bioassays are performed as described for the other SEP constructs.

Example 9

Efficacy Studies for SEP-3-L42

SEP-3-L42 was reformulated in Citrate Buffer (20 mM sodium citrate+100 mM sodium chloride) plus 0.25% rat serum albumin (RSA) and was administered intravenously to normal male rats (5 rats per group) at doses of 0, 1, 5, or 10 µg/kg, tiw, on Days 1, 3, and 6. Blood samples were collected 4 days after the last injection (Day 9) and analyzed for hematologic parameters. There were no statistically significant differences in red blood cell (RBC), hemoglobin (HGB), hematocrit (HCT), and reticulocyte count (RET) values at 4 days after the last injection with SEP-3-L42 at these doses when compared with those of the control group.

Example 10

Pharmacokinetic Studies for SEP-3-L42

SEP-3-L42 was reformulated in Citrate Buffer (20 mM sodium citrate+100 mM sodium chloride) plus 0.25% RSA, pH6.9, and was administered intravenously as a single dose to normal male rats at a dose level of 5 ug/kg. Blood samples were collected at 0, 1, 2, 4, 6, 12, 24, 48, 72, 96, 120, 144, 168 hours after the dosing. The plasma SEP-3-L42 concentration was determined by anti-EPO ELISA kit (R & D Systems, Human Erythropoietin Quantikine IVD Immunoassay Kit #DEP00) according to the manufacturers instructions. The results are shown in FIG. 29.

Figure 29:
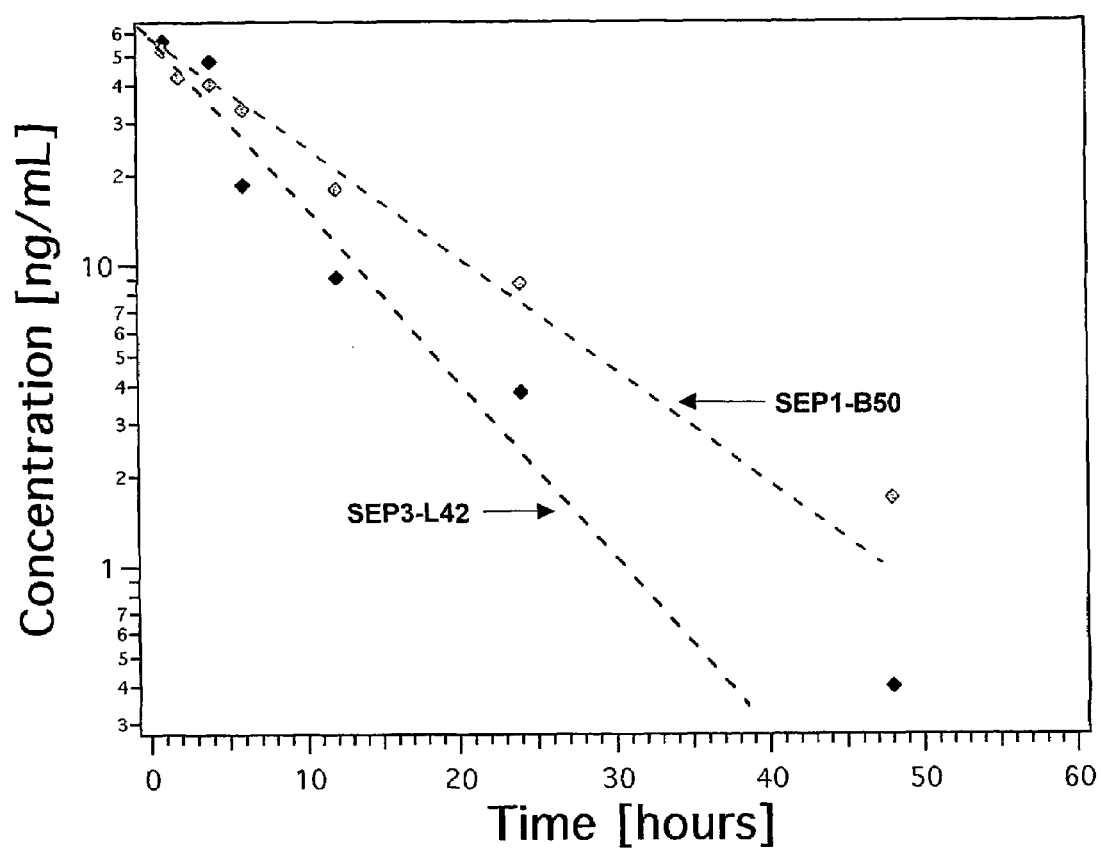
FIG. 29 shows a representative pharmacokinetic profile comparing plasma concentration in nanograms per milliliter (ng/ml) of SEP3-L42 and SEP1-B50 versus time in hours.

As shown in FIG. 29, SEP-1-B50 exhibited slightly slower clearance compared to SEP3-L42. Despite its circulating half-life, SEP3-L42 failed to exhibit statistically significant differences in promoting red blood cell production at the doses tested. In contrast, the SEP-1-B50 stimulated red blood cell production at the same doses. This illustrates that polymer structure can be exploited for fine-tuning in vivo biological properties, including pharmacokinetic behavior and potency.

Example 11

Efficacy Studies for SEP-1-L30

SEP-1-L30 was reformulated in Citrate Buffer (20 mM sodium citrate+100 mM sodium chloride) plus 0.25% RSA and was administered intravenously to normal male rats (5 rats per group) at doses of 0, 1, 5, 25, or 50 µg/kg, tiw, on Days 1, 3, and 5. Blood samples were collected 4 and 8 days after the last injection (Days 9 and 13) and analyzed for hematologic parameters. There were no statistically significant differences in RBC, HGB, and HCT values at any interval after treatment with SEP-1-L30, when compared with those of the control group. Reticulocyte counts were higher at 4 days after the last injection (Day 9) for rats treated with 25 and 50 µg/kg (statistically significant difference when compared with those of the control group). No other differences in hematologic parameters were observed at either Day 9 or Day 13 for any of the animals treated with SEP-1-L30. [Data not shown]

Example 12

Pharmacokinetic Studies for SEP-1-L30

SEP-1-L30 was reformulated in Citrate Buffer (20 mM sodium citrate+100 mM sodium chloride) plus 0.25% RSA, pH6.9, and was administered intravenously to normal male rats as a single dose at a dose level of 5 or 25 ug/kg. Blood samples were collected at 0, 1, 2, 4, 6, 12, 24, 48, 72, 96, 120, 144, and 168 hours after the dosing. Plasma concentration of SEP-1-L30 was determined by ELISA kit (R & D Systems, Human Erythropoietin Quantikine IVD Immunoassay Kit #DEP00) according to manufacturers instructions. No SEP-1-L30 was detectable at any of the time points at the doses given.

Example 13

Efficacy Studies for SEP-1-B50

SEP-1-B50 was reformulated in sterile PBS (phosphate buffered saline) plus 0.25% RSA and was administered intravenously to normal male rats (5 rats per group) at doses of 0, 1, 5, 25, or 125 µg/kg, tiw, on Days 1, 3, and 6. Blood samples were collected 4, 9, and 14 days after the last injection (Days 10, 15, and 20) and analyzed for hematologic parameters. The data is shown in Table VII below. A dose-related response in increased RBC, HGB, HCT, and RET was observed at 4 days after the last injection (Day 10) for animals receiving 5, 25, and 125 µg/kg SEP-1-B50 (statistically significant difference when compared with those of the control group). RBC, HGB, and HCT for these animals remained higher than control values on Day 15 and continued to be significantly higher than control values through Day 20 (14 days after the last injection) for animals treated at 125 µg/kg. RET production was reduced after Day 10, with significantly lower counts on Days 15 and 20 for the 25 and 125 µg/kg animals.

TABLE VII

Hematology Findings Following Multiple Doses of SEP-1-B50

|  | Day 10 | Day 15 | Day 20 |
|---|---|---|---|
| RBC |  |  |  |
| Control | 7.01 ± 0.301 | 6.86 ± 0.391 | 6.96 ± 0.178 |
| 1 µg/kg | 7.07 ± 0.482 | 6.85 ± 0.446 | 7.00 ± 0.315 |
| 5 µg/kg | 7.16 ± 0.402 | 7.27 ± 0.229 | 6.92 ± 0.238 |
| 25 µg/kg | 7.98 ± 0.484** | 7.73 ± 0.448* | 7.20 ± 0.331 |
| 125 µg/kg | 8.71 ± 0.512** | 8.89 ± 0.598** | 8.25 ± 0.641** |
| HGB |  |  |  |
| Control | 14.2 ± 0.49 | 14.0 ± 0.61 | 13.9 ± 0.36 |
| 1 µg/kg | 14.4 ± 1.18 | 14.2 ± 0.44 | 14.1 ± 0.30 |
| 5 µg/kg | 15.6 ± 0.43* | 15.3 ± 0.33* | 14.4 ± 0.30 |
| 25 µg/kg | 16.1 ± 0.49** | 15.1 ± 0.57 | 13.8 ± 0.22 |
| 125 µg/kg | 16.9 ± 0.82** | 16.4 ± 0.32** | 15.0 ± 1.07* |
| HCT |  |  |  |
| Control | 41.1 ± 1.39 | 40.5 ± 0.93 | 40.9 ± 1.33 |
| 1 µg/kg | 42.6 ± 1.82 | 40.6 ± 1.83 | 41.2 ± 1.13 |
| 5 µg/kg | 44.7 ± 1.69* | 44.1 ± 1.27 | 41.5 ± 0.90 |
| 25 µg/kg | 46.6 ± 1.50** | 43.6 ± 1.61 | 40.3 ± 1.05 |
| 125 µg/kg | 49.8 ± 2.13** | 48.4 ± 3.95** | 44.3 ± 3.39* |
| RET |  |  |  |
| Control | 2.4 ± 1.14 | 2.5 ± 1.10 | 0.9 ± 0.13 |
| 1 µg/kg | 3.8 ± 1.14 | 2.3 ± 0.46 | 1.3 ± 0.41 |
| 5 µg/kg | 6.6 ± 3.60* | 1.8 ± 0.48 | 0.8 ± 0.26 |
| 25 µg/kg | 6.2 ± 1.12* | 1.1 ± 0.24* | 0.2 ± 0.21** |
| 125 µg/kg | 8.4 ± 1.60** | 0.9 ± 0.50** | 0.3 ± 0.36** |

*Significant difference from control, $p < 0.05$
**Significant difference from control, $p < 0.01$ Example 14

Pharmacokinetic Studies for SEP-1-B50

SEP-1-B50 was reformulated in Citrate Buffer (20 mM sodium citrate+100 mM sodium chloride) plus 0.25% RSA, pH6.9, and was administered intravenously to normal male rats as a single dose at a dose level of 5 or 25 ug/kg. Blood samples were collected at 0, 1, 2, 4, 6, 12, 24, 48, 72, 96, 120, 144, 168 hours after dosing. Plasma concentration of SEP-1-B50 was determined by ELISA kit (R & D Systems, Human Erythropoietin Quantikine IVD Immunoassay Kit #DEP00) according to manufacturers instructions. The elimination half-lives were determined to be 9.7 and 9.9 hours for 5 and 25 ug/kg dose, respectively. The observed MRT (mean residence time) was 13.9 and 14.4 hours for the 5 and 25 ug/kg dose, respectively. A representative pharmacokinetic profile for SEP-1-B50 is shown in FIG. 29.

Example 15

Efficacy Studies for SEP-1-B51

SEP-1-B51 was administered intravenously to normal male rats in two experiments.

Experiment 1:

SEP-1-B51 was reformulated in Citrate Buffer (20 mM sodium citrate+100 mM sodium chloride) plus 0.25% RSA and was administered intravenously to male rats (5 rats per group) at doses of 0, 1,5. or 25 /µg/kg, tiw, on Days 1, 3, and 6, and blood samples collected at 4, 9, and 14 days after the last injection (Days 10, 15, and 20) for analysis of hematologic parameters. The data is shown in Table VIII below. Four days after the third and last intravenous injection with SEP-1-B51 (Day 10), a statistically significant increase in RBC, HGB, HCT, and absolute reticulocyte counts (ART) was observed for animals receiving 25 µg/kg SEP-1-B51, when compared with the values for the control group. The RBC value for these animals remained higher than the control value on Day 15 and was comparable to the control value on Day 20. Reticulocyte production was reduced after Day 10, with significantly lower counts observed for the 5 and 25 µg/kg animals on Day 15.

TABLE VIII

Hematology Findings Following Multiple Doses of SEP-1-B51

|  | Day 10 | Day 15 | Day 20 |
|---|---|---|---|
| RBC |  |  |  |
| Control | 5.66 ± 0.497 | 5.62 ± 0.385 | 5.90 ± 0.286 |
| 1 ug/kg | 5.32 ± 0.275 | 5.23 ± 0.470 | 5.77 ± 0.200 |
| 5 ug/kg | 6.22 ± 0.377 | 6.18 ± 0.298 | 6.39 ± 0.369 |
| 25 ug/kg | 6.70 ± 0.257** | 6.25 ± 0.348* | 5.94 ± 0.294 |
| HGB |  |  |  |
| Control | 14.3 ± 1.10 | 14.2 ± 0.88 | 14.8 ± 0.72 |
| 1 ug/kg | 13.3 ± 0.41 | 13.2 ± 0.93 | 14.3 ± 0.37 |
| 5 ug/kg | 15.1 ± 0.53 | 14.8 ± 0.30 | 15.4 ± 0.25 |
| 25 ug/kg | 16.5 ± 0.52** | 15.0 ± 0.91 | 14.3 ± 0.64 |
| HCT |  |  |  |
| Control | 36.8 ± 3.08 | 36.2 ± 2.59 | 37.9 ± 1.93 |
| 1 ug/kg | 34.5 ± 1.21 | 33.4 ± 2.56 | 37.1 ± 0.82 |
| 5 ug/kg | 39.9 ± 1.51 | 38.6 ± 0.91 | 40.2 ± 1.36 |
| 25 ug/kg | 43.8 ± 1.83** | 39.3 ± 2.77 | 37.2 ± 1.60 |
| ART |  |  |  |
| Control | 0.29 ± 0.089 | 0.28 ± 0.086 | 0.21 ± 0.034 |
| 1 ug/kg | 0.34 ± 0.50 | 0.23 ± 0.055 | 0.19 ± 0.075 |
| 5 ug/kg | 0.28 ± 0.059 | 0.11 ± 0.021** | 0.20 ± 0.081 |
| 25 ug/kg | 0.48 ± 0.121* | 0.06 ± 0.054** | 1.45 ± 3.100 |

**significant difference from control $p < 0.01$
*significant difference from control $p < 0.05$ Experiment 2.

SEP-1-B51 was reformulated in Citrate Buffer (20 mM sodium citrate+100 mM sodium chloride) plus 0.25% human serum albumin and was administered intravenously to male rats (5 rats per group) at doses of 0, 1, 5, or 25 µg/kg, tiw, on Days 1, 3, and 5, and blood samples collected at 2, 4, and 6 days after the last injection (Days 7, 9, and 11) for analysis of hematologic parameters. In addition, blood samples for measurement of hematocrit only [as packed cell volume (PCV)] were collected daily on the remaining study days (Days 2, 3, 4, 5, 6, 8, 10, 12, and 13). The data is shown in Table IX below. HCT (PCV or calculated) values were significantly increased for animals receiving 5 and 25 µg/kg beginning 2 days after the first injection (Day 3) and continuing through 6 days after the third and last injection (Day 11). RBC and HGB were also significantly increased on the days that they were measured (2, 4, and 6 days after the last dose; Days 7, 9, and 11) for animals receiving 5 and 25 µg/kg. ART was significantly increased only for the 25 µg/kg group at 2 and 4 days after the last dose (Days 7 and 9).

TABLE IX

Hematology Findings Following Multiple Doses[V] of SEP-1-B51

|  | Day 7 | Day 9 | Day 11 |
|---|---|---|---|
| RBC |  |  |  |
| Control | 5.61 ± 0.679 | 5.23 ± 0.467 | 5.34 ± 0.405 |
| 1 ug/kg | 6.08 ± 0.141 | 5.70 ± 0.300 | 5.67 ± 0.547 |
| 5 ug/kg | 6.29 ± 0.459 | 6.07 ± 0.308** | 6.11 ± 0.248* |
| 25 ug/kg | 6.61 ± 0.295** | 6.24 ± 0.268** | 6.38 ± 0.173** |
| HGB |  |  |  |
| Control | 13.7 ± 1.07 | 12.9 ± 0.79 | 13.3 ± 0.93 |
| 1 ug/kg | 14.6 ± 0.27 | 13.9 ± 0.19 | 13.9 ± 0.90 |
| 5 ug/kg | 15.8 ± 0.50** | 14.9 ± 0.53** | 14.8 ± 0.18* |
| 25 ug/kg | 16.7 ± 0.86** | 15.1 ± 0.66** | 14.6 ± 0.69* |
| HCT |  |  |  |
| Control | 35.6 ± 3.61 | 33.2 ± 2.39 | 34.5 ± 3.19 |
| 1 ug/kg | 38.9 ± 0.82 | 35.9 ± 0.94 | 35.9 ± 2.43 |
| 5 ug/kg | 41.3 ± 1.92** | 39.1 ± 1.01** | 39.2 ± 0.78* |
| 25 ug/kg | 44.4 ± 2.08** | 39.7 ± 2.23** | 39.6 ± 2.32** |
| ART |  |  |  |
| Control | 0.50 ± 0.158 | 0.36 ± 0.093 | 0.34 ± 0.079 |
| 1 ug/kg | 0.30 ± 0.044* | 0.30 ± 0.026 | 0.25 ± 0.054 |
| 5 ug/kg | 0.45 ± 0.125 | 0.36 ± 0.056 | 0.25 ± 0.045 |
| 25 ug/kg | 0.78 ± 0.117** | 0.71 ± 0.152** | 0.32 ± 0.099 |

*Significant difference from control, p < 0.05
**Significant difference from control, p < 0.01
[V]Note:
Day 7 (2 days post 3rd dose);
Day 9 (4 days post 3rd dose);
Day 11 (6 days post 3rd dose)

Additional groups of rats were treated with a single intravenous dose of SEP-1-B51 at 25 µg/kg, and blood samples were collected at 48 hr after injection for analysis of hematologic parameters. Blood samples for measurement of hematocrit only (as packed cell volume) were collected at 8, 24, and 72 hr and at 7 days after injection (Days 1, 2, 4, and 8). HCT, HGB, and ART values for the rats treated intravenously with SEP-1-B51 were higher than those of the control animals (statistically significantly) on Day 3 (2 days after injection), and HCT was also significantly increased in these animals on Day 4.

Example 16

Efficacy Studies in Polycythemic and Hypoxic Model for SEP-1-B51

Groups of 10 normal mice each (vehicle control, recombinant glycosylated human erythropoietin produced in CHO-cells ("rhEPO") at 4 dose levels, and SEP-1-B51 at 4 dose levels: 0.32, 1, 5, 25 ug/kg/dose assuming 100 mU/ng) were exposed 18 hr per day to atmospheric air maintained at 506.5 mb in a simulated high altitude chamber for 20 days. The rhEPO or SEP-1-B51, formulated in Citrate Buffer plus 0.25% human serum albumin, was injected intravenously (IV) in a 200 µL-volume on the $4^{th}$ post-hypoxic day. Two days later, each mouse was injected intraperitoneally (i.p.) with 0.2 µCi of $^{59}$Fe. RBC-radioiron uptake was estimated 3 days later by measuring the amount of radioactivity present in 500 µL of blood taken by cardiac puncture.

Figure 30:
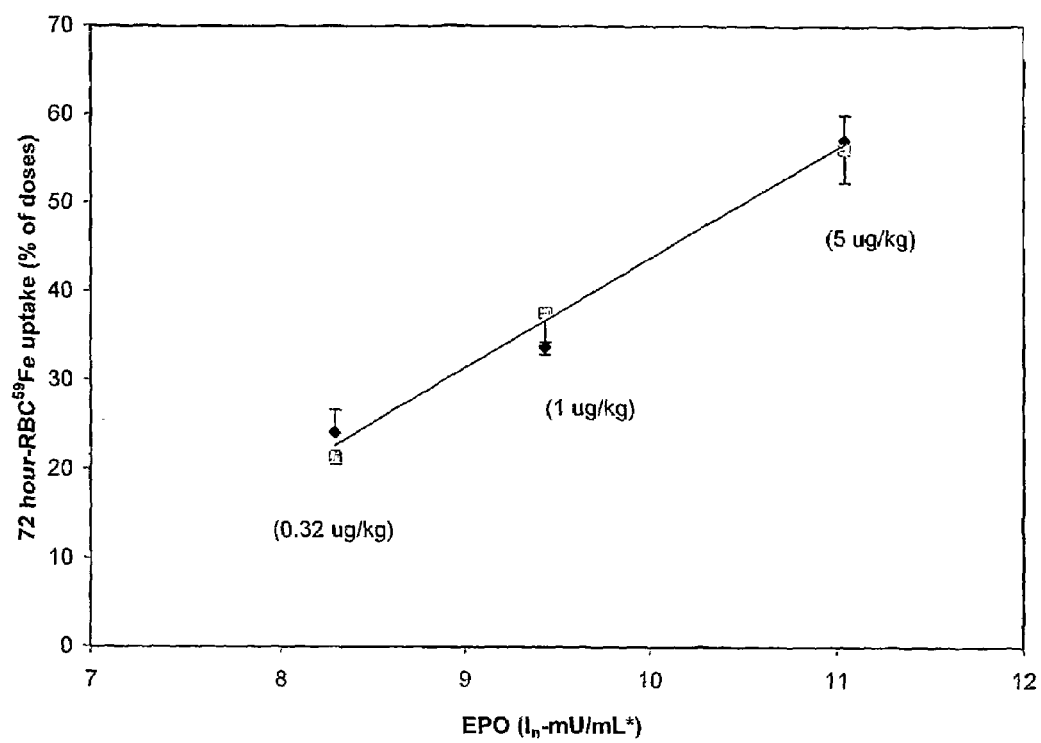
FIG. 30 shows linear regression analyses of the in vivo activity as measured by the 72-hour red blood cell (RBC)-$^{59}$Fe uptake (as a % of dose) for SEP 1-B51 and recombinant glycosylated human erythropoietin produced in CHO-cells ("rhEPO") in a hypoxic rat model.

The 72-hour RBC-$^{59}$Fe uptake (% of dose) for SEP-1-B51 and rhEPO showed a clear dose related response in increased $^{59}$Fe uptake with increasing dose up to 5 µg/kg, above which the response plateaued (25 µg/kg). The three lowest dose levels were therefore used to calculate linear regression. The linear regression analyses of SEP-1-B51 and rhEPO are presented in FIG. 30. The responses of SEP-1-B51 and rhEPO were essentially the same. The "potency ratio" of SEP-1-B51 to rhEPO was 1.0035 (95% confidence interval of 0.6947 to 1.4498) and the potency of SEP-1-B51 determined in this assay was 100 mU/ng (95% confidence interval of 69-145).

SEP-1-B51 exhibits in vivo activity similar to that of rhEPO and acts in dose-dependent manner, including a response plateau at higher doses due to induction of a negative feedback mechanism typical for rhEPO in this model. This illustrates that the polymer structures attached at precise user-defined glycosylation sites in the SEP-1-B51 molecule mimic the in vivo activity contributed by the sugar chains of rhEPO.

Example 17

Pharmacokinetic Studies for SEP-1-B51

Groups of normal male rats were dosed intravenously with a singe dose of 5 ug/kg SEP-1-B51, formulated in Citrate Buffer plus 0.25% human serum albumin, or rhEPO (equivalent to 500 U/kg) and bled at 5, 30, 60 minutes, 2, 4, 8, and 24 hours, and 2, 3, 4, 5, 6, and 7 days following the dose. The SEP-1-B51 or rhEPO concentrations in the plasma samples were determined by ELISA assays using a R & D Systems anti-EPO ELISA kit (R & D Systems, Human Erythropoietin Quantikine IVD Immunoassay Kit #DEP00) according to manufacturers instructions.

A least squares analysis of the logarithms of the concentrations was performed, yielding the pharmacokinetic parameters listed in Table X below. The change in plasma concentration of SEP-1-B51 with time in male rats receiving a single intravenous dose of 5 µg/kg could be described by a mono-exponential pharmacokinetic disposition function with half-life of 10.5±0.5 hours. The volume of distribution of the central compartment (Vc) for SEP-1-B51 was 32.5±2.0 mL/kg. The clearance (CL) was 2.15 mL/hr/kg, with mean residence time (MRT) of 15.1±0.7 hours. By comparison, the change in plasma concentration of rhEPO in male rats receiving an intravenous dose of 5 µg/kg was best described using a bi-exponential pharmacokinetic disposition function, with α half-life of 1.24±0.22 hours and β half-life of 5.51±0.40 hours. The Vc for rhEPO was 57.0±3.2 mL/kg. The CL was 16.0±0.5 mL/hr/kg, about 8 fold greater than that of SEP-1-B51. The mean residence time (MRT) of rhEPO was 5.73±0.17 hours, about 3 fold shorter than that of SEP-1-B51.

TABLE X

Pharmacokinetic Parameters for SEP-1-B51 Compared to rhEPO

| Curve | AUC (ng/mL-hr) | Cmax (ng/mL) | Vc (mL/kg) | CL (mL/hr/kg) |
|---|---|---|---|---|
| SEP-1-B51 | 2326 ± 121 | 154 ± 9 | 32.5 ± 2.0 | 2.15 ± 0.11 |
| rhEPO | 312 ± 9 | 87.9 ± 5.0 | 57.0 ± 3.2 | 16.0 ± 0.5 |

| Curve | MRT (Hours) | T1/2α (Hours) | T1/2β (Hours) |
|---|---|---|---|
| SEP-1-B51 | 15.1 ± 0.7 | 10.5 ± 0.5 | N/A |
| rhEPO | 5.73 ± 0.17 | 1.24 ± 0.22 | 5.51 ± 0.40 |

Figure 31:
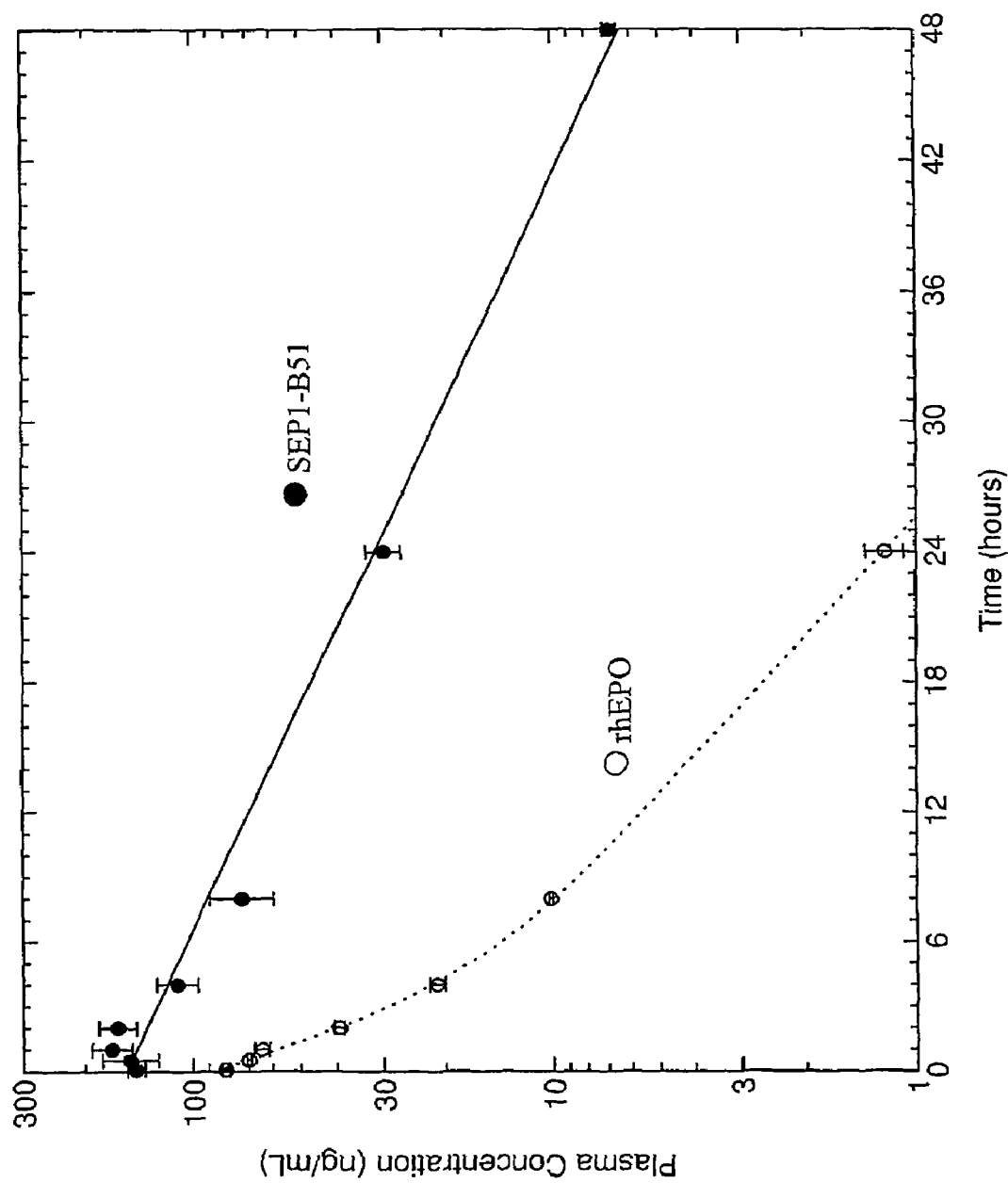
FIG. 31 shows a representative pharmacokinetic profile for clearance in rats comparing plasma concentration in ng/ml of SEP1-B51 and rhEPO versus time in hours following a single IV dose of 5 μg/kg for each compound.

The graphic presentation of SEP-1-B51 and rhEPO plasma clearance is in FIG. 31. These data illustrate a significant increase in circulating half-life for SEP-1-B51 over the glycosylated recombinant human EPO, and that this increase is due to the polymer structures attached at precise user-defined sites in the molecule.

Example 18

Synthesis Of Polymer-Modified Synthetic Rantes Proteins

Figure 32:
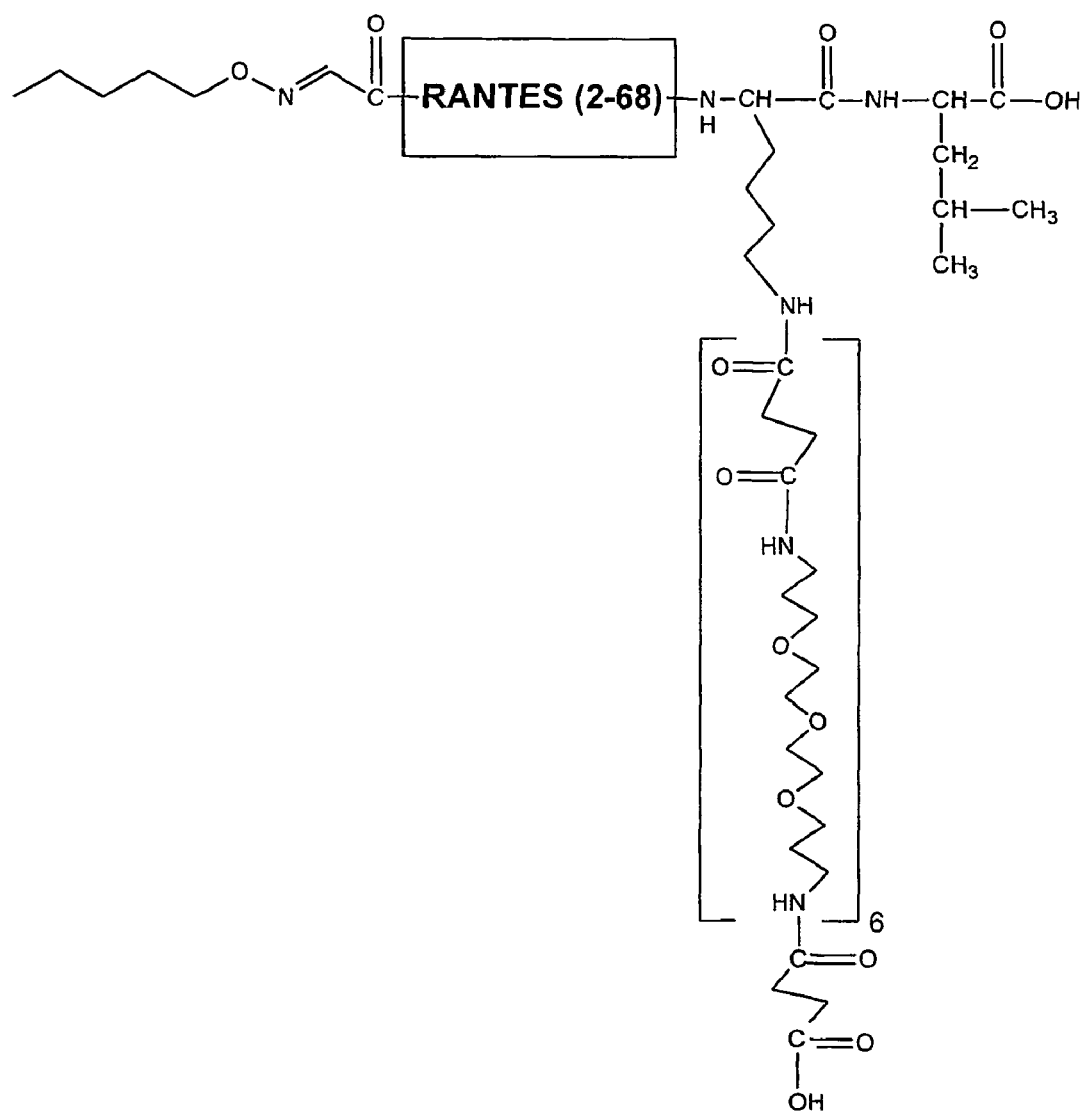
FIG. 32 depicts a synthetic chemokine designated RANTES G1755-01, which is a precision polymer-modified synthetic analog of RANTES prepared as described in Example 18.
Figure 33:
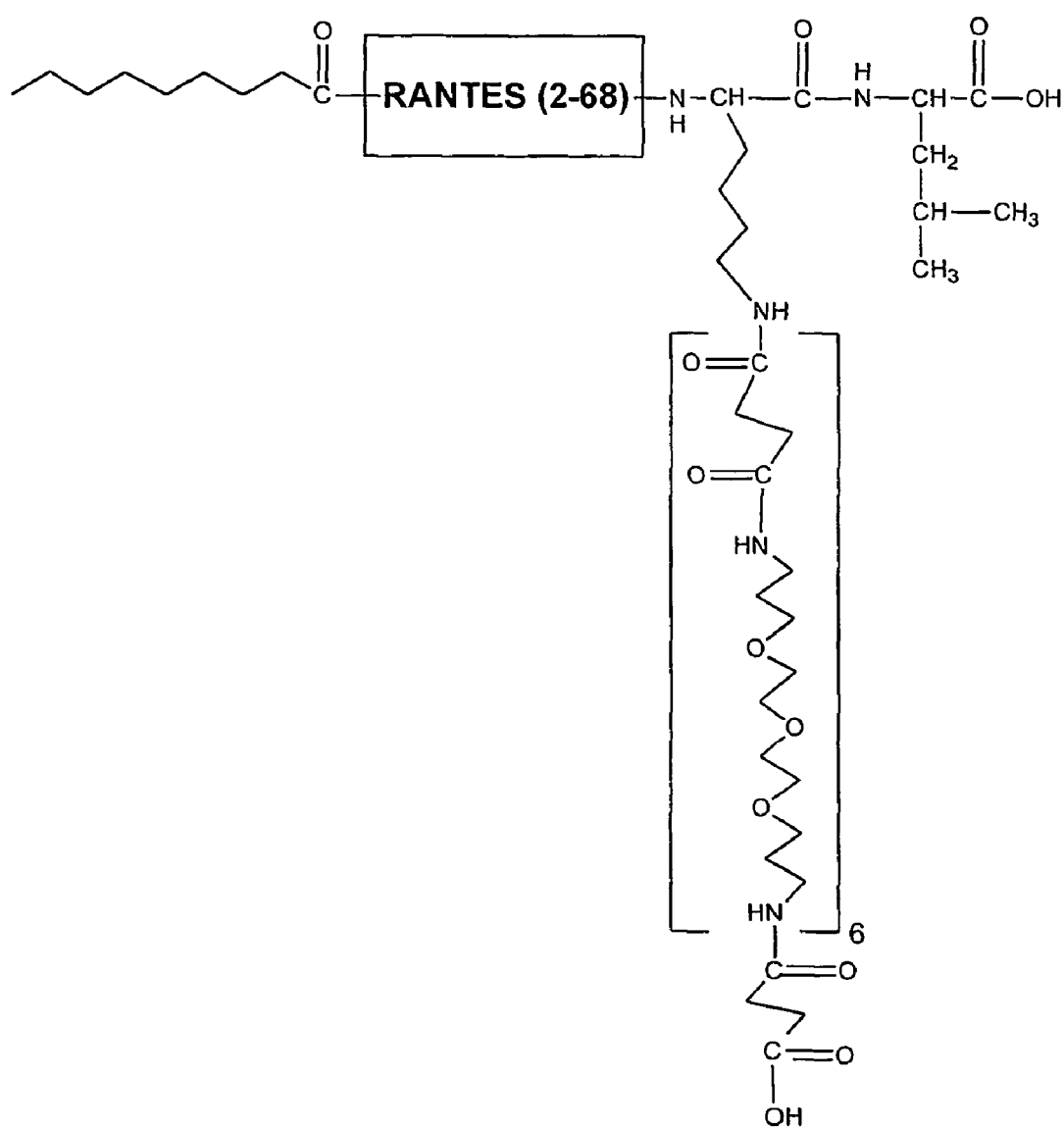
FIG. 33 depicts a synthetic chemokine designated RANTES G1755, which is a precision polymer-modified synthetic analog of RANTES prepared as described in Example 19.
Figure 34:
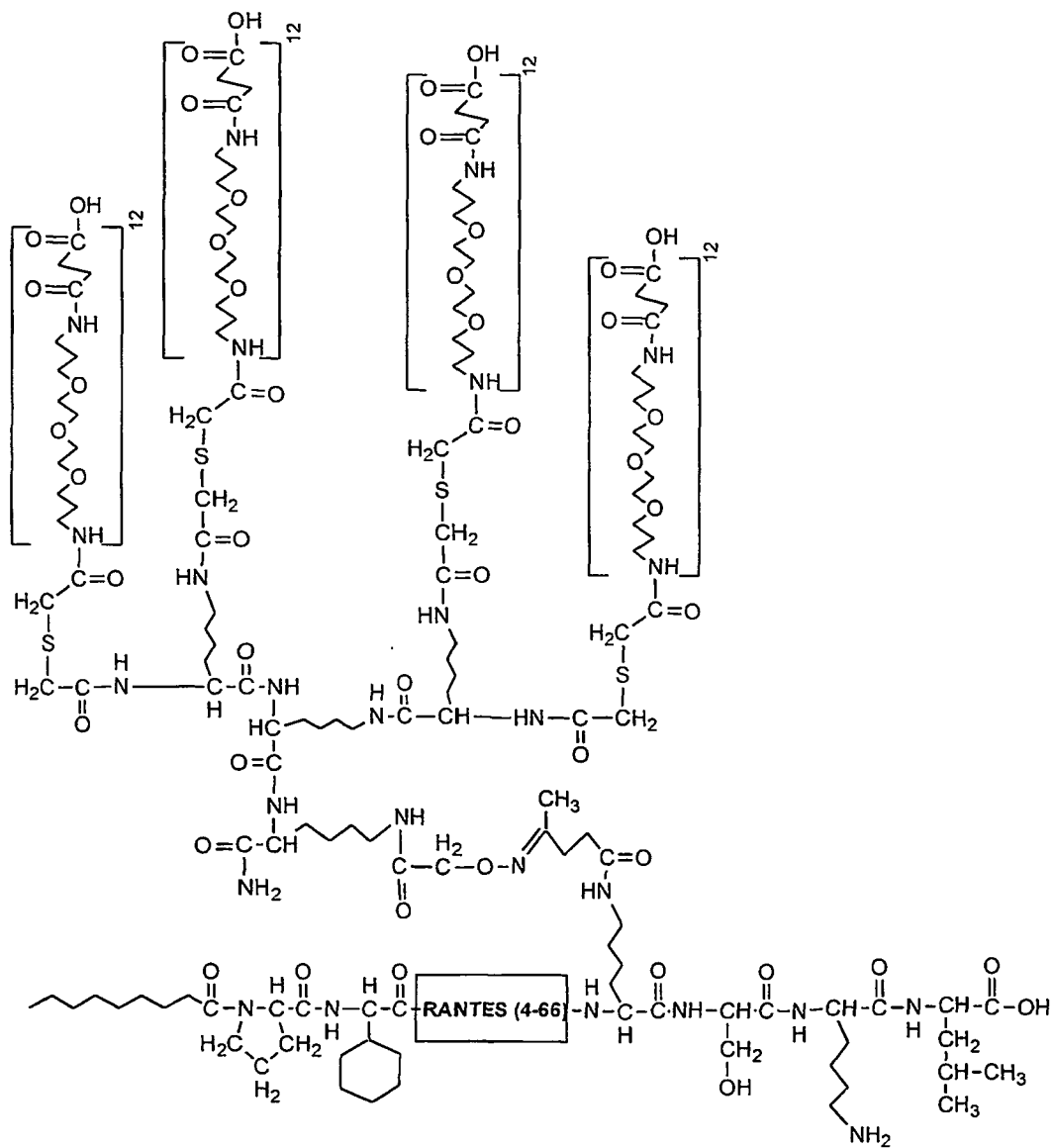
FIG. 34 depicts a synthetic chemokine designated RANTES G1805, which is a precision polymer-modified synthetic analog of RANTES prepared as described in Example 20.
Figure 35:
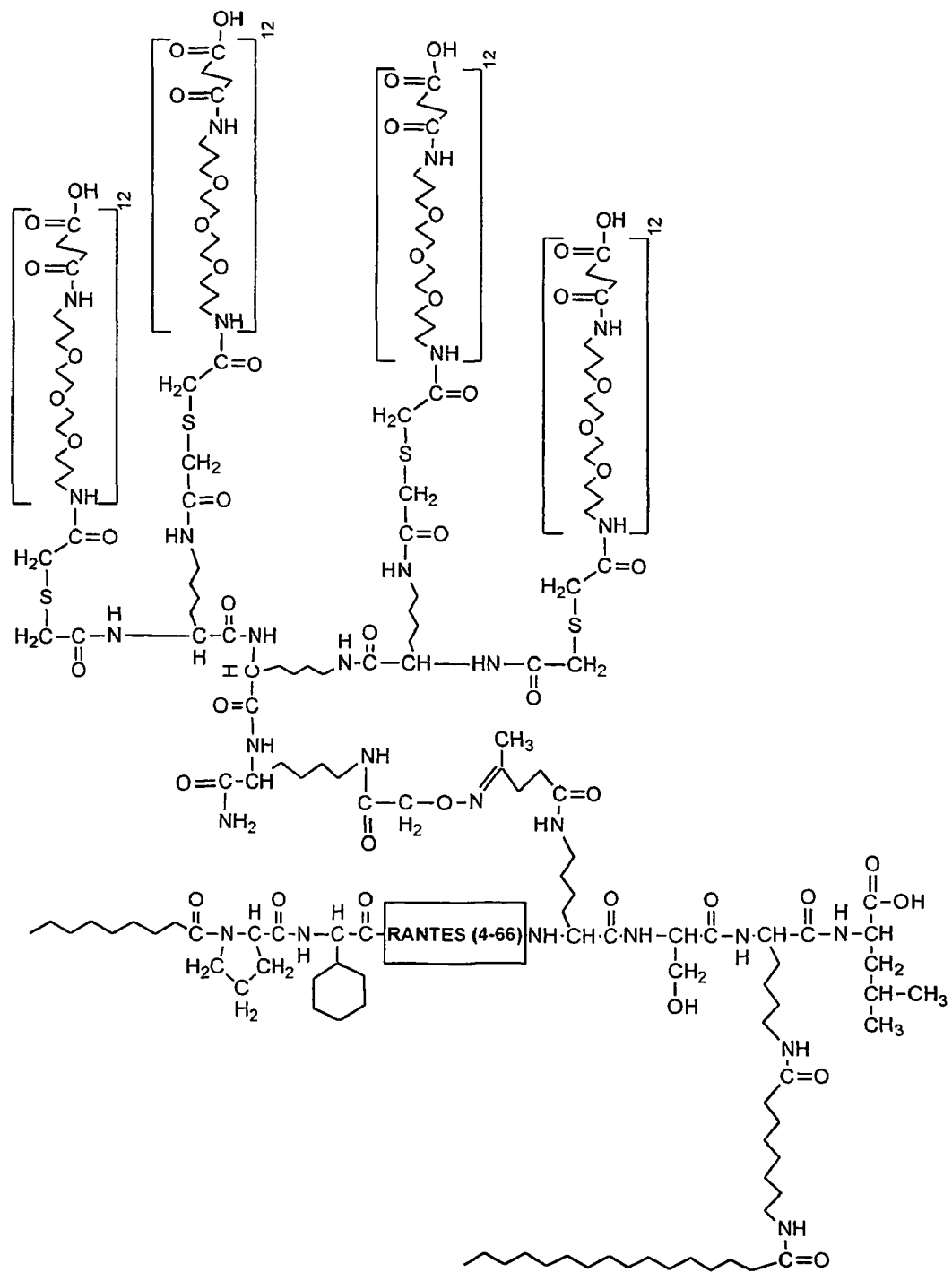
FIG. 35 depicts a synthetic chemokine designated RANTES G1806, which is a precision polymer-modified synthetic analog of RANTES prepared as described in Example 21.

In order to further illustrate the polymer modified proteins of the present invention, two polymer-modified derivatives of RANTES 2-68 (RANTES G1755-01; FIG. 32 and RANTES G1755; FIG. 33) and two polymer-modified derivatives of RANTES 4-66 (RANTES G1805; FIG. 34 and RANTES G1806; FIG. 35) were prepared. The structures of these polymer-modified proteins are shown in FIGS. 32–35.

Preparation of RANTES Analog G1755-01

The RANTES analog, G1755-01, depicted in FIG. 32 was synthesized as follows.

1. Preparation of AOP-[RANTES(2-33)]-thioester aminooxypetane-glyoxalyl-PYSSDTTPCC FAYIARPLPR AHIKEYFYTS GK-thioester (residues of 1–32 of SEQ ID NO:4)

The N-terminal peptide segment AOP-[RANTES(2-33)]-α-thioester (thioester also depicted as —C(O)SR) containing an N-terminal aminooxypentane-glyoxalyl oxime moiety (AOP) was synthesized by assembly of the RANTES(2-33) sequence on a thioester-generating resin (Hackeng, et al., PNAS (1999) 96: 10068–10073), and then modified at the N-terminus by direct coupling of an aminooxypentane-glyoxalyl oxime moiety [i.e. $CH_3(CH_2)_4$—O—N=CHCOOH] to the resin following standard protocols (Wilken et al., Chemistry & Biology (1999) 6(1):43–51). The peptide-resin was cleaved with hydrogen fluoride and purified by reverse-phase HPLC to yield the α-carboxy thioester peptide AOP-RANTES(2-33)-thioester. Observed mass=4179.6 Da; Calculated mass=4178.6 Da (average isotope composition).

2. Preparation of [RANTES(34-68)]-Lys69(GP6)-Leu70 CSNPAVVFVT RKNRQVCANP EKKWVREYIN SLEMSK(GP6)L (residues 33–69 of SEQ ID NO:4) where GP6 is bound to the $N^\epsilon$ of Lys 69:

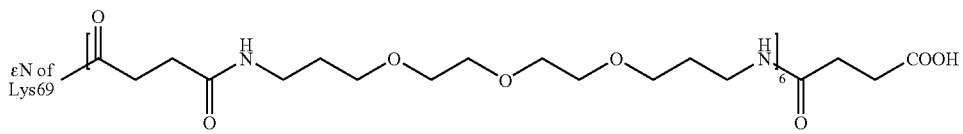

a. Solid Phase Peptide and On-{Peptide-Resin} Water-soluble Polymer Synthesis

The C-terminal peptide segment [RANTES(34-68)]-Lys69(Fmoc)-Leu70 was synthesized by conventional SPPS on a Boc-Leu-OCH2-Pam-resin using the in situ neutralization/HBTU activation protocols for Boc chemistry SPPS as described in Schnolzer, et al, Int. J. Pep. Protein Res. (1992) 40:180–193.

After completion of chain assembly, the Fmoc group on the epsilon nitrogen of Lys69 was removed from the protected peptide-resin with 20% piperidine in DMF treatment. Succinic anhydride was then coupled in an HOBT solution in DMF containing DIEA to the epsilon nitrogen on Lys69. After washing, the free carboxyl group of the resin-bound succinic acid was activated by addition of CDI in DMF. After another wash cycle, 50% TTD in 0.5M HOBT in DMF was added. After washing, the resin-bound polymer was ready for the next cycle of succinic anhydride coupling/CDI activation/TTD coupling. After 6 cycles, succinic anhydride was coupled to the last TTD amine in HOBT/DMF plus DIEA solution.

The peptide/linear water-soluble polymer resin was cleaved from the resin with hydrogen fluoride and the product purified by reverse-phase preparative HPLC to yield [RANTES(34-68)]-Lys69(GP6)-Leu70. Observed mass=6253 Da; Calculated mass=6252 Da (average isotope composition).

3. Preparation of G1755-01

```
                                              (SEQ ID NO.:4)
aminooxypentane-glyoxalyl-PYSSDTTPCC FAYIARPLPR

AHIKEYFYTS GKCSNPAVVF VTRKNRQVCA NPEKKWVREY

INSLEMSK(GP6)L
```

The N-terminal and C-terminal peptide segments described above were joined together by native chemical ligation as described Dawson et al, Science 266:776–779

(1994). The full-length polypeptide product in reduced form was purified using reverse-phase HPLC with a linear gradient of acetonitrile versus water containing 0.1% trifluoroacetic acid. Observed mass=10,060 Da.

The full-length polypeptide with GP6 attached was folded with concomitant formation of 2 disulfide bonds in aqueous buffer containing a cysteine-cystine redox couple, and purified by reverse-phase HPLC following standard protocols (Wilken et al., Chemistry & Biology (1999) 6(1):43–51). The folded product was homogeneous on HPLC. Observed mass=10,056 Da; Calculated mass=10,058 Da (average isotope composition).

Example 19

Preparation of RANTES Analog G1755

The G1755 compound depicted in FIG. 33 was synthesized as follows.
1. Preparation of n-nonanoyl-RANTES(2-33) n-nonanoyl-PYSSDTTPCC FAYIARPLPR AHIKEYFYTS GK-thioester (residues 1–32 of SEQ ID NO:4);

n-nonanoyl-RANTES(2-33) was synthesized on a thioester-producing resin as described above in Example 18, and then modified at the N-terminus by direct coupling of n-nonanoic acid to the resin. The peptide resin was cleaved with hydrogen fluoride and purified by reverse-phase HPLC to yield n-nonanoyl-RANTES(2-33). Observed mass=4177.0 Da; Calculated mass=4177.6 Da (average isotope composition).

2. Preparation of RANTES(34-68)-Lys69(GP6)-Leu70 CSNPAVVFVT RKNRQVCANP EKKWVREYIN SLEMSK(GP6)L (residues 33–69 of SEQ ID NO:4)

a. Solid Phase Peptide and On-{Peptide-Resin} Water-soluble Polymer Synthesis

RANTES(34-68)-Lys69(Fmoc)-Leu70 was synthesized by conventional solid phase peptide synthesis on a Boc-Leu-OCH2-Pam-resin using the in situ neutralization/HBTU activation protocols for Boc chemistry solid phase peptide synthesis as described above in Example 18.

After completion of chain assembly the Fmoc group on the epsilon nitrogen of Lys69 was removed from the protected peptide-resin and the GP6 construct was synthesized on the peptide resin as described above in Example 18. The peptide/linear water soluble polymer resin was cleaved with hydrogen fluoride and the product purified by reverse-phase preparative HPLC to yield RANTES(34-68)-Lys69(GP6)-Leu70. Observed mass=6252.9 Da; Calculated mass=6252.2 Da (average isotope composition).

3. Preparation of G1755

```
                                              (SEQ ID NO.:5)
nonanoyl-PYSSDTTPCC FAYIARPLPR AHIKEYFYTS

GKCSNPAVVF VTRKNRQVCA NPEKKWVREY INSLEMSK(GP6) L
``` a. Assembly of Full-Length Polypeptide By Native Chemical Ligation

The N-terminal and C-terminal peptide segments were joined together by native chemical ligation as described above in Example 18. The full-length polypeptide in reduced form was purified using reverse-phase HPLC with a linear gradient of acetonitrile versus water containing 0.1% trifluoroacetic acid. Observed mass=10060.7 Da; Calculated mass=10058.7 Da (average isotope composition).

b. Folding and Purification of Polypeptide Modified with Water-soluble Polymer

The full-length polypeptide with GP6 attached was folded with concomitant formation of 2 disulfide bonds in aqueous buffer containing a cysteine-cystine redox couple, and purified by reverse-phase HPLC as described above in Example 18. The folded product was homogeneous on HPLC. Observed mass=10057.4 Da; Calculated mass=10054.7 Da (average isotope composition).

Example 20

Preparation of RANTES Analog G1805

The G1805 compound depicted in FIG. 34 was synthesized as follows.
1. Preparation of n-nonanoyl-RANTES(2-33)(Tyr3Chg)-thioester nonanoyl-PXSSDTTPCC FAYIARPLPR AHIKEYFYTS GK-thioester (residues 1–32 of SEQ ID NO:7)

where X=L-Cyclohexylglycine (Chg)

n-nonanoyl-RANTES(2-33)(Tyr3Chg) was synthesized on a thioester-producing resin as described above in Example 18, and then modified at the N-terminus by direct coupling of n-nonanoic acid to the resin. The peptide resin was cleaved with hydrogen fluoride and purified by reverse-phase HPLC to yield n-nonanoyl-RANTES(2-33) (Tyr3Chg). Observed mass=41512.0 Da; Calculated mass=4152.6 Da (average isotope composition).

2. Preparation of RANTES(34-68)(Met67Lys(Lev))-Lys69-Leu70 CSNPAVVFVT RKNRQVCANP EKKWVREYIN SLEK(Lev)SKL (residues 69–69 of SEQ ID NO:6)

RANTES(34-68)(Met67Lys)-Lys69(Fmoc)-Leu70 was synthesized by conventional SPPS on a Boc-Leu-OCH2-Pam-resin using the in situ neutralization/HBTU activation protocols for Boc chemistry SPPS as described above in Example 18.

After completion of chain assembly the Fmoc group on the epsilon nitrogen of Lys67 was removed from the protected peptide-resin with 20% piperidine in DMF treatment. Levulinic acid was activiated as the symmetrical anhydride with 1,3-di-isopropylcarbodi-imide and coupled to the epsilon nitrogen of Lys67. The peptide-resin was cleaved with hydrogen fluoride and the product purified by reverse-phase preparative HPLC to yield RANTES(34-68)(Met67Lys (Lev))-Lys69-Leu70. Observed mass=4433.2 Da; Calculated mass=4434.2 Da (average isotope composition).

3. Preparation of G1806

```
                                              (SEQ ID NO.:6)
nonanoyl-PXSSDTTPCC FAYIARPLPR AHIKEYFYTS

GKCSNPAVVF VTRKNRQVCA NPEKKWVREY

INSLEK(Lev-GP29)SKL
``` where X=L-Cyclohexylglycine (Chg), and where GP29=branched oxime-linked water-soluble polymer construct depicted in FIG. 34 and prepared as described in Example 4.

a. Assembly of Full-Length Polypeptide By Native Chemical Ligation

The N-terminal and C-terminal peptide segments were joined together by native chemical ligation as described above in Example 18. The full-length polypeptide in reduced form was purified using reverse-phase HPLC with a linear gradient of acetonitrile versus water containing 0.1% trifluoroacetic acid. Observed mass=8213.6 Da; Calculated mass=8216.6 Da (average isotope composition).

b. Attachment of GP29 to the of Ligated, Full-Length Polypeptide

The lyophilized full-length polypeptide was dissolved and co-lyophilized with an equimolar amount of the aminooxyacetyl (AoA)-containing branched water-soluble polymer construct GP29. The dried powder was dissolved and purified by reverse-phase HPLC to yield the full-length polypeptide with GP29 covalently attached by an oxime bond to the Veto functionality on the modified side chain of the lysine at position 67. Observed mass=23,836 Da; Calculated mass=23,845 Da (average isotope composition). Alternatively, GP29 was covalently attached after folding the polypeptide, however this was observed to give a lower yield.

c. Folding and Purification of Polypeptide containing Oxime-Linked GP29

The full-length polypeptide with GP29 attached was folded with concomitant formation of 2 disulfide bonds in aqueous buffer containing a cysteine-cystine redox couple, and purified by reverse-phase HPLC as described above in Example 18. The folded product was homogeneous on HPLC. Observed mass=23,832 Da; Calculated mass=23,840 Da (average isotope composition).

Example 21

Preparation of RANTES Analog G1806

The RANTES analog, G1806, depicted in FIG. 35, was synthesized as follows.

1. Preparation of n-nonanoyl-RANTES(2-33)(Tyr3Chg)-thioester nonanoyl-PXSSDTTPCC FAYIARPLPR AHIKEYFYTS GK-thioester (residues 1–=of SEQ ID NO:7)

where X=L-Cyclohexylglycine (Chg)

Peptide segment n-nonanoyl-RANTES(2-33)(Tyr3Chg)-thioester (thioester also depicted as —COSR, where R is alkyl group) was synthesized on a thioester producing resin as described above in Example 18, and then modified at the N-terminus by direct coupling of n-nonanoic acid to the resin. The peptide resin was cleaved with hydrogen fluoride and purified by reverse-phase HPLC to yield n-nonanoyl-RANTES(2-33) Tyr3Chg. Observed mass=4152.0 Da; Calculated mass=4152.6 Da (average isotope composition).

2. Preparation of RANTES(34-68)(Met67Lys(Lev))-Lys69(Palm)-Leu70 CSNPAVVFVT RKNRQVCANP EKKWVREYIN SLEK(Lev)SK (Palm) L (residues 33–69 of SEQ ID NO:6)

where K(lev) is a levulinic acid-modified epsilon nitrogen of Lys67 of the Met67Lys change from wild type RANTES; and where K(Palm) is a palmitate-modified epsilon nitrogen of Lys69 attached through an amino-octanoic moiety, having the structure:

[εNitrogen Lys69]—C(O)—$CH_2$—$CH_2$—$CH_2$—$CH_2$—$CH_2$—$CH_2$—$CH_2$—NH—C(O)—$(CH_2)_{14}$—$CH_3$ RANTES(34-68)(Met67Lys)-Lys69(Palm)-Leu70 was synthesized by conventional SPPS on a Boc-Leu-OCH2-Pam-resin using the in situ neutralization/HBTU activation protocols for Boc chemistry solid phase peptide synthesis as described above in Example 18. After coupling Boc-Lys (Fmoc)-OH at position 69, the Fmoc group was removed with 20% piperidine in DMF. Fmoc-8-amino-octanoic acid was activated with HBTU/DIEA and coupled to the epsilon nitrogen of Lys69. After Fmoc group removal, palmitic acid was activated with 1-hydroxy-7-azabenzotriazole (HATU) and 1,3-di-isopropylcarbodi-imide and coupled to the resin. The chain assembly was then completed using standard Boc chemistry SPPS procedures as described in Example 18. After completion of chain assembly the Fmoc group on the epsilon nitrogen of Lys67 was removed with 20% piperidine in DMF treatment. Levulinic acid was activated as the symmetrical anhydride with 1,3-di-isopropylcarbodi-imide and coupled to the epsilon nitrogen of Lys67. The peptide resin was cleaved with hydrogen fluoride and the product purified by reverse-phase preparative HPLC to yield RANTES(34-68)(Met67Lys(Lev))-Lys69(Palmitate)-Leu70. Observed mass=4813.7 Da; Calculated mass=4813.8 Da (average isotope composition).

3. Preparation of G1806

```
21 nonanoyl-PXSSDTTPCC FAYIARPLPR AHIKEYFYTS            (SEQ ID NO.:7)

GKCSNPAVVF VTRKNRQVCA NPEKKWVREY INSLEK(Lev-GP29)SK(Palm)L
``` where X=L-Cyclohexylglycine (Chg), and where palmitate ("Palm") fatty acid attachment is through an amino-octanoic moiety:

[εNitrogen Lys69]—C(O)—$CH_2$—$CH_2$—$CH_2$—$CH_2$—$CH_2$—$CH_2$—$CH_2$—NH—C(O)—$(CH_2)_{14}$—$CH_3$ a. Assembly of Fatty Acid Modified Full Length Polypeptide By Native Chemical Ligation The N-terminal and C-terminal peptide segments were joined together by native chemical ligation as described in Example 18. The full-length polypeptide in reduced form was purified using reverse-phase HPLC with a linear gradient of acetonitrile versus water containing 0.1% trifluoroacetic acid. Observed mass=8598.2 Da; Calculated mass=8596.3 Da (average isotope composition).

b. Attachment of the Water-soluble Polymer GP29 to Ligated, Fatty Acid Modified Full Length Polypeptide The lyophilized full length polypeptide was dissolved and co-lyophilized with an equimolar amount of the AoA-containing polymer GP29. The dried powder was dissolved and purified by reverse-phase HPLC to yield the full length polypeptide with GP29 covalently attached by an oxime bond to the keto functionality on the modified side chain of the lysine at position 67. Observed mass=24,217 Da; Calculated mass=24,224. Da (average isotope composition). Alternatively, GP29 can be covalently attached after folding the polypeptide, however this was observed to give a lower yield.

c. Folding and Purification of Polypeptide Containing Oxime-linked GP29 and Fatty Acid The full length polypeptide with GP29 attached was folded with concomitant formation of 2 disulfide bonds in aqueous buffer containing a cysteine-cystine redox couple, and purified by reverse-phase HPLC as described above in Example 18. The folded product was homogeneous on HPLC. Observed mass=24,210 Da; Calculated mass=24,220 Da (average isotope composition).

Figure 36:
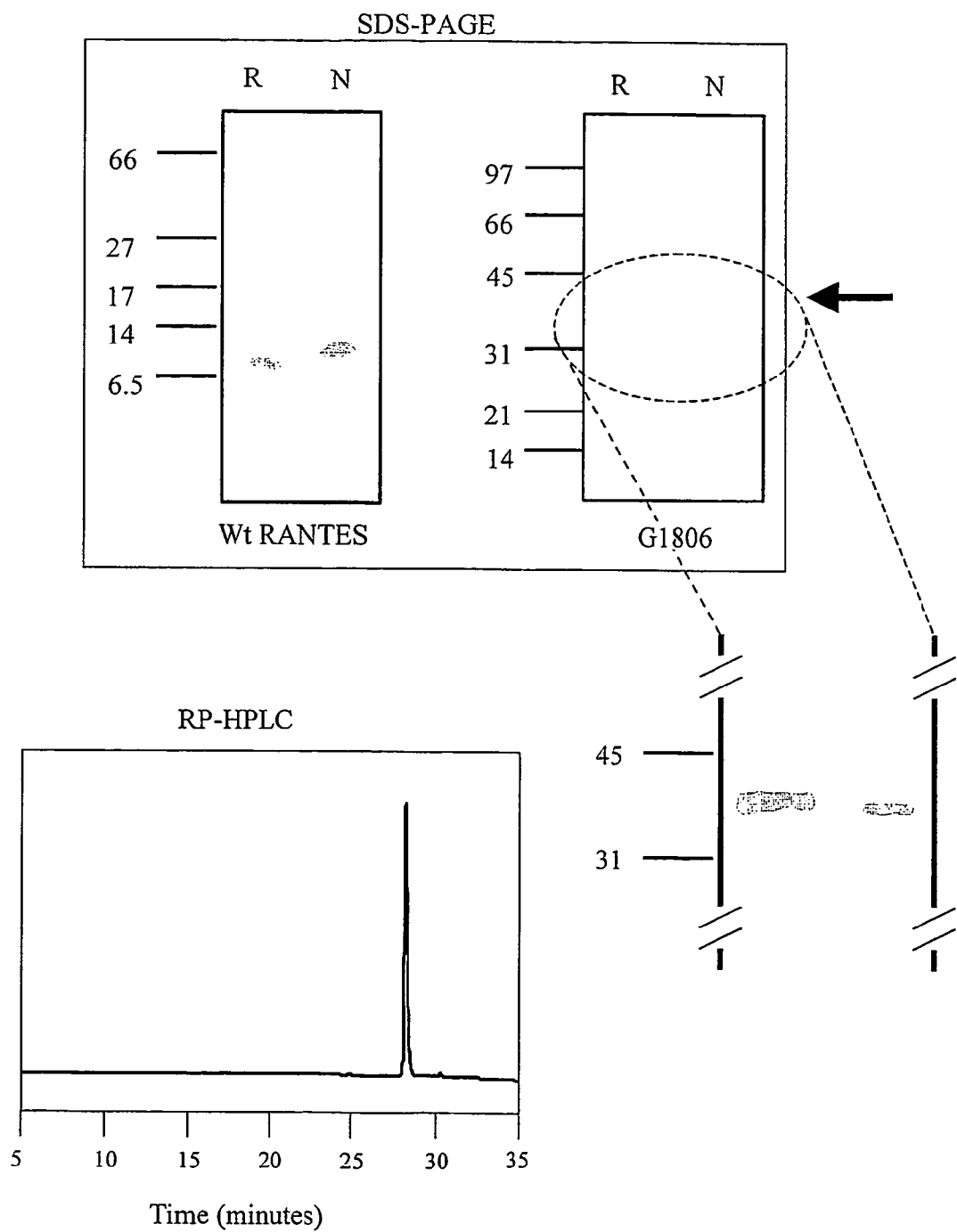
FIG. 36 shows a representative analytical data for the synthetic chemokine analogs prepared in Examples 18–21. As shown, a representative SDS-PAGE gel compares the relative molecular weights of wild type (Wt) RANTES to synthetic chemokine analog RANTES G1806 under reducing (R) and non-reducing conditions (N).

FIG. 36 shows analytical data representative of the final folded, purified synthetic Rantes analogs. In particular, a representative SDS-PAGE gel comparing the relative molecular weights of wild type (Wt) RANTES to synthetic chemokine analog RANTES G1806 under reducing (R) and non-reducing conditions (N) in shown in FIG. 36. The relative molecular weights are depicted on the left hand side of each gel, which corresponds to a molecular weight standard run on the same gel (not shown). Also shown is a representative RP-HPLC chromatogram of the folded, purified G1806 product. This illustrates the purity and increased relative molecular weight of the precision polymer-modified constructs compared to wild type, native RANTES.

Figure 37:
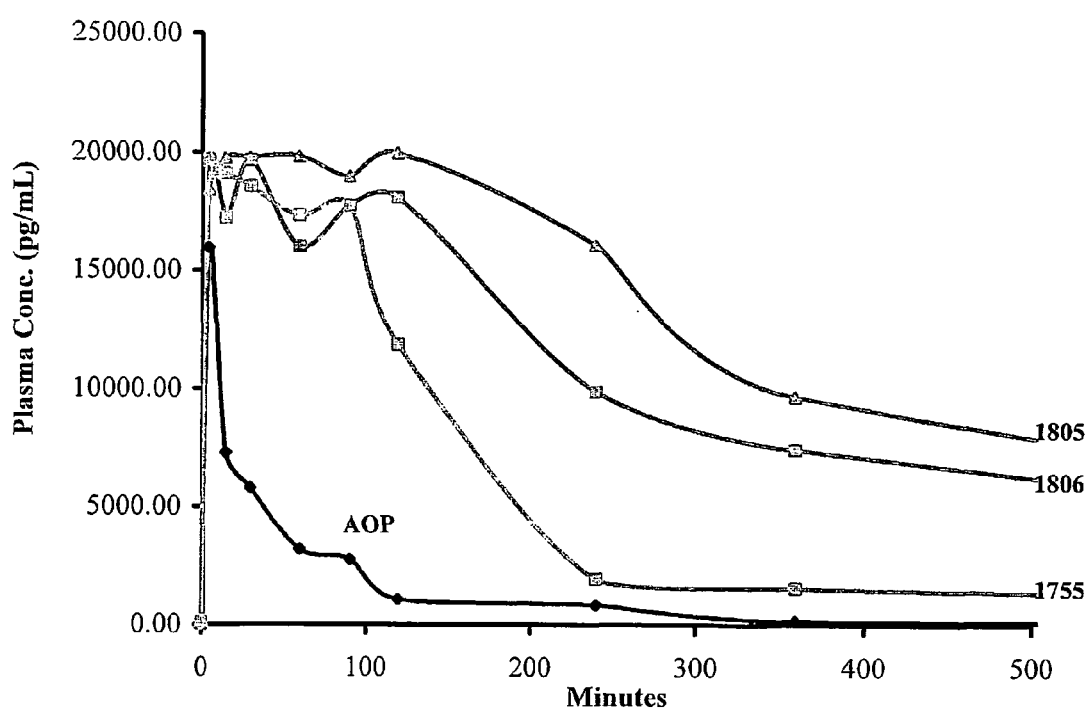
FIG. 37 shows a pharmacokinetic profile for clearance in rats comparing plasma concentration in picograms per milliliter (pg/ml) of synthetic Rantes analogs G1755, G1806, and G1805 versus time in minutes following a single TV dose of Equimolar amounts/kilo gram (kg) weight of each animal for each compound.

Example 22

Cell Fusion Assays for G1755-01, G1755, G1805 and G1806

Cell fusion assays were performed to examine the anti-HIV activity of the various polymer-modified RANTES analogs. The ability of a given panel of compounds to inhibit CCR5-dependent cell fusion was determined using cells engineered to contain viral envelop proteins fusing with cells bearing CD4 and CCR5 and containing a reporter system. CCR5-mediated viral envelope-mediated cell fusion assays were carried out essentially as described in Simmons et al. (Science (1997) 276:276–279) using the cell lines HeLa-P5L and HeLa-Env-ADA, both of which were kindly provided by the laboratory of M. Alizon (Paris). Briefly, HeLa-P5L cells were seeded in 96-well plates ($10^4$ cells per well in 100 μl). Twenty-four hours later medium was removed and medium containing $10^4$ HeLa-Env-ADA cells per well plus chemokines was added (200 μl final volume). After a further twenty-four hours, cells were washed once in PBS and lysed in 50 μl PBS/0.5% NP-40 for 15 min at room temperature. Lysates were assayed for β-galactosidase activity by the addition of 50 μl 2×CPRG substrate (16 mM chlorophenol red-β-D-galactopyranoside; 120 mM $Na_2HPO_4$, 80 mM $NaH_2PO_4$, 20 mM KCl, 20 mM $MgSO_4$, and 10 mM β-mercaptoethanol) followed by incubation for 1–2 hours in the dark at room temperature. The absorbance at 575 nm was then read on a Labsystems microplate reader. From these values, percentage inhibition $[100\times(OD_{(test)}-OD_{(negative\ control)})/OD_{(positive\ control)}-OD_{(negative\ control)})]$ was calculated at each inhibitor concentration. A plot of percentage fusion inhibition against inhibitor concentration allowed the calculation of $IC_{50}$ values for each compound.

Representative results are depicted in Table XII below.

TABLE XI

HeLa P4-CCR5/HeLa-Env-ADA Cell Fusion Data

| Compound | EC50 |
|---|---|
| AOP-RANTES (2–68) | $1.81 \times 10^{-9}$ M |
| NNY-RANTES (2–68) | $3.23 \times 10^{-10}$ M |
| RANTES G 1755-01 | $11.00 \times 10^{-9}$ M |
| RANTES G1755 | $1.87 \times 10^{-9}$ M |
| RANTES G 1805 | $1.40 \times 10^{-9}$ M |
| RANTES G 1806 | $2.98 \times 10^{-10}$ M |

These results demonstrate the substantial retention of anti-fusion activity following site-specific modification with either the linear or branched water-soluble polymer constructs. This result was surprising given the observed increase in activity of various RANTES analogs when a hydrophobic moiety, such as a fatty acid, was attached to the C-terminus, which supported the hypothesis that increasing the hydrophobic nature of the RANTES analogs in general would increase anti-fusion activity. In contrast, the water-soluble polymers used for modification, particularly the branched water-soluble polymers, were quite hydrophilic and negatively charged, yet only a marginal reduction in activity was observed that was well within the target potency range sought for in vivo activity. Even more unexpected was the relative retention in activity of the RANTES analogs modified with the large, negatively charged branched water-soluble polymer constructs compared to the smaller, linear water-soluble polymer constructs, and that the small linear and large branched polymer modified analogs had substantially the same effect on activity. This later observation is believed to be due in part to anti-aggregation properties when water-soluble polymer modifications are made internal to the pendant C-terminal residue of wild type RANTES at an aggregation region, as designed, and/or the localized anti-fusion properties of the water-soluble polymers.

The additional potency-increasing changes compensated for the marginal activity loss from attachment of water-soluble polymers, relative to AOP-RANTES and NNY-RANTES. These changes included the introduction of one or more hydrophobic amino acid derivatives to the N-terminus, and addition of a hydrophobic fatty acid moiety to the C-terminus. These results indicate that additional changes in combination with the monodisperse polyamide ethylene polymers (or other water-soluble polymers) can improve overall potency of NNY- and AOP-type modified chemokine molecules, such as AOP- or NNY-RANTES having the combined Pro2Thz and Tyr3Chg change to the N-terminus and/or the addition of a lipid moiety to the C-terminus.

Example 23

Pharmacokinetic Studies for G1755, G1805, and G1806

Pharmacokinetic studies of polymer-modified RANTES analogs were performed in male Sprague-Dawley rats as follows. RANTES analogs G1755, G1805, and G1806, prepared as described above (along with AOP-RANTES as control), were formulated for intravenous (IV) injection just prior to injection from lyophilized protein stock in phosphate buffered saline at pH 7.0. Formulations were prepared so as to provide equimolar doses of the RANTES analogs to individual test animals [400 μg/kg (AOP-RANTES); 510 μg/kg (G1755); 1210 μg/kg (G1805); and 1225 μg/kg (G1806) (μg analog/kg animal)]. Final concentrations were adjusted where necessary to provide a total dose volume of 1 ml/kg for each animal (i.e., dose volumes were held constant). Each formulated analog was administered intravenously via the tail of the rats on day 1 of the experiment, and each animal received a single dose.

Following injection, approximately 0.25 ml of blood were collected from the tail vein/artery over the course of the experiment at each sample collection time point, and plasma or serum samples were prepared using EDTA as anticoagulant following standard protocols and the National Institutes of Health animal care guidelines and recommended testing procedures. Sample collection times were adjusted based on initial data collection to avoid collection of more than 14 samples of 0.25 ml from any animal within 3 weeks (as established by the National Institutes of Health animal care guidelines). Additional samples were collected at weekly intervals where detectable blood levels persisted beyond the initial samples. The plasma concentration of each RANTES analog at each time point was determined using Quantikine®Elisa, Human RANTES Immunoassay, (R&D Systems Catalog#DRN00), per the manufacturers instructions. Overall health of the animals was monitored over the course of the experiment, including weight, eating habits, disposition, appearance etc., and no apparent side effects were observed. Representative results are depicted in FIG. 37.

These results demonstrate the substantive increase in circulating half-life provided by attachment of water-soluble polymers to the various precursor RANTES analogs, with the apparent increase in half-life of G1805>G1806>G1755>AOP-RANTES. Relative to AOP-RANTES, the increase was about 40-fold for G1805, 20-fold for G1806, and 10-fold for G1755. Collectively, the balance of retained high potency and significantly improved circulating half-life for the water-soluble polymer modified RANTES analogs is expected to enhance the therapeutic efficacy of these compounds in an in vivo setting, and reduce the number and amount of doses needed for treatment.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A composition comprising an isolated synthetic bioactive protein having the formula Protein-$h_k U_k$Polymer-J*, wherein Protein comprises a polypeptide chain of a ribosomally specified protein, said polypeptide chain comprising one or more non-overlapping peptide segments covalently bonded by one or more chemical ligation sites, U is a residue of a unique functional group covalently bonded to a mutually reactive unique functional group of a side chain h of one or more internal amino acids of one or more of said non-overlapping peptide segments, where k is a discrete integer selected from 1 to 6, Polymer is a substantially non-antigenic water-soluble polymer, and J* is a pendant group having a net charge under physiological conditions selected from the group consisting of negative, neutral and positive, and wherein the composition is uniform with respect to the attachment sites of the Polymer to the Protein; and wherein said synthetic bioactive protein comprises a monomer molecular weight of greater than 25,000 Daltons.

2. The composition of claim 1, wherein said polypeptide chain comprises one or more irregular amino acids.

3. The composition of claim 2, wherein said irregular amino acid has a side chain group other than that of one of the 20 genetically encoded amino acids.

4. The composition of claim 3, wherein said irregular amino acid is selected from the group consisting of a pseudo amino acid and a hydrophobic amino acid delivative.

5. The composition of claim 1, wherein said side chain h is a non-natural side chain.

6. The composition of claim 1, wherein one or more of substituents U, Polymer and J* are separated by a spacer or linker, so as to have the formula:

-$U_k$-s1-B-s2-Polymer-s3-J* where s1, s2, and s3 are spacer or linker moieties that may be the same or different, and may be individually present or absent, and B is a branching core substituent having three or more arms that may be the same or different.

7. The composition of claim 6, wherein one arm of a B substituent is joined to a U substituent, and a second arm of said B substituent is joined to Polymer.

8. The composition of claim 6, wherein B comprises four or more arms.

9. The composition of claim 6, wherein at least one of said arms comprises a residue of a bond selected from the group consisting of oxime, amide, amine, urethane, thioether, ester, thioester, hydrazide, oxazolidine, and thiazolidine.

10. The composition of claim 6, wherein B comprises a branching core selected from the group consisting of amino, carboxylate and mixed amino-carboxylate.

11. The composition of claim 10, wherein said amino branching core comprises lysine, said carboxylate branching core comprises glutamic or aspartic acid, and said mixed amino-carboxylate branching core comprises gamma-glutamic acid.

12. The composition of claim 6, wherein B-s2-Polymer-s3-J* comprises a molecular weight of between 1,500 and 80,000 Daltons.

13. The composition of claim 6, wherein side chain h is 2 or more, and wherein one or more of B-s2-Polymer-s3-J* is different.

14. The composition of claim 6, wherein B-s2-Polymer-s3-J* comprises a net charge under physiological conditions that is selected from the group consisting of negative, neutral and positive.

15. The composition of claim 6, wherein B-s2-Polymer-s3-J* is mono-disperse.

16. The composition of claim 1, wherein Polymer is a polyamide of the formula —[C(O)—X—C(O)NH—Y—NH]$_z$ or —[NH—Y—NH—C(O)—X—C(O)]$_z$—, where X and Y are divalent radicals that may be the same or different and may be branched or linear, and z is an integer from 2 to 100, and where either or both of X and Y comprises a water-soluble repeat unit that may be linear or branched.

17. The composition of claim 16, wherein said X is a divalent radical of the formula —NH—X'— or —X'—NH—, where X' is a divalent radical comprising a water-soluble repeat unit that may be linear or branched.

18. The composition of claim 16, wherein said Y is a divalent radical of the formula —CO—Y'— or —Y'—CO—, where Y' is a divalent radical.

19. The composition of claim 16, wherein z is a discrete integer from 2 to 50.

20. The composition of claim 16, wherein said water-soluble repeat unit comprises an ethylene oxide repeat unit of the formula —(CH$_2$—CH$_2$—O)— or —(O—CH$_2$—CH$_2$)—.

21. The composition of claim 20, wherein said ethylene oxide repeat unit has the formula —(CH$_2$CH$_2$—O)$_m$— or —(O—CH$_2$CH$_2$)$_m$—, where m is a discrete integer from 2 to 50.

22. The composition of claim 1, wherein J* is an ionizable group having a net charge under physiological conditions selected from the group consisting of negative and positive.

23. The composition of claim 22, wherein said ionizable group is selected from carboxyl, amine, and hydroxyl.

24. The composition of claim 16, having an increased circulating half-life in a mammal compared to a corresponding synthetic bioactive protein that is devoid of said water-soluble polymer.

25. A composition comprising a synthetic bioactive protein comprising a polypeptide chain comprising an amino acid sequence of a ribosomally specified glycoprotein, said polypeptide chain having one or more water-soluble polymers attached thereto and a monomer polypeptide molecular weight of greater than 25 kDa, wherein the composition is uniform with regard to the amino acid attachment sites of the polymer, and wherein the polymer is attached to at least one internal amino acid of the protein.

26. The composition of claim 25, wherein said synthetic bioactive protein possesses a bioactivity that mimics a bioactivity associated with said ribosomally specified glycoprotein.

27. The composition of claim 26, wherein said ribosomally specified glycoprotein is a cytokine.

28. A composition comprising a synthetic bioactive protein comprising a polypeptide chain comprising an amino acid sequence of a ribosomally specified glycoprotein, said polypeptide chain having one or more water-soluble polymers attached thereto, wherein said polypeptide chain together with said attached one or more water-soluble polymers has a molecular weight greater than 25 kDa, wherein the composition is uniform with regard to the amino acid attachment sites of the polymer, and wherein the polymer is attached to at least one internal amino acid of the protein, and wherein said synthetic bioactive protein possesses a bioactivity that mimics a bioactivity associated with a cytokine selected from the group consisting of an erythropoiesis stimulating protein, Rantes, and granulocyte colony stimulating factor.

29. The composition of claim 25, wherein said ribosomally specified glycoprotein comprises one or more glycosylation sites.

30. The composition of claim 29, wherein said water-soluble polymer is attached to said polypeptide chain at one or more sites corresponding to said one or more glycosylation sites.

31. The composition of claim 30, wherein said water-soluble polymer is attached to said polypeptide chain exclusively at one or more sites corresponding to said one or more glycosylation sites.

32. The composition of claim 25, wherein said ribosomally specified glycoprotein is a recombinantly produced glycoprotein.

33. The composition of claim 32, wherein said recombinantly produced glycoprotein is a non-natural glycoprotein.

34. The composition of claim 33, wherein said non-natural glycoprotein has one or more non-natural glycosylation sites.

35. The composition of claim 25, wherein said polypeptide chain comprises one or more irregular amino acids.

36. The composition of claim 25, wherein said water-soluble polymer comprises a molecular weight of between 1,500 and 80,000 Daltons.

37. The composition of claim 25, wherein said water-soluble polymer comprises a net charge under physiological conditions that is selected from the group consisting of negative, neutral and positive.

38. The composition of claim 25, wherein said water-soluble polymer is selected from the group consisting of polyalkylene oxide, polyamide alkylene oxide and derivatives thereof.

39. The composition of claim 25, wherein said water-soluble polymer is a polyamide of the formula

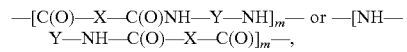

where X and Y are divalent radicals that may be the same or different and may be branched or linear, and m is an integer from 2 to 100, and where either or both of X and Y comprises a water-soluble repeat unit that may be linear or branched.

40. The composition of claim 39, wherein m is a discrete integer from 2 to 50.

41. The composition of claim 39, wherein said water-soluble repeat unit comprises an ethylene oxide repeat unit of the formula

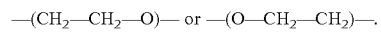

42. A method of treating a human disease or condition that comprises administering to an individual in need of such treatment an effective amount of a pharmaceutical composition comprising a polymer-modified bioactive protein having a monomer polypeptide molecular weight greater than about 25 kDa, wherein the polymer-modified bioactive protein possesses a bioactivity that mimics a bioactivity associated with a natural human protein receptor or fragment thereof, protein receptor ligand or fragment thereof, or a cytokine, wherein the composition is uniform with regard to the attachment sites of the polymer to the protein, and wherein the polymer is attached to at least one internal amino acid of the protein.

43. The method of claim 42, wherein said bioactive protein is a synthetic protein having a bioactivity of a cytokine.

44. The method of claim 43, wherein said cytokine is selected from the group consisting of an interleukin, an erythropoiesis stimulating protein, an interferon, a lymphokine, a chemokine, a growth factor, a colony stimulating factor, and a signal peptide hormone.

45. A method of producing a polymer-modified polypeptide chain of a synthetic bioactive polymer-modified protein, said method comprising providing peptide segments comprising non-overlapping amino acid sequences of a polypeptide chain of said synthetic bioactive polymer-modified protein, wherein one or more of said peptide segments comprises an irregular amino acid having a first chemoselective functional group attached thereto, and reacting said irregular amino acid with a water-soluble polymer having a second chemoselective functional group attached thereto, wherein the second chemoselective group is uniquely and mutually reactive with the first chemoselective group, to obtain at least one of said peptide segments having a polymer attached thereto, chemically ligating said peptide segments to obtain a polymer-modified polypeptide chain of said synthetic bioactive polymer-modified protein.

46. The method of claim 45, wherein said polypeptide chain comprises an amino acid sequence of a ribosomally specified protein.

47. The method of claim 46, wherein said ribosomally specified protein is a mammalian protein.

48. The method of claim 47, wherein said mammalian protein is a cytokine.

49. The method of claim 48, wherein said cytokine is selected from the group consisting of an interleukin, an erythropoiesis stimulating protein, an interferon, a lymphokine, a chemokine, a growth factor, a colony stimulating factor, and a signal peptide hormone.

50. The method of claim 45, which further comprises folding said polymer-modified polypeptide chain whereby a synthetic bioactive polymer-modified protein is produced.

51. The method of claim 45, wherein one or more of said peptide segments are partially protected.

52. The method of claim 45, wherein one or more of said peptide segments are unprotected.

53. The method of claim 45, wherein said chemically ligating comprises a chemoselective ligation chemistry selected from the group consisting of native chemical ligation, extended native chemical ligation and pseudo native chemical ligation.

54. The method of claim 45, wherein said water-soluble polymer comprises a molecular weight of between 1,500 and 80,000 Daltons.

55. A method of producing a polymer-modified polypeptide chain of a synthetic bioactive polymer-modified protein, said method comprising:
   a. chemically ligating peptide segments comprising non-overlapping amino acid sequences of said synthetic bioactive polymer-modified protein to form a full length polypeptide chain corresponding to the amino acid sequence of said synthetic bioactive polymer-modified protein, wherein one or more of said peptide segments comprises an irregular amino acid having a first unique chemoselective group attached thereto; and
   b. chemically ligating a water-soluble polymer to said full length polypeptide chain, said water-soluble polymer comprising a second chemoselective group that is mutually and uniquely reactive with said first unique chemoselective group, whereby a polymer-modified polypeptide chain of said synthetic bioactive polymer-modified protein is produced.

56. The method of claim 55, which further comprises folding said polymer-modified polypeptide chain whereby a synthetic bioactive polymer-modified protein is produced.

57. A method of producing a synthetic bioactive polymer-modified protein, said method comprising
   a. chemically ligating peptide segments comprising non-overlapping amino acid sequences of said synthetic bioactive polymer-modified protein to form a full length polypeptide chain corresponding to the amino acid sequence of said synthetic bioactive polymer-modified protein, wherein one or more of said peptide segments comprises a non-native side chain comprising a first unique chemoselective group that is unreactive with a side chain functional group of an amino acid of a genetically encoded amino acid;
   b. folding said full length polypeptide chain to form a folded polypeptide chain; and
   c. chemically ligating a water-soluble polymer to said folded polypeptide chain, said water-soluble polymer comprising a second chemoselective group that is mutually and uniquely reactive with said first unique chemoselective group, whereby a polymer-modified polypeptide chain of said synthetic bioactive polymer-modified protein is produced.

58. A molecularly homogeneous water-soluble polymer of the formula:

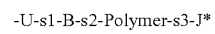

wherein:
   U is a residue of a unique functional group covalently bonded to a mutually reactive unique functional group of a side chain of an internal amino acid of a peptide,
   B comprises a branching core joined to Polymer through amide bonds, and
   Y is $-(CH_2-(CH_2-CH_2-O)_3-CH_2-CH_2-CH_2)_z-$ or $-(CH_2-CH_2-CH_2-(O-CH_2-CH_2)_3-CH_2)_z-$, where z is 6 to 36,
   Polymer is a polyamide having a molecular weight greater than about 5,000 Da of the formula $-[C(O)-X-C(O)-NH-Y-NH]_n-$ or $-[NH-Y-NH-C(O)-X-C(O)]_n-$, where X and Y are divalent radicals that may be the same or different and may be branched or linear, and n is a discrete integer from 2 to 50, and where either or both of X and Y comprises a substantially non-antigenic water-soluble repeat unit that may be linear or branched,
   J* is a residue of a substantially non-antigenic pendant group having a net charge under physiological conditions selected from the group consisting of negative, positive and neutral, and
   s1, s2, and s3 are spacer or linker moieties that may be the same or different, and may be individually present or absent.

59. The water-soluble polymer of claim 58, wherein J* comprises an ionizable group that comprises a net negative charge under physiological conditions.

60. The water-soluble polymer of claim 58, wherein X is $-X'-NH-$ or $-NH-X'-$, wherein X' is a divalent radical comprising a water-soluble repeat unit that may be linear or branched.

61. The water-soluble polymer of claim 58, wherein Y is $-Y'-NH-$ or $-NH-Y'-$, wherein Y' is divalent radical.

62. The water-soluble polymer of claim 61, wherein Y' comprises a polyethylene oxide of formula $(-CH_2-CH_2-O-)_z$ or $(O-CH_2-CH_2-)_z$ where z is 2 to 50.

* * * * *

UNITED STATES PATENT AND TRADEMARK OFFICE
CERTIFICATE OF CORRECTION

| | | |
|---|---|---|
| PATENT NO. | : 7,118,737 B2 | Page 1 of 1 |
| APPLICATION NO. | : 10/332385 | |
| DATED | : October 10, 2006 | |
| INVENTOR(S) | : Gerd G. Kochendoerfer et al. | |

It is certified that error appears in the above-identified patent and that said Letters Patent is hereby corrected as shown below:

Column 113, line 46, claim 4, replace "delivative" with -- derivative --.

Signed and Sealed this

Seventeenth Day of April, 2007

JON W. DUDAS
*Director of the United States Patent and Trademark Office*